(12) United States Patent
Howard et al.

(10) Patent No.: US 8,598,217 B2
(45) Date of Patent: Dec. 3, 2013

(54) IMIDAZOLE DERIVATIVES AND THEIR USE AS MODULATORS OF CYCLIN DEPENDENT KINASES

(75) Inventors: Steven Howard, Cambridge (GB); Paul Neil Mortenson, Cambridge (GB); Steven Douglas Hiscock, Cambridge (GB); Alison Jo-Anne Woolford, Cambridge (GB); Andrew James Woodhead, Cambridge (GB); Gianni Chessari, Cambridge (GB); Marc O'Reilly, Cambridge (GB); Miles Stuart Congreve, Royston (GB); Claudio Dagostin, Cambridge (GB); Young Shin Cho, Cambridge, MA (US); Fan Yang, Roxbury, MA (US); Christine Hiu-Tung Chen, Waltham, MA (US); Christopher Thomas Brain, North Reading, MA (US); Bharat Lagu, Acton, MA (US); Yaping Wang, Boxborough, MA (US); Sunkyu Kim, Arlington, MA (US); John Giraldes, Quincy, MA (US); Michael Joseph Luzzio, Groton, CT (US); Lawrence Blas Perez, Hopkinton, MA (US)

(73) Assignees: Astex Therapeutics Ltd., Cambridge (GB); Novartis AG, Basel (CH)

( * ) Notice: Subject to any disclaimer, the term of this patent is extended or adjusted under 35 U.S.C. 154(b) by 132 days.

(21) Appl. No.: 13/266,976

(22) PCT Filed: Apr. 30, 2010

(86) PCT No.: PCT/GB2010/050725
§ 371 (c)(1),
(2), (4) Date: Jan. 5, 2012

(87) PCT Pub. No.: WO2010/125402
PCT Pub. Date: Nov. 4, 2010

(65) Prior Publication Data
US 2012/0101064 A1  Apr. 26, 2012

Related U.S. Application Data

(60) Provisional application No. 61/174,293, filed on Apr. 30, 2009.

(51) Int. Cl.
| | | |
|---|---|---|
| *A61K 31/496* | (2006.01) |
| *A61K 31/4545* | (2006.01) |
| *A61K 31/4439* | (2006.01) |
| *A61K 31/4725* | (2006.01) |
| *A61K 31/4353* | (2006.01) |
| *A61K 31/4178* | (2006.01) |
| *A61K 31/4184* | (2006.01) |
| *A61P 35/00* | (2006.01) |
| *C07D 471/04* | (2006.01) |
| *C07D 401/06* | (2006.01) |
| *C07D 417/10* | (2006.01) |
| *C07D 413/06* | (2006.01) |
| *C07D 403/10* | (2006.01) |

(52) U.S. Cl.
USPC ........... 514/396; 514/397; 514/399; 514/400; 514/303; 514/341; 514/394; 514/365; 514/234.5; 514/318; 514/319; 514/322; 514/323; 514/307; 514/218; 514/81; 514/253.05; 514/253.09; 544/364; 544/139; 544/131; 544/363; 546/274.7; 546/273.1; 546/118; 546/144;546/199;548/303.1; 548/312.1

(58) Field of Classification Search
USPC ......... 514/396, 397, 399, 400, 303, 341, 394, 514/365, 253.05, 253.09, 234.5, 318, 319, 514/322, 323, 307, 218, 81; 544/364, 139, 544/131, 363; 546/274.7, 273.1, 118, 144, 546/199; 548/303.1, 312.1
See application file for complete search history.

(56) References Cited

U.S. PATENT DOCUMENTS

| | | |
|---|---|---|
| 6,603,000 B2 | 8/2003 | Yee et al. |
| 2003/0028017 A1 | 2/2003 | Yee et al. |
| 2006/0270686 A1 | 11/2006 | Kelly et al. |

FOREIGN PATENT DOCUMENTS

| | | |
|---|---|---|
| DE | 4142075 | 6/1993 |
| JP | 06-041116 | 2/1994 |

(Continued)

*Primary Examiner* — Sreeni Padmanabhan
*Assistant Examiner* — Irina Neagu
(74) *Attorney, Agent, or Firm* — Heslin Rothenberg Farley & Mesiti P.C.

(57) ABSTRACT

The invention provides compounds of the formula (I):

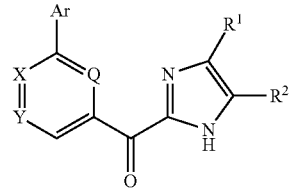

and salts, tautomers, solvates and N-oxides thereof;
wherein Q is CH or N; X is N, $N^+$—$O^-$ or $CR^3$; Y is N, $N^+$—$O^-$ or $CR^{3a}$; $R^1$ and $R^2$ are independently selected from hydrogen and various substituents as defined in the claims; or $R^1$ and $R^2$ together with the atoms to which they are attached, link to form an optionally substituted carbocyclic or heterocyclic aromatic or non-aromatic ring of 4 to 7 members; $R^3$ is selected from hydrogen and various substituents; and $R^{3a}$ is selected from hydrogen and various substituents as defined in the claims. Also provided are pharmaceutical compositions containing the compounds of formula (I), processes for making the compounds and the medical uses of the compounds. The compounds of formula (I) have activity as inhibitors of CDK kinases and are useful in the treatment of inter alia proliferative diseases such as cancers.

18 Claims, No Drawings

(56) References Cited

FOREIGN PATENT DOCUMENTS

| WO | WO 92/17468 | 10/1992 |
| WO | WO 99/38829 | 8/1999 |
| WO | WO 01/00579 | 1/2001 |
| WO | WO 01/10842 | 2/2001 |
| WO | 01/51456 A2 | 7/2001 |
| WO | WO 02/00647 | 1/2002 |
| WO | WO 02/062766 | 8/2002 |
| WO | WO 2005/049603 | 6/2005 |
| WO | WO 2005/058834 | 6/2005 |
| WO | WO 2005/080346 | 9/2005 |
| WO | 2008/013963 A2 | 1/2008 |
| WO | WO 2008/044045 | 4/2008 |
| WO | WO 2009/014637 | 1/2009 |

IMIDAZOLE DERIVATIVES AND THEIR USE AS MODULATORS OF CYCLIN DEPENDENT KINASES

CROSS REFERENCE TO RELATED APPLICATIONS

This application is a national stage filing under section 371 of International Application No. PCT/GB2010/050725, filed on Apr. 30, 2010, and published in English on Nov. 4, 2010, as WO 2010/125402, and claims priority to U.S. Provisional Application No. 61/174,293, filed on Apr. 30, 2009. The entire disclosures of each of the prior applications are hereby incorporated herein by reference.

FIELD OF THE INVENTION

This invention relates to compounds that inhibit or modulate the Cyclin dependent Kinases (CDK) kinases, to the use of the compounds in the treatment or prophylaxis of disease states or conditions mediated by the kinases, pharmaceutical compositions containing the compounds, processes for their preparation and novel chemical intermediates.

BACKGROUND OF THE INVENTION

Protein kinases constitute a large family of structurally related enzymes that are responsible for the control of a wide variety of signal transduction processes within the cell (Hardie, G. and Hanks, S. (1995) *The Protein Kinase Facts Book. I and II*, Academic Press, San Diego, Calif.). The kinases may be categorized into families by the substrates they phosphorylate (e.g., protein-tyrosine, protein-serine/threonine, lipids, etc.). Sequence motifs have been identified that generally correspond to each of these kinase families (e.g., Hanks, S. K., Hunter, T., *FASEB J.*, 9:576-596 (1995); Knighton, et al., *Science*, 253:407-414 (1991); Hiles, et al., *Cell*, 70:419-429 (1992); Kunz, et al., *Cell*, 73:585-596 (1993); Garcia-Bustos, et al., *EMBO J.*, 13:2352-2361 (1994)).

Protein kinases may be characterized by their regulation mechanisms. These mechanisms include, for example, autophosphorylation, transphosphorylation by other kinases, protein-protein interactions, protein-lipid interactions, and protein-polynucleotide interactions. An individual protein kinase may be regulated by more than one mechanism.

Kinases regulate many different cell processes including, but not limited to, proliferation, differentiation, apoptosis, motility, transcription, translation and other signalling processes, by adding phosphate groups to target proteins. These phosphorylation events act as molecular on/off switches that can modulate or regulate the target protein biological function. Phosphorylation of target proteins occurs in response to a variety of extracellular signals (hormones, neurotransmitters, growth and differentiation factors, etc.), cell cycle events, environmental or nutritional stresses, etc. Examples of such stimuli include environmental and chemical stress signals (e.g., osmotic shock, heat shock, ultraviolet radiation, bacterial endotoxin, and $H_2O_2$), cytokines (e.g., interleukin-1 (IL-1) and tumor necrosis factor-$\alpha$ (TNF-$\alpha$)), and growth factors (e.g., granulocyte macrophage-colony-stimulating factor (GM-CSF), and fibroblast growth factor (FGF)). An extracellular stimulus may affect one or more cellular responses related to cell growth, migration, differentiation, secretion of hormones, activation of transcription factors, muscle contraction, glucose metabolism, control of protein synthesis, and regulation of the cell cycle.

Many diseases are associated with abnormal cellular responses triggered by protein kinase-mediated events as described above. These diseases include, but are not limited to, autoimmune diseases, inflammatory diseases, bone diseases, metabolic diseases, neurological and neurodegenerative diseases, cancer, cardiovascular diseases, allergies and asthma, Alzheimer's disease, and hormone-related diseases.

Accordingly, there has been a substantial effort in medicinal chemistry to find protein kinase inhibitors that are effective as therapeutic agents.

Cyclin Dependent Kinases

Initiation, progression, and completion of the mammalian cell cycle are regulated by various cyclin-dependent kinase (CDK) complexes, which are critical for cell growth. These complexes comprise at least a catalytic (the CDK itself) and a regulatory (cyclin) subunit. Some of the more important complexes for cell cycle regulation include cyclin A (CDK1—also known as cdc2, and CDK2), cyclin B1-B3 (CDK1) and cyclin D1-D3 (CDK2, CDK4, CDK5, CDK6), cyclin E (CDK2). Each of these complexes is involved in a particular phase of the cell cycle.

The process of eukaryotic cell division may be broadly divided into a series of sequential phases termed G1, S, G2 and M. Correct progression through the various phases of the cell cycle has been shown to be critically dependent upon the spatial and temporal regulation of CDKs and a diverse set of their cognate protein partners termed cyclins. CDKs are homologous serine-threonine kinase proteins that are able to utilise ATP as a substrate in the phosphorylation of diverse polypeptides in a sequence dependent context. Cyclins are a family of proteins characterised by a homology region, containing approximately 100 amino acids, termed the "cyclin box" which is used in binding to, and defining selectivity for, specific CDK partner proteins.

Modulation of the expression levels, degradation rates, and activation levels of various CDKs and cyclins throughout the cell cycle leads to the cyclical formation of a series of CDK/cyclin complexes, in which the CDKs are enzymatically active. The formation of these complexes controls passage through discrete cell cycle checkpoints and thereby enables the process of cell division to continue. Failure to satisfy the pre-requisite biochemical criteria at a given cell cycle checkpoint, i.e. failure to form a required CDK/cyclin complex, can lead to cell cycle arrest and/or cellular apoptosis. Aberrant cellular proliferation, as manifested in cancer, can often be attributed to loss of correct cell cycle control. Inhibition of CDK enzymatic activity therefore provides a means by which abnormally dividing cells can have their division arrested and/or be killed. The diversity of CDKs, and CDK complexes, and their critical roles in mediating the cell cycle, provides a broad spectrum of potential therapeutic targets selected on the basis of a defined biochemical rationale.

Progression from the G1 phase to the S phase of the cell cycle is primarily regulated by CDK2, CDK3, CDK4 and CDK6 via association with members of the D and E type cyclins. The D-type cyclins in complex with CDK4 and 6 appear to be key to the transition from G1 to S phase, where CDK2/cyclin E also plays a critical role Subsequent progression through S phase and entry into G2 is thought to require the CDK2/cyclin A complex. Both mitosis, and the G2 to M phase transition which triggers it, are regulated by complexes of CDK1 (also known as cdc2) and the A and B type cyclins.

During G1 phase Retinoblastoma protein (Rb), and related pocket proteins such as p130, are substrates for CDK(2, 4, & 6)/cyclin complexes. Progression through G1 is in part facilitated by hyperphosphorylation, and thus inactivation, of Rb and p130 by the CDK(4/6)/cyclin-D and CDK2/cyclin E complexes.

Hyperphosphorylation of Rb and p130 causes the release of transcription factors, such as E2F, and thus the expression of genes necessary for progression through G1 and for entry into S-phase, such as the gene for cyclin E. Expression of cyclin E facilitates formation of the CDK2/cyclin E complex which amplifies, or maintains, E2F levels via further phosphorylation of Rb.

The exact role of CDK3 in the cell cycle is not clear. As yet no cognate cyclin partner has been identified, but a dominant negative form of CDK3 delayed cells in G1, thereby suggesting that CDK3 has a role in regulating the G1/S transition.

Progression through the G1-S phase of the cell cycle requires phosphorylation of the retinoblastoma (Rb) protein by CDK4 or the highly homologous CDK6 in complex with their activating subunits, the D-type cyclins, D1, D2 and D3. Hyperphosphorylation of Rb diminishes its ability to repress gene transcription through the E2F family of transcription factors and consequently allows synthesis of several genes, the protein products of which are necessary for DNA replication. Rb phosphorylations at CDK4 and 6 specific sites are also required for the subsequent phosphorylations by CDK2 enzyme complex. Thus, the catalytic activities for CDK4 or CDK6 regulate a critical checkpoint for the G1-S transition and the commitment to cell division. Moreover, D-cyclins also bind to p21 and p27, the cellular inhibitors of CDK2 complexes, to titrate the proteins away from their target, further activating the kinase activity of CDK2.

Not all members of the CDK family are involved exclusively in cell cycle control, however. Although most CDKs have been implicated in regulation of the cell cycle there is evidence that certain members of the CDK family are involved in other biochemical processes. This is exemplified by CDK5 which is necessary for correct neuronal development and which has also been implicated in the phosphorylation of several neuronal proteins such as Tau, NUDE-1, synapsin1, DARPP32 and the Munc18/Syntaxin1A complex. Neuronal CDK5 is conventionally activated by binding to the p35/p39 proteins. CDK5 activity can, however, be deregulated by the binding of p25, a truncated version of p35. Conversion of p35 to p25, and subsequent deregulation of CDK5 activity, can be induced by ischemia, excitotoxicity, and β-amyloid peptide. Consequently p25 has been implicated in the pathogenesis of neurodegenerative diseases, such as Alzheimer's, and is therefore of interest as a target for therapeutics directed against these diseases.

CDK7 is a nuclear protein that has cdc2 CAK activity and binds to cyclin H. CDK7 has been identified as component of the TFIIH transcriptional complex which has RNA polymerase II C-terminal domain (CTD) activity. This has been associated with the regulation of HIV-1 transcription via a Tat-mediated biochemical pathway. CDK8 binds cyclin C and has been implicated in the phosphorylation of the CTD of RNA polymerase II. Similarly the CDK9/cyclin-T1 complex (P-TEFb complex) has been implicated in elongation control of RNA polymerase II. PTEF-b is also required for activation of transcription of the HIV-1 genome by the viral transactivator Tat through its interaction with cyclin T1. Thus CDKs 7, 8, and 9 are implicated in the regulation of transcription and therefore CDK7, CDK8, CDK9 and the P-TEFb complex are therefore potential targets for anti-viral therapeutics.

At a molecular level mediation of CDK/cyclin complex activity requires a series of stimulatory and inhibitory phosphorylation, or dephosphorylation, events. CDK phosphorylation is performed by a group of CDK activating kinases (CAKs) and/or kinases such as wee1, Myt1 and Mik1. Dephosphorylation is performed by phosphatases such as cdc25(a & c), pp2a, or KAP.

CDK/cyclin complex activity may be further regulated by two families of endogenous cellular proteinaceous inhibitors: the Kip/Cip family, or the INK family. The INK proteins specifically bind CDK4 and CDK6. $p16^{ink4}$ (also known as MTS1) is a potential tumour suppressor gene that is mutated, or deleted, in a large number of primary cancers. The Kip/Cip family contains proteins such as $p21^{Cip1,Waf1}$, $p27^{Kip1}$ and $p57^{kip2}$. p21 is induced by p53 and is able to inactivate the CDK2/cyclin(E/A) complexes. Atypically low levels of p27 expression have been observed in breast, colon and prostate cancers. Conversely over expression of cyclin E in solid tumours has been shown to correlate with poor patient prognosis. Overexpression of cyclin D1 has been associated with oesophageal, breast, squamous, and non-small cell lung carcinomas.

The pivotal roles of CDKs, and their associated proteins, in co-ordinating and driving the cell cycle in proliferating cells have been outlined above. Some of the biochemical pathways in which CDKs play a key role have also been described. The development of monotherapies for the treatment of proliferative disorders, such as cancers, using therapeutics targeted generically at CDKs, or at specific CDKs, is therefore potentially highly desirable. CDK inhibitors could conceivably also be used to treat other conditions such as viral infections, autoimmune diseases and neuro-degenerative diseases, amongst others. CDK targeted therapeutics may also provide clinical benefits in the treatment of the previously described diseases when used in combination therapy with either existing, or new, therapeutic agents. CDK targeted anticancer therapies could potentially have advantages over many current antitumour agents as they would not directly interact with DNA and should therefore reduce the risk of secondary tumour development.

There is evidence that particular components of the CDK4/cyclin D-INK4 proteins-Rb family regulatory machinery act as tumour suppressors or protooncogenes, whose mutations occur so frequently (>90%) as to suggest that perturbing "the RB pathway" may be involved in the formation of cancer cells. RB loss and mutations inactivating p16INK4a function occurs in many tumour types. Mutually exclusive events resulting in RB or p16INK4a inactivation through mutation, deletion, or epigenetic silencing, or in the overexpression of cyclin D1 or CDK4 or mutation in CDK4, provide genetic evidence for operation of this signaling pathway in tumour surveillance.

Cancers that experience INK4a and RB loss of function, mutation in CDK4 and cyclin D1 or CDK4 activation or overexpression, include retinoblastomas, small cell lung carcinomas, non-small lung carcinomas, sarcomas, gliomas, pancreatic cancers, head, neck and breast cancers and mantle cell lymphomas in particular small cell lung cancer, non-small cell lung cancer, pancreatic cancer, breast cancer, glioblastoma multiforme, T cell ALL and mantle cell lymphoma.

Therefore one subset of cancers is retinoblastomas, small cell lung carcinomas, non-small lung carcinomas, sarcomas, gliomas, pancreatic cancers, head, neck and breast cancers and mantle cell lymphomas.

Another subset of cancers are small cell lung cancer, non-small cell lung cancer, pancreatic cancer, breast cancer, glioblastoma multiforme, T cell ALL and mantle cell lymphoma.

CDK4 activation can occur in tumours with ras or raf mutations or growth factor activation. Therefore tumours with ras, raf and EGFR, IGFR, FGFR, cKit, PDGFR activation may also be treated with CDK4 inhibiting compounds.

Amplification or translocation of CDK4 or CDK6 has been demonstrated in several sarcomas and leukemias (Am J Pathol. 2002 August; 161(2): 405-411). In addition, CDK4 amplification and overexpression have been implicated in glioma development, in this case, mutually exclusive mutations of p16INK4a or CDK4 were observed. Also, a mutation in CDK4 has been described in patients with familial melanoma and it has recently been reported that CDK4 knockout mice harbouring this point mutation (R24C) are highly susceptible to melanoma development after chemical treatment.

SUMMARY OF THE INVENTION

The invention provides compounds that have cyclin dependent kinase inhibiting or modulating activity, and which are useful in preventing or treating disease states or conditions mediated by the kinases.

Thus, for example, the compounds of the invention will be useful in alleviating or reducing the incidence of cancer.

In a first aspect, the invention provides a compound of the formula (I):

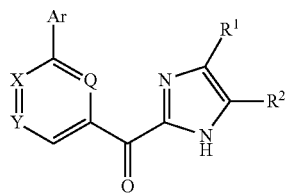

or a salt, tautomer, solvate or N-oxide thereof;
wherein:
Q is CH or N;
X is N, N$^+$—O$^-$ or CR$^3$;
Y is N, N$^+$—O$^-$ or CR$^{3a}$;
R$^1$ and R$^2$ are independently selected from hydrogen; halogen; cyano; hydroxyl; C$_{1-8}$ alkyl; C$_{1-8}$ alkoxyl; C$_{2-8}$ alkenyl; C$_{2-8}$ alkynyl; C$_{3-8}$ cycloalkyl; C$_{2-8}$ cycloalkenyl; aryl; heterocyclyl; heteroaryl; OR$^5$; C=OR$^5$; C(=O)OR$^5$; OC=OR$^5$; S(O)$_n$R$^5$; NR$^7$R$^8$; N(R$^7$)C(=O)R$^8$; C(=O)NR$^7$R$^8$; SO$_2$NR$^9$R$^{10}$; wherein the C$_{1-8}$ alkyl, C$_{1-8}$ alkoxyl, C$_{2-8}$ alkenyl and C$_{2-8}$ alkynyl moieties are each optionally substituted by one or more substituents R$^{11}$; and the C$_{3-8}$ cycloalkyl, C$_{2-6}$ cycloalkenyl, aryl, heterocyclyl and heteroaryl are each optionally substituted by one or more substituents R$^{12}$;
n is 0, 1 or 2;
m is 0, 1, 2, or 3;
or R$^1$ and R$^2$ together with the atoms to which they are attached, link to form an aromatic or non-aromatic ring of 4 to 7 members, wherein said aromatic or non-aromatic ring contains 0, 1 or 2 heteroatom ring members selected from O, N and S, wherein the aromatic or non-aromatic ring is optionally substituted by one or more substituents R$^{13}$;
R$^3$ is selected from hydrogen; hydroxy; halogen; cyano; OR$^5$; C(=O)R$^5$; OC(=O)R$^5$; C(=O)OR$^5$; S(O)$_n$R$^5$; NR$^7$R$^8$; N(R$^7$)C(=O)R$^8$; C(=O)NR$^7$R$^8$; SO$_2$NR$^9$R$^{10}$; C$_{1-6}$ alkyl; C$_{2-6}$ alkenyl; C$_{2-6}$ alkynyl; C$_{3-6}$ cycloalkyl; 5 or 6 membered aryl; and 5 or 6 membered heteroaryl;
R$^{3a}$ is selected from hydrogen; halogen; cyano; OR$^5$; C(=O)R$^5$; OC(=O)R$^5$; C(=O)OR$^5$; S(O)$_n$R$^5$; NR$^7$R$^8$; N(R$^7$)C(=O)R$^8$; C(=O)NR$^7$R$^8$; SO$_2$NR$^9$R$^{10}$; C$_{1-6}$ alkyl; C$_{2-6}$ alkenyl; C$_{2-6}$ alkynyl; C$_{3-6}$ cycloalkyl; 5 or 6 membered aryl; and 5 or 6 membered heteroaryl;
wherein, in R$^3$ and R$^{3a}$, the C$_{1-6}$ alkyl, C$_{1-6}$ alkoxyl, C$_{2-6}$ alkenyl and C$_{2-6}$ alkynyl moieties are each optionally substituted by one or more substituents R$^{11}$; and the C$_{3-6}$ cycloalkyl, 5- or 6-membered aryl, and 5- or 6-membered heteroaryl moieties are each optionally substituted by one or more substituents R$^{12}$;
R$^5$ is selected from C$_{1-8}$ alkyl; C$_{3-8}$ cycloalkyl; aryl; heteroaryl; and heterocyclyl;
R$^7$ and R$^8$ are the same or different, and independently are selected from hydrogen; C$_{1-8}$ alkyl; C$_{3-8}$ cycloalkyl; aryl; heteroaryl; and heterocyclyl; or NR$^7$R$^8$ forms a non-aromatic four to seven membered ring optionally containing a second heteroatom selected from O, N and S, and optionally substituted by one or more substituents R$^{12}$;
R$^9$ and R$^{10}$ are the same or different, and independently are selected from hydrogen; C$_{1-8}$ alkyl; C$_{3-8}$ cycloalkyl; aryl; heteroaryl; and heterocyclyl; or NR$^9$R$^{10}$ forms a non-aromatic four to seven membered ring optionally containing a second heteroatom selected from O, N and S, and optionally substituted by one or more substituents R$^{12}$;
wherein, in R$^5$, R$^7$, R$^8$, R$^9$ and R$^{10}$, the C$_{1-8}$ alkyl moiety is optionally substituted by one or more substituents R$^{11}$; and the C$_{3-8}$ cycloalkyl, aryl, heteroaryl and heterocyclyl moieties are each optionally substituted by one or more substituents R$^{12}$;
R$^{11}$ is selected from the group consisting of halogen; cyano; =O; hydroxyl; C$_{1-6}$ alkyl; C$_{1-6}$ alkoxy; C$_{2-6}$ alkenyl; C$_{2-6}$ alkynyl; C$_{3-6}$ cycloalkyl; C$_{3-6}$ cycloalkenyl; aryl; heteroaryl; heterocyclyl; —(CH$_2$)$_m$—NR$^{7a}$R$^{8a}$; —(CH$_2$)$_m$—C(=O)OR$^{5a}$; —(CH$_2$)$_m$—OC(=O)R$^{5a}$; —(CH$_2$)$_m$—C(=O)R$^{5a}$; —(CH$_2$)$_m$—S(O)$_n$R$^5$; —(CH$_2$)$_m$—N(R$^{7a}$)C(=O)R$^{8a}$; —(CH$_2$)$_m$—C(=O)NR$^{7a}$R$^{8a}$; —(CH$_2$)$_m$—SO$_2$NR$^{9a}$R$^{10a}$; —(CH$_2$)$_m$-aryl; —(CH$_2$)$_m$—O-aryl; —O—(CH$_2$)$_m$-aryl; —(CH$_2$)$_m$-heterocyclyl; —O—(CH$_2$)$_m$-heterocyclyl; and —(CH$_2$)$_m$—O-heterocyclyl;
R$^{12}$ is selected from the group consisting of halogen; cyano; =O; hydroxyl; —O—P(O)(OH)$_2$; C$_{1-6}$ alkyl; C$_{1-6}$ alkoxyl; C$_{2-6}$ alkenyl; C$_{2-6}$ alkynyl; C$_{3-6}$ cycloalkyl; C$_{3-6}$ cycloalkenyl; —(CH$_2$)$_m$—NR$^{7a}$R$^{8a}$; —(CH$_2$)$_m$—C(=O)OR$^{5a}$; —(CH$_2$)$_m$—OC(=O)R$^{5a}$; —(CH$_2$)$_m$—C(=O)R$^{5a}$; —(CH$_2$)$_m$—S(O)$_n$R$^{5a}$; —(CH$_2$)$_m$—N(R$^7$)C(=O)R$^{8a}$; —(CH$_2$)$_m$—C(=O)NR$^{7a}$R$^{8a}$; —(CH$_2$)$_m$—SO$_2$NR$^{9a}$R$^{10a}$; —(CH$_2$)$_m$-aryl; —(CH$_2$)$_m$-O-aryl; —O—(CH$_2$)$_m$-aryl; —(CH$_2$)$_m$-heterocyclyl; —O—(CH$_2$)m-heterocyclyl; and —(CH$_2$)$_m$—O-heterocyclyl;
wherein, in R$^{11}$ and R$^{12}$, the C$_{1-6}$ alkyl, C$_{1-6}$ alkoxyl, C$_{2-6}$ alkenyl and C$_{2-6}$ alkynyl moieties are each optionally substituted by one or more substituents R$^{14}$; and the C$_{3-8}$ cycloalkyl, C$_{3-6}$ cycloalkenyl, aryl, heterocyclyl and heteroaryl moieties are each optionally substituted by one or more substituents R$^{15}$;
R$^{13}$ is selected from the group consisting of halogen; cyano; hydroxyl; =O; an oxide (when R$^{13}$ is attached to N or S); a dioxide (when R$^{13}$ is attached to S); C$_{1-6}$ alkyl optionally substituted by one or more substituents R$^{11}$; C$_{1-6}$ alkoxyl optionally substituted by one or more substituents R$^{11}$; C$_{2-6}$ alkenyl optionally substituted by one or more substituents R$^{11}$; C$_{2-6}$ alkynyl optionally substituted by one or more substituents R$^{11}$; C$_{3-6}$ cycloalkyl optionally substituted by one or more substituents R$^{12}$; C$_{3-6}$ cycloalkenyl optionally substituted by one or more substituents R$^{12}$; aryl optionally substituted by one or more substituents $R^{12}$; heteroaryl optionally substituted by one or more substituents $R^{12}$; heterocyclyl optionally substituted by one or more substituents $R^{12}$; $-(CH_2)_m-NR^7R^8$; $-(CH_2)_m-C(=O)OR^5$; $-(CH_2)_m-OC(=O)R^5$; $-(CH_2)_m-C(=O)R^5$; $-(CH_2)_m-S(O)_nR^5$; $-(CH_2)_m-N(R^7)C(=O)R^8$; $-(CH_2)_m-C(=O)NR^7R^8$; $-(CH_2)_m-SO_2NR^9R^{10}$; $-(CH_2)_m$-aryl; $-(CH_2)_m$-O-aryl; $-O-(CH_2)_m$-aryl; $-(CH_2)_m$-heterocyclyl; $-O-(CH_2)_m$-heterocyclyl; and $-(CH_2)_m$-O-heterocyclyl wherein the aryl or heterocyclyl can be optionally substituted by one or more substituents $R^{12}$; and Ar is selected from 6-membered aryl optionally substituted by one or more substituents $R^{13}$; 5 or 6-membered heteroaryl optionally substituted by one or more substituents $R^{13}$; bicyclic aryl optionally substituted by one or more substituents $R^{13}$; and bicyclic heteroaryl optionally substituted by one or more substituents $R^{13}$;

$R^{14}$ is selected from hydroxy; halogen; cyano; $C_{1-4}$ alkyl; $C_{1-4}$ alkoxy; $C_{1-4}$ alkoxy-$C_{2-4}$ alkoxy; hydroxy-$C_{2-4}$ alkoxy; $(CH_2)_m-NR^{7a}R^{8a}$; $-(CH_2)_m-C(=O)OR^{5a}$; $-(CH_2)_m-OC(=O)R^{5a}$; $-(CH_2)_m-C(=O)R^{5a}$; $-(CH_2)_m-S(O)_nR^{5a}$; $-(CH_2)_m-N(R^{7a})C(=O)R^{8a}$; $-(CH_2)_m-C=ONR^{7a}R^{8a}$; and $-(CH_2)_m-SO_2NR^{9a}R^{10a}$;

$R^{15}$ is selected from hydroxy; halogen; cyano; $C_{1-4}$ alkyl; $C_{1-4}$ alkoxy; $C_{1-4}$ alkoxy-$C_{2-4}$ alkoxy; hydroxy-$C_{2-4}$ alkoxy; $(CH_2)_m-NR^{7a}R^{8a}$; $-(CH_2)_m-C(=O)OR^{5a}$; $-(CH_2)_m-OC(=O)R^{5a}$; $-(CH_2)_m-C(=O)R^{5a}$; $-(CH_2)_m-S(O)_nR^{5a}$; $-(CH_2)_m-N(R^{7a})C(=O)R^{8a}$; $-(CH_2)_m-C(=O)NR^{7a}R^{8a}$; and $-(CH_2)_m-SO_2NR^{9a}R^{10a}$;

$R^{5a}$ is selected from $C_{1-8}$ alkyl optionally substituted by one or more substituents selected from amino, hydroxy, $C_{1-4}$ alkoxy, halogen and cyano; $C_{3-8}$ cycloalkyl optionally substituted by one or more substituents selected from hydroxy, $C_{1-4}$ alkyl, $C_{1-4}$ alkoxy, halogen and cyano; aryl optionally substituted by one or more substituents selected from hydroxy, $C_{1-4}$ alkyl, $C_{1-4}$ alkoxy, halogen and cyano; heteroaryl optionally substituted by one or more substituents selected from hydroxy, $C_{1-4}$ alkyl, $C_{1-4}$ alkoxy, halogen and cyano; and heterocyclyl optionally substituted by one or more substituents selected from hydroxy, $C_{1-4}$ alkyl, $C_{1-4}$ alkoxy, halogen and cyano;

$R^{7a}$ and $R^{8a}$ are the same or different, and independently are selected from hydrogen; $C_{1-8}$ alkyl optionally substituted by one or more substituents selected from hydroxy, $C_{1-4}$ alkoxy, halogen and cyano; $C_{3-8}$ cycloalkyl optionally substituted by one or more substituents hydroxy, $C_{1-4}$ alkyl, $C_{1-4}$ alkoxy, halogen and cyano; aryl optionally substituted by one or more substituents hydroxy, $C_{1-4}$ alkyl, $C_{1-4}$ alkoxy, halogen and cyano; heteroaryl optionally substituted by one or more substituents selected from hydroxy, $C_{1-4}$ alkyl, $C_{1-4}$ alkoxy, halogen and cyano; and heterocyclyl optionally substituted by one or more substituents selected from hydroxy, $C_{1-4}$ alkyl, $C_{1-4}$ alkoxy, halogen and cyano; or $NR^{7a}R^{8a}$ forms a non-aromatic four to seven membered ring optionally containing a second heteroatom selected from O, N and S, and optionally substituted by one or more substituents selected from hydroxyl, $C_{1-4}$ alkyl, $C_{1-4}$ acyl, $C_{1-4}$ alkoxycarbonyl and $C_{1-4}$ alkylsulphonyl; and $R^{9a}$ and $R^{10a}$ are the same or different, and independently are selected from hydrogen; $C_{1-8}$ alkyl optionally substituted by one or more substituents selected from hydroxy, $C_{1-4}$ alkoxy, halogen and cyano; $C_{3-8}$ cycloalkyl optionally substituted by one or more substituents selected from hydroxy, $C_{1-4}$ alkyl, $C_{1-4}$ alkoxy, halogen and cyano; aryl optionally substituted by one or more substituents selected from hydroxy, $C_{1-4}$ alkyl, $C_{1-4}$ alkoxy, halogen and cyano; heteroaryl optionally substituted by one or more substituents selected from hydroxy, $C_{1-4}$ alkyl, $C_{1-4}$ alkoxy, halogen and cyano; and heterocyclyl optionally substituted by one or more substituents selected from hydroxy, $C_{1-4}$ alkyl, $C_{1-4}$ alkoxy, halogen and cyano.

In another aspect, the invention provides a compound of the formula (I), or a salt, tautomer, solvate or N-oxide thereof, as hereinbefore defined;

wherein:

X is N, $N^+-O^-$ or $CR^3$;

Y is N, $N^+-O^-$ or $CR^{3a}$;

$R^1$ and $R^2$ are independently selected from hydrogen; halogen; cyano; hydroxyl; $C_{1-8}$ alkyl; $C_{1-8}$ alkoxyl; $C_{2-8}$ alkenyl; $C_{2-8}$ alkynyl; $C_{3-8}$ cycloalkyl; $C_{2-8}$ cycloalkenyl; aryl; heterocyclyl; heteroaryl; $OR^5$; $C=OR^5$; $C(=O)OR^5$; $OC=OR^5$; $S(O)_nR^5$; $NR^7R^8$; $N(R^7)C(=O)R^8$; $C(=O)NR^7R^8$; $SO_2NR^9R^{10}$; wherein the $C_{1-8}$ alkyl, $C_{1-8}$ alkoxyl, $C_{2-8}$ alkenyl and $C_{2-8}$ alkynyl moieties are each optionally substituted by one or more substituents $R^{11}$; and the $C_{3-8}$ cycloalkyl, $C_{2-6}$ cycloalkenyl, aryl, heterocyclyl and heteroaryl are each optionally substituted by one or more substituents $R^{12}$;

n is 0, 1 or 2;

m is 0, 1, 2, or 3;

or $R^1$ and $R^2$ together with the atoms to which they are attached, link to form an aromatic or non-aromatic ring of 4 to 7 members, wherein said aromatic or non-aromatic ring contains 0, 1 or 2 heteroatom ring members selected from O, N and S, wherein the aromatic or non-aromatic ring is optionally substituted by one or more substituents $R^{13}$;

$R^3$ is selected from hydrogen; halogen; cyano; $OR^5$; $C(=O)R^5$; $OC(=O)R^5$; $C(=O)OR^5$; $S(O)_nR^5$; $NR^7R^8$; $N(R^7)C(=O)R^8$; $C(=O)NR^7R^8$; $SO_2NR^9R^{10}$; $C_{1-6}$ alkyl; $C_{2-6}$ alkenyl; $C_{2-6}$ alkynyl; $C_{3-6}$ cycloalkyl; 5 or 6 membered aryl; and 5 or 6 membered heteroaryl;

$R^{3a}$ is selected from hydrogen; halogen; cyano; $OR^5$; $C(=O)R^5$; $OC(=O)R^5$; $C(=O)OR^5$; $S(O)_nR^5$; $NR^7R^8$; $N(R^7)C(=O)R^8$; $C(=O)NR^7R^8$; $SO_2NR^9R^{10}$; $C_{1-6}$ alkyl; $C_{2-6}$ alkenyl; $C_{2-6}$ alkynyl; $C_{3-6}$ cycloalkyl; 5 or 6 membered aryl; and 5 or 6 membered heteroaryl;

wherein, in $R^3$ and $R^{3a}$, the $C_{1-6}$ alkyl, $C_{1-6}$ alkoxyl, $C_{2-6}$ alkenyl and $C_{2-6}$ alkynyl moieties are each optionally substituted by one or more substituents $R^{11}$; and the $C_{3-6}$ cycloalkyl, 5- or 6-membered aryl, and 5- or 6-membered heteroaryl moieties are each optionally substituted by one or more substituents $R^{12}$;

$R^5$ is selected from $C_{1-8}$ alkyl; $C_{3-8}$ cycloalkyl; aryl; heteroaryl; and heterocyclyl;

$R^7$ and $R^8$ are the same or different, and independently are selected from hydrogen; $C_{1-8}$ alkyl; $C_{3-8}$ cycloalkyl; aryl; heteroaryl; and heterocyclyl; or $NR^7R^8$ forms a non-aromatic four to seven membered ring optionally containing a second heteroatom selected from O, N and S, and optionally substituted by one or more substituents $R^{12}$;

$R^9$ and $R^{10}$ are the same or different, and independently are selected from hydrogen; $C_{1-8}$ alkyl; $C_{3-8}$ cycloalkyl; aryl; heteroaryl; and heterocyclyl; or $NR^9R^{10}$ forms a non-aromatic four to seven membered ring optionally containing a second heteroatom selected from O, N and S, and optionally substituted by one or more substituents $R^{12}$;

wherein, in $R^5$, $R^7$, $R^8$, $R^9$ and $R^{10}$, the $C_{1-8}$ alkyl moiety is optionally substituted by one or more substituents $R^{11}$; and the $C_{3-8}$ cycloalkyl, aryl, heteroaryl and heterocyclyl moieties are each optionally substituted by one or more substituents $R^{12}$;

$R^{11}$ is selected from the group consisting of halogen; cyano; =O; hydroxyl; $C_{1-6}$ alkyl; $C_{1-6}$ alkoxy; $C_{2-6}$ alkenyl; $C_{2-6}$ alkynyl; $C_{3-6}$ cycloalkyl; $C_{3-6}$ cycloalkenyl; aryl; heteroaryl; heterocyclyl; —$(CH_2)_m$—$NR^{7a}R^{8a}$; —$(CH_2)_m$—C(=O)OR$^{5a}$; —$(CH_2)_m$—OC(=O)R$^{5a}$; —$(CH_2)_m$—C(=O)R$^{5a}$; —$(CH_2)_m$—S(O)$_n$R$^5$; —$(CH_2)_m$—N(R$^{7a}$)C(=O)R$^{8a}$; —$(CH_2)_m$—C(=O)NR$^{7a}$R$^{8a}$; —$(CH_2)_m$—SO$_2$NR$^{9a}$R$^{10a}$; —$(CH_2)_m$-aryl; —$(CH_2)_m$—O-aryl; —O—$(CH_2)_m$-aryl; —$(CH_2)_m$-heterocyclyl; —O—$(CH_2)_m$-heterocyclyl; and —$(CH_2)_m$—O-heterocyclyl;

$R^{12}$ is selected from the group consisting of halogen; cyano; =O; hydroxyl; $C_{1-6}$ alkyl; $C_{1-6}$ alkoxyl; $C_{2-6}$ alkenyl; $C_{2-6}$ alkynyl; $C_{3-6}$ cycloalkyl; $C_{3-6}$ cycloalkenyl; —$(CH_2)_m$—NR$^{7a}$R$^{8a}$; —$(CH_2)_m$—C(=O)OR$^{5a}$; —$(CH_2)_m$—OC(=O)R$^{5a}$; —$(CH_2)_m$—C(=O)R$^{5a}$; —$(CH_2)_m$—S(O)$_n$R$^{5a}$; —$(CH_2)_m$—N(R$^7$)C(=O)R$^{8a}$; —$(CH_2)_m$—C(=O)NR$^{7a}$R$^{8a}$; —$(CH_2)_m$—SO$_2$NR$^{9a}$R$^{10a}$; —$(CH_2)_m$-aryl; —$(CH_2)_m$—O-aryl; —O—$(CH_2)_m$-aryl; —$(CH_2)_m$-heterocyclyl; —O—$(CH_2)$m-heterocyclyl; and —$(CH_2)_m$—O-heterocyclyl;

wherein, in $R^{11}$ and $R^{12}$, the $C_{1-6}$ alkyl, $C_{1-6}$ alkoxyl, $C_{2-6}$ alkenyl and $C_{2-6}$ alkynyl moieties are each optionally substituted by one or more substituents $R^{14}$; and the $C_{3-8}$ cycloalkyl, $C_{3-6}$ cycloalkenyl, aryl, heterocyclyl and heteroaryl moieties are each optionally substituted by one or more substituents $R^{15}$;

$R^{13}$ is selected from the group consisting of halogen; cyano; hydroxyl; =O; an oxide (when $R^{13}$ is attached to N or S); a dioxide (when $R^{13}$ is attached to S); $C_{1-6}$ alkyl optionally substituted by one or more substituents $R^{11}$; $C_{1-6}$ alkoxyl optionally substituted by one or more substituents $R^{11}$; $C_{2-6}$ alkenyl optionally substituted by one or more substituents $R^{11}$; $C_{2-6}$ alkynyl optionally substituted by one or more substituents $R^{11}$; $C_{3-6}$ cycloalkyl optionally substituted by one or more substituents $R^{12}$; $C_{3-6}$ cycloalkenyl optionally substituted by one or more substituents $R^{12}$; aryl optionally substituted by one or more substituents $R^{12}$; heteroaryl optionally substituted by one or more substituents $R^{12}$; heterocyclyl optionally substituted by one or more substituents $R^{12}$; $(CH_2)_m$—NR$^7$R$^8$; —$(CH_2)_m$—C(=O)OR$^5$; —$(CH_2)_m$—OC(=O)R$^5$; —$(CH_2)_m$—C(=O)R$^5$; —$(CH_2)_m$—S(O)$_n$R$^5$; —$(CH_2)_m$—N(R$^7$)C(=O)R$^8$; —$(CH_2)_m$—C(=O)NR$^7$R$^8$; —$(CH_2)_m$—SO$_2$NR$^9$R$^{10}$; —$(CH_2)_m$-aryl; —$(CH_2)_m$—O-aryl; —O—$(CH_2)_m$-aryl; —$(CH_2)_m$-heterocyclyl; —O—$(CH_2)_m$-heterocyclyl; and —$(CH_2)_m$—O-heterocyclyl wherein the aryl or heterocyclyl can be optionally substituted by one or more substituents $R^{12}$; and Ar is selected from 6-membered aryl optionally substituted by one or more substituents $R^{13}$; 5 or 6-membered heteroaryl optionally substituted by one or more substituents $R^{13}$; bicyclic aryl optionally substituted by one or more substituents $R^{13}$; and bicyclic heteroaryl optionally substituted by one or more substituents $R^{13}$;

$R^{14}$ is selected from hydroxy; halogen; cyano; $C_{1-4}$ alkyl; $C_{1-4}$ alkoxy; $C_{1-4}$ alkoxy-$C_{2-4}$ alkoxy; hydroxy-$C_{2-4}$ alkoxy; $(CH_2)_m$—NR$^{7a}$R$^{8a}$; —$(CH_2)_m$—C(=O)OR$^{5a}$; —$(CH_2)_m$—OC(=O)R$^{5a}$; —$(CH_2)_m$—C(=O)R$^{5a}$; —$(CH_2)_m$—S(O)$_n$R$^{5a}$; —$(CH_2)_m$—N(R$^{7a}$)C(=O)R$^{8a}$; —$(CH_2)_m$—C=ONR$^{7a}$R$^{8a}$; and —$(CH_2)_m$—SO$_2$NR$^{9a}$R$^{10a}$;

$R^{15}$ is selected from hydroxy; halogen; cyano; $C_{1-4}$ alkyl; $C_{1-4}$ alkoxy; $C_{1-4}$ alkoxy-$C_{2-4}$ alkoxy; hydroxy-$C_{2-4}$ alkoxy; $(CH_2)_m$—NR$^{7a}$R$^{8a}$; —$(CH_2)_m$—C(=O)OR$^{5a}$; —$(CH_2)_m$—OC(=O)R$^{5a}$; —$(CH_2)_m$—C(=O)R$^{5a}$; —$(CH_2)_m$—S(O)$_n$R$^{5a}$; —$(CH_2)_m$—N(R$^{7a}$)C(=O)R$^{8a}$; —$(CH_2)_m$—C(=O)NR$^{7a}$R$^{8a}$; and —$(CH_2)_m$—SO$_2$NR$^{9a}$R$^{10a}$;

$R^{5a}$ is selected from $C_{1-8}$ alkyl optionally substituted by one or more substituents selected from hydroxy, $C_{1-4}$ alkoxy, halogen and cyano; $C_{3-8}$ cycloalkyl optionally substituted by one or more substituents selected from hydroxy, $C_{1-4}$ alkyl, $C_{1-4}$ alkoxy, halogen and cyano; aryl optionally substituted by one or more substituents selected from hydroxy, $C_{1-4}$ alkyl, $C_{1-4}$ alkoxy, halogen and cyano; heteroaryl optionally substituted by one or more substituents selected from hydroxy, $C_{1-4}$ alkyl, $C_{1-4}$ alkoxy, halogen and cyano; and heterocyclyl optionally substituted by one or more substituents selected from hydroxy, $C_{1-4}$ alkyl, $C_{1-4}$ alkoxy, halogen and cyano;

$R^{7a}$ and $R^{8a}$ are the same or different, and independently are selected from hydrogen; $C_{1-8}$ alkyl optionally substituted by one or more substituents selected from hydroxy, $C_{1-4}$ alkoxy, halogen and cyano; $C_{3-8}$ cycloalkyl optionally substituted by one or more substituents hydroxy, $C_{1-4}$ alkyl, $C_{1-4}$ alkoxy, halogen and cyano; aryl optionally substituted by one or more substituents hydroxy, $C_{1-4}$ alkyl, $C_{1-4}$ alkoxy, halogen and cyano; heteroaryl optionally substituted by one or more substituents selected from hydroxy, $C_{1-4}$ alkyl, $C_{1-4}$ alkoxy, halogen and cyano; and heterocyclyl optionally substituted by one or more substituents selected from hydroxy, $C_{1-4}$ alkyl, $C_{1-4}$ alkoxy, halogen and cyano; or NR$^{7a}$R$^{8a}$ forms a non-aromatic four to seven membered ring optionally containing a second heteroatom selected from O, N and S, and optionally substituted by one or more substituents selected from hydroxyl, $C_{1-4}$ alkyl, $C_{1-4}$ acyl, $C_{1-4}$ alkoxycarbonyl and $C_{1-4}$ alkylsulphonyl; and $R^{9a}$ and $R^{10a}$ are the same or different, and independently are selected from hydrogen; $C_{1-8}$ alkyl optionally substituted by one or more substituents selected from hydroxy, $C_{1-4}$ alkoxy, halogen and cyano; $C_{3-8}$ cycloalkyl optionally substituted by one or more substituents selected from hydroxy, $C_{1-4}$ alkyl, $C_{1-4}$ alkoxy, halogen and cyano; aryl optionally substituted by one or more substituents selected from hydroxy, $C_{1-4}$ alkyl, $C_{1-4}$ alkoxy, halogen and cyano; heteroaryl optionally substituted by one or more substituents selected from hydroxy, $C_{1-4}$ alkyl, $C_{1-4}$ alkoxy, halogen and cyano; and heterocyclyl optionally substituted by one or more substituents selected from hydroxy, $C_{1-4}$ alkyl, $C_{1-4}$ alkoxy, halogen and cyano.

The invention also provides inter alia:

A compound of the formula (I) or any sub-groups or examples thereof as defined herein for use in the prophylaxis or treatment of a disease state or condition mediated by a cyclin dependent kinase (particularly CDK-4 and/or CDK-6).

A method for the prophylaxis or treatment of a disease state or condition mediated by a cyclin dependent kinase (particularly CDK-4 and/or CDK-6), which method comprises administering to a subject in need thereof a compound of the formula (I) or any sub-groups or examples thereof as defined herein.

A method for alleviating or reducing the incidence of a disease state or condition mediated by a cyclin dependent kinase (particularly CDK-4 and/or CDK-6), which method comprises administering to a subject in need thereof a compound of the formula (I) or any sub-groups or examples thereof as defined herein.

A method for treating a disease or condition comprising or arising from abnormal cell growth in a mammal, which method comprises administering to the mammal a compound of the formula (I) or any sub-groups or examples thereof as defined herein in an amount effective in inhibiting abnormal cell growth.

A method for alleviating or reducing the incidence of a disease or condition comprising or arising from abnormal cell growth in a mammal, which method comprises administering to the mammal a compound of the formula (I) or any sub-groups or examples thereof as defined herein in an amount effective in inhibiting abnormal cell growth.

A method for treating a disease or condition comprising or arising from abnormal cell growth in a mammal, the method comprising administering to the mammal a compound of the formula (I) or any sub-groups or examples thereof as defined herein in an amount effective to inhibit a CDK kinase (such as CDK4 or CDK6).

A method for alleviating or reducing the incidence of a disease or condition comprising or arising from abnormal cell growth in a mammal, the method comprising administering to the mammal a compound of the formula (I) or any sub-groups or examples thereof as defined herein in an amount effective to inhibit a CDK kinase (such as CDK4 or CDK6).

A method of inhibiting a cyclin dependent kinase (particularly CDK-4 and/or CDK-6), which method comprises contacting the kinase with a kinase-inhibiting compound of the formula (I) or any sub-groups or examples thereof as defined herein.

A method of modulating a cellular process (for example cell division) by inhibiting the activity of a cyclin dependent kinase (particularly CDK-4 and/or CDK-6) using a compound of the formula (I) or any sub-groups or examples thereof as defined herein.

A compound of the formula (I) or any sub-groups or examples thereof as defined herein for use in the prophylaxis or treatment of a disease state as described herein.

The use of a compound of the formula (I) or any sub-groups or examples thereof as defined herein for the manufacture of a medicament, wherein the medicament is for any one or more of the uses defined herein.

A pharmaceutical composition comprising a compound of the formula (I) or any sub-groups or examples thereof as defined herein and a pharmaceutically acceptable carrier.

A pharmaceutical composition comprising a compound of the formula (I) or any sub-groups or examples thereof as defined herein and a pharmaceutically acceptable carrier in a form suitable for oral administration.

A pharmaceutical composition for administration in an aqueous solution form, the pharmaceutical composition comprising a compound of the formula (I) or any sub-groups or examples thereof as defined herein in the form of a salt having a solubility in water of greater than 25 mg/ml, typically greater than 50 mg/ml and preferably greater than 100 mg/ml.

A compound of the formula (I) or any sub-groups or examples thereof as defined herein for use in medicine.

A method for the diagnosis and treatment of a disease state or condition mediated by a cyclin dependent kinase, which method comprises (i) screening a patient to determine whether a disease or condition from which the patient is or may be suffering is one which would be susceptible to treatment with a compound having activity against cyclin dependent kinases (particularly CDK-4 and/or CDK-6); and (ii) where it is indicated that the disease or condition from which the patient is thus susceptible, thereafter administering to the patient a compound of the formula (I) or any sub-groups or examples thereof as defined herein.

The use of a compound of the formula (I) or any sub-groups or examples thereof as defined herein for the manufacture of a medicament for the treatment or prophylaxis of a disease state or condition in a patient who has been screened and has been determined as suffering from, or being at risk of suffering from, a disease or condition which would be susceptible to treatment with a compound having activity against cyclin dependent kinase (particularly CDK-4 and/or CDK-6).

A compound of the formula (I) or any sub-groups or examples thereof as defined herein for use in inhibiting tumour growth in a mammal.

A compound of the formula (I) or any sub-groups or examples thereof as defined herein for use in inhibiting the growth of tumour cells (e.g. in a mammal).

A method of inhibiting tumour growth in a mammal (e.g. a human), which method comprises administering to the mammal (e.g. a human) an effective tumour growth-inhibiting amount of a compound of the formula (I) or any sub-groups or examples thereof as defined herein.

A method of inhibiting the growth of tumour cells (e.g. tumour cells present in a mammal such as a human), which method comprises contacting the tumour cells with an effective tumour cell growth-inhibiting amount of a compound of the formula (I) or any sub-groups or examples thereof as defined herein.

A compound as defined herein for any of the uses and methods set forth above, and as described elsewhere herein.

GENERAL PREFERENCES AND DEFINITIONS

In this section, as in all other sections of this application, unless the context indicates otherwise, references to a compound of formula (I) includes all subgroups of formula (I) as defined herein and the term 'subgroups' includes all preferences, embodiments, examples and particular compounds defined herein.

Moreover, a reference to a compound of formula (I) and sub-groups thereof includes ionic forms, salts, solvates, isomers, tautomers, N-oxides, esters, prodrugs, isotopes and protected forms thereof, as discussed below: —preferably, the salts or tautomers or isomers or N-oxides or solvates thereof: —and more preferably, the salts or tautomers or N-oxides or solvates thereof.

The following general preferences and definitions shall apply to each of Ar, $R^1$, $R^2$, $R^3$, $R^{3a}$, $R^4$, $R^5$, $R^{5a}$, $R^7$, $R^8$, $R^{7a}$, $R^{8a}$, $R^9$, $R^{10}$, $R^{9a}$, $R^{10a}$, $R^{11}$, $R^{12}$, $R^{13}$, $R^{14}$, $R^{15}$, X, Y, m and n and their various sub-groups, sub-definitions, examples and embodiments unless the context indicates otherwise.

Any references to formula (I) herein shall also be taken to refer to and any sub-group of compounds within formula (I) and any preferences and examples thereof unless the context requires otherwise.

As used herein, the term "treatment" and the related terms "treat" and "treating" refer to both prophylactic or preventative treatment as well as curative or palliative treatment of the condition (e.g. cancer). Thus, the term encompasses situations where the condition (e.g. cancer) is already being experienced by a subject or patient, as well as situations where condition (e.g. cancer) is not currently being experienced but is expected to arise. The term "treatment", "treat", "treating" and related terms also cover both complete and partial reduction or prevention of the condition. Thus, for example in the context of pain, the compound of the invention may prevent existing condition from worsening, assist in the management of the condition or reduce or even eliminate the condition. When used in a prophylactic sense, the compounds may prevent any condition from developing or they may lessen the extent of condition that may develop.

As used herein, the term "modulation", as applied to the activity of a kinase, is intended to define a change in the level of biological activity of the protein kinase. Thus, modulation encompasses physiological changes which effect an increase or decrease in the relevant protein kinase activity. In the latter case, the modulation may be described as "inhibition". The modulation may arise directly or indirectly, and may be mediated by any mechanism and at any physiological level, including for example at the level of gene expression (including for example transcription, translation and/or post-translational modification), at the level of expression of genes encoding regulatory elements which act directly or indirectly on the levels of kinase activity. Thus, modulation may imply elevated/suppressed expression or over- or under-expression of a kinase, including gene amplification (i.e. multiple gene copies) and/or increased or decreased expression by a transcriptional effect, as well as hyper- (or hypo-) activity and (de)activation of the protein kinase(s) (including (de)activation) by mutation(s). The terms "modulated", "modulating" and "modulate" are to be interpreted accordingly.

As used herein, the term "mediated", as used e.g. in conjunction with a kinase as described herein (and applied for example to various physiological processes, diseases, states, conditions, therapies, treatments or interventions) is intended to operate limitatively so that the various processes, diseases, states, conditions, treatments and interventions to which the term is applied are those in which the kinase plays a biological role. In cases where the term is applied to a disease, state or condition, the biological role played by a kinase may be direct or indirect and may be necessary and/or sufficient for the manifestation of the symptoms of the disease, state or condition (or its aetiology or progression). Thus, kinase activity (and in particular aberrant levels of kinase activity, e.g. kinase over-expression) need not necessarily be the proximal cause of the disease, state or condition: rather, it is contemplated that the kinase mediated diseases, states or conditions include those having multifactorial aetiologies and complex progressions in which the kinase in question is only partially involved. In cases where the term is applied to treatment, prophylaxis or intervention, the role played by the kinase may be direct or indirect and may be necessary and/or sufficient for the operation of the treatment, prophylaxis or outcome of the intervention. Thus, a disease state or condition mediated by a kinase includes the development of resistance to any particular cancer drug or treatment.

The term "upregulation of a kinase" as used herein is defined as including elevated expression or over-expression of the kinase, including gene amplification (i.e. multiple gene copies) and increased expression by a transcriptional effect, and hyperactivity and activation of the kinase, including activation by mutations and stabilisation.

The term "overexpression" means elevated levels of a kinase in the cell compared to normal levels. This can be due to gene amplification or upregulation of the pathway comprising the gene, or due to elevated levels of the protein in the cell due to stabilisation of the protein or reduction in the rate of destruction of the protein.

References to the prophylaxis or treatment of a disease state or condition such as cancer include within their scope alleviating or reducing the incidence of cancer.

The term "intervention" is a term of art used herein to define any agency which effects a physiological change at any level. Thus, the intervention may comprise the induction or repression of any physiological process, event, biochemical pathway or cellular/biochemical event. The interventions of the invention typically effect (or contribute to) the therapy, treatment or prophylaxis of a disease or condition.

As used herein, the term "combination", as applied to two or more compounds and/or agents (also referred to herein as the components), is intended to define material in which the two or more compounds/agents are associated. The terms "combined" and "combining" in this context are to be interpreted accordingly.

The association of the two or more compounds/agents in a combination may be physical or non-physical. Examples of physically associated combined compounds/agents include:
  compositions (e.g. unitary formulations) comprising the two or more compounds/agents in admixture (for example within the same unit dose);
  compositions comprising material in which the two or more compounds/agents are chemically/physicochemically linked (for example by crosslinking, molecular agglomeration or binding to a common vehicle moiety);
  compositions comprising material in which the two or more compounds/agents are chemically/physicochemically co-packaged (for example, disposed on or within lipid vesicles, particles (e.g. micro- or nanoparticles) or emulsion droplets);
  pharmaceutical kits, pharmaceutical packs or patient packs in which the two or more compounds/agents are co-packaged or co-presented (e.g. as part of an array of unit doses);

Examples of non-physically associated combined compounds/agents include:
  material (e.g. a non-unitary formulation) comprising at least one of the two or more compounds/agents together with instructions for the extemporaneous association of the at least one compound to form a physical association of the two or more compounds/agents;
  material (e.g. a non-unitary formulation) comprising at least one of the two or more compounds/agents together with instructions for combination therapy with the two or more compounds/agents;
  material comprising at least one of the two or more compounds/agents together with instructions for administration to a patient population in which the other(s) of the two or more compounds/agents have been (or are being) administered;
  material comprising at least one of the two or more compounds/agents in an amount or in a form which is specifically adapted for use in combination with the other(s) of the two or more compounds/agents.

As used herein, the term "in combination" may refer to compounds/agents that are administered as part of the same overall treatment regimen. As such, the posology of each of the two or more compounds/agents may differ: each may be administered at the same time or at different times. It will therefore be appreciated that the compounds/agents of the combination may be administered sequentially (e.g. before or after) or simultaneously, either in the same pharmaceutical formulation (i.e. together), or in different pharmaceutical formulations (i.e. separately). Simultaneously in the same formulation is as a unitary formulation whereas simultaneously in different pharmaceutical formulations is non-unitary. The posologies of each of the two or more compounds/agents in a combination therapy may also differ with respect to the route of administration.

As used herein, the term "pharmaceutical kit" defines an array of one or more unit doses of a pharmaceutical composition together with dosing means (e.g. measuring device) and/or delivery means (e.g. inhaler or syringe), optionally all contained within common outer packaging. In pharmaceutical kits comprising a combination of two or more compounds/agents, the individual compounds/agents may unitary or non-unitary formulations. The unit dose(s) may be contained within a blister pack. The pharmaceutical kit may optionally further comprise instructions for use.

As used herein, the term "pharmaceutical pack" defines an array of one or more unit doses of a pharmaceutical composition, optionally contained within common outer packaging. In pharmaceutical packs comprising a combination of two or more compounds/agents, the individual compounds/agents may unitary or non-unitary formulations. The unit dose(s) may be contained within a blister pack. The pharmaceutical pack may optionally further comprise instructions for use.

As used herein, the term "patient pack" defines a package, prescribed to a patient, which contains pharmaceutical compositions for the whole course of treatment. Patient packs usually contain one or more blister pack(s). Patient packs have an advantage over traditional prescriptions, where a pharmacist divides a patient's supply of a pharmaceutical from a bulk supply, in that the patient always has access to the package insert contained in the patient pack, normally missing in patient prescriptions. The inclusion of a package insert has been shown to improve patient compliance with the physician's instructions.

The following general preferences and definitions shall apply to the groups described herein unless the context indicates otherwise.

The term "aryl" as used herein refer to a carbocyclic group having aromatic character. An "aryl" group may be monocyclic or polycyclic. Preferred aryl groups are monocyclic and bicyclic aryl groups having from 6 to 12 ring members, more usually 6 to 10 ring members. Where the aryl group is polycyclic one or more rings may be non-aromatic provided that at least one ring is aromatic. In such polycyclic systems, the group may be attached by the aromatic ring, or by a non-aromatic ring. Particular aryl groups include phenyl, naphthyl, indenyl, and tetrahydronaphthyl groups.

The term "heteroaryl" is used herein to denote a heterocyclic group having aromatic character. A "heteroaryl" group may be monocyclic or polycyclic. Preferred heteroaryl groups are monocyclic and bicyclic aryl groups having from 5 to 12 ring members, more usually 5 to 10 ring members. Where the heteroaryl group is polycyclic one or more rings may be non-aromatic provided that at least one ring is aromatic. In such polycyclic systems, the group may be attached by the aromatic ring, or by a non-aromatic ring.

Examples of heteroaryl groups are monocyclic and bicyclic groups containing from five to twelve ring members, and more usually from five to ten ring members. The heteroaryl group can be, for example, a five membered or six membered monocyclic ring or a bicyclic structure formed from fused five and six membered rings or two fused six membered rings or, by way of a further example, two fused five membered rings. Each ring may contain up to about four heteroatoms typically selected from nitrogen, sulphur and oxygen. Typically the heteroaryl ring will contain up to 4 heteroatoms, more typically up to 3 heteroatoms, more usually up to 2, for example a single heteroatom. In one embodiment, the heteroaryl ring contains at least one ring nitrogen atom. The nitrogen atoms in the heteroaryl rings can be basic, as in the case of an imidazole or pyridine, or essentially non-basic as in the case of an indole or pyrrole nitrogen. In general the number of basic nitrogen atoms present in the heteroaryl group, including any amino group substituents of the ring, will be less than five.

Examples of five membered heteroaryl groups include but are not limited to pyrrole, furan, thiophene, imidazole, furazan, oxazole, oxadiazole, oxatriazole, isoxazole, thiazole, isothiazole, pyrazole, triazole and tetrazole groups.

Examples of six membered heteroaryl groups include but are not limited to pyridine, pyrazine, pyridazine, pyrimidine and triazine.

A bicyclic heteroaryl group may be, for example, a group selected from:

a) a benzene ring fused to a 5- or 6-membered ring containing 1, 2 or 3 ring heteroatoms;
b) a pyridine ring fused to a 5- or 6-membered ring containing 1, 2 or 3 ring heteroatoms;
c) a pyrimidine ring fused to a 5- or 6-membered ring containing 1 or 2 ring heteroatoms;
d) a pyrrole ring fused to a a 5- or 6-membered ring containing 1, 2 or 3 ring heteroatoms;
e) a pyrazole ring fused to a a 5- or 6-membered ring containing 1 or 2 ring heteroatoms;
f) a pyrazine ring fused to a 5- or 6-membered ring containing 1 or 2 ring heteroatoms;
g) an imidazole ring fused to a 5- or 6-membered ring containing 1 or 2 ring heteroatoms;
h) an oxazole ring fused to a 5- or 6-membered ring containing 1 or 2 ring heteroatoms;
i) an isoxazole ring fused to a 5- or 6-membered ring containing 1 or 2 ring heteroatoms;
j) a thiazole ring fused to a 5- or 6-membered ring containing 1 or 2 ring heteroatoms;
k) an isothiazole ring fused to a 5- or 6-membered ring containing 1 or 2 ring heteroatoms;
l) a thiophene ring fused to a 5- or 6-membered ring containing 1, 2 or 3 ring heteroatoms;
m) a furan ring fused to a 5- or 6-membered ring containing 1, 2 or 3 ring heteroatoms;
n) a cyclohexyl ring fused to a 5- or 6-membered ring containing 1, 2 or 3 ring heteroatoms; and
o) a cyclopentyl ring fused to a 5- or 6-membered ring containing 1, 2 or 3 ring heteroatoms.

Particular examples of bicyclic heteroaryl groups containing a five membered ring fused to another five membered ring include but are not limited to imidazothiazole (e.g. imidazo [2,1-b]thiazole) and imidazoimidazole (e.g. imidazo[1,2-a] imidazole).

Particular examples of bicyclic heteroaryl groups containing a six membered ring fused to a five membered ring include but are not limited to benzofuran, benzothiophene, benzimidazole, benzoxazole, isobenzoxazole, benzisoxazole, benzothiazole, benzisothiazole, isobenzofuran, indole, isoindole, indolizine, indoline, isoindoline, purine (e.g., adenine, guanine), indazole, pyrazolopyrimidine (e.g. pyrazolo[1,5-a]pyrimidine), triazolopyrimidine (e.g. [1,2,4]triazolo[1,5-a]pyrimidine), benzodioxole, imidazopyridine and pyrazolopyridine (e.g. pyrazolo[1,5-a]pyridine) groups.

Particular examples of bicyclic heteroaryl groups containing two fused six membered rings include but are not limited to quinoline, isoquinoline, chroman, thiochroman, chromene, isochromene, chroman, isochroman, benzodioxan, quinolizine, benzoxazine, benzodiazine, pyridopyridine, quinoxaline, quinazoline, cinnoline, phthalazine, naphthyridine and pteridine groups.

One sub-group of heteroaryl groups comprises pyridyl, pyrrolyl, furanyl, thienyl, imidazolyl, oxazolyl, oxadiazolyl, oxatriazolyl, isoxazolyl, thiazolyl, isothiazolyl, pyrazolyl, pyrazinyl, pyridazinyl, pyrimidinyl, triazinyl, triazolyl, tetrazolyl, quinolinyl, isoquinolinyl, benzfuranyl, benzthienyl, chromanyl, thiochromanyl, benzimidazolyl, benzoxazolyl, benzisoxazole, benzthiazolyl and benzisothiazole, isobenzofuranyl, indolyl, isoindolyl, indolizinyl, indolinyl, isoindolinyl, purinyl (e.g., adenine, guanine), indazolyl, benzodioxolyl, chromenyl, isochromenyl, isochromanyl, benzodioxanyl, quinolizinyl, benzoxazinyl, benzodiazinyl, pyridopyridinyl, quinoxalinyl, quinazolinyl, cinnolinyl, phthalazinyl, naphthyridinyl and pteridinyl groups.

Examples of polycyclic heteroaryl groups containing an aromatic ring and a non-aromatic ring include tetrahydroisoquinoline, tetrahydroquinoline, dihydrobenzthiene, dihydrobenzfuran, 2,3-dihydro-benzo[1,4]dioxine, benzo[1,3]dioxole, 4,5,6,7-tetrahydrobenzofuran, tetrahydrotriazolopyrazine, indoline and indane groups.

A further example of a bicyclic heteroaryl group containing one aromatic ring and one non-aromatic ring is a 5,6-dihydro-8H-imidazo[1,2-a]pyrazinyl ring, e.g. a 5,6-dihydro-8H-imidazo[1,2-a]pyrazin-7-yl ring.

The term "nitrogen-containing heteroaryl ring" indicates a heteroaryl group with at least one ring nitrogen atom. Each ring may, in addition, contain up to about three other heteroatoms typically selected from nitrogen, sulphur and oxygen. Typically the heteroaryl ring will contain up to 3 heteroatoms, for example 1, 2 or 3, more usually up to 2 nitrogens, for example a single nitrogen. The nitrogen atoms in the heteroaryl rings can be basic, as in the case of an imidazole or pyridine, or essentially non-basic as in the case of an indole or pyrrole nitrogen. In general the number of basic nitrogen atoms present in the heteroaryl group, including any amino group substituents of the ring, will be less than five.

Examples of nitrogen-containing heteroaryl groups include, but are not limited to, pyridyl, pyrrolyl, imidazolyl, oxazolyl, oxadiazolyl, thiadiazolyl, oxatriazolyl, isoxazolyl, thiazolyl, isothiazolyl, furazanyl, pyrazolyl, pyrazinyl, pyrimidinyl, pyridazinyl, triazinyl, triazolyl (e.g., 1,2,3-triazolyl, 1,2,4-triazolyl), tetrazolyl, quinolinyl, isoquinolinyl, benzimidazolyl, benzoxazolyl, benzisoxazole, benzthiazolyl and benzisothiazole, indolyl, 3H-indolyl, isoindolyl, indolizinyl, isoindolinyl, purinyl (e.g., adenine[6-aminopurine], guanine [2-amino-6-hydroxypurine]), indazolyl, quinolizinyl, benzoxazinyl, benzodiazinyl, pyridopyridinyl, quinoxalinyl, quinazolinyl, cinnolinyl, phthalazinyl, naphthyridinyl and pteridinyl.

Examples of nitrogen-containing polycyclic heteroaryl groups containing an aromatic ring and a non-aromatic ring include tetrahydroisoquinolinyl, tetrahydroquinolinyl, and indolinyl.

The term "heterocyclyl" as used herein refers to a non-aromatic heterocyclic ring. Such non-aromatic heterocyclic rings can have from 3 to 12 ring members, typically 4 to 12 ring members, and more usually from 5 to 10 ring members.

The heterocyclyl groups can be monocyclic or polycyclic and preferably are monocyclic or bicyclic. The heterocyclyl rings typically have from 1 to 5 heteroatom ring members (more usually 1, 2, 3 or 4 heteroatom ring members) usually selected from nitrogen, oxygen and sulphur. Polycyclic groups such as bicyclic groups can be fused ring systems, bridged ring systems or spiro ring systems. As used herein, the term "fused ring system" means a ring system in which two rings share two atoms whereas the term "bridged ring system" refers to ring systems in which two rings share more than two atoms, see for example *Advanced Organic Chemistry*, by Jerry March, 4$^{th}$ Edition, Wiley Interscience, pages 131-133, 1992. As used herein, the term "spiro ring system" refers to a ring system in which two rings share a single atom.

Examples of fused heterocyclyl ring systems include structures such as:

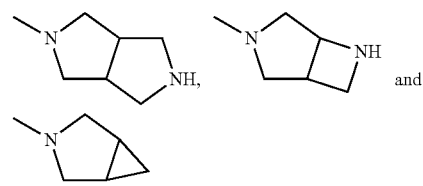

Examples of spiro heterocyclyl ring systems include structures such as:

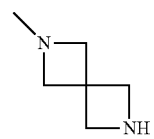

The term "non-aromatic group" embraces unsaturated ring systems without aromatic character, partially saturated and fully saturated carbocyclic and heterocyclic ring systems. The terms "unsaturated" and "partially saturated" refer to rings wherein the ring structure(s) contains atoms sharing more than one valence bond i.e. the ring contains at least one multiple bond e.g. a C=C, C≡C or N=C bond. The terms "fully saturated" and "saturated" refer to rings where there are no multiple bonds between ring atoms. Saturated carbocyclic groups include cycloalkyl groups as defined below. Partially saturated carbocyclic groups include cycloalkenyl groups as defined below, for example cyclopentenyl, cyclohexenyl, cycloheptenyl and cyclooctenyl. Saturated heterocyclic groups include piperidine, morpholine, thiomorpholine. Partially saturated heterocyclic groups include pyrazolines, for example 2-pyrazoline and 3-pyrazoline.

The heterolic groups can contain, for example, cyclic ether moieties (e.g. as in tetrahydrofuran and dioxane), cyclic thioether moieties (e.g. as in tetrahydrothiophene and dithiane), cyclic amine moieties (e.g. as in pyrrolidine), cyclic amide moieties (e.g. as in pyrrolidone), cyclic thioamides, cyclic thioesters, cyclic ester moieties (e.g. as in butyrolactone), cyclic sulphones (e.g. as in sulpholane and sulpholene), cyclic sulphoxides, cyclic sulphonamides and combinations thereof (e.g. morpholine and thiomorpholine and its S-oxide and S,S-dioxide). Further examples of heterocyclic groups are those containing a cyclic urea moiety (e.g. as in imidazolidin-2-one), Examples of monocyclic non-aromatic heterocyclic groups include 5-, 6- and 7-membered monocyclic heterocyclic groups. Particular examples include morpholine, piperidine (e.g. 1-piperidinyl, 2-piperidinyl, 3-piperidinyl and 4-piperidinyl), N-alkyl piperidines such as N-methyl piperidine, pyrrolidine (e.g. 1-pyrrolidinyl, 2-pyrrolidinyl and 3-pyrrolidinyl), pyrrolidone, pyran (2H-pyran or 4H-pyran), dihydrothiophene, dihydropyran, dihydrofuran, dihydrothiazole, tetrahydrofuran, tetrahydrothiophene, dioxane, tetrahydropyran (e.g. 4-tetrahydro pyranyl), imidazoline, imidazolidinone, oxazoline, thiazoline, 2-pyrazoline, pyrazolidine, piperazine, N-alkyl piperazines such as N-methyl piperazine, thiomorpholine and its S-oxide and S,S-dioxide (particularly thiomorpholine), azetidine, piperidone and piperazone.

The term "saturated heterocyclic ring" as used herein to a cyclic group containing no multiple bonds (e.g. double bonds) between adjacent ring members and containing one or more heteroatom ring members with the remaining ring members being carbon atoms. Unless stated otherwise, the saturated heterocyclic ring contains one or two heteroatom ring members selected from O, N and S and oxidized forms of N and S. Preferred saturated heterocyclic groups are those having 5 or six ring members. Examples of saturated heterocyclic groups include azetidine, pyrrolidine, piperidine, azepine, morpholine, thiomorpholine, thiomorpholine S-oxide and S,S-dioxide, piperazine, and N-methyl piperazine. Particular saturated heterocyclic groups are pyrrolidine, piperidine, morpholine, piperazine, and N-methyl piperazine.

One particular sub-set of heterocyclyl rings consists of saturated groups such as azetidine, pyrrolidine, piperidine, morpholine, thiomorpholine, thiomorpholine S,S-dioxide, piperazine, N-alkyl piperazines, and N-alkyl piperidines.

The term "nitrogen-containing heterocyclic ring" indicates a heterocyclic ring which must contain at least one ring nitrogen atom. The heterocylic groups can contain, for example cyclic amine moieties (e.g. as in pyrrolidine), cyclic amides (such as a pyrrolidinone, piperidone or caprolactam), cyclic sulphonamides (such as an isothiazolidine 1,1-dioxide, [1,2] thiazinane 1,1-dioxide or [1,2]thiazepane 1,1-dioxide) and combinations thereof.

Particular examples of nitrogen-containing heterocyclic groups include aziridine, morpholine, thiomorpholine, piperidine (e.g. 1-piperidinyl, 2-piperidinyl, 3-piperidinyl and 4-piperidinyl), pyrrolidine (e.g. 1-pyrrolidinyl, 2-pyrrolidinyl and 3-pyrrolidinyl), pyrrolidone, dihydrothiazole, imidazoline, imidazolidinone, oxazoline, thiazoline, 6H-1,2,5-thiadiazine, 2-pyrazoline, 3-pyrazoline, pyrazolidine, piperazine, and N-alkyl piperazines such as N-methyl piperazine.

When sulphur is present in a heteroaryl or heterocyclic ring, it may, where the nature of the adjacent atoms and groups permits, exist as —S—, —S(O)— or —S(O)$_2$—.

When nitrogen is present in a heteroaryl or heterocyclic ring, it may, where the nature of the adjacent atoms and groups permits, exist as N or N$^+$—O$^-$.

The term "cycloalkyl" as used herein is used in its conventional sense to denote a cyclic alkyl group of the empirical formula $C_nH_{2n-1}$ where n is an integer.

Typical examples are three, four, five, six and seven membered saturated carbocyclic rings. Particular examples of cycloalkyl groups include cyclopropyl, cyclobutyl, cyclopentyl, cyclohexyl and cycloheptyl.

Further examples of cycloalkyl groups include bridged ring systems such as bicycloalkanes although such bridged ring systems are generally less preferred. Examples of bridged ring systems include bicyclo[2.2.1]heptane, bicyclo [2.2.2]octane and bicyclo[3.2.1]octane.

The term "cycloalkenyl" as used herein is used in its conventional sense to mean a cyclic hydrocarbon group containing one or more carbon-carbon double bonds, and more preferably a single carbon-carbon double bond. Examples of cycloalkenyl groups include, but are not limited to, cyclopropenyl, cyclobutenyl, cyclopentenyl, cyclopentadienyl and cyclohexenyl. Within the sub-set of cycloalkenyl groups the cycloalkenyl groups have from 3 to 8 carbon atoms, and particular examples are $C_{3-6}$ cycloalkenyl groups.

The prefix "$C_{x-y}$" (where x and y are integers) as used herein refers to the number of carbon atoms in a given group. Thus, a $C_{1-8}$ alkyl group contains from 1 to 8 carbon atoms, a $C_{3-6}$ cycloalkyl group contains from 3 to 6 carbon atoms, a $C_{1-4}$ alkoxy group contains from 1 to 4 carbon atoms, and so on.

The term "alkyl" as used herein is used in its conventional sense to mean a group of the empirical formula $C_nH_{2n+1}$ where n is an integer (e.g. 1 to 6). The term "alkyl" covers both straight chain and branched chain alkyl groups. Within the sub-set of alkyl groups having 1 to 8 carbon atoms, particular examples are $C_{1-6}$ alkyl groups, such as $C_{1-4}$ alkyl groups (e.g. $C_{1-3}$ alkyl groups or $C_{1-2}$ alkyl groups or $C_{2-3}$ alkyl groups or $C_{2-4}$ alkyl groups). Particular examples of alkyl groups include methyl, ethyl, propyl, isopropyl, n-butyl, isobutyl, tert-butyl, n-pentyl, 2-pentyl, 3-pentyl, 2-methyl butyl, 3-methyl butyl, and n-hexyl and its isomers.

The term "alkenyl" as used herein is used in its conventional sense to mean an acyclic hydrocarbon group containing one or more carbon-carbon double bonds, and more preferably a single carbon-carbon double bond. The term "alkenyl" as used herein covers both straight chain and branched chain alkenyl groups. Within the sub-set of alkenyl groups having 2 to 8 carbon atoms, particular examples are $C_{2-6}$ alkenyl groups, such as $C_{2-4}$ alkenyl groups (e.g. $C_{2-3}$ alkenyl groups). Particular examples of alkenyl groups include, but are not limited to, ethenyl (vinyl), 1-propenyl, 2-propenyl (allyl), isopropenyl, butenyl, buta-1,4-dienyl, pentenyl, and hexenyl.

The term "alkynyl" as used herein is used in its conventional sense to mean a hydrocarbon group containing a carbon-carbon triple bond. Within the sub-set of alkynyl groups having 2 to 8 carbon atoms, particular examples are $C_{2-6}$ alkynyl groups, such as $C_{2-4}$ alkynyl groups. Particular examples of alkynyl groups include, but are not limited to, ethynyl and 2-propynyl (propargyl) groups. A preferred akynyl group is a propargyl group.

The term "alkoxy" as used herein is used in its conventional sense to mean a group of the empirical formula $OC_nH_{2n+1}$ where n is an integer (e.g. 1 to 8 carbon atoms, particular examples are $C_{1-6}$). Examples of alkoxy alkyl groups are methox, ethoxy, propoxy, isopropoxy, butoxy, 1-methylpropoxy, 2-methylpropoxy and tert-butoxy.

The prefix "aza" as used herein (e.g. as in "azaindolyl" or "azobenzoimidazolyl" refers to a group (e.g. an indole or benzoimidazole group) in which one of the carbon ring members has been replaced by a nitrogen atom.

The term "optionally substituted" indicates that the specified groups can, unless the context indicates otherwise, be unsubstituted or substituted by one or more substituents as indicated. The specific group may be optionally substituted by one or more (e.g. 1, 2 or 3) substituent groups.

Specific Embodiments of and Preferences for X, Y, Ar, $R^1$ to $R^5$ and $R^7$ to $R^{15}$, m and n

Q

In formula (I), Q can be CH or N.
In one general embodiment, Q is CH.
In another general embodiment, Q is N.

X and Y

In formula (I), X is N, $N^+$—$O^-$ or $CR^3$ and Y is N, $N^+$—$O^-$ or $CR^{3a}$.

In one embodiment Y is N or $CR^{3a}$.
In one embodiment, Y is $CR^{3a}$.
In one embodiment, $R^{3a}$ is selected from hydrogen; halogen (e.g. chlorine) and 5-membered heteroaryl rings containing 1 or 2 heteroatoms selected from N and S and being optionally substituted with $C_{1-6}$ alkyl (e.g. unsubstituted thiophene or pyrazoyl substituted with $C_{1-8}$ alkyl (e.g. —$CH_3$)).
In one embodiment $R^{3a}$ is selected from hydrogen; and halogen (e.g. chlorine).
In one embodiment, Y is CH.
In one embodiment, X is $CR^3$.
In one embodiment $R^3$ is selected from hydrogen; hydroxy; halogen (e.g. fluorine or chlorine); cyano; $OR^5$ (e.g. OMe); and $C(=O)NR^7R^8$ (e.g. $C(=O)NH_2$ or $C(=O)N(Me)_2$).
In one embodiment, $R^3$ is selected from halogen (e.g. chlorine or fluorine); cyano; and $OR^5$, wherein $R^5$ is $C_{1-4}$ alkyl (e.g. methyl).
In one embodiment, $R^3$ is selected from halogen (e.g. chlorine or fluorine) and cyano.
In one embodiment, X is N or C—CN.
In one embodiment, X is C—CN.
In another embodiment, X is N (i.e. unsubstituted nitrogen).
In one embodiment, X is C—CN and Y is CH.
In one embodiment, X is N and Y is CH.

Ar

In formula (I), Ar is selected from 6-membered aryl optionally substituted by one or more substituents $R^{13}$; 5 or 6-membered heteroaryl optionally substituted by one or more substituents $R^{13}$; bicyclic aryl optionally substituted by one or more substituents $R^{13}$; and bicyclic heteroaryl optionally substituted by one or more substituents $R^{13}$.

In one embodiment, Ar is a nitrogen containing heteroaryl. In one embodiment, Ar is nitrogen containing heteroaryl wherein the nitrogen atom in the heteroaryl ring is beta to the point of attachment. In a further embodiment, Ar is nitrogen containing heteroaryl wherein the nitrogen atom is unsubstituted.

In another embodiment, Ar is selected from phenyl; naphthyl; 5-membered heteroaryl rings containing a nitrogen ring member and optionally a further heteroatom ring member selected from O, N and S; 6-membered heteroaryl rings containing one or two nitrogen ring members; bicyclic heteroaryl rings containing 9 or 10 ring members of which one or two are heteroatoms selected from O, N and S; each of the moieties Ar being optionally substituted by one or more substituents $R^{13}$.

In one embodiment, Ar is selected from phenyl, pyridyl, thiophene, pyrazolyl, imidazolyl, thiazolyl, isoxazolyl, pyrimidinyl, naphthyl, indolyl, azaindolyl, isoquinolinyl, quinolinyl, pyridopyridyl, pyrazolopyridinyl, pyrrolopyridine, benzoimidazolyl, azobenzoimidazolyl, 2,3-dihydrobenzfuranyl, dihydro-benzodioxine, naphthyridine, and dihydro pyrrolopyrazolyl, optionally substituted by one or more substituents $R^{13}$.

In a further embodiment, Ar is selected from phenyl, pyridyl, pyrazolyl, imidazolyl, thiazolyl, pyrimidinyl, naphthyl, isoquinolinyl, benzoimidazolyl, azobenzoimidazolyl, pyridopyrazolyl, quinolinyl, pyridopyridyl, indolyl, azaindolyl, isoquinolinyl, and 2,3-dihydrobenzfuranyl, each optionally substituted by one or more substituents $R^{13}$.

In one embodiment, Ar is a bicyclic ring. In another embodiment, Ar is a bicyclic heteroaryl ring. In one embodiment, Ar is a 5,6 bicyclic heteroaryl ring. In another embodiment, Ar is a 6,6 bicyclic heteroaryl ring.

In one embodiment, Ar is an isoquinolinyl ring (e.g. a 4-isoquinolinyl ring) optionally substituted by one or more substituents $R^{13}$.

In one embodiment, Ar is a pyrazolyl ring (e.g. a 3-pyrazolyl ring) optionally substituted by one or more substituents $R^{13}$. In one embodiment, Ar is a pyrazolyl ring (e.g. a 3-pyrazolyl ring) substituted by two or three substituents $R^{13}$ (e.g. $C_{1-4}$ alkyl).

In one embodiment, Ar is a pyrazolyl ring (e.g. a 3-pyrazolyl ring) optionally substituted by two or three methyl groups.

In one embodiment, Ar is an azaindole ring (e.g. a 6-azaindol-4-yl ring) optionally substituted by one or more substituents $R^{13}$.

Ar can be optionally substituted by one or more substituents $R^{13}$.

In one embodiment, Ar is unsubstituted or is substituted by one or more substituents selected from halogen, $C_{1-4}$ alkoxy, $C_{1-4}$ alkyl, amino, mono- or di-$C_{1-2}$ alkylamino, mono- or di-$C_{1-2}$ alkylamino-$C_{1-2}$ alkyl.

In one embodiment, Ar is unsubstituted.

In another embodiment, Ar is substituted by at least one substituent.

In one embodiment, when Ar is nitrogen containing heteroaryl wherein the nitrogen atom in the heteroaryl ring is beta to the point of attachment, Ar is substituted by at least one substituent positioned α' (alpha-prime) to the point of attachment; i.e. adjacent the point of attachment and on the opposite side of the ring to the beta nitrogen atom.

In this application, references to alpha, alpha prime and beta positions in connection with the group Ar refer to the location of a substituent group relative to the point of attachment of the group Ar.

For example, when Ar is a pyridyl group as shown below, the arrow indicates the point of attachment of the group Ar to the ring containing the moiety X—Y. The alpha position is the position 2 adjacent the point of attachment. The beta position is the position numbered 3. The beta-prime position is the position numbered 5 and the alpha-prime position is the position numbered 6.

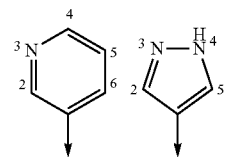

For the pyrazole ring, the alpha and alpha prime positions are numbered 2 and 5 respectively and the beta position is numbered 3. Alternatively, the alpha and alpha prime positions can be the positions numbered 5 and 2 respectively in which case the beta position is numbered 4.

$R^1$ and $R^2$

In formula (I), $R^1$ and $R^2$ are independently selected from hydrogen; halogen; cyano; hydroxyl; $C_{1-8}$ alkyl optionally substituted by one or more substituents $R^{11}$; $C_{2-8}$ alkenyl optionally substituted by one or more substituents $R^{11}$; $C_{2-8}$ alkynyl optionally substituted by one or more substituents $R^{11}$; $C_{3-8}$ cycloalkyl optionally substituted by one or more substituents $R^{12}$; aryl optionally substituted by one or more substituents $R^{12}$; heterocyclyl optionally substituted by one or more substituents $R^{12}$; heteroaryl optionally substituted by one or more substituents $R^{12}$; $OR^5$; $C(=O)R^5$; $C(=O)OR^5$; $OC(=O)R^5$; $(SO)_nR^5$; $NR^7R^8$; $N(R)^7C(=O)R^8$; $C(=O)NR^7R^8$; $SO_2NR^9R^{10}$;

n is 0, 1 or 2;
m is 0, 1, 2, or 3;
or $R^1$ and $R^2$ together with the atoms to which they are attached, link to form an aromatic or non-aromatic ring of 4 to 7 members and containing 0, 1 or 2 heteroatom ring members selected from O, N and S and oxidised forms of N and S, wherein the aromatic or non-aromatic ring is optionally substituted by one or more substituents $R^{13}$.

In one embodiment, $R^1$ and $R^2$ together with the carbon atoms to which they are attached form a 4 to 7 membered aromatic or non-aromatic ring optionally substituted by one or more substituents $R^{13}$.

For example, $R^1$ and $R^2$ together with the carbon atoms to which they are attached can form a 6-membered aromatic ring optionally containing one or two nitrogen ring members, and optionally substituted by one or more substituents $R^{13}$.

In one embodiment $R^1$ and $R^2$ together with the atoms to which they are attached, link to form an aromatic ring of 6 members, wherein said aromatic ring contains 0, 1 or 2 nitrogen heteroatom ring members (for example link to form phenyl, pyridine or pyrimidine), wherein the aromatic ring is optionally substituted by one or more substituents $R^{13}$.

In another embodiment, $R^1$ and $R^2$ together with the carbon atoms to which they are attached form a benzene ring optionally substituted by one or more substituents $R^{13}$.

In another embodiment, the imidazole ring and $R^1$ and $R^2$ together form a group selected from groups AA, AB, AC and AD below.

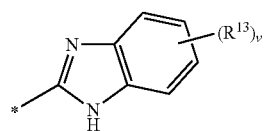

AA

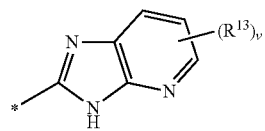

AB

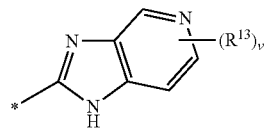

AC

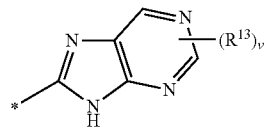

AD

In each case, v is 0, 1 or 2.
In one particular embodiment, the imidazole ring and $R^1$ and $R^2$ together form a group AA.

In another particular embodiment, the imidazole ring and $R^1$ and $R^2$ together form a group AB.

In one embodiment, v is 0.
In another embodiment v is 1.
In another embodiment, v is 2.

When $R^1$ and $R^2$ together with the carbon atoms to which they are attached form a 4 to 7 membered aromatic or non-aromatic ring, typically one or two substituents $R^{13}$ are present and these may be selected from the group consisting of halogen; cyano; hydroxyl; =O; an oxide (when $R^{13}$ is attached to N or S); a dioxide (when $R^{13}$ is attached to S); $C_{1-6}$ alkyl optionally substituted by one or more substituents $R^{11}$; $C_{1-6}$ alkoxyl optionally substituted by one or more substituents $R^{11}$; $C_{2-6}$ alkenyl optionally substituted by one or more substituents $R^{11}$; $C_{2-6}$ alkynyl optionally substituted by one or more substituents $R^{11}$; $C_{3-6}$ cycloalkyl optionally substituted by one or more substituents $R^{12}$; $C_{3-6}$ cycloalkenyl optionally substituted by one or more substituents $R^{12}$; aryl optionally substituted by one or more substituents $R^{12}$; heteroaryl optionally substituted by one or more substituents $R^{12}$; heterocyclyl optionally substituted by one or more substituents $R^{12}$; $(CH_2)_m-NR^7R^8$; $-(CH_2)_m-C(=O)OR^5$; $-(CH_2)_m-OC(=O)R^5$; $-(CH_2)_m-C(=O)R^5$; $-(CH_2)_m-S(O)_nR^5$; $-(CH_2)_m-N(R^7)C(=O)R^8$; $-(CH_2)_m-C(=O)NR^7R^8$; $-(CH_2)_m-SO_2NR^9R^{10}$; $-(CH_2)_m$-aryl; $-(CH_2)_m-O$-aryl; $-O-(CH_2)_m$-aryl; $-(CH_2)_m$-heterocyclyl; $-O-(CH_2)_m$-heterocyclyl; and $-(CH_2)_m-O$-heterocyclyl wherein the aryl or heterocyclyl can be optionally substituted by one or more substituents $R^{12}$.

In one embodiment, $R^{13}$ is selected from the group consisting of halogen; cyano; hydroxyl; $C_{1-6}$ alkyl optionally substituted by one or more substituents $R^{11}$; $C_{1-6}$ alkoxyl optionally substituted by one or more substituents $R^{11}$; heteroaryl optionally substituted by one or more substituents $R^{12}$; heterocyclyl optionally substituted by one or more substituents $R^{12}$; $(CH_2)_m-NR^7R^8$; $-(CH_2)_m-C=ONR^7R^8$; wherein $NR^7R^8$, $R^{11}$, $R^{12}$, and m are as defined herein.

The moiety $R^{12}$ is selected from the group consisting of halogen; cyano; =O; hydroxyl; $-O-P(O)(OH)_2$; $C_{1-6}$ alkyl; $C_{1-6}$ alkoxyl; $C_{2-6}$ alkenyl; $C_{2-6}$ alkynyl; $C_{3-6}$ cycloalkyl; $C_{3-6}$ cycloalkenyl; $-(CH_2)_m-NR^{7a}R^{8a}$; $-(CH_2)_m-C(=O)OR^{5a}$; $-(CH_2)_m-OC(=O)R^{5a}$; $-(CH_2)_m-C(=O)R^{5a}$; $-(CH_2)_m-S(O)_nR^{5a}$; $-(CH_2)_m-N(R^7)C(=O)R^{8a}$; $-(CH_2)_m-C(=O)NR^{7a}R^{8a}$; $-(CH_2)_m-SO_2NR^{9a}R^{10a}$; $-(CH_2)_m$-aryl; $-(CH_2)_m-O$-aryl; $-O-(CH_2)_m$-aryl; $-(CH_2)_m$-heterocyclyl; $-O-(CH_2)_m$-heterocyclyl; and $-(CH_2)_m-O$-heterocyclyl; wherein the $C_{1-6}$ alkyl, $C_{1-6}$ alkoxyl, $C_{2-6}$ alkenyl and $C_{2-6}$ alkynyl moieties are each optionally substituted by one or more substituents $R^{14}$; and the $C_{3-8}$ cycloalkyl, $C_{3-6}$ cycloalkenyl, aryl, heterocyclyl and heteroaryl moieties are each optionally substituted by one or more substituents $R^{15}$; and $R^{5a}$, $R^{7a}$, $R^{8a}$, $R^{9a}$, $R^{10a}$, $R^{14}$, $R^{15}$ and m are as defined herein.

In one embodiment, $R^{12}$ is selected from the group consisting of halogen; cyano; =O; hydroxyl; $C_{1-6}$ alkyl; $C_{1-6}$ alkoxyl; $C_{2-6}$ alkenyl; $C_{2-6}$ alkynyl; $C_{3-6}$ cycloalkyl; $C_{3-6}$ cycloalkenyl; $-(CH_2)_m-NR^{7a}R^{8a}$; $-(CH_2)_m-COOR^{5a}$; $-(CH_2)_m-OC=OR^{5a}$; $-(CH_2)_m-C=OR^{5a}$; $-(CH_2)_m-S(O)_nR^{5a}$; $-(CH_2)_m-NR^7C=OR^{8a}$; $-(CH_2)_m-C=ONR^{7a}R^{8a}$; $-(CH_2)_m-SO_2NR^{9a}R^{10a}$; $-(CH_2)_m$-aryl; $-(CH_2)_m-O$-aryl; $-O-(CH_2)_m$-aryl; $-(CH_2)_m$-heterocyclyl; $-O-(CH_2)_m$-heterocyclyl; and $-(CH_2)_m-O$-heterocyclyl; wherein the $C_{1-6}$ alkyl, $C_{1-6}$ alkoxyl, $C_{2-6}$ alkenyl and $C_{2-6}$ alkynyl moieties are each optionally substituted by one or more substituents $R^{14}$; and the $C_{3-8}$ cycloalkyl, $C_{3-6}$ cycloalkenyl, aryl, heterocyclyl and heteroaryl moieties are each optionally substituted by one or more substituents $R^{15}$.

In one embodiment, $R^1$ and $R^2$ together with the carbon atoms to which they are attached may form a 4 to 7 membered aromatic or non-aromatic ring substituted by one or two substituents $R^{13}$ selected from:

hydroxyl;

fluorine;

chlorine;

cyano;

5-9 membered monocyclic or bicyclic heterocyclic groups containing one nitrogen ring member and optionally a second heteroatom ring member selected from oxygen, nitrogen and sulphur, wherein the said heterocyclic groups are optionally substituted by $C_{1-6}$ alkyl, hydroxyl, OP(=O)(OH)$_2$, OC(O)$R^{5a}$ or $NR^{7a}R^{8a}$;

5 or 6 membered heteroaryl optionally substituted by $C_{1-4}$ alkyl;

a 9 membered heteroaryl group containing a six membered non-aromatic ring having 0, 1 or 2 nitrogen ring members fused to an imidazole ring;

—O—(CH$_2$)$_m$-heterocycyl where m is 0, 1 or 2 and the heterocyclyl is a 4 to 7 membered saturated ring containing one nitrogen heteroatom ring member and optionally a second heteroatom ring member selected from O, N and S, and wherein the said saturated ring is optionally substituted by one or $C_{1-6}$ alkyl groups; $C_{1-6}$ alkoxyl optionally substituted by one or more substituents selected from hydroxyl and $NR^{7a}R^{8a}$;

$C_{1-6}$ alkyl optionally substituted by one or more substituents $NR^{7a}R^{8a}$; (CH$_2$)$_m$—NR$^7$R$^8$ where m is 1, 2 or 3 and NR$^7$R$^8$ forms a non-aromatic four to seven membered ring optionally containing a second heteroatom selected from O, N and S, and optionally substituted by one or more substituents $R^{12a}$ selected from $C_{1-6}$ alkyl and $NR^{7a}R^{8a}$; and —(CH$_2$)$_m$—C(=O)NR$^7$R$^8$;

wherein m is 0, and $R^7$, $R^{7a}$, $R^8$ and $R^{8a}$ are as defined herein.

In another embodiment, $R^1$ and $R^2$ together with the carbon atoms to which they are attached may form a 4 to 7 membered aromatic or non-aromatic ring substituted by one or two substituents $R^{13}$ selected from:

hydroxyl;

fluorine;

chlorine;

cyano;

5-7 membered heterocyclic groups containing one nitrogen ring member and optionally a second heteroatom ring member selected from oxygen, nitrogen and sulphur, wherein the said heterocyclic groups are optionally substituted by $C_{1-6}$ alkyl or $NR^{7a}R^{8a}$;

5 or 6 membered heteroaryl optionally substituted by $C_{1-4}$ alkyl;

$C_{1-6}$ alkoxyl optionally substituted by one or more substituents selected from hydroxyl and $NR^{7a}R^{8a}$;

$C_{1-6}$ alkyl optionally substituted by one or more substituents $NR^{7a}R^{8a}$;

(CH$_2$)$_m$—NR$^7$R$^8$ where m is 1, 2 or 3 and NR$^7$R$^8$ forms a non-aromatic four to seven membered ring optionally containing a second heteroatom selected from O, N and S, and optionally substituted by one or more substituents $R^{12a}$ selected from $C_{1-6}$ alkyl and $NR^{7a}R^{8a}$; and —(CH$_2$)$_m$—C(=O)NR$^7$R$^8$;

wherein m is 0, and $R^7$, $R^{7a}$, $R^8$ and $R^{8a}$ are as defined herein.

In a further embodiment, $R^1$ and $R^2$ together with the carbon atoms to which they are attached may form a 4 to 7 membered aromatic or non-aromatic ring substituted by one or two substituents $R^{13}$ selected from:

hydroxy;

fluorine;

5-7 membered non-aromatic heterocyclic groups containing a nitrogen ring member and optionally a second heteroatom ring member selected from O, N and S, the heterocyclic groups being optionally substituted by one or two substituents selected from $C_{1-4}$ alkyl and $NR^{7b}R^{8b}$;

$C_{1-4}$ alkoxy optionally substituted by one or two substituents independently selected from hydroxy and $NR^{7b}R^{8b}$;

$C_{1-4}$ alkyl optionally substituted by $NR^{7b}R^{8b}$;

5-membered heteroaryl groups containing a nitrogen ring member and up to two further heteroatom ring members selected from N, S and O provided that no more than one of the two further heteroatom ring members can be O or S; wherein the heteroaryl group is optionally substituted by $C_{1-4}$ alkyl; and —C(=O)NR$^{7b}$R$^{8b}$;

wherein $R^{7b}$ and $R^{8b}$ are each selected from hydrogen and $C_{1-4}$ alkyl, or $NR^{7b}R^{8b}$ forms a saturated heterocyclic group selected from pyrrolidine, piperidine, piperazine, azepine, diazepine, morpholine and thiomorpholine, wherein the saturated heterocyclic group is optionally substituted by $C_{1-4}$ alkyl, amino, mono-$C_{1-4}$ alkyl or di-$C_{1-4}$ alkyl.

In one embodiment, $R^{13}$ is selected from the group consisting nitrogen-containing heteroaryl optionally substituted by one or more substituents $R^{12}$; (CH$_2$)$_m$—NR$^7$R$^8$; —(CH$_2$)$_m$—C(=O)R$^5$ wherein m is zero; —(CH$_2$)$_m$—C(=O)NR$^7$R$^8$ wherein m is zero; (CH$_2$)$_m$-heterocyclyl, —O—(CH$_2$)$_m$-heterocyclyl, and —(CH$_2$)$_m$—O-heterocyclyl wherein the heterocyclyl are nitrogen-containing heterocyclic groups and can be optionally substituted by one or more substituents $R^{12}$.

In another embodiment, $R^{13}$ is selected from —(CH$_2$)$_m$-heterocyclyl wherein m is zero or one and the heterocyclyl can be optionally substituted by one or more substituents $R^{12}$. In one embodiment m is zero and in another embodiment m is one.

In another embodiment, $R^{13}$ is selected from —(CH$_2$)$_m$-heterocyclyl wherein the heterocyclyl is a nitrogen-containing heterocyclyl and the heterocyclyl can be optionally substituted by one or more substituents $R^{12}$. In another embodiment, $R^{13}$ is selected from —(CH$_2$)$_m$-heterocyclyl wherein the heterocyclyl is a saturated nitrogen-containing heterocyclyl and the heterocyclyl can be optionally substituted by one or more substituents $R^{12}$.

In one embodiment, $R^{13}$ is selected from —(CH$_2$)$_m$-heterocyclyl wherein the heterocyclyl is a nitrogen-containing heterocyclyl and the heterocyclyl is substituted by one or more substituents $R^{12}$. In another embodiment, $R^{13}$ is selected from —(CH$_2$)$_m$-heterocyclyl wherein the heterocyclyl is a saturated nitrogen-containing heterocyclyl and the heterocyclyl is substituted by one or more substituents $R^{12}$. In one embodiment $R^{12}$ is selected from the group consisting of halogen; cyano; =O; hydroxyl; $C_{1-6}$ alkyl; $C_{1-6}$ alkoxyl; $C_{2-6}$ alkenyl; $C_{2-6}$ alkynyl; $C_{3-6}$ cycloalkyl; $C_{3-6}$ cycloalkenyl; —(CH$_2$)$_m$—NR$^{7a}$R$^{8a}$; —(CH$_2$)$_m$—C(=O)OR$^{5a}$; —(CH$_2$)$_m$—OC(=O)R$^{5a}$; —(CH$_2$)$_m$—C(=O)R$^{5a}$; —(CH$_2$)$_m$—S(O)$_n$R$^{5a}$; —(CH$_2$)$_m$—N(R$^7$)C(=O)R$^{8a}$; —(CH$_2$)$_m$—C(=O)NR$^{7a}$R$^{8a}$; —(CH$_2$)$_m$—SO$_2$NR$^{9a}$R$^{10a}$; —(CH$_2$)$_m$-aryl; —(CH$_2$)$_m$—O-aryl; —O—(CH$_2$)$_m$-aryl; —(CH$_2$)$_m$-heterocyclyl; —O—(CH$_2$)$_m$-heterocyclyl; and —(CH$_2$)$_m$—O-heterocyclyl. In another embodiment $R^{12}$ is selected from the group consisting of $C_{1-6}$ alkyl (e.g. methyl) and —$(CH_2)_m$—$NR^{7a}R^{8a}$ (e.g. NMe$_2$).

In one embodiment, $R^{13}$ is selected from —O—$(CH_2)_m$-heterocyclyl or $C_{1-6}$ alkoxyl optionally substituted by one or more substituents $R^{11}$. In one embodiment, $R^{13}$ is selected $C_{1-6}$ alkoxyl (e.g. $C_{1-4}$ alkoxyl or $C_{1-2}$ alkoxyl) optionally substituted by one or more substituents $R^{11}$, wherein $R^{11}$ is selected from the group consisting of halogen; cyano; =O; hydroxyl; $C_{1-6}$ alkyl; $C_{1-6}$ alkoxy; $C_{2-6}$ alkenyl; $C_{2-6}$ alkynyl; $C_{3-6}$ cycloalkyl; $C_{3-6}$ cycloalkenyl; aryl; heteroaryl; heterocyclyl; —$(CH_2)_m$—$NR^{7a}R^{8a}$; —$(CH_2)_m$—$C(=O)OR^{5a}$; —$(CH_2)_m$—$OC(=O)R^{5a}$; —$(CH_2)_m$—$C(=O)R^{5a}$; —$(CH_2)_m$—$S(O)_nR^5$; —$(CH_2)_m$—$N(R^{7a})C(=O)R^{8a}$; —$(CH_2)_m$—$C(=O)NR^{7a}R^{8a}$; —$(CH_2)_m$—$SO_2NR^{9a}R^{10a}$; —$(CH_2)_m$-aryl; —$(CH_2)_m$—O-aryl; —O—$(CH_2)_m$-aryl; —$(CH_2)_m$-heterocyclyl; —O—$(CH_2)_m$-heterocyclyl; and —$(CH_2)_m$—O-heterocyclyl.

In one embodiment, $R^{13}$ is selected from $C_2$ alkoxyl optionally substituted by one or more substituents $R^{11}$, wherein $R^{11}$ is selected from —$(CH_2)_m$—$NR^{7a}R^{8a}$; —$(CH_2)_m$-heterocyclyl; —O—$(CH_2)_m$-heterocyclyl; and —$(CH_2)_m$—O-heterocyclyl. In one embodiment $R^{11}$ is —$(CH_2)_m$—$NR^{7a}R^{8a}$ and in a further embodiment, m is zero and $R^{7a}$ and $R^{8a}$ are $C_{1-4}$ alkyl (e.g. methyl).

In one embodiment, $R^{13}$=—$(CH_2)_m$—$C(=O)R^5$ wherein $R^5$ is selected from $C_{1-8}$ alkyl; $C_{3-8}$ cycloalkyl; aryl; heteroaryl; and heterocyclyl. In one embodiment $R^5$ is heterocyclyl, and in another embodiment $R^5$ is nitrogen-containing heterocyclyl.

In one embodiment, one or two substituents $R^{13}$ are present. Within this sub-group of compounds, in one embodiment one substituent $R^{13}$ is present. In another embodiment, two substituents $R^{13}$ are present. When two substituents are present, it is preferred that at least one is selected from halogen, $C_{1-4}$ alkyl and $C_{1-4}$ alkoxy.

In one embodiment, $R^{14}$ is selected from hydroxy; halogen; cyano; $C_{1-4}$ alkoxy; $C_{1-4}$ alkoxy-$C_{2-4}$ alkoxy; and hydroxy-$C_{2-4}$ alkoxy.

In one embodiment, $R^{15}$ is selected from hydroxy; halogen; cyano; $C_{1-4}$ alkyl; $C_{1-2}$ alkoxy; $C_{1-2}$ alkoxy-$C_{2-4}$ alkoxy; hydroxy-$C_{2-4}$ alkoxy; $(CH_2)_m$—$NR^{7a}R^{8a}$; —$(CH_2)_m$—$C(=O)OR^{5a}$; —$(CH_2)_m$—$OC(=O)R^{5a}$; —$(CH_2)_m$—$C(=O)R^{5a}$; —$(CH_2)_m$—$(SO)_nR^{5a}$; —$(CH_2)_m$—$N(R^{7a})C(=O)R^{8a}$; —$(CH_2)_m$—$C(=O)NR^{7a}R^{8a}$; and —$(CH_2)_m$—$SO_2NR^{9a}R^{10a}$.

Preferred Subgroups of Compounds

One preferred subgroup of compounds within formula (I) can be represented by formula (II):

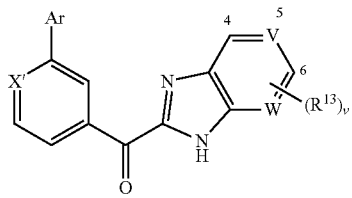

(II)

or a salt, solvate, tautomer or N-oxide thereof; wherein X' is N or C—CN; V and W are selected from N, CH and C—$R^{13}$; v is 0, 1 or 2; and Ar and $R^{13}$ are as defined herein.

In one embodiment V is C—$R^{13}$ and W is CH or N.

In one embodiment X' is N. In one embodiment X' is C—CN.

In one embodiment within formula (II), there is provided a compound of the formula (IIa):

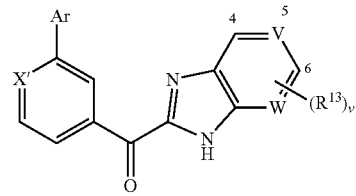

(IIa)

or a salt, solvate, tautomer or N-oxide thereof; wherein:

X' is N or C—CN;

V and W are selected from N, CH and C—$R^{13}$;

v is 0, 1 or 2;

$R^{13}$ is selected from the group $R^{13a}$ consisting of halogen; cyano; hydroxyl; =O; an oxide (when $R^{13}$ is attached to N or S); $C_{1-6}$ alkyl optionally substituted by one or more substituents $R^{11a}$; $C_{1-6}$ alkoxyl optionally substituted by one or more substituents $R^{11a}$; $C_{3-6}$ cycloalkyl optionally substituted by one or more substituents $R^{12a}$; heterocyclyl optionally substituted by one or more substituents $R^{12a}$; $(CH_2)_m$—$NR^{7b}R^{8b}$; —$(CH_2)_m$—$C(=O)OR^{5b}$; —$(CH_2)_m$—$C(=O)NR^{7b}R^{8b}$; —$(CH_2)_m$-heterocyclyl; —O—$(CH_2)_m$-heterocyclyl; and —$(CH_2)_m$—O-heterocyclyl wherein the heterocyclyl can be optionally substituted by one or more substituents $R^{12a}$;

Ar is as defined herein;

$R^{11a}$ is selected from the group consisting of halogen; cyano; =O; hydroxyl; $C_{1-6}$ alkyl; $C_{1-6}$ alkoxy; heterocyclyl; —$(CH_2)_m$—$NR^{7b}R^{8b}$; —$(CH_2)_m$—$C(=O)NR^{7b}R^{8b}$; —$(CH_2)_m$-heterocyclyl; —O—$(CH_2)_m$-heterocyclyl; and —$(CH_2)_m$—O-heterocyclyl;

$R^{12a}$ is selected from the group consisting of hydroxyl; $C_{1-6}$ alkyl; $C_{1-6}$ alkoxyl; —$(CH_2)_m$—$NR^{7b}R^{8b}$; —$(CH_2)_m$—$C(=O)NR^{7b}R^{8b}$; —$(CH_2)_m$-heterocyclyl; —O—$(CH_2)_m$-heterocyclyl; and —$(CH_2)_m$—O-heterocyclyl;

$R^{5b}$ is hydrogen or $C_{1-4}$ alkyl;

$R^{7b}$ and $R^{8b}$ are the same or different, and independently are selected from hydrogen; $C_{1-8}$ alkyl optionally substituted by one or more substituents selected from hydroxyl and $C_{1-4}$ alkoxy and cyano; $C_{3-8}$ cycloalkyl optionally substituted by one or more substituents hydroxy, $C_{1-4}$ alkyl, $C_{1-4}$ alkoxy and cyano; and heterocyclyl optionally substituted by one or more substituents selected from hydroxy, $C_{1-4}$ alkyl, $C_{1-4}$ alkoxy and cyano; or $NR^{7b}R^{8b}$ forms a non-aromatic four to seven membered ring optionally containing a second heteroatom selected from O, N and S, and optionally substituted by one or more substituents selected from hydroxyl, $C_{1-4}$ alkyl, $C_{1-4}$ acyl, $C_{1-4}$ alkoxycarbonyl and $C_{1-4}$ alkylsulphonyl.

In one embodiment X' is N. In one embodiment X' is C—CN.

In another embodiment within formula (II), there is provided a compound of the formula (IIb):

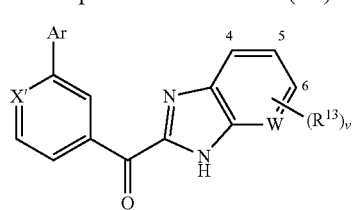

(IIb)

or a salt, solvate, tautomer or N-oxide thereof; wherein X' is N or C—CN; W is selected from N, CH and C—R$^{13}$; v is 0, 1 or 2; and Ar and R$^{13}$ are as defined defined herein.

In one embodiment X' is N. In one embodiment X' is C—CN.

Within formulae (II), (IIa) and (IIb), the moiety Ar may be for example, selected from unsubstituted or substituted (as defined herein) isoquinoline, pyrazole and azaindole (particularly 6-aza-indol-4-yl) groups.

Accordingly, in another embodiment within formula (II), there is provided a compound of the formula (III):

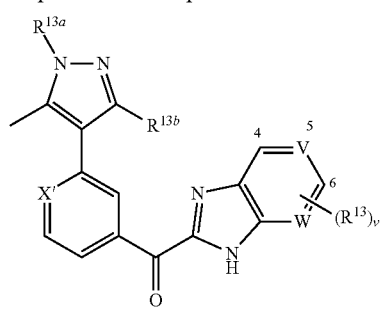

(III)

or a salt, solvate, tautomer or N-oxide thereof; X' is N or C—CN; W is CH or N; V is CH, N or C—R$^{13}$; R$^{13a}$ and R$^{13b}$ are each selected from R$^{13}$; and v and R$^{13}$ are as defined herein.

In one embodiment within formula (III), R$^{13a}$ is selected from hydrogen and C$_{1-3}$ alkyl; and R$^{13b}$ is selected from hydrogen and C$_{1-3}$ alkyl wherein the C$_{1-3}$ alkyl is optionally substituted by one or more fluorine atoms.

In another embodiment, R$^{13a}$ is hydrogen or methyl (more preferably methyl) and R$^{13b}$ is methyl.

In one embodiment X' is N. In one embodiment X' is C—CN.

In another embodiment within formula (II), there is provided a compound of the formula (IV):

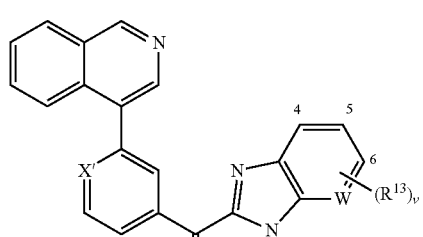

(IV)

or a salt, solvate, tautomer or N-oxide thereof; wherein X', W, R$^{13}$ and v are as defined herein.

In one embodiment X' is N. In one embodiment X' is C—CN.

Within formulae (II), (IIa), (IIb), (III) and (IV) it is preferred that a substituent R$^{13}$ is attached to the 5- or 6-position of the benzimidazole (or aza-benzoimidazole or diaza-benzoimidazole) ring.

Within formula (IV), one particular subgroup of compounds is the group of compounds having the formula (V):

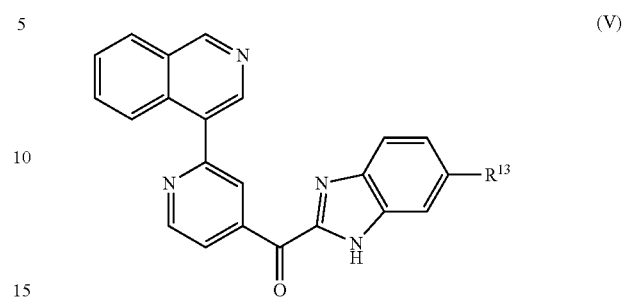

(V)

or a salt, solvate, tautomer or N-oxide thereof, wherein R$^{13}$ is as defined herein.

In another embodiment within formula (II), there is provided a compound of the formula (VI):

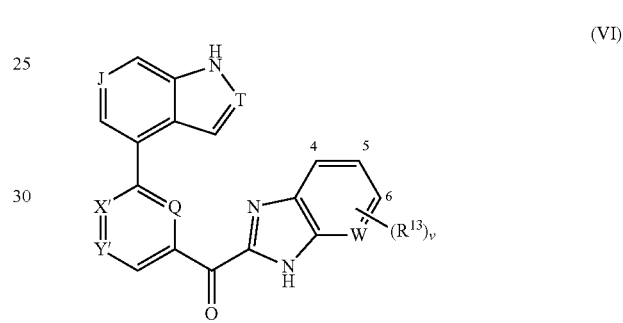

(VI)

or a salt, solvate, tautomer or N-oxide thereof, wherein J is CH, C—R$^{13}$ or N, T is CH or N, v is 0, 1 or 2 and R$^{13}$ is as defined herein.

In one embodiment within formula (VI), J is CH or N and T is CH.

In another embodiment within formula (VI), J is N and T is CH.

In another embodiment within formula (VI), J is CH and T is CH.

In each of formulae (I), (II), (IIa), (IIb), (III), (IV), (V) and (VI) (for example in each of formulae (I), (II), (IIa), (IIb), (III), (IV) and (V)), a substituent group R$^{13}$ can be selected from:

(a) —O$_m$—(C$_{1-4}$-alkylene)$_n$-[Sol], where m is 0 or 1 and n is 0 or 1 and the alkylene is straight chain or branched, provided that when m and n are both 1 and Sol is linked by a nitrogen atom to C$_{1-4}$-alkylene, there must be at least two carbon atoms in the C$_{1-4}$-alkylene in line between O and [Sol];

(b) —(C=O)-[Sol];

(c) (SO$_2$)-[Sol]

(d) mono- or dihydroxy-C$_{2-4}$-alkoxy, provided that when two hydroxyl groups are present, they are not attached to the same carbon atom; and wherein [Sol] is selected from:

(i) NR$^{18}$R$^{19}$ where R$^{18}$ is selected from hydrogen and C$_{1-3}$ alkyl where the C$_{1-3}$ alkyl is optionally substituted by hydroxyl, amino or mono- or di-methylamino; and R$^{19}$ is selected from R$^{18}$ and monocyclic and bicyclic saturated heterocylic rings containing from 4 to 8 ring members and containing a nitrogen ring member and optionally a second heteroatom ring member selected from N and O; and wherein the monocyclic and bicyclic saturated heterocylic rings are optionally substituted by one or more substituents selected from $C_{1-4}$ alkyl, hydroxy, amino, mono-$C_{1-2}$-alkylamino and mono-$C_{1-2}$-alkylamino and optionally substituted 4 to 6 membered saturated heterocyclic rings containing a nitrogen ring member and optionally a second ring member selected from nitrogen and oxygen wherein the optional substituents for the 4 to 6 membered saturated heterocyclic rings are selected from hydroxyl and methyl; and (ii) monocyclic and bicyclic saturated heterocyclic rings containing from 4 to 8 ring members and containing a nitrogen ring member and optionally a second heteroatom ring member selected from N and O; and wherein the monocyclic and bicyclic saturated heterocylic rings are optionally substituted by one or more substituents selected from $C_{1-4}$ alkyl, hydroxy, —OP(=O)(OH)$_2$, amino, amino-$C_{1-4}$alkanoyloxy, mono-$C_{1-2}$-alkylamino and mono-$C_{1-2}$-alkylamino and optionally substituted 4 to 6 membered saturated heterocyclic rings containing a nitrogen ring member and optionally a second ring member selected from nitrogen and oxygen wherein the optional substituents for the 4 to 6 membered saturated heterocyclic rings are selected from hydroxyl and methyl.

In one embodiment, [Sol] is selected from:
(i) NR$^{18}$R$^{19}$ where R$^{18}$ is selected from hydrogen and $C_{1-3}$ alkyl where the $C_{1-3}$ alkyl is optionally substituted by hydroxyl, amino or mono- or di-methylamino; and R$^{19}$ is selected from R$^{18}$ and monocyclic and bicyclic saturated heterocylic rings containing from 4 to 8 ring members and containing a nitrogen ring member and optionally a second heteroatom ring member selected from N and O; and wherein the monocyclic and bicyclic saturated heterocylic rings are optionally substituted by one or more substituents selected from $C_{1-4}$ alkyl, hydroxy, amino, mono-$C_{1-2}$-alkylamino and mono-$C_{1-2}$-alkylamino and optionally substituted 4 to 6 membered saturated heterocyclic rings containing a nitrogen ring member and optionally a second ring member selected from nitrogen and oxygen wherein the optional substituents for the 4 to 6 membered saturated heterocyclic rings are selected from hydroxyl and methyl; and (ii) monocyclic and bicyclic saturated heterocyclic rings containing from 4 to 8 ring members and containing a nitrogen ring member and optionally a second heteroatom ring member selected from N and O; and wherein the monocyclic and bicyclic saturated heterocylic rings are optionally substituted by one or more substituents selected from $C_{1-4}$ alkyl, hydroxy, amino, mono-$C_{1-2}$-alkylamino and mono-$C_{1-2}$-alkylamino and optionally substituted 4 to 6 membered saturated heterocyclic rings containing a nitrogen ring member and optionally a second ring member selected from nitrogen and oxygen wherein the optional substituents for the 4 to 6 membered saturated heterocyclic rings are selected from hydroxyl and methyl.

When only one substituent group R$^{13}$ is present, it may, for example, be selected from (a), (b) and (c) above.

When more than one (e.g. two) substituent group R$^{13}$ is present, one may be selected from (a), (b) and (c) above and the other(s) may be selected from hydroxy, methyl, methoxy and fluorine, for example.

Particular substituent groups R$^{13}$ include groups A to Z in the table below. The asterisks indicate the point of attachment to the benzoimidazole or aza- or diaza-benzoimidazole group.

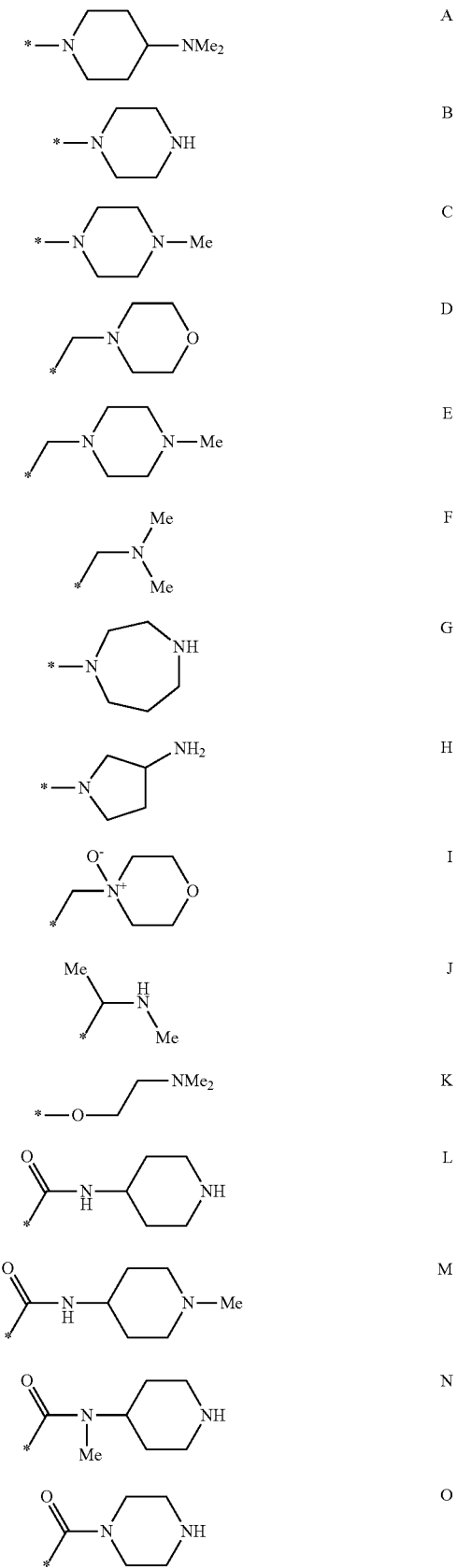

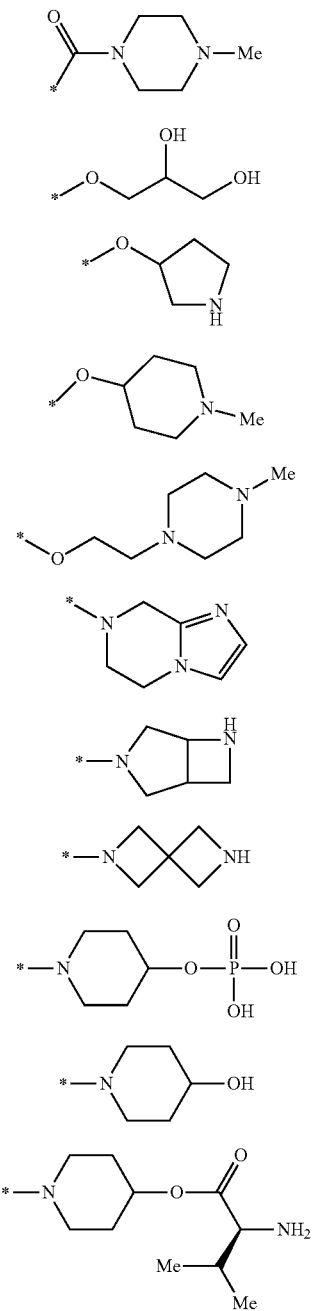

In one embodiment, a subset of substituent groups $R^{13}$ consists of groups A to Q.

One preferred group is group A.

In one particular embodiment, the invention provides a compound of the formula (I) or a salt, tautomer, solvate or N-oxide thereof; wherein:

Q is CH;

X is N, $N^+$—$O^-$ or $CR^3$;

Y is N or $CR^{3a}$;

$R^3$ is selected from hydrogen; hydroxy; halogen (e.g. fluorine or chlorine); cyano; $OR^5$ (e.g. OMe); and C(=O)$NR^7R^8$ (e.g. C(=O)$NH_2$ or C(=O)$N(Me)_2$);

$R^{3a}$ is selected from hydrogen; halogen (e.g. chlorine) and 5-membered heteroaryl rings containing 1 or 2 heteroatoms selected from N and S and being optionally substituted with $C_{1-6}$ alkyl (e.g. unsubstituted thiophene or pyrazoyl substituted with $C_{1-8}$ alkyl (e.g. —$CH_3$));

$R^1$ and $R^2$ are independently selected from hydrogen; $C_{1-8}$ alkyl (e.g. methyl) optionally substituted by one or more substituents $R^{11}$ (for example a heterocyclyl group such as piperidinyl wherein the heterocyclyl (e.g. piperidinyl) group is substituted with a substituent $R^{15}$ such as —$(CH_2)_m$—$NR^{7a}R^{8a}$ (for example wherein $R^{7a}$ and $R^{7b}$ are both methyl) and heteroaryl (e.g. pyrazolyl) optionally substituted by one or more substituents $R^{12}$ e.g. $C_{1-6}$ alkyl such as methyl;

or $R^1$ and $R^2$ together with the atoms to which they are attached, link to form an aromatic ring of 6 members, wherein said aromatic ring contains 0, 1 or 2 nitrogen heteroatom ring members (for example wherein said aromatic ring is a benzene, pyridine or pyrimidine ring), wherein the aromatic ring is optionally substituted by one or more (e.g. 1 or 2) substituents $R^{13}$, for example where $R^{13}$ is selected from the group consisting of:

halogen (e.g. fluorine, chlorine);

hydroxy;

—$C_{1-6}$ alkyl (e.g. methyl or ethyl) optionally substituted by one or more substituents $R^{11}$ (e.g. $R^{11}$ substituents selected from heterocyclyl such as N-methyl piperazinyl, morpholinyl, N-oxide morpholinyl; and —$(CH_2)_m$—$NR^{7a}R^{8a}$ such as NHMe, $N(Me)_2$);

—$C_{1-6}$ alkoxyl (e.g. methoxy, ethoxy or propoxy) optionally substituted by one or more substituents $R^{11}$ e.g. $R^{11}$ substituents selected from hydroxyl, —$(CH_2)_m$—$NR^{7a}R^{8a}$ such as $N(Me)_2$ (e.g. to form OMe, —$OCH_2CH_2N(Me)_2$, —$OCH_2CH(OH)CH_2OH$);

heterocyclyl (e.g. pyrrolidinyl, piperazinyl, piperidinyl, diazepinyl, azabicyclohexyl, diazaspiroheptyl, diazabicycloheptyl) optionally substituted by one or more substituents $R^{12}$ e.g. where $R^{12}$ is selected from hydroxyl; =O, $C_{1-6}$ alkyl (e.g. methyl, isopropyl); —$(CH_2)_m$—$NR^{7a}R^{8a}$ (e.g. $NH_2$, $N(Me)_2$), —$(CH_2)_m$—OC(=O)$R^{5a}$ (e.g. —OC(=O)—CH(CH(CH_3)_2)NH_2$); —$(CH_2)_m$—C(=O)$OR^{5a}$ (e.g. —C(=O)O$^tBu$); —O—P(O)(OH)$_2$ and heterocyclyl (e.g. piperidinyl);

—$(CH_2)_m$—$NR^7R^8$ (e.g. —NH-pyrrolidinyl);

—$(CH_2)_m$—C(=O)$R^5$ (e.g. —C(=O)-piperazinyl, —C(=O)—(N-methyl-piperazinyl));

—$(CH_2)_m$—C(=O)$NR^7R^8$ (e.g. —C(=O)NH—(N-methyl-piperidinyl), —C(=O)NH-piperidinyl, —C(=O)NMe-piperidinyl;

—$(CH_2)_m$—$SO_2NR^9R^{10}$ (e.g. —$SO_2N(CH_3)$(CH_2CH_2NH_2$), —$SO_2$-piperazinyl); and —O—$(CH_2)_m$-heterocyclyl (e.g. O-pyrrolidinyl, —O—(N-methylpiperidinyl), and —O—$CH_2CH_2$—(N-methylpiperazinyl).

Ar is selected from:

6-membered aryl (e.g. phenyl) optionally substituted by one two or three substituents $R^{13}$;

5 or 6-membered heteroaryl (e.g. pyridyl, thiophene, pyrazolyl, imidazolyl, thiazolyl, isoxazolyl, pyrimidinyl) optionally substituted by one, two or three substituents $R^{13}$;

bicyclic aryl (e.g. naphthyl), optionally substituted by one, two or three substituents $R^{13}$; and bicyclic heteroaryl (e.g. indolyl, azaindolyl, isoquinolinyl, quinolinyl, pyridopyridyl, pyrazolopyridinyl, pyrrolopyridine, benzoimidazolyl, azobenzoimidazolyl, 2,3-dihydrobenzfuranyl, dihydro-benzodioxine, naphthyridine, dihydropyrrolopyrazolyl) optionally substituted by one, two or three substituents $R^{13}$;

e.g. wherein the R¹³ substituents on the group Ar are selected from:
halogen (e.g. fluorine);
—$C_{1-6}$ alkyl (e.g. methyl, isopropyl) optionally substituted by one or more substituents $R^{11}$ (e.g. substituents selected from the group consisting of hydroxyl and —$(CH_2)_m$—$NR^{7a}R^{8a}$; e.g. to form $CH_3$, $CH(CH_3)_2$, $CH_2OH$, $CH_2NHCH_2CH_3$);
$C_{1-6}$ alkoxyl optionally substituted by one or more substituents $R^{11}$ (e.g. OMe);
aryl optionally substituted by one or more substituents $R^{12}$ (e.g. unsubstituted phenyl);
heterocyclyl optionally substituted by one or more substituents $R^{12}$ (e.g. piperazinyl, piperazinyl-boc);
—$(CH_2)_m$—$NR^7R^8$ (e.g. $NH_2$); and
—$(CH_2)_m$—$SO_2NR^9R^{10}$ (e.g. —$SO_2NHMe$).

The various functional groups and substituents making up the compounds of the formula (I) are typically chosen such that the molecular weight of the compound of the formula (I) does not exceed 1000. More usually, the molecular weight of the compound will be less than 750, for example less than 700, or less than 650, or less than 600, or less than 550. More preferably, the molecular weight is less than 525 and, for example, is 500 or less.

Particular compounds of the invention are as illustrated in the examples below and include:
[2-(2,6-Difluoro-phenyl)-pyridin-4-yl]-[5-(1-methyl-1H-pyrazol-4-yl)-1H-imidazol-2-yl]-methanone;
[2-(2-Fluoro-6-methoxy-phenyl)-pyridin-4-yl]-[6-(4-methyl-piperazin-1-yl)-1H-benzoimidazol-2-yl]-methanone;
[6-(4-Dimethylamino-piperidin-1-yl)-1H-benzoimidazol-2-yl]-[2-(2-fluoro-6-methoxy-phenyl)-pyridin-4-yl]-methanone;
(6'-Fluoro-2'-methoxy-biphenyl-3-yl)-(5-morpholin-4-ylmethyl-1H-benzoimidazol-2-yl)-methanone;
1H-Imidazol-2-yl)-[3-(2-methyl-thiazol-4-yl)-phenyl]-methanone;
(1H-Imidazol-2-yl)-(2-phenyl-pyridin-4-yl)-methanone;
(1H-Imidazol-2-yl)-[3-(2H-pyrazol-3-yl)-phenyl]-methanone;
(1H-Imidazol-2-yl)-(3-thiophen-3-yl-phenyl)-methanone;
[2-(4-Hydroxymethyl-phenyl)-pyridin-4-yl]-(1H-imidazol-2-yl)-methanone;
(1H-Imidazol-2-yl)-[2-(3-methoxy-phenyl)-pyridin-4-yl]-methanone;
(3-Chloro-5-thiophen-3-yl-phenyl)-(1H-imidazol-2-yl)-methanone;
(3'-Amino-biphenyl-3-yl)-(1H-imidazol-2-yl)-methanone;
(3-Chloro-5-thiazol-4-yl-phenyl)-(1H-imidazol-2-yl)-methanone;
(3,5-Di-thiophen-3-yl-phenyl)-(1H-imidazol-2-yl)-methanone;
(1H-Imidazol-2-yl)-[3-(1-methyl-1H-pyrazol-3-yl)-5-thiophen-3-yl-phenyl]-methanone;
[2-(2,3-Difluoro-6-methoxy-phenyl)-pyridin-4-yl]-(1H-imidazol-2-yl)-methanone;
[2-(2,3-Difluoro-6-methoxy-phenyl)-pyridin-4-yl]-(5-dimethylaminomethyl-1H-benzoimidazol-2-yl)-methanone;
[2-(3,5-Dimethyl-isoxazol-4-yl)-pyridin-4-yl]-(5-morpholin-4-ylmethyl-1H-benzoimidazol-2-yl)-methanone;
(5-Morpholin-4-ylmethyl-1H-benzoimidazol-2-yl)-(2-phenyl-pyridin-4-yl)-methanone;
[2-(2,6-Difluoro-phenyl)-pyridin-4-yl]-(5-morpholin-4-ylmethyl-1H-benzoimidazol-2-yl)-methanone;
[2-(2,6-Difluoro-phenyl)-pyridin-4-yl]-(1H-imidazol-2-yl)-methanone;
[2-(4-Hydroxymethyl-phenyl)-pyridin-4-yl]-(5-morpholin-4-ylmethyl-1H-benzoimidazol-2-yl)-methanone;
[2-(2-Fluoro-6-methoxy-phenyl)-pyridin-4-yl]-(5-morpholin-4-ylmethyl-1H-benzoimidazol-2-yl)-methanone;
[2-(2,3-Difluoro-6-methoxy-phenyl)-pyridin-4-yl]-(5-morpholin-4-ylmethyl-1H-benzoimidazol-2-yl)-methanone;
[2-(2-Methoxy-phenyl)-pyridin-4-yl]-(5-morpholin-4-ylmethyl-1H-benzoimidazol-2-yl)-methanone;
[4-(4-Dimethylamino-piperidin-1-ylmethyl)-1H-imidazol-2-yl]-[2-(2-fluoro-6-methoxy-phenyl)-pyridin-4-yl]-methanone;
(6-Chloro-2'-methoxy-biphenyl-3-yl)-(5-dimethylaminomethyl-1H-benzoimidazol-2-yl)-methanone;
[2-(2-Fluoro-6-methoxy-phenyl)-1-oxy-pyridin-4-yl]-[5-(4-oxy-morpholin-4-ylmethyl)-1H-benzoimidazol-2-yl]-methanone;
(4-Dimethylaminomethyl-1H-benzoimidazol-2-yl)-(2-isoquinolin-4-yl-pyridin-4-yl)-methanone (e.g. formate salt);
[2-(2,3-Difluoro-6-methoxy-phenyl)-pyridin-4-yl]-(4-dimethylaminomethyl-1H-benzoimidazol-2-yl)-methanone (e.g. hydrochloride salt);
(4-Hydroxy-1H-benzoimidazol-2-yl)-(2-isoquinolin-4-yl-pyridin-4-yl)-methanone (e.g. methanesulfonate salt);
(2-Isoquinolin-4-yl-pyridin-4-yl)-[4-(1-methylamino-ethyl)-1H-benzoimidazol-2-yl]-methanone (e.g. trifluoroacetate salt);
(5,6-Dimethoxy-1H-benzoimidazol-2-yl)-(5'-ethylaminomethyl-[2,3']bipyridinyl-4-yl)-methanone (e.g. formate salt);
[5-(2-Dimethylamino-ethoxy)-1H-benzoimidazol-2-yl]-(2-isoquinolin-4-yl-pyridin-4-yl)-methanone;
(6-Dimethylaminomethyl-1H-benzoimidazol-2-yl)-(2-isoquinolin-4-yl-pyridin-4-yl)-methanone;
2-(2-Isoquinolin-4-yl-pyridine-4-carbonyl)-3H-benzoimidazole-5-carboxylic acid piperidin-4-ylamide (e.g. formate salt);
(2-Isoquinolin-4-yl-pyridin-4-yl)-[5-(4-methyl-piperazin-1-ylmethyl)-1H-benzoimidazol-2-yl]-methanone (e.g. formate salt);
(2-Isoquinolin-4-yl-pyridin-4-yl)-[6-(piperazine-1-carbonyl)-1H-benzoimidazol-2-yl]-methanone (e.g. formate salt);
5-[5-(4-Dimethylamino-piperidin-1-yl)-1H-benzoimidazole-2-carbonyl]-2'-methoxy-biphenyl-2-carbonitrile (e.g. trifluoroacetate salt);
[5-(4-Dimethylamino-piperidin-1-yl)-1H-benzoimidazol-2-yl]-(2-isoquinolin-4-yl-pyridin-4-yl)-methanone (e.g. hydrochloride salt);
(2-Isoquinolin-4-yl-pyridin-4-yl)-[5-(4-methyl-piperazin-1-yl)-1H-benzoimidazol-2-yl]-methanone;
(2-Isoquinolin-4-yl-pyridin-4-yl)-(5-piperazin-1-yl-1H-benzoimidazol-2-yl)-methanone;
[5-(3-Amino-pyrrolidin-1-yl)-1H-benzoimidazol-2-yl]-(2-isoquinolin-4-yl-pyridin-4-yl)-methanone;
(5-[1,4]Diazepan-1-yl-1H-benzoimidazol-2-yl)-(2-isoquinolin-4-yl-pyridin-4-yl)-methanone;
(5,7-Difluoro-1H-benzoimidazol-2-yl)-(5'-ethylaminomethyl-[2,3']bipyridinyl-4-yl)-methanone (e.g. hydrochloride salt);
(5,7-Difluoro-1H-benzoimidazol-2-yl)-(5'-ethylaminomethyl-4'-methyl-[2,3']bipyridinyl-4-yl)-methanone (e.g. hydrochloride salt);
[6-(4-Dimethylamino-piperidin-1-yl)-1H-benzoimidazol-2-yl]-(5'-ethylaminomethyl-[2,3']bipyridinyl-4-yl)-methanone (e.g. formate salt);
(2-Isoquinolin-4-yl-pyridin-4-yl)-[6-(4-methyl-piperazine-1-carbonyl)-1H-benzoimidazol-2-yl]methanone;

[5-(2,3-Dihydroxy-propoxy)-1H-benzoimidazol-2-yl]-(2-isoquinolin-4-yl-pyridin-4-yl)-methanone;

2-(2-Isoquinolin-4-yl-pyridine-4-carbonyl)-3H-benzoimidazole-5-carboxylic acid methyl-piperidin-4-yl amide;

2-(2-Isoquinolin-4-yl-pyridine-4-carbonyl)-3H-benzoimidazole-5-carboxylic acid (1-methyl-piperidin-4-yl)-amide;

4-(5,6-Dimethoxy-1H-benzoimidazole-2-carbonyl)-2-(5-ethylaminomethyl-pyridin-3-yl)-benzonitrile;

[2-(2,3-Difluoro-6-methoxy-phenyl)-pyridin-4-yl]-[5-(4-dimethylamino-piperidin-1-yl)-1H-benzoimidazol-2-yl]-methanone;

[5-(4-Isopropyl-piperazin-1-yl)-1H-benzoimidazol-2-yl]-(2-isoquinolin-4-yl-pyridin-4-yl)-methanone;

4-{4-[6-(4-dimethylamino-piperidin-1-yl)-1H-benzoimidazole-2-carbonyl]-4'-methyl[2,3']bipyridinyl-6'-yl}piperazine-1-carboxylic acid tert-butyl ester;

[6-(4-Dimethylamino-piperidin-1-yl)-1H-benzoimidazol-2-yl]-(4'-methyl-6'-piperazin-1-yl-[2,3']bipyridinyl-4-yl)-methanone;

[6-(4-Dimethylamino-piperidin-1-yl)-1H-benzoimidazol-2-yl]-[2-(7-methyl-1H-indol-3-yl)-pyridin-4-yl]-methanone;

[6-(4-Dimethylamino-piperidin-1-yl)-1H-benzoimidazol-2-yl]-[2-(5-methyl-1H-pyrazol-4-yl)-pyridin-4-yl]-methanone;

[6-(4-Dimethylamino-piperidin-1-yl)-1H-benzoimidazol-2-yl]-(4'-methyl-[2,3']bipyridinyl-4-yl)-methanone;

[6-(4-Dimethylamino-piperidin-1-yl)-1H-benzoimidazol-2-yl]-[2-(1H-indol-3-yl)-pyridin-4-yl]-methanone;

[6-(4-Dimethylamino-piperidin-1-yl)-1H-benzoimidazol-2-yl]-[2-(1H-indol-4-yl)-pyridin-4-yl]-methanone;

[6-(4-Dimethylamino-piperidin-1-yl)-1H-benzoimidazol-2-yl]-(2-pyrazolo[1,5-a]pyridin-3-yl-pyridin-4-yl)-methanone (e.g. methanesulfonate salt);

[6-(4-Dimethylamino-piperidin-1-yl)-1H-benzoimidazol-2-yl]-[2-(1H-pyrrolo[2,3-b]pyridin-5-yl)-pyridin-4-yl]-methanone;

[6-(4-Dimethylamino-piperidin-1-yl)-1H-benzoimidazol-2-yl]-[2-(1H-pyrrolo[3,2-b]pyridin-6-yl)-pyridin-4-yl]-methanone;

[6-(4-Dimethylamino-piperidin-1-yl)-1H-benzoimidazol-2-yl]-(2-quinolin-3-yl-pyridin-4-yl)-methanone;

[6-(4-Dimethylamino-piperidin-1-yl)-1H-benzoimidazol-2-yl]-(2-naphthalen-1-yl-pyridin-4-yl)-methanone;

[2,4']Bipyridinyl-4-yl-[6-(4-dimethylamino-piperidin-1-yl)-1H-benzoimidazol-2-yl]-methanone;

[2,3']Bipyridinyl-4-yl-[6-(4-dimethylamino-piperidin-1-yl)-1H-benzoimidazol-2-yl]-methanone;

[6-(4-Dimethylamino-piperidin-1-yl)-1H-benzoimidazol-2-yl]-(4'-methoxy-[2,3']bipyridinyl-4-yl)-methanone;

[6-(4-Dimethylamino-piperidin-1-yl)-1H-benzoimidazol-2-yl]-(6'-fluoro-4'-methyl-[2,3']bipyridinyl-4-yl)-methanone;

2-{4-[6-(4-Dimethylamino-piperidin-1-yl)-1H-benzoimidazole-2-carbonyl]-pyridin-2-yl}-N-methyl-benzenesulfonamide;

[6-(4-Dimethylamino-piperidin-1-yl)-1H-benzoimidazol-2-yl]-[2-(1,5-dimethyl-1H-pyrazol-4-yl)-pyridin-4-yl]-methanone;

[6-(4-Dimethylamino-piperidin-1-yl)-1H-benzoimidazol-2-yl]-[2-(4-isopropyl-pyrimidin-5-yl)-pyridin-4-yl]-methanone;

[6-(4-Dimethylamino-piperidin-1-yl)-1H-benzoimidazol-2-yl]-[2-(2,4-dimethyl-thiazol-5-yl)-pyridin-4-yl]-methanone;

[6-(4-Dimethylamino-piperidin-1-yl)-1H-benzoimidazol-2-yl]-[2-(2-methyl-2H-pyrazol-3-yl)-pyridin-4-yl]-methanone;

[6-(4-Dimethylamino-piperidin-1-yl)-1H-benzoimidazol-2-yl]-[2-(5-fluoro-2-methoxy-phenyl)-pyridin-4-yl]-methanone;

[6-(4-Dimethylamino-piperidin-1-yl)-1H-benzoimidazol-2-yl]-[2-(1,3,5-trimethyl-1H-pyrazol-4-yl)-pyridin-4-yl]-methanone;

[6-(4-Dimethylamino-piperidin-1-yl)-1H-benzoimidazol-2-yl]-[2-(4-piperidin-1-yl-phenyl)-pyridin-4-yl]-methanone (trifluoroacetate salt);

[2-(2,3-Dihydro-benzofuran-7-yl)-pyridin-4-yl]-[6-(4-dimethylamino-piperidin-1-yl)-1H-benzoimidazol-2-yl]-methanone (hydrochloride salt);

[6-(4-Dimethylamino-piperidin-1-yl)-1H-benzoimidazol-2-yl]-[2-(3,5-dimethyl-1H-pyrazol-4-yl)-pyridin-4-yl] methanone (formate salt);

(5'-Amino-[2,3']bipyridinyl-4-yl)-[6-(4-dimethylamino-piperidin-1-yl)-1H-benzoimidazol-2-yl]-methanone (formate salt);

[2-(2,3-Dihydro-benzo[1,4]dioxin-6-yl)-pyridin-4-yl]-[6-(4-dimethylamino-piperidin-1-yl)-1H-benzoimidazol-2-yl]-methanone;

[6-(4-Dimethylamino-piperidin-1-yl)-7-fluoro-1H-benzoimidazol-2-yl]-(2-isoquinolin-4-yl-pyridin-4-yl)-methanone (e.g. trifluoroacetate salt);

[2-(4-Dimethylamino-piperidin-1-yl)-9H-purin-8-yl]-(2-isoquinolin-4-yl-pyridin-4-yl)-methanone;

(2-[1,4]Diazepan-1-yl-9H-purin-8-yl)-(2-isoquinolin-4-yl-pyridin-4-yl)-methanone;

[5-(4-Dimethylamino-piperidin-1-yl)-3H-imidazo[4,5-b]pyridin-2-yl]-(2-isoquinolin-4-yl-pyridin-4-yl)-methanone;

[5-(4-Dimethylamino-piperidin-1-yl)-3H-imidazo[4,5-b]pyridin-2-yl]-[2-(1,3,5-trimethyl-1H-pyrazol-4-yl)-pyridin-4-yl]methanone;

4-[6-(4-Dimethylamino-piperidin-1-yl)-1H-benzoimidazole-2-carbonyl]-2-isoquinolin-4-yl-benzonitrile;

4-[5-(4-Dimethylamino-piperidin-1-yl)-1H-benzoimidazole-2-carbonyl]-2-(3,5-dimethyl-1H-pyrazol-4-yl)-benzonitrile;

4-[5-(4-Dimethylamino-piperidin-1-yl)-1H-benzoimidazole-2-carbonyl]-2-pyridin-3-yl-benzonitrile;

4-[5-(4-Dimethylamino-piperidin-1-yl)-3H-imidazo[4,5-b]pyridine-2-carbonyl]-2-(1H-pyrrolo[2,3-c]pyridin-4-yl)-benzonitrile;

4-[6-(4-Dimethylamino-piperidin-1-yl)-1H-benzoimidazole-2-carbonyl]-2-(1H-pyrrolo[2,3-c]pyridin-4-yl)-benzonitrile;

4-[6-(4-Dimethylamino-piperidin-1-yl)-1H-benzoimidazole-2-carbonyl]-2-[1,6]naphthyridin-8-yl-benzonitrile;

4-[5-(4-Dimethylamino-piperidin-1-yl)-3H-imidazo[4,5-b]pyridine-2-carbonyl]-2-[1,6]naphthyridin-8-yl-benzonitrile;

4-[5-(4-Dimethylamino-piperidin-1-yl)-3H-imidazo[4,5-b]pyridine-2-carbonyl]-2-(3,5-dimethyl-1H-pyrazol-4-yl)-benzonitrile;

[5-(4-dimethylamino-piperidin-1-yl)-3H-imidazo[4,5-b]pyridin-2-yl]-[2-(2,3-difloro-6-methoxy-phenyl)-pyridin-4-yl]-methanone;

[6-(4-dimethylamino-piperidin-1-yl)-1H-benzoimidazol-2-yl]-[2-(5-methyl-imidazol-1-yl)-pyridin-4-yl]-methanone (e.g. hydrochloride salt);

[6-(4-Dimethylamino-piperidin-1-yl)-1H-benzoimidazol-2-yl]-[2-(4-methyl-imidazol-1-yl)-pyridin-4-yl]-methanone (e.g. hydrochloride salt);

[6-(4-Dimethylamino-piperidin-1-yl)-1H-benzoimidazol-2-yl]-[2-(2-methyl-benzoimidazol-1-yl)-pyridin-4-yl]-methanone;
[6-(4-Dimethylamino-piperidin-1-yl)-1H-benzoimidazol-2-yl]-[2-(2,5-dimethyl-imidazol-1-yl)-pyridin-4-yl]-methanone;
[6-(4-Dimethylamino-piperidin-1-yl)-1H-benzoimidazol-2-yl]-[2-(2,4-dimethyl-imidazol-1-yl)-pyridin-4-yl]-methanone;
[6-(4-Dimethylamino-piperidin-1-yl)-1H-benzoimidazol-2-yl]-(2-imidazo[4,5-c]pyridin-3-yl-pyridin-4-yl)-methanone;
[6-(4-Dimethylamino-piperidin-1-yl)-1H-benzoimidazol-2-yl]-(2-imidazo[4,5-c]pyridin-1-yl-pyridin-4-yl)-methanone;
[6-(4-Dimethylamino-piperidin-1-yl)-1H-benzoimidazol-2-yl]-(2-imidazo[4,5-b]pyridin-3-yl-pyridin-4-yl)-methanone;
[6-(4-Dimethylamino-piperidin-1-yl)-1H-benzoimidazol-2-yl]-(2-imidazo[4,5-b]pyridin-1-yl-pyridin-4-yl)-methanone;
(2-Benzoimidazol-1-yl-pyridin-4-yl)-[6-(4-dimethylamino-piperidin-1-yl)-1H-benzoimidazol-2-yl]-methanone;
[5-(2,3-Difluoro-6-methoxy-phenyl)-pyridin-3-yl]-(5-dimethylaminomethyl-1H-benzoimidazol-2-yl)-methanone;
[5-(4-Dimethylamino-piperidin-1-yl)-3H-imidazo[4,5-b]pyridin-2-yl]-(2-isoquinolin-4-yl-pyridin-4-yl)-methanone;
[5-(4-Dimethylamino-piperidin-1-yl)-3H-imidazo[4,5-b]pyridin-2-yl]-[2-(1,3,5-trimethyl-1H-pyrazol-4-yl)-pyridin-4-yl]-methanone;
[5-(4-dimethylamino-piperidin-1-yl)-3H-imidazo[4,5-b]pyridin-2-yl]-2-(2,3-difloro-6-methoxy-phenyl)-pyridin-4-yl]-methanone;
(5-[1,4]Diazepan-1-yl-3H-imidazo[4,5-b]pyridin-2-yl)-(2-isoquinolin-4-yl-pyridin-4-yl)-methanone;
(2-Isoquinolin-4-yl-pyridin-4-yl)-5-piperazin-1-yl-3H-imidazo[4,5-b]pyridin-2-yl)-methanone;
4-[5-(4-Dimethylamino-piperidin-1-yl)-3H-imidazo[4,5-b]pyridine-2-carbonyl]-2-isoquinolin-4-yl-benzonitrile;
2-Isoquinolin-4-yl-4-(5-piperazin-1-yl-3H-imidazo[4,5-b]pyridine-2-carbonyl)-benzonitrile;
[5-(4-Dimethylamino-piperidin-1-yl)-3H-imidazo[4,5-b]pyridine-2-yl]-[2-(3,5-dimethyl-1H-pyrazol-4-yl)-pyridin-4-yl]-methanone;
4-[5-(4-Dimethylamino-piperidin-1-yl)-3H-imidazo[4,5-b]pyridine-2-carbonyl]-2-(3,5-dimethyl-1H-pyrazol-4-yl)-benzonitrile;
[2-(3,5-Dimethyl-1H-pyrazol-4-yl)-pyridin-4-yl]-(5-piperazin-1-yl-3H-imidazo[4,5-b]pyridin-2-yl)-methanone;
(5-[1,4]Diazepan-1-yl-3H-imidazo[4,5-b]-pyridin-2-yl)-[2-(3,5-dimethyl-1H-pyrazol-4-yl)-pyridin-4-yl]-methanone;
(5-[1,4]Diazepan-1-yl-3H-imidazo[4,5-b]-pyridin-2-yl)-[2-(1,3,5-trimethyl-1H-pyrazol-4-yl)-pyridin-4-yl]-methanone;
[5-(3-Amino-pyrrolidin-1-yl)-3H-imidazole[4,5-b]pyridine-2-yl]-2-(isoquinolin-4-yl-pyridin-4-yl)-methanone;
4-[5-(4-Dimethylamino-piperidin-1-yl)-3H-imidazo[4,5-b]pyridine-2-carbonyl]-2-(1,3,5-trimethyl-1H-pyrazol-4-yl)-benzonitrile;
2-(3-Methyl-isoquinolin-4-yl)-4-[5-(piperazine-1-carbonyl)-1H-benzoimidazole-2-carbonyl]-benzonitrile;
5-[5-(4-Dimethylamino-piperidin-1-yl)-1H-benzoimidazole-2-carbonyl]-2-methoxy-biphenyl-2-carboxylic acid amide;

4-[5-(4-Dimethylamino-piperidin-1-yl)-3H-imidazo[4,5-b]pyridine-2-carbonyl]-2-(2-methyl-imidazo[1,2-a]pyridin-3-yl)-benzonitrile;
2-(3,5-Dimethyl-1H-pyrazol-4-yl)-4-[6-(piperazine-1-carbonyl)-1H-benzoimidazole-2-carbonyl]-benzonitrile;
(2-Isoquinolin-4-yl-pyridin-4-yl)-[5-(piperazine-1-carbonyl)-3H-imidazo[4,5-b]pyridin-2-yl]-methanone;
4-(5-[1,4']Bipiperidinyl-1'-yl-3H-imidazo[4,5-b]pyridine-2-carbonyl)-2-(3,5-dimethyl-1H-pyrazol-4-yl)-benzonitrile;
2-Isoquinolin-4-yl-4-[6-(piperazine-1-carbonyl)-1H-benzoimidazole-2-carbonyl]-benzonitrile;
4-(6-Chloro-1H-benzoimidazole-2-carbonyl)-2-[1,6]naphthyridin-8-yl-benzonitrile;
(2-Isoquinolin-4-yl-pyridin-4-yl)-[6-(piperazine-1-sulfonyl)-1H-benzoimidazol-2-yl]-methanone;
[6-(piperazine-1-carbonyl)-1H-benzoimidazol-2-yl]-[2-(1,3,5-trimethyl-1H-pyrazol-4-yl)-pyridin-4-yl]-methanone;
4-[6-(piperazine-1-carbonyl)-1H-benzoimidazole-2-carbonyl]-2-(1,3,5-trimethyl-1H-pyrazol-4-yl)-benzonitrile;
2-(3,5-Dimethyl-1-phenyl-1H-pyrazol-4-yl)-4-[6-(piperazine-1-carbonyl)-1H-benzoimidazole-2-carbonyl]-benzonitrile;
2-(4-Cyano-3-isoquinolin-4-yl-benzoyl)-3H-benzoimidazole-5-sulfonic acid (2-amino-ethyl)-methyl-amide;
2-(3,5-Dimethyl-isoxazol-4-yl)-4-[6-(piperazine-1-carbonyl)-1H-benzoimidazole-2-carbonyl]-benzonitrile;
[6-(4-Dimethylamino-piperidin-1-yl)-1H-benzoimidazol-2-yl]-[3-(3,5-dimethyl-1H-pyrazol-4-yl)-4-fluoro-phenyl]-methanone;
4-(5-piperazin-1-yl-3H-imidazo[4,5-b]pyridine-2-carbonyl)-2-(1,3,5-trimethyl-1H-pyrazol-4-yl)-benzonitrile;
(5-[1,4']Bipiperidinyl-1'-yl-3H-imidazo[4,5-b]pyridin-2-yl)-(2-isoquinolin-4-yl-pyridin-4-yl)-methanone;
4-[2-(2-Isoquinolin-4-yl-pyridine-4-carbonyl)-3H-imidazo[4,5-b]pyridin-6-yl]-[1,4]diazepane-1-carboxylic acid tert-butyl ester;
(2-Isoquinolin-4-yl-pyridin-4-yl)-[6-(piperazine-1-carbonyl)-1H-benzoimidazol-2-yl]-methanone;
4-[2-(2-Isoquinolin-4-yl-pyridine-4-carbonyl)-3H-imidazo[4,5-b]pyridin-5-yl]-piperazine-1-carboxylic acid tert-butyl ester; and
4-[2-(4-Cyano-3-isoquinolin-4-yl-benzoyl)-3H-imidazo[4,5-b]pyridin-5-yl]-piperazine-1-carboxylic acid tert-butyl ester;
and salts, solvates, tautomers and N-oxides thereof.

A further group of specific compounds of the invention consists of the compounds:
4-[5-(pyrrolidin-3-yloxy)-3H-imidazo[4,5-b]pyridine-2-carbonyl]-2-(1,3,5-trimethyl-1H-pyrazol-4-yl)-benzonitrile;
4-[5-(4-dimethylamino-piperidin-1-yl)-3H-imidazo[4,5-b]pyridine-2-carbonyl]-2-(1,3,5-trimethyl-1H-pyrazol-4-yl)-benzamide;
4-[5-(4-dimethylamino-piperidin-1-yl)-3H-imidazo[4,5-b]pyridine-2-carbonyl]-N,N-dimethyl-2-(1,3,5-trimethyl-1H-pyrazol-4-yl)-benzamide;
[6-(4-dimethylamino-piperidin-1-yl)-1H-benzoimidazol-2-yl]-(3-isoquinolin-4-yl-4-methoxy-phenyl)-methanone;
[6-(4-dimethylamino-piperidin-1-yl)-1H-benzoimidazol-2-yl]-(4-hydroxy-3-isoquinolin-4-yl-phenyl)-methanone;
4-[5-(4-dimethylamino-piperidin-1-yl)-3H-imidazo[4,5-b]pyridine-2-carbonyl]-2-(2-methyl-5,6-dihydro-4H-pyrrolo[1,2-b]pyrazol-3-yl)-benzonitrile;
4-[5-(4-hydroxy-piperidin-1-yl)-3H-imidazo[4,5-b]pyridine-2-carbonyl]-2-(1H-pyrrolo[2,3-c]pyridin-4-yl)-benzonitrile;

(S)-2-amino-3-methyl-butyric-acid-1-{2-[4-cyano-3-(1H-pyrrolo[2,3-c]pyridin-4-yl)-benzoyl]-3H-imidazo[4,5-b]pyridin-5-yl}-piperidin-4-yl ester;
phosphoric-acid-mono-(1-{2-[4-cyano-3-(1H-pyrrolo[2,3-c]pyridin-4-yl)-benzoyl]-3H-imidazo[4,5-b]pyridin-5-yl}-piperidin-4-yl)ester;
4-[5-(4-dimethylamino-piperidin-1-yl)-3H-imidazo[4,5-b]pyridine-2-carbonyl]-2-(5-methoxy-1H-pyrrolo[2,3-c]pyridin-4-yl)-benzonitrile;
4-[5-(pyrrolidin-3-yloxy)-3H-imidazo[4,5-b]pyridine-2-carbonyl]-2-(1H-pyrrolo[2,3-c]pyridin-4-yl)-benzonitrile;
4-{5-[2-(4-methyl-piperazin-1-yl)-ethoxy]-3H-imidazo[4,5-b]pyridine-2-carbonyl}-2-(1,3,5-trimethyl-1H-pyrazol-4-yl)-benzonitrile;
4-[5-(5,6-dihydro-8H-imidazo[1,2-a]pyrazin-7-yl)-3H-imidazo[4,5-b]pyridine-2-carbonyl]-2-(1,3,5-trimethyl-1H-pyrazol-4-yl)-benzonitrile;
4-[5-(5,6-dihydro-8H-imidazo[1,2-a]pyrazin-7-yl)-3H-imidazo[4,5-b]pyridine-2-carbonyl]-2-(1,3,5-trimethyl-1H-pyrazol-4-yl)-benzonitrile;
4-[5-(3,6-diaza-bicyclo[3.2.0]hept-3-yl)-3H-imidazo[4,5-b]pyridine-2-carbonyl]-2-(1,3,5-trimethyl-1H-pyrazol-4-yl)-benzonitrile;
4-[5-(2,6-diaza-spiro[3.3]hept-2-yl)-3H-imidazo[4,5-b]pyridine-2-carbonyl]-2-(1,3,5-trimethyl-1H-pyrazol-4-yl)-benzonitrile;
4-[5-(2,6-diaza-spiro[3.3]hept-2-yl)-3H-imidazo[4,5-b]pyridine-2-carbonyl]-2-(1H-pyrrolo[2,3-c]pyridin-4-yl)-benzonitrile;
4-[5-(3,3-dimethyl-2-oxo-piperazin-1-yl)-3H-imidazo[4,5-b]pyridine-2-carbonyl]-2-(1,3,5-trimethyl-1H-pyrazol-4-yl)-benzonitrile;
4-[5-(pyrrolidin-3-ylamino)-3H-imidazo[4,5-b]pyridine-2-carbonyl]-2-(1,3,5-trimethyl-1H-pyrazol-4-yl)-benzonitrile;
4-[5-(3-amino-pyrrolidin-1-yl)-3H-imidazo[4,5-b]pyridine-2-carbonyl]-2-(1,3,5-trimethyl-1H-pyrazol-4-yl)-benzonitrile; and
4-[5-(6-amino-3-aza-bicyclo[3.1.0]hex-3-yl)-3H-imidazo[4,5-b]pyridine-2-carbonyl]-2-(1,3,5-trimethyl-1H-pyrazol-4-yl)-benzonitrile;
and salts, solvates, tautomers and N-oxides thereof.

Advantages of the Compounds of the Invention

The compounds of the formula (I) have a number of advantages. For example, the compounds of formula (I) have advantageous ADMET and physiochemical properties.

Salts, Solvates, Tautomers, Isomers, N-Oxides, Esters, Prodrugs and Isotopes

A reference to a compound of the formulae (I) and sub-groups thereof also includes ionic forms, salts, solvates, isomers, tautomers, N-oxides, esters, prodrugs, isotopes and protected forms thereof, for example, as discussed below; preferably, the salts or tautomers or isomers or N-oxides or solvates thereof; and more preferably, the salts or tautomers or N-oxides or solvates thereof.

Salts

Many compounds of the formula (I) can exist in the form of salts, for example acid addition salts or, in certain cases salts of organic and inorganic bases such as carboxylate, sulphonate and phosphate salts. All such salts are within the scope of this invention, and references to compounds of the formula (I) include the salt forms of the compounds.

The salts of the present invention can be synthesized from the parent compound that contains a basic or acidic moiety by conventional chemical methods such as methods described in *Pharmaceutical Salts: Properties, Selection, and Use*, P. Heinrich Stahl (Editor), Camille G. Wermuth (Editor), ISBN: 3-90639-026-8, Hardcover, 388 pages, August 2002. Generally, such salts can be prepared by reacting the free acid or base forms of these compounds with the appropriate base or acid in water or in an organic solvent, or in a mixture of the two; generally, nonaqueous media such as ether, ethyl acetate, ethanol, isopropanol, or acetonitrile are used.

Acid addition salts may be formed with a wide variety of acids, both inorganic and organic. Examples of acid addition salts include salts formed with an acid selected from the group consisting of acetic, 2,2-dichloroacetic, adipic, alginic, ascorbic (e.g. L-ascorbic), L-aspartic, benzenesulphonic, benzoic, 4-acetamidobenzoic, butanoic, (+) camphoric, camphor-sulphonic, (+)-(1S)-camphor-10-sulphonic, capric, caproic, caprylic, cinnamic, citric, cyclamic, dodecylsulphuric, ethane-1,2-disulphonic, ethanesulphonic, 2-hydroxyethanesulphonic, formic, fumaric, galactaric, gentisic, glucoheptonic, D-gluconic, glucuronic (e.g. D-glucuronic), glutamic (e.g. L-glutamic), α-oxoglutaric, glycolic, hippuric, hydrobromic, hydrochloric, hydriodic, isethionic, (+)-L-lactic, (±)-DL-lactic, lactobionic, maleic, malic, (−)-L-malic, malonic, (±)-DL-mandelic, methanesulphonic, naphthalene-2-sulphonic, naphthalene-1,5-disulphonic, 1-hydroxy-2-naphthoic, nicotinic, nitric, oleic, orotic, oxalic, palmitic, pamoic, phosphoric, propionic, L-pyroglutamic, salicylic, 4-aminosalicylic, sebacic, stearic, succinic, sulphuric, tannic, (+)-L-tartaric, thiocyanic, p-toluenesulphonic, undecylenic and valeric acids, as well as acylated amino acids and cation exchange resins.

One particular group of salts consists of salts formed from acetic, hydrochloric, hydriodic, phosphoric, nitric, sulphuric, citric, lactic, succinic, maleic, malic, isethionic, fumaric, benzenesulphonic, toluenesulphonic, methanesulphonic (mesylate), ethanesulphonic, naphthalenesulphonic, valeric, acetic, propanoic, butanoic, malonic, glucuronic and lactobionic acids.

One sub-group of salts consists of salts formed from hydrochloric, acetic, methanesulphonic, adipic, L-aspartic and DL-lactic acids.

Another sub-group of salts consists of the acetate, mesylate, ethanesulphonate, DL-lactate, adipate, D-glucuronate, D-gluconate and hydrochloride salts.

If the compound is anionic, or has a functional group which may be anionic (e.g., —COOH may be –COO−), then a salt may be formed with a suitable cation.

Examples of suitable inorganic cations include, but are not limited to, alkali metal ions such as Na+ and K+, alkaline earth metal cations such as $Ca^{2+}$ and $Mg^{2+}$, and other cations such as $Al^{3+}$. Examples of suitable organic cations include, but are not limited to, ammonium ion (i.e., $NH_4^+$) and substituted ammonium ions (e.g., $NH_3R^+$, $NH_2R_2^+$, $NHR_3^+$, $NR_4^+$). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is $N(CH_3)_4^+$.

Where the compounds of the formula (I) contain an amine function, these may form quaternary ammonium salts, for example by reaction with an alkylating agent according to methods well known to the skilled person. Such quaternary ammonium compounds are within the scope of formula (I).

The compounds of the invention may exist as mono- or di-salts depending upon the pKa of the acid from which the salt is formed.

The salt forms of the compounds of the invention are typically pharmaceutically acceptable salts, and examples of pharmaceutically acceptable salts are discussed in Berge et al., 1977, "Pharmaceutically Acceptable Salts," *J. Pharm. Sci.*, Vol. 66, pp. 1-19. However, salts that are not pharmaceutically acceptable may also be prepared as intermediate forms which may then be converted into pharmaceutically acceptable salts. Such non-pharmaceutically acceptable salts forms, which may be useful, for example, in the purification or separation of the compounds of the invention, also form part of the invention.

Preferred salts for use in the preparation of liquid (e.g. aqueous) compositions of the compounds of formulae (I) and sub-groups and examples thereof as described herein are salts having a solubility in a given liquid carrier (e.g. water) of greater than 10 mg/ml of the liquid carrier (e.g. water), more typically greater than 15 mg/ml and preferably greater than 20 mg/ml.

In one embodiment of the invention, there is provided a pharmaceutical composition comprising an aqueous solution containing a compound of the formula (I) and sub-groups and examples thereof as described herein in the form of a salt in a concentration of greater than 10 mg/ml, typically greater than 15 mg/ml and preferably greater than 20 mg/ml.

N-Oxides

Compounds of the formula (I) containing an amine function may also form N-oxides. A reference herein to a compound of the formula (I) that contains an amine function also includes the N-oxide.

Where a compound contains several amine functions, one or more than one nitrogen atom may be oxidised to form an N-oxide. Particular examples of N-oxides are the N-oxides of a tertiary amine or a nitrogen atom of a nitrogen-containing heterocycle.

N-Oxides can be formed by treatment of the corresponding amine with an oxidizing agent such as hydrogen peroxide or a per-acid (e.g. a peroxycarboxylic acid), see for example *Advanced Organic Chemistry*, by Jerry March, 4$^{th}$ Edition, Wiley Interscience, pages. More particularly, N-oxides can be made by the procedure of L. W. Deady (*Syn. Comm.* 1977, 7, 509-514) in which the amine compound is reacted with m-chloroperoxybenzoic acid (MCPBA), for example, in an inert solvent such as dichloromethane.

Geometric Isomers and Tautomers

Compounds of the formula (I) may exist in a number of different geometric isomeric, and tautomeric forms and references to compounds of the formula (I) include all such forms. For the avoidance of doubt, where a compound can exist in one of several geometric isomeric or tautomeric forms and only one is specifically described or shown, all others are nevertheless embraced by formula (I).

For example, in compounds of the formula (I), the imidazole ring can exist in the two tautomeric forms A and B below. For simplicity, the general formula (I) illustrates form A but the formula is to be taken as embracing both tautomeric forms.

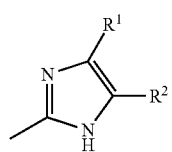

A

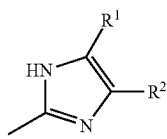

B

Other examples of tautomeric forms include, for example, keto-, enol-, and enolate-forms, as in, for example, the following tautomeric pairs: keto/enol (illustrated below), imine/enamine, amide/imino alcohol, amidine/amidine, nitroso/oxime, thioketone/enethiol, and nitro/aci-nitro.

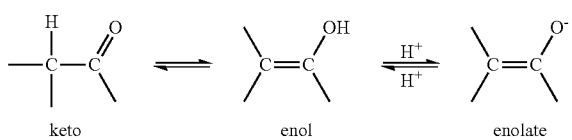

Optical Isomers

Where compounds of the formula (I) contain one or more chiral centres, and can exist in the form of two or more optical isomers, references to compounds of the formula (I) include all optical isomeric forms thereof (e.g. enantiomers, epimers and diastereoisomers), either as individual optical isomers, or mixtures (e.g. racemic mixtures) or two or more optical isomers, unless the context requires otherwise.

The optical isomers may be characterised and identified by their optical activity (i.e. as + and − isomers, or d and l isomers) or they may be characterised in terms of their absolute stereochemistry using the "R and S" nomenclature developed by Cahn, Ingold and Prelog, see *Advanced Organic Chemistry* by Jerry March, 4$^{th}$ Edition, John Wiley & Sons, New York, 1992, pages 109-114, and see also Cahn, Ingold & Prelog, *Angew. Chem. Int. Ed. Engl.*, 1966, 5, 385-415.

Optical isomers can be separated by a number of techniques including chiral chromatography (chromatography on a chiral support) and such techniques are well known to the person skilled in the art.

As an alternative to chiral chromatography, optical isomers can be separated by forming diastereoisomeric salts with chiral acids such as (+)-tartaric acid, (−)-pyroglutamic acid, (−)-di-toluoyl-L-tartaric acid, (+)-mandelic acid, (−)-malic acid, and (−)-camphorsulphonic, separating the diastereoisomers by preferential crystallisation, and then dissociating the salts to give the individual enantiomer of the free base.

Where compounds of the formula (I) exist as two or more optical isomeric forms, one enantiomer in a pair of enantiomers may exhibit advantages over the other enantiomer, for example, in terms of biological activity. Thus, in certain circumstances, it may be desirable to use as a therapeutic agent only one of a pair of enantiomers, or only one of a plurality of diastereoisomers. Accordingly, the invention provides compositions containing a compound of the formula (I) having one or more chiral centres, wherein at least 55% (e.g. at least 60%, 65%, 70%, 75%, 80%, 85%, 90% or 95%) of the compound of the formula (I) is present as a single optical isomer (e.g. enantiomer or diastereoisomer). In one general embodiment, 99% or more (e.g. substantially all) of the total amount of the compound of the formula (I) may be present as a single optical isomer (e.g. enantiomer or diastereoisomer).

Isotopic Variations

The present invention includes all pharmaceutically acceptable isotopically-labeled compounds of the invention, i.e. compounds of formula (I), wherein one or more atoms are replaced by atoms having the same atomic number, but an atomic mass or mass number different from the atomic mass or mass number usually found in nature.

Examples of isotopes suitable for inclusion in the compounds of the invention comprise isotopes of hydrogen, such as $^2$H and $^3$H, carbon, such as $^{11}$C, $^{13}$C and $^{14}$C, chlorine, such as $^{36}$Cl, fluorine, such as $^{18}$F, iodine, such as $^{123}$I and $^{125}$I, nitrogen, such as $^{13}$N and $^{15}$N, oxygen, such as $^{15}$O, $^{17}$O and $^{18}$O, phosphorus, such as $^{32}$P, and sulphur, such as $^{35}$S.

Certain isotopically-labelled compounds of formula (I), for example, those incorporating a radioactive isotope, are useful in drug and/or substrate tissue distribution studies. The radioactive isotopes tritium, i.e. $^3$H, and carbon-14, i.e. $^{14}$C, are particularly useful for this purpose in view of their ease of incorporation and ready means of detection.

Substitution with heavier isotopes such as deuterium, i.e. $^2$H, may afford certain therapeutic advantages resulting from greater metabolic stability, for example, increased in vivo half-life or reduced dosage requirements, and hence may be preferred in some circumstances.

Substitution with positron emitting isotopes, such as $^{11}$C, $^{18}$F, $^{15}$O and $^{13}$N, can be useful in Positron Emission Topography (PET) studies for examining substrate receptor occupancy.

Isotopically-labeled compounds of formula (I) can generally be prepared by conventional techniques known to those skilled in the art or by processes analogous to those described in the accompanying Examples and Preparations using an appropriate isotopically-labeled reagents in place of the non-labeled reagent previously employed.

Esters

Esters such as carboxylic acid esters and acyloxy esters of the compounds of formula (I) bearing a carboxylic acid group or a hydroxyl group are also embraced by Formula (I). Examples of esters are compounds containing the group —C(=O)OR, wherein R is an ester substituent, for example, a $C_{1-7}$ alkyl group, a $C_{3-20}$ heterocyclyl group, or a $C_{5-20}$ aryl group, preferably a $C_{1-7}$ alkyl group. Particular examples of ester groups include, but are not limited to, —C(=O)OCH$_3$, —C(=O)OCH$_2$CH$_3$, —C(=O)OC(CH$_3$)$_3$, and —C(=O)OPh. Examples of acyloxy (reverse ester) groups are represented by —OC(=O)R, wherein R is an acyloxy substituent, for example, a $C_{1-7}$ alkyl group, a $C_{3-20}$ heterocyclyl group, or a $C_{5-20}$ aryl group, preferably a $C_{1-7}$ alkyl group. Particular examples of acyloxy groups include, but are not limited to, —OC(=O)CH$_3$ (acetoxy), —OC(=O)CH$_2$CH$_3$, —OC(=O)C(CH$_3$)$_3$, —OC(=O)Ph, and —OC(=O)CH$_2$Ph.

In one embodiment of the invention, formula (I) includes within its scope esters of compounds of the formula (I) bearing a carboxylic acid group or a hydroxyl group. In another embodiment of the invention, formula (I) does not include within its scope esters of compounds of the formula (I) bearing a carboxylic acid group or a hydroxyl group Solvates Also encompassed by formula (I) are any polymorphic forms of the compounds, and solvates such as hydrates.

The compounds of the invention may form solvates, for example with water (i.e., hydrates) or common organic solvents. As used herein, the term "solvate" means a physical association of the compounds of the present invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. The term "solvate" is intended to encompass both solution-phase and isolatable solvates. Non-limiting examples of suitable solvates include compounds on the invention in combination with water, isopropanol, ethanol, methanol, DMSO, ethyl acetate, acetic acid or ethanolamine and the like. The compounds of the invention may exert their biological effects whilst they are in solution.

Solvates are well known in pharmaceutical chemistry. They can be important to the processes for the preparation of a substance (e.g. in relation to their purification, the storage of the substance (e.g. its stability) and the ease of handling of the substance and are often formed as part of the isolation or purification stages of a chemical synthesis. A person skilled in the art can determine by means of standard and long used techniques whether a hydrate or other solvate has formed by the isolation conditions or purification conditions used to prepare a given compound. Examples of such techniques include thermogravimetric analysis (TGA), differential scanning calorimetry (DSC), X-ray crystallography (e.g. single crystal X-ray crystallography or X-ray powder diffraction) and Solid State NMR (SS-NMR, also known as Magic Angle Spinning NMR or MAS-NMR). Such techniques are as much a part of the standard analytical toolkit of the skilled chemist as NMR, IR, HPLC and MS.

Alternatively the skilled person can deliberately form a solvate using crystallisation conditions that include an amount of the solvent required for the particular solvate. Thereafter the standard methods described above, can be used to establish whether solvates had formed.

Furthermore, the compounds of the present invention may have one or more polymorph or amorphous crystalline forms and as such are intended to be included in the scope of the invention.

Complexes

Formula (I) also includes within its scope complexes (e.g. inclusion complexes or clathrates with compounds such as cyclodextrins, or complexes with metals) of the compounds. Inclusion complexes, clathrates and metal complexes can be formed by means of methods well known the skilled person.

Prodrugs

Also encompassed by formula (I) are any pro-drugs of the compounds of the formula (I). By "prodrugs" is meant for example any compound that is converted in vivo into a biologically active compound of the formula (I).

For example, some prodrugs are esters of the active compound (e.g., a physiologically acceptable metabolically labile ester). During metabolism, the ester group (—C(=O)OR) is cleaved to yield the active drug. Such esters may be formed by esterification, for example, of any of the carboxylic acid groups (—C(=O)OH) in the parent compound, with, where appropriate, prior protection of any other reactive groups present in the parent compound, followed by deprotection if required.

Examples of such metabolically labile esters include those of the formula —C(=O)OR wherein R is:

$C_{1-7}$alkyl (e.g., -Me, -Et, -nPr, -iPr, -nBu, -sBu, -iBu, -tBu);
$C_{1-7}$-aminoalkyl (e.g., aminoethyl; 2-(N,N-diethylamino) ethyl; 2-(4-morpholino)ethyl); and
acyloxy-$C_{1-7}$alkyl (e.g., acyloxymethyl; acyloxyethyl; pivaloyloxymethyl; acetoxymethyl; 1-acetoxyethyl; 1-(1-methoxy-1-methyl)ethyl-carbonxyloxyethyl; 1-(benzoyloxy) ethyl; isopropoxy-carbonyloxymethyl; 1-isopropoxy-carbonyloxyethyl; cyclohexyl-carbonyloxymethyl; 1-cyclohexyl-carbonyloxyethyl; cyclohexyloxy-carbonyloxymethyl; 1-cyclohexyloxy-carbonyloxyethyl; (4-tetrahydropyranyloxy)carbonyloxymethyl; 1-(4-tetrahydropyranyloxy)carbonyloxyethyl; (4-tetrahydropyranyl) carbonyloxymethyl; and 1-(4-tetrahydropyranyl)carbonyloxyethyl).

Also, some prodrugs are activated enzymatically to yield the active compound, or a compound which, upon further chemical reaction, yields the active compound (for example, as in antigen-directed enzyme pro-drug therapy (ADEPT), gene-directed enzyme pro-drug therapy (GDEPT), and ligand-directed enzyme pro-drug therapy (LIDEPT), etc.). For example, the prodrug may be a sugar derivative or other glycoside conjugate, or may be an amino acid ester derivative.

Also encompassed by formulae (I), and sub-groups thereof are any polymorphic forms of the compounds, solvates (e.g. hydrates) and complexes (e.g. inclusion complexes or clathrates with compounds such as cyclodextrins, or complexes with metals) of the compounds.

Biological Activity

The compounds of the formulae (I) and sub-groups thereof are inhibitors of cyclin dependent kinases. For example, compounds of the invention are inhibitors of cyclin dependent kinases, and in particular cyclin dependent kinases selected from CDK1, CDK2, CDK3, CDK4, CDK5, CDK6 and CDK9, and more particularly selected from CDK1, CDK2, CDK3, CDK4, CDK5 and CDK9.

Preferred compounds are compounds that inhibit CDK4 and/or CDK6 kinases.

One particular group of compounds consists of compounds that are selective inhibitors of CDK4 and/or CDK6, and in particular are selective for these kinases by comparison with CDK1 and CDK2 kinases.

As a consequence of their activity in modulating or inhibiting CDKs play a role in the regulation of the cell cycle, apoptosis, transcription, differentiation and CNS function. Therefore, CDK inhibitors could be useful in the treatment of diseases in which there is a disorder of proliferation, apoptosis or differentiation such as cancer. These include tumours harbouring mutations in ras, Raf, Growth Factor Receptors or over-expression of Growth Factor Receptors. Furthermore tumours with hypermethylated promoter regions of CDK inhibitors as well as tumours over-expressing cyclin partners of the cyclin dependent kinases may also display sensitivity. In particular RB+ve tumours may be particularly sensitive to CDK inhibitors. RB−ve tumours may also be sensitive to CDK inhibitors.

Examples of cancers which may be treated (or inhibited) include, but are not limited to, a carcinoma, for example a carcinoma of the bladder, breast, colon (e.g. colorectal carcinomas such as colon adenocarcinoma and colon adenoma), kidney, epidermis, liver, lung, for example adenocarcinoma, small cell lung cancer and non-small cell lung carcinomas, oesophagus, gall bladder, ovary, pancreas e.g. exocrine pancreatic carcinoma, stomach, cervix, endometrium, thyroid, nose, head and neck, prostate, gastrointestinal system, e.g. gastrointestinal stromal tumours or skin, for example squamous cell carcinoma; a hematopoietic tumour of lymphoid lineage, for example leukemia, acute lymphocytic leukemia, chronic lymphocytic leukaemia, B-cell lymphoma (such as diffuse large B cell lymphoma), T-cell lymphoma, Hodgkin's lymphoma, non-Hodgkin's lymphoma, hairy cell lymphoma, or Burkett's lymphoma; a hematopoietic tumour of myeloid lineage, for example acute and chronic myelogenous leukemias, myeloproliferative syndrome, myelodysplastic syndrome, or promyelocytic leukemia; multiple myeloma; thyroid follicular cancer; a tumour of mesenchymal origin, for example fibrosarcoma, Ewing's sarcoma or habdomyosarcoma; a tumour of the central or peripheral nervous system, for example astrocytoma, neuroblastoma, glioma or schwannoma; melanoma; seminoma; teratocarcinoma; osteosarcoma; xeroderma pigmentosum; keratoctanthoma; thyroid follicular cancer; or Kaposi's sarcoma.

One subset of cancers which the compounds of the invention may be useful in the treatment of includes sarcomas, leukemias, glioma, familial melanoma and melanoma. Thus, in the pharmaceutical compositions, uses or methods of this invention for treating a disease or condition comprising abnormal cell growth, the disease or condition comprising abnormal cell growth in one embodiment is a cancer.

Another subset of cancers includes human breast cancers (e.g. primary breast tumours, node-negative breast cancer, invasive duct adenocarcinomas of the breast, non-endometrioid breast cancers); and mantle cell lymphomas. In addition, other cancers are colorectal and endometrial cancers.

Another subset of cancers includes hematopoietic tumours of lymphoid lineage, for example leukemia, chronic lymphocytic leukaemia, mantle cell lymphoma and B-cell lymphoma (such as diffuse large B cell lymphoma).

Within this subset, one particular cancer is chronic lymphocytic leukaemia. Another particular cancer is mantle cell lymphoma. A further particular cancer is diffuse large B cell lymphoma Another subset of cancers includes breast cancer, ovarian cancer, colon cancer, prostate cancer, oesophageal cancer, squamous cancer and non-small cell lung carcinomas.

The cancers may be cancers which are sensitive to inhibition of any one or more cyclin dependent kinases selected from CDK1, CDK2, CDK3, CDK4, CDK5 and CDK6, and, in particular, one or more CDK kinases selected from CDK4 and CDK6.

A further subset of cancers, namely cancers wherein compounds having CDK4 inhibitory activity may be of particular therapeutic benefit, comprises retinoblastomas, small cell lung carcinomas, non-small lung carcinomas, sarcomas, gliomas, pancreatic cancers, head, neck and breast cancers and mantle cell lymphomas.

Another subset of cancers wherein compounds having CDK4 inhibitory activity may be of particular therapeutic benefit comprises small cell lung cancer, non-small cell lung cancer, pancreatic cancer, breast cancer, glioblastoma multiforme, T cell ALL and mantle cell lymphoma.

Whether or not a particular cancer is one which is sensitive to inhibition by a cyclin dependent kinase such as CDK4 or CDK6 may be determined by means of a cell growth assay as set out in the examples below or by a method as set out in the section headed "Methods of Diagnosis".

CDKs are also known to play a role in apoptosis, proliferation, differentiation and transcription and therefore CDK inhibitors could also be useful in the treatment of the following diseases other than cancer; viral infections, for example herpes virus, pox virus, Epstein-Barr virus, Sindbis virus, adenovirus, HIV, HPV, HCV and HCMV; prevention of AIDS development in HIV-infected individuals; chronic inflammatory diseases, for example systemic lupus erythematosus, autoimmune mediated glomerulonephritis, rheumatoid arthritis, psoriasis, inflammatory bowel disease, and autoimmune diabetes mellitus; cardiovascular diseases for example cardiac hypertrophy, restenosis, atherosclerosis; neurodegenerative disorders, for example Alzheimer's disease, AIDS-related dementia, Parkinson's disease, amyotropic lateral sclerosis, retinitis pigmentosa, spinal muscular atropy and cerebellar degeneration; glomerulonephritis; myelodysplastic syndromes, ischemic injury associated myocardial infarctions, stroke and reperfusion injury, arrhythmia, atherosclerosis, toxin-induced or alcohol related liver diseases, haematological diseases, for example, chronic anemia and aplastic anemia; degenerative diseases of the musculoskeletal system, for example, osteoporosis and arthritis, aspirin-sensitive rhinosinusitis, cystic fibrosis, multiple sclerosis, kidney diseases, ophthalmic diseases including age related macular degeneration, uveitis, and cancer pain.

Thus, in the pharmaceutical compositions, uses or methods of this invention for treating a disease or condition comprising abnormal cell growth, the disease or condition comprising abnormal cell growth in one embodiment is a cancer.

One group of cancers includes human breast cancers (e.g. primary breast tumours, node-negative breast cancer, invasive duct adenocarcinomas of the breast, non-endometrioid breast cancers); and mantle cell lymphomas. In addition, other cancers are colorectal and endometrial cancers.

Another sub-set of cancers includes hematopoietic tumours of lymphoid lineage, for example leukemia, chronic lymphocytic leukaemia, mantle cell lymphoma and B-cell lymphoma (such as diffuse large B cell lymphoma).

One particular cancer is chronic lymphocytic leukaemia.
Another particular cancer is mantle cell lymphoma.
Another particular cancer is diffuse large B cell lymphoma
Another sub-set of cancers includes multiple myeloma.
Another sub-set of cancers includes breast cancer, ovarian cancer, colon cancer, prostate cancer, oesophageal cancer, squamous cancer and non-small cell lung carcinomas.

Another sub-set of cancers includes breast cancer, pancreatic cancer, colorectal cancer, lung cancer, and melanoma.

A further sub-set of cancers, namely cancers wherein compounds having CDK4 inhibitory activity may be of particular therapeutic benefit, comprises retinoblastomas, small cell lung carcinomas, non-small lung carcinomas, sarcomas, gliomas, pancreatic cancers, head, neck and breast cancers and mantle cell lymphomas.

Another sub-set of cancers wherein compounds having CDK4 inhibitory activity may be of particular therapeutic benefit comprises small cell lung cancer, non-small cell lung cancer, pancreatic cancer, breast cancer, glioblastoma multiforme, T cell ALL and mantle cell lymphoma.

A further subset of cancers which the compounds of the invention may be useful in the treatment of includes sarcomas, leukemias, glioma, familial melanoma and melanoma.

Another set of cancers which the compounds of the present invention may be useful in the treatment of includes:
Mantle cell lymphoma (cyclin D1 translocation)
Squamous cell esophageal cancer (Cyclin D1 amplification)
Liposarcoma (CDK4 amplification)
Breast cancer (Cyclin D1 amplification)
Melanoma (p16 inactivation, activating mutation in CDK4)
Glioma (CDK6 amplification, p16 inactivation)
Mesothelioma (p16 inactivation)
T-cell lymphoblastic lymphoma/leukemia (CDK6 amplification), and
Multiple myeloma (Cyclin D translocation)

A further subset of cancers which the compounds of the present invention may be useful in the treatment of includes:
Pancreatic cancer
Prostate cancer
NSCLC
Rhabdomyosarcoma
a sarcoma such as Osteosarcoma
Teratoma
Gastric cancer and
Renal cancer Another preferred use of the compounds of the invention comprises the treatment of a cancer selected from pancreatic cancer, NSCLC, mantle cell lymphoma, squamous cell esophageal cancer, liposarcoma, breast cancer, and multiple myeloma.

A further preferred use of the compounds of the invention comprises the treatment of a cancer selected from a cancer determined to have a cyclin D (e.g. D1) translocation, Cyclin D (e.g. D1) amplification, CDK4 amplification, p16 inactivation, or activating mutation in CDK4.

One subset of non-cancer conditions that the compounds of the invention will be useful in treating consists of viral infections, type II or non-insulin dependent diabetes mellitus, autoimmune diseases, head trauma, stroke, epilepsy, neurodegenerative diseases such as Alzheimer's, motor neurone disease, progressive supranuclear palsy, corticobasal degeneration and Pick's disease for example autoimmune diseases and neurodegenerative diseases.

A further subset of disease states and conditions where the compounds of the invention will be useful consists of viral infections, autoimmune diseases and neurodegenerative diseases.

Patients with neurofibromatosis 1 (NF1) are predisposed to develop multiple neurofibromas (NFs) and are at risk for transformation of NFs to malignant peripheral nerve sheath tumors (MPNSTs). CDKN2A/p16 inactivation occurs during the malignant transformation of NFs in NF1 patients and raises the possibility that p16 immunohistochemistry may provide ancillary information in the distinction of NF from MPNST.

Therefore compounds of the invention may be useful in treating neurofibromatosis 1 (NF1) tumours.

Cell cycle regulators play crucial roles in the preadipocyte proliferation and adipocyte differentiation. Cyclin-dependent kinase 4 (CDK4) mediates with D-type cyclins entry of cells into cell cycle in response to external stimuli. CDK4 plays a role in body weight, adipogenesis, and beta cell proliferation. CDK4 null mice develop type 2 diabetes (T2D). Furthermore, CDK4 variants are associated with obesity-associated tumors/cancer. It has been found that the CDK4 IVS4-nt40GG genotype is a risk variant for T2D-associated obesity and that the AA genotype is associated with BMI<30 in T2D. Hence, CDK4 IVS4-nt40A allele is protective and G allele confers risk for obesity in T2D patients.

Therefore compounds of the invention may be useful in treating human obesity, T2D-associated obesity and obesity-associated tumors/cancer.

The activity of the compounds of the invention as inhibitors of cyclin dependent kinases (e.g. CDK4 or CDK6) can be measured using the assays set forth in the examples below and the level of activity exhibited by a given compound can be defined in terms of the $IC_{50}$ value. Preferred compounds of the present invention are compounds having an $IC_{50}$ value of less than 1 micromolar, more preferably less than 0.1 micromolar.

Advantages of the Compounds of the Invention

Compounds of the formulae (I) and sub-groups thereof as defined herein have advantages over prior art compounds. In particular, preferred compounds of the invention are selective for CDK4 or CDK6 over CDK2. Preferred compounds have a 10-30 fold selectivity for CDK4 over CDK2.

Considerable evidence implicates misregulation of the D-Cyclin-CDK4/6-INK4-Rb pathway in diseases of uncontrolled cell growth. Although Rb loss occurs in some human tumours, the majority of cancers retain wild-type Rb. Up-regulation of this pathway including overexpression of cyclin D1, mutation of CDK4, mutation or depletion of pRb or deletion of p16-INK4, is associated with more than 90% of all human tumours.

In addition, activating events upstream of the CDK4/6 kinase e.g. Ras mutations or Raf mutations or hyperactive or over-expressed receptors such as Her-2/Neu in breast cancer can also lead to a cancer cell growth advantage.

Analysis of cancer genetics has highlighted a number of specific aberrations in the D-Cyclin-CDK4/6-INK4-Rb pathway leading to uncontrolled cell proliferation and tumour formation. These include; p16 tumour suppressor protein mutations e.g. in melanomas; p16 tumour suppressor protein deletion e.g. in a range of lung cancers; p16 methylation e.g. epigenetic modification of p16 tumour suppressor protein leading to lung cancers, ras mutant cell lines lung cancers, pancreatic cancers and colorectal cancers; cyclin D over-expression e.g. breast cancers, lung cancers and multiple myeloma. The advantage of a selective CDK4 inhibitor would be to target these specific cancers caused by aberrations in the D-Cyclin-CDK4/6-INK4-Rb pathway.

Further advantages of the compounds of the invention include reduced P450 affinity, and reduced toxicity in particular due to its reduced effect on healthy cells.

Methods for the Preparation of Compounds of the Formula (I)

Compounds of the formula (I) may be prepared by the methods described herein or methods analogous thereto.

In this section, the moieties Ar, X, Y, $R^1$ and $R^2$ are as defined in relation to formula (I) and subgroups and embodiments thereof unless indicated to the contrary.

In one embodiment, compounds of the formula (I) may be prepared by the reaction of a compound of the formula (X):

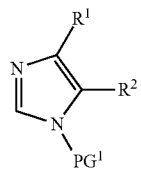

(X)

where $PG^1$ is a protecting group, with an alkyl lithium compound such as butyl lithium, followed by reaction with a compound of the formula (XI)

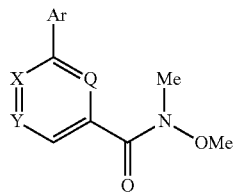

(XI)

The reaction of the compound of formula (X) with the alkyl lithium to form a metallated intermediate (not shown) may typically be carried out in a polar aprotic solvent such as tetrahydrofuran (THF) at a low temperature (for example at −78° C. Subsequent addition of the compound of formula (XI) may be carried out at −78° C. and the reaction mixture then allowed to warm to room temperature.

In this embodiment, the protecting group $PG^1$ may be, for example, a dialkylaminomethyl protecting group such as dialkylaminomethyl.

In another embodiment, compounds of the formula (I) may be prepared by the reaction of a compound of the formula (X) with a compound of the formula (XII)

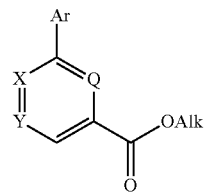

(XII)

where Alk is a methyl or ethyl group, in the presence of a lithium dialkylamide such as lithium diisopropylamide (LDA). The reaction may typically be carried out in a polar aprotic solvent such as tetrahydrofuran (THF) at a low temperature (for example at −78° C.).

In this embodiment, the protecting group $PG^1$ may be, for example, a dialkylaminomethyl protecting group such as dialkylaminomethyl, a tert-butoxycarbonyl (Boc) group, a $CH(OEt)_2$ group or a trialkylsilylalkoxymethyl group such as trimethylsilylethoxymethyl (SEM).

In a further embodiment, compounds of the formula (I) may be prepared by the reaction of a compound of the formula (XIII):

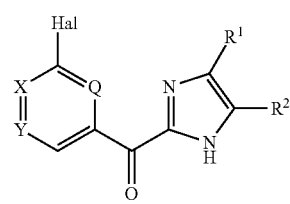

(XIII)

where Hal is chlorine, bromine or iodine with an aryl or heteroaryl boronate or aryl boronic acid in the presence of a palladium catalyst and base under Suzuki reaction conditions. Many aryl or heteroaryl boronates or boronic acids suitable for use in preparing compounds of the invention are commercially available. Where the boronates are not commercially available, they may be prepared by methods known in the art, for example as described in the review article by N. Miyaura and A. Suzuki, *Chem. Rev.* 1995, 95, 2457. Thus, boronates may be prepared by reacting the corresponding bromo-compound with an alkyl lithium such as butyl lithium and then reacting with a borate ester. The resulting boronate ester derivative may, if desired, be hydrolysed to give the corresponding boronic acid.

The reaction between the compound of formula (XIII) and an aryl/heteroaryl boronate or aryl/heteroaryl boronic acid may be carried out in the presence of a base such as potassium phosphate and a palladium catalyst. Examples of palladium catalysts include $Pd_2(dba)_3$, $PdCl_2(PPh_3)_2$, $Pd(P^tButyl_3)_2$ and $Pd(PPh_3)_4$.

The reaction may typically be carried out in a solvent or mixture of solvents, for example mixtures of polar and non-polar solvents such as mixtures of water, ethanol and toluene. The reaction may be carried out at an elevated temperature and may usefully be conducted in sealed tube, for example in a microwave reactor.

Instead of using arylboronates or aryl boronic acids and Suzuki reaction conditions, a compound of the formula (XIII) may be reacted with an organotin compound of the formula Ar—Sn(Butyl)$_3$ in a polar non-protic solvent such as dioxane in the presence of a palladium catalyst such as $Pd(PPh_3)_4$. As with the Suzuki reaction, the reaction with the organotin compound may be carried out in a sealed tube at an elevated temperature, for example in a microwave reactor.

Intermediate compounds of the formula (XIII) may be prepared by metallation of a compound of the formula (X) as described above followed by reaction with a compound of the formula (XIV):

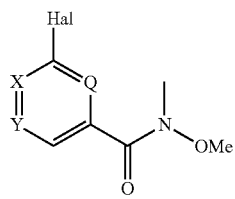

(XIV)

under conditions analogous to those described above for the reaction of compounds of the formula (X) with compounds of the formula (XI).

In a further embodiment, the compounds of formula (I) may be prepared by the oxidation of a compound of the formula (XV):

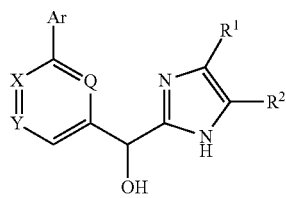

(XV)

or a protected derivative thereof, using an oxidizing agent such as manganese dioxide in a solvent such as dichloromethane, and thereafter where necessary removing any protecting group or groups.

Compounds of the formula (XV) may be prepared by the metallation of a compound of the formula (X) above, using an organometallic reagent such as an alkyl lithium (e.g. butyl lithium), followed by reaction of the metallated intermediate (not shown) with a compound of the formula (XVI):

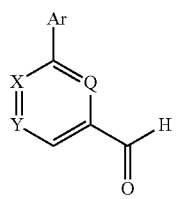

(XVI)

The reaction is typically carried out in a polar aprotic solvent such as tetrahydrofuran (THF) at a low temperature (for example at −78° C.

In this embodiment, the protecting group $PG^1$ is advantageously an SEM group.

Compounds of the formula (XVI) may be prepared by the reduction of a compound of the formula (XI), for example using diisobutyl aluminium hydride (DIBAL) as the reducing agent.

Compounds of the formula (XI) may be prepared by the reaction of a compound of the formula (XIV) with an aryl or heteroaryl boronic acid or boronate under Suzuki reaction conditions as described above.

Compounds of the formula (XIV) may be prepared by the reaction of the corresponding carboxylic acids of the formula (XVIII):

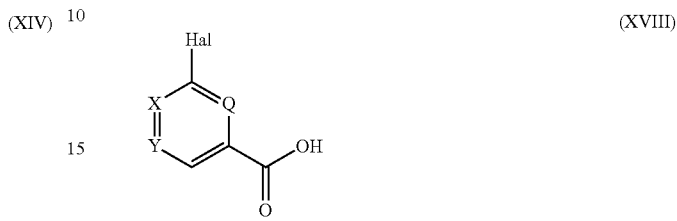

(XVIII)

with N,O-dimethyl hydroxylamine in the presence of 2-chloro-4,6-dimethoxy[1,3,5]triazine or a combination of 1-hydroxybenzotriazole (HOBt) and 1-ethyl-3-(3'-dimethylaminopropyl)-carbodiimide (EDC) and a base such as triethylamine or diisopropylethylamine.

Compounds of the formula (XII) above may be prepared by the reaction of a compound of the formula (XIX):

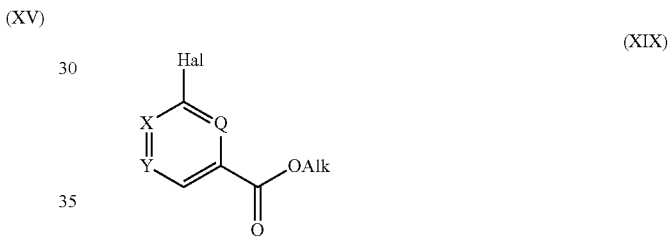

(XIX)

with an aryl or heteroaryl boronic acid or boronate under Suzuki reaction conditions as described above.

Compounds of the formula (XIX) can be prepared by halogenation of a compound of the formula (XX):

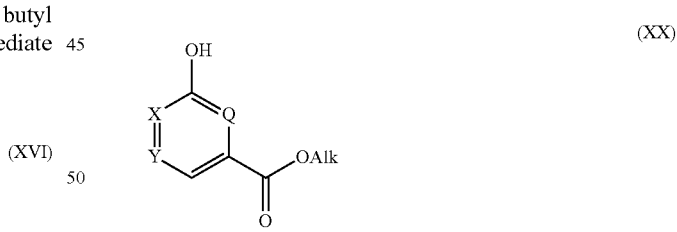

(XX)

For example, to prepare a compound wherein Hal is chlorine, the compound of formula (XX) may be reacted with a chlorinating reagent such as phosphorus oxychloride, for example in dimethylformamide.

Alternatively, the conversion of the hydroxy-compound (XX) to a halogenated compound (XIX) may be accomplished using the conditions described in WO2005/058830 or methods analogous thereto.

Compounds of the formula (XX) may be prepared by the methods described in Yonezawa et al., *Heterocycles*, (2004), 63(12), 2735-2746 or methods analogous thereto.

In an alternative synthesis of compounds of the formula (XIX) wherein X is C—CN, Y is CH and Q is N, a compound of the formula (XXI):

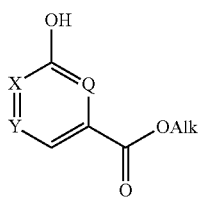

can be treated with hydrogen peroxide to form the pyridine N-oxide and then reacted with a chlorinating agent such as phosphorus oxychloride under conditions described in WO2009/151098 or conditions analogous thereto.

Once formed, many compounds of the formula (I) may be converted into other compounds of the formula (I) using standard functional group interconversions. Examples of interconversions of one compound of the formula (I) to another compound of the formula (I) may be found in the examples below. Additional examples of functional group interconversions and reagents and conditions for carrying out such conversions may be found in, for example, *Advanced Organic Chemistry*, by Jerry March, 4$^{th}$ edition, 119, Wiley Interscience, New York, *Fiesers' Reagents for Organic Synthesis*, Volumes 1-17, John Wiley, edited by Mary Fieser (ISBN: 0-471-58283-2), and *Organic Syntheses*, Volumes 1-8, John Wiley, edited by Jeremiah P. Freeman (ISBN: 0-471-31192-8).

In many of the reactions described above, it may be necessary to protect one or more groups to prevent reaction from taking place at an undesirable location on the molecule. Examples of protecting groups, and methods of protecting and deprotecting functional groups, can be found in *Protective Groups in Organic Synthesis* (T. Green and P. Wuts; 3rd Edition; John Wiley and Sons, 1999). A hydroxy group may be protected, for example, as an ether (—OR) or an ester (—OC(=O)R), for example, as: a t-butyl ether; a benzyl, benzhydryl (diphenylmethyl), or trityl (triphenylmethyl) ether; a trimethylsilyl or t-butyldimethylsilyl ether; or an acetyl ester (—OC(=O)CH$_3$, —OAc). An aldehyde or ketone group may be protected, for example, as an acetal (R—CH(OR)$_2$) or ketal (R$_2$C(OR)$_2$), respectively, in which the carbonyl group (>C=O) is converted to a diether (>C(OR)$_2$), by reaction with, for example, a primary alcohol. The aldehyde or ketone group is readily regenerated by hydrolysis using a large excess of water in the presence of acid. An amine group may be protected, for example, as an amide (—NRCO—R) or a urethane (—NRCO—OR), for example, as: a methyl amide (—NHCO—CH$_3$); a benzyloxy amide (—NHCO—OCH$_2$C$_6$H$_5$, —NH-Cbz); as a t-butoxy amide (—NHCO—OC(CH$_3$)$_3$, —NH-Boc); a 2-biphenyl-2-propoxy amide (—NHCO—OC(CH$_3$)$_2$C$_6$H$_4$C$_6$H$_5$, —NH-Bpoc), as a 9-fluorenylmethoxy amide (—NH-Fmoc), as a 6-nitroveratryloxy amide (—NH-Nvoc), as a 2-trimethylsilylethyloxy amide (—NH-Teoc), as a 2,2,2-trichloroethyloxy amide (—NH-Troc), as an allyloxy amide (—NH-Alloc), or as a 2(-phenylsulphonyl)ethyloxy amide (—NH-Psec). Other protecting groups for amines, such as cyclic amines and heterocyclic N—H groups, include toluenesulphonyl (tosyl) and methanesulphonyl (mesyl) groups and benzyl groups such as a para-methoxybenzyl (PMB) group. A carboxylic acid group may be protected as an ester for example, as: an C$_{1-7}$ alkyl ester (e.g., a methyl ester; a t-butyl ester); a C$_{1-7}$ haloalkyl ester (e.g., a C$_{1-7}$ trihaloalkyl ester); a triC$_{1-7}$alkylsilyl-C$_{1-7}$ alkyl ester; or a C$_{5-20}$ aryl-C$_{1-7}$ alkyl ester (e.g., a benzyl ester; a nitrobenzyl ester); or as an amide, for example, as a methyl amide. A thiol group may be protected, for example, as a thioether (—SR), for example, as: a benzyl thioether; an acetamidomethyl ether (—S—CH$_2$NHC(=O)CH$_3$).

Methods of Purification

The compounds may be isolated and purified by a number of methods well known to those skilled in the art and examples of such methods include chromatographic techniques such as column chromatography (e.g. flash chromatography) and HPLC. Preparative LC-MS is a standard and effective method used for the purification of small organic molecules such as the compounds described herein. The methods for the liquid chromatography (LC) and mass spectrometry (MS) can be varied to provide better separation of the crude materials and improved detection of the samples by MS. Optimisation of the preparative gradient LC method will involve varying columns, volatile eluents and modifiers, and gradients. Methods are well known in the art for optimising preparative LC-MS methods and then using them to purify compounds. Such methods are described in Rosentreter U, Huber U.; Optimal fraction collecting in preparative LC/MS; *J Comb Chem.;* 2004; 6(2), 159-64 and Leister W, Strauss K, Wisnoski D, Zhao Z, Lindsley C., Development of a custom high-throughput preparative liquid chromatography/mass spectrometer platform for the preparative purification and analytical analysis of compound libraries; *J Comb Chem.;* 2003; 5(3); 322-9.

One such system for purifying compounds via preparative LC-MS is described in the experimental section below although a person skilled in the art will appreciate that alternative systems and methods to those described could be used. In particular, normal phase preparative LC based methods might be used in place of the reverse phase methods described here. Most preparative LC-MS systems utilise reverse phase LC and volatile acidic modifiers, since the approach is very effective for the purification of small molecules and because the eluents are compatible with positive ion electrospray mass spectrometry. Employing other chromatographic solutions e.g. normal phase LC, alternatively buffered mobile phase, basic modifiers etc as outlined in the analytical methods described above could alternatively be used to purify the compounds.

Pharmaceutical Formulations

While it is possible for the active compound to be administered alone, it is preferable to present it as a pharmaceutical composition (e.g. formulation) comprising at least one active compound of the invention together with one or more pharmaceutically acceptable carriers, adjuvants, excipients, diluents, fillers, buffers, stabilisers, preservatives, lubricants, or other materials well known to those skilled in the art and optionally other therapeutic or prophylactic agents.

Thus, the present invention further provides pharmaceutical compositions, as defined above, and methods of making a pharmaceutical composition comprising admixing at least one active compound, as defined above, together with one or more pharmaceutically acceptable carriers, excipients, buffers, adjuvants, stabilizers, or other materials, as described herein.

The term "pharmaceutically acceptable" as used herein pertains to compounds, materials, compositions, and/or dosage forms which are, within the scope of sound medical judgment, suitable for use in contact with the tissues of a subject (e.g. human) without excessive toxicity, irritation, allergic response, or other problem or complication, commensurate with a reasonable benefit/risk ratio. Each carrier, excipient, etc. must also be "acceptable" in the sense of being compatible with the other ingredients of the formulation.

Pharmaceutical compositions containing compounds of the formula (I) can be formulated in accordance with known techniques, see for example, Remington's Pharmaceutical Sciences, Mack Publishing Company, Easton, Pa., USA.

Accordingly, in a further aspect, the invention provides compounds of the formula (I) and sub-groups thereof as defined herein in the form of pharmaceutical compositions.

The pharmaceutical compositions can be in any form suitable for oral, parenteral, topical, intranasal, ophthalmic, otic, rectal, intra-vaginal, or transdermal administration. Where the compositions are intended for parenteral administration, they can be formulated for intravenous, intramuscular, intraperitoneal, subcutaneous administration or for direct delivery into a target organ or tissue by injection, infusion or other means of delivery. The delivery can be by bolus injection, short term infusion or longer term infusion and can be via passive delivery or through the utilisation of a suitable infusion pump or syringe driver.

Pharmaceutical formulations adapted for parenteral administration include aqueous and non-aqueous sterile injection solutions which may contain anti-oxidants, buffers, bacteriostats, co-solvents, surface active agents, organic solvent mixtures, cyclodextrin complexation agents, emulsifying agents (for forming and stabilizing emulsion formulations), liposome components for forming liposomes, gellable polymers for forming polymeric gels, lyophilisation protectants and combinations of agents for, inter alia, stabilising the active ingredient in a soluble form and rendering the formulation isotonic with the blood of the intended recipient. Pharmaceutical formulations for parenteral administration may also take the form of aqueous and non-aqueous sterile suspensions which may include suspending agents and thickening agents (R. G. Strickly, Solubilizing Excipients in oral and injectable formulations, Pharmaceutical Research, Vol 21(2) 2004, p 201-230).

Liposomes are closed spherical vesicles composed of outer lipid bilayer membranes and an inner aqueous core and with an overall diameter of <100 μm. Depending on the level of hydrophobicity, moderately hydrophobic drugs can be solubilized by liposomes if the drug becomes encapsulated or intercalated within the liposome. Hydrophobic drugs can also be solubilized by liposomes if the drug molecule becomes an integral part of the lipid bilayer membrane, and in this case, the hydrophobic drug is dissolved in the lipid portion of the lipid bilayer.

The formulations may be presented in unit-dose or multi-dose containers, for example sealed ampoules, vials and pre-filled syringes, and may be stored in a freeze-dried (lyophilised) condition requiring only the addition of the sterile liquid carrier, for example water for injections, immediately prior to use.

The pharmaceutical formulation can be prepared by lyophilising a compound of formula (I), or sub-groups thereof. Lyophilisation refers to the procedure of freeze-drying a composition. Freeze-drying and lyophilisation are therefore used herein as synonyms.

Extemporaneous injection solutions and suspensions may be prepared from sterile powders, granules and tablets.

Pharmaceutical compositions of the present invention for parenteral injection can also comprise pharmaceutically acceptable sterile aqueous or non-aqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), carboxymethylcellulose and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

The compositions of the present invention may also contain adjuvants such as preservatives, wetting agents, emulsifying agents, and dispersing agents. Prevention of the action of microorganisms may be ensured by the inclusion of various antibacterial and antifungal agents, for example, paraben, chlorobutanol, phenol, sorbic acid, and the like. It may also be desirable to include agents to adjust tonicity such as sugars, sodium chloride, and the like. Prolonged absorption of the injectable pharmaceutical form may be brought about by the inclusion of agents which delay absorption such as aluminum monostearate and gelatin.

In one preferred embodiment of the invention, the pharmaceutical composition is in a form suitable for i.v. administration, for example by injection or infusion. For intravenous administration, the solution can be dosed as is, or can be injected into an infusion bag (containing a pharmaceutically acceptable excipient, such as 0.9% saline or 5% dextrose), before administration.

In another preferred embodiment, the pharmaceutical composition is in a form suitable for sub-cutaneous (s.c.) administration.

Pharmaceutical dosage forms suitable for oral administration include tablets (coated or uncoated), capsules (hard or soft shell), caplets, pills, lozenges, syrups, solutions, powders, granules, elixirs and suspensions, sublingual tablets, wafers or patches such as buccal patches.

Thus, tablet compositions can contain a unit dosage of active compound together with an inert diluent or carrier such as a sugar or sugar alcohol, eg; lactose, sucrose, sorbitol or mannitol; and/or a non-sugar derived diluent such as sodium carbonate, calcium phosphate, calcium carbonate, or a cellulose or derivative thereof such as microcrystalline cellulose (MCC), methyl cellulose, ethyl cellulose, hydroxypropyl methyl cellulose, and starches such as corn starch. Tablets may also contain such standard ingredients as binding and granulating agents such as polyvinylpyrrolidone, disintegrants (e.g. swellable crosslinked polymers such as crosslinked carboxymethylcellulose), lubricating agents (e.g. stearates), preservatives (e.g. parabens), antioxidants (e.g. BHT), buffering agents (for example phosphate or citrate buffers), and effervescent agents such as citrate/bicarbonate mixtures. Such excipients are well known and do not need to be discussed in detail here.

Tablets may be designed to release the drug either upon contact with stomach fluids (immediate release tablets) or to release in a controlled manner (controlled release tablets) over a prolonged period of time or with a specific region of the GI tract.

Capsule formulations may be of the hard gelatin or soft gelatin variety and can contain the active component in solid, semi-solid, or liquid form. Gelatin capsules can be formed from animal gelatin or synthetic or plant derived equivalents thereof.

The solid dosage forms (eg; tablets, capsules etc.) can be coated or un-coated. Coatings may act either as a protective film (e.g. a polymer, wax or varnish) or as a mechanism for controlling drug release. The coating (e.g. a Eudragit™ type polymer) can be designed to release the active component at a desired location within the gastro-intestinal tract. Thus, the coating can be selected so as to degrade under certain pH conditions within the gastrointestinal tract, thereby selectively release the compound in the stomach or in the ileum, duodenum or colon.

Instead of, or in addition to, a coating, the drug can be presented in a solid matrix comprising a release controlling agent, for example a release delaying agent which may be adapted to release the compound in a controlled manner in the gastrointestinal tract. Alternatively the drug can be presented in a polymer coating e.g. a polymethacrylate polymer coating, which may be adapted to selectively release the compound under conditions of varying acidity or alkalinity in the gastrointestinal tract. Alternatively, the matrix material or release retarding coating can take the form of an erodible polymer (e.g. a maleic anhydride polymer) which is substantially continuously eroded as the dosage form passes through the gastrointestinal tract. As a further alternative, the active compound can be formulated in a delivery system that provides osmotic control of the release of the compound. Osmotic release and other delayed release or sustained release formulations may be prepared in accordance with methods well known to those skilled in the art.

The pharmaceutical compositions typically comprise from approximately 1% (w/w) to approximately 95% (w/w) active ingredient and from 99% (w/w) to 5% (w/w) of a pharmaceutically acceptable excipient or combination of excipients. Preferably, the compositions comprise from approximately 20% (w/w) to approximately 90% (w/w) active ingredient and from 80% (w/w) to 10% of a pharmaceutically excipient or combination of excipients. Pharmaceutical compositions according to the invention may be, for example, in unit dose form, such as in the form of ampoules, vials, suppositories, dragées, tablets or capsules.

The pharmaceutically acceptable excipient(s) can be selected according to the desired physical form of the formulation and can, for example, be selected from diluents (e.g solid diluents such as fillers or bulking agents; and liquid diluents such as solvents and co-solvents), disintegrants, buffering agents, lubricants, flow aids, release controlling (e.g. release retarding or delaying polymers or waxes) agents, binders, granulating agents, pigments, plasticizers, antioxidants, preservatives, flavouring agents, taste masking agents, tonicity adjusting agents and coating agents.

The skilled person will have the expertise to select the appropriate amounts of ingredients for use in the formulations. For example tablets and capsules typically contain 0-20% disintegrants, 0-5% lubricants, 0-5% flow aids and/or 0-99% (w/w) fillers/or bulking agents (depending on drug dose). They may also contain 0-10% (w/w) polymer binders, 0-5% (w/w) antioxidants, 0-5% (w/w) Pigments. Slow release tablets would in addition contain 0-99% (w/w) polymers (depending on dose). The film coats of the tablet or capsule typically contain 0-10% (w/w) polymers, 0-3% (w/w) pigments, and/or 0-2% (w/w) plasticizers.

Parenteral formulations typically contain 0-20% (w/w) buffers, 0-50% (w/w) cosolvents, and/or 0-99% (w/w) Water for Injection (WFI) (depending on dose and if freeze dried). Formulations for intramuscular depots may also contain 0-99% (w/w) oils.

Pharmaceutical compositions for oral administration can be obtained by combining the active ingredient with solid carriers, if desired granulating a resulting mixture, and processing the mixture, if desired or necessary, after the addition of appropriate excipients, into tablets, dragee cores or capsules. It is also possible for them to be incorporated into a polymer or waxy matrix that allow the active ingredients to diffuse or be released in measured amounts.

The compounds of the invention can also be formulated as solid dispersions. Solid dispersions are homogeneous extremely fine disperse phases of two or more solids. Solid solutions (molecularly disperse systems), one type of solid dispersion, are well known for use in pharmaceutical technology (see (Chiou and Riegelman, J. Pharm. Sci., 60, 1281-1300 (1971)) and are useful in increasing dissolution rates and increasing the bioavailability of poorly water-soluble drugs.

This invention also provides solid dosage forms comprising the solid solution described above. Solid dosage forms include tablets, capsules and chewable tablets. Known excipients can be blended with the solid solution to provide the desired dosage form. For example, a capsule can contain the solid solution blended with (a) a disintegrant and a lubricant, or (b) a disintegrant, a lubricant and a surfactant. In addition a capsule can contain a bulking agent, such as lactose or microcrystalline cellulose. A tablet can contain the solid solution blended with at least one disintegrant, a lubricant, a surfactant, a bulking agent and a glidant. A chewable tablet can contain the solid solution blended with a bulking agent, a lubricant, and if desired an additional sweetening agent (such as an artificial sweetener), and suitable flavours. Solid solutions may also be formed by spraying solutions of drug and a suitable polymer onto the surface of inert carriers such as sugar beads ('non-pareils'). These beads can subsequently be filled into capsules or compressed into tablets.

The pharmaceutical formulations may be presented to a patient in "patient packs" containing an entire course of treatment in a single package, usually a blister pack. Patient packs have an advantage over traditional prescriptions, where a pharmacist divides a patient's supply of a pharmaceutical from a bulk supply, in that the patient always has access to the package insert contained in the patient pack, normally missing in patient prescriptions. The inclusion of a package insert has been shown to improve patient compliance with the physician's instructions.

Compositions for topical use and nasal delivery include ointments, creams, sprays, patches, gels, liquid drops and inserts (for example intraocular inserts). Such compositions can be formulated in accordance with known methods.

Examples of formulations for rectal or intra-vaginal administration include pessaries and suppositories which may be, for example, formed from a shaped moldable or waxy material containing the active compound.

Compositions for administration by inhalation may take the form of inhalable powder compositions or liquid or powder sprays, and can be administrated in standard form using powder inhaler devices or aerosol dispensing devices. Such devices are well known. For administration by inhalation, the powdered formulations typically comprise the active compound together with an inert solid powdered diluent such as lactose.

The compounds of the formula (I) will generally be presented in unit dosage form and, as such, will typically contain sufficient compound to provide a desired level of biological activity. For example, a formulation may contain from 1 nanogram to 2 grams of active ingredient, e.g. from 1 nanogram to 2 milligrams of active ingredient. Within this range, particular sub-ranges of compound are 0.1 milligrams to 2 grams of active ingredient (more usually from 10 milligrams to 1 gram, e.g. 50 milligrams to 500 milligrams), or 1 microgram to 20 milligrams (for example 1 microgram to 10 milligrams, e.g. 0.1 milligrams to 2 milligrams of active ingredient).

For oral compositions, a unit dosage form may contain from 1 milligram to 2 grams, more typically 10 milligrams to 1 gram, for example 50 milligrams to 1 gram, e.g. 100 milligrams to 1 gram, of active compound.

The active compound will be administered to a patient in need thereof (for example a human or animal patient) in an amount sufficient to achieve the desired therapeutic effect.
Methods of Treatment The compounds of the formula (I) and sub-groups as defined herein will be useful in the prophylaxis or treatment of a range of disease states or conditions mediated by cyclin dependent kinases (particularly CDK4 and/or CDK6). Examples of such disease states and conditions are set out above.

The compounds are generally administered to a subject in need of such administration, for example a human or animal patient, preferably a human.

The compounds will typically be administered in amounts that are therapeutically or prophylactically useful and which generally are non-toxic. However, in certain situations (for example in the case of life threatening diseases), the benefits of administering a compound of the formula (I) may outweigh the disadvantages of any toxic effects or side effects, in which case it may be considered desirable to administer compounds in amounts that are associated with a degree of toxicity.

The compounds may be administered over a prolonged term to maintain beneficial therapeutic effects or may be administered for a short period only. Alternatively they may be administered in a continuous manner or in a manner that provides intermittent dosing (e.g. a pulsatile manner).

A typical daily dose of the compound of formula (I) can be in the range from 100 picograms to 100 milligrams per kilogram of body weight, more typically 5 nanograms to 25 milligrams per kilogram of bodyweight, and more usually 10 nanograms to 15 milligrams per kilogram (e.g. 10 nanograms to 10 milligrams, and more typically 1 microgram per kilogram to 20 milligrams per kilogram, for example 1 microgram to 10 milligrams per kilogram) per kilogram of bodyweight although higher or lower doses may be administered where required. The compound of the formula (I) can be administered on a daily basis or on a repeat basis every 2, or 3, or 4, or 5, or 6, or 7, or 10 or 14, or 21, or 28 days for example.

The compounds of the invention may be administered orally in a range of doses, for example 1 to 1500 mg, 2 to 800 mg, or 5 to 500 mg, e.g. 2 to 200 mg or 10 to 1000 mg, particular examples of doses including 10, 20, 50 and 80 mg. The compound may be administered once or more than once each day. The compound can be administered continuously (i.e. taken every day without a break for the duration of the treatment regimen). Alternatively, the compound can be administered intermittently (i.e. taken continuously for a given period such as a week, then discontinued for a period such as a week and then taken continuously for another period such as a week and so on throughout the duration of the treatment regimen. Examples of treatment regimens involving intermittent administration include regimens wherein administration is in cycles of one week on, one week off; or two weeks on, one week off; or three weeks on, one week off; or two weeks on, two weeks off; or four weeks on two weeks off; or one week on three weeks off—for one or more cycles, e.g. 2, 3, 4, 5, 6, 7, 8, 9 or 10 or more cycles.

In one particular dosing schedule, a patient will be given an infusion of a compound of the formula (I) for periods of one hour daily for up to ten days in particular up to five days for one week, and the treatment repeated at a desired interval such as two to four weeks, in particular every three weeks.

More particularly, a patient may be given an infusion of a compound of the formula (I) for periods of one hour daily for 5 days and the treatment repeated every three weeks.

In another particular dosing schedule, a patient is given an infusion over 30 minutes to 1 hour followed by maintenance infusions of variable duration, for example 1 to 5 hours, e.g. 3 hours.

In a further particular dosing schedule, a patient is given a continuous infusion for a period of 12 hours to 5 days, an in particular a continuous infusion of 24 hours to 72 hours.

Ultimately, however, the quantity of compound administered and the type of composition used will be commensurate with the nature of the disease or physiological condition being treated and will be at the discretion of the physician.

It has also been discovered that cyclin-dependent kinase inhibitors can be used in combination with other anticancer agents. The compounds as defined herein can be administered as the sole therapeutic agent or they can be administered in combination therapy with one of more other compounds (or therapies) for treatment of a particular disease state, for example a neoplastic disease such as a cancer as hereinbefore defined. Examples of other therapeutic agents or treatments that may be administered together (whether concurrently or at different time intervals) with the compounds of the formula (I) include but are not limited to:

Topoisomerase I inhibitors
    Antimetabolites
    Tubulin targeting agents
    DNA binder and topoisomerase II inhibitors
    Alkylating Agents
    Monoclonal Antibodies.
    Anti-Hormones
    Signal Transduction Inhibitors
    Proteasome Inhibitors
    DNA methyl transferases
    Cytokines and retinoids
    Chromatin targeted therapies
    Radiotherapy, and,
    Other therapeutic or prophylactic agents; for example agents that reduce or alleviate some of the side effects associated with chemotherapy. Particular examples of such agents include anti-emetic agents and agents that prevent or decrease the duration of chemotherapy-associated neutropenia and prevent complications that arise from reduced levels of red blood cells or white blood cells, for example erythropoietin (EPO), granulocyte macrophage-colony stimulating factor (GM-CSF), and granulocyte-colony stimulating factor (G-CSF). Also included are agents that inhibit bone resorption such as bisphosphonate agents e.g. zoledronate, pamidronate and ibandronate, agents that suppress inflammatory responses (such as dexamethazone, prednisone, and prednisolone) and agents used to reduce blood levels of growth hormone and IGF-I in acromegaly patients such as synthetic forms of the brain hormone somatostatin, which includes octreotide acetate which is a long-acting octapeptide with pharmacologic properties mimicking those of the natural hormone somatostatin. Further included are agents such as leucovorin, which is used as an antidote to drugs that decrease levels of folic acid, or folinic acid it self and agents such as megestrol acetate which can be used for the treatment of side-effects including oedema and thromoembolic episodes.

Each of the compounds present in the combinations of the invention may be given in individually varying dose schedules and via different routes.

Where the compound of the formula (I) is administered in combination therapy with one, two, three, four or more other therapeutic agents (preferably one or two, more preferably one), the compounds can be administered simultaneously or sequentially. When administered sequentially, they can be administered at closely spaced intervals (for example over a period of 5-10 minutes) or at longer intervals (for example 1, 2, 3, 4 or more hours apart, or even longer periods apart where required), the precise dosage regimen being commensurate with the properties of the therapeutic agent(s).

The compounds of the invention may also be administered in conjunction with non-chemotherapeutic treatments such as radiotherapy, photodynamic therapy, gene therapy; surgery and controlled diets.

For use in combination therapy with another chemotherapeutic agent, the compound of the formula (I) and one, two, three, four or more other therapeutic agents can be, for example, formulated together in a dosage form containing two, three, four or more therapeutic agents. In an alternative, the individual therapeutic agents may be formulated separately and presented together in the form of a kit, optionally with instructions for their use.

In one embodiment the pharmaceutical composition contains a compound of formula I together with a pharmaceutically acceptable carrier and optionally another therapeutic agent.

A person skilled in the art would know through his or her common general knowledge the dosing regimes and combination therapies to use.

Methods of Diagnosis

Prior to administration of a compound of the formula (I), a patient may be screened to determine whether a disease or condition from which the patient is or may be suffering is one which would be susceptible to treatment with a compound having activity against cyclin dependent kinases.

For example, a biological sample taken from a patient may be analysed to determine whether a condition or disease, such as cancer, that the patient is or may be suffering from is one which is characterised by a genetic abnormality or abnormal protein expression which leads to over-activation of CDK activity or to sensitisation of a pathway to normal CDK activity. Examples of such abnormalities that result in activation or sensitisation of the CDK4 signal include up-regulation of cyclin D, or loss of p16, or presence of activating mutation in CDK4 and 6. The term up-regulation includes elevated expression or over-expression, including gene amplification (i.e. multiple gene copies) and increased expression by a transcriptional effect, and hyperactivity and activation, including activation by mutations.

Thus, the patient may be subjected to a diagnostic test to detect a marker characteristic of up-regulation of cyclin D, or loss of p16, or presence of activating mutations in CDK4 and 6. The term diagnosis includes screening. By marker we include genetic markers including, for example, the measurement of DNA composition to identify mutations of CDK4 and 6. The term marker also includes markers which are characteristic of up regulation of cyclin D, including enzyme activity, enzyme levels, enzyme state (e.g. phosphorylated or not) and mRNA levels of the aforementioned proteins. Tumours with upregulation of cyclin D, or loss of p16 may be particularly sensitive to CDK inhibitors. Tumours may preferentially be screened for upregulation of cyclin D, or loss of p16 prior to treatment. Thus, the patient may be subjected to a diagnostic test to detect a marker characteristic of up-regulation of cyclin D, or loss of p16.

The diagnostic tests are typically conducted on a biological sample selected from tumour biopsy samples, blood samples (isolation and enrichment of shed tumour cells), stool biopsies, sputum, chromosome analysis, pleural fluid, peritoneal fluid, or urine.

Methods of identification and analysis of mutations and up-regulation of proteins are well known to a person skilled in the art. Screening methods could include, but are not limited to, standard methods such as reverse-transcriptase polymerase chain reaction (RT-PCR) or in-situ hybridisation.

In screening by RT-PCR, the level of mRNA in the tumour is assessed by creating a cDNA copy of the mRNA followed by amplification of the cDNA by PCR. Methods of PCR amplification, the selection of primers, and conditions for amplification, are known to a person skilled in the art. Nucleic acid manipulations and PCR are carried out by standard methods, as described for example in Ausubel, F. M. et al., eds. Current Protocols in Molecular Biology, 2004, John Wiley & Sons Inc., or Innis, M. A. et-al., eds. PCR Protocols: a guide to methods and applications, 1990, Academic Press, San Diego. Reactions and manipulations involving nucleic acid techniques are also described in Sambrook et al., 2001, $3^{rd}$ Ed, Molecular Cloning: A Laboratory Manual, Cold Spring Harbor Laboratory Press. Alternatively a commercially available kit for RT-PCR (for example Roche Molecular Biochemicals) may be used, or methodology as set forth in U.S. Pat. Nos. 4,666,828; 4,683,202; 4,801,531; 5,192,659, 5,272,057, 5,882,864, and 6,218,529 and incorporated herein by reference.

An example of an in-situ hybridisation technique for assessing mRNA expression would be fluorescence in-situ hybridisation (FISH) (see Angerer, 1987 Meth. Enzymol., 152: 649).

Generally, in situ hybridization comprises the following major steps: (1) fixation of tissue to be analyzed; (2) prehybridization treatment of the sample to increase accessibility of target nucleic acid, and to reduce nonspecific binding; (3) hybridization of the mixture of nucleic acids to the nucleic acid in the biological structure or tissue; (4) post-hybridization washes to remove nucleic acid fragments not bound in the hybridization, and (5) detection of the hybridized nucleic acid fragments. The probes used in such applications are typically labeled, for example, with radioisotopes or fluorescent reporters. Preferred probes are sufficiently long, for example, from about 50, 100, or 200 nucleotides to about 1000 or more nucleotides, to enable specific hybridization with the target nucleic acid(s) under stringent conditions. Standard methods for carrying out FISH are described in Ausubel, F. M. et al., eds. Current Protocols in Molecular Biology, 2004, John Wiley & Sons Inc and Fluorescence In Situ Hybridization: Technical Overview by John M. S. Bartlett in Molecular Diagnosis of Cancer, Methods and Protocols, 2nd ed.; ISBN: 1-59259-760-2; March 2004, pps. 077-088; Series: Methods in Molecular Medicine.

Alternatively, the protein products expressed from the mRNAs may be assayed by immunohistochemistry of tumour samples, solid phase immunoassay with microtiter plates, Western blotting, 2-dimensional SDS-polyacrylamide gel electrophoresis, ELISA, flow cytometry and other methods known in the art for detection of specific proteins. Detection methods would include the use of site specific antibodies. The skilled person will recognize that all such well-known techniques for detection of upregulation of cyclin D, or loss of p16, or detection of CDK4 and 6 variants could be applicable in the present case.

Therefore, all of these techniques could also be used to identify tumours particularly suitable for treatment with the compounds of the invention.

Patients with mantle cell lymphoma (MCL) could be selected for treatment with a compound of the invention using diagnostic tests outlined herein. MCL is a distinct clinicopathologic entity of non-Hodgkin's lymphoma, characterized by proliferation of small to medium-sized lymphocytes with co-expression of CD5 and CD20, an aggressive and incurable clinical course, and frequent t(11;14)(q13;q32) translocation. Over-expression of cyclin D1 mRNA, found in mantle cell lymphoma (MCL), is a critical diagnostic marker. Yatabe et al (Blood. 2000 Apr. 1; 95(7):2253-61) proposed that cyclin D1-positivity should be included as one of the standard criteria for MCL, and that innovative therapies for this incurable disease should be explored on the basis of the new criteria. Jones et al (J Mol. Diagn. 2004 May; 6(2):84-9) developed a real-time, quantitative, reverse transcription PCR assay for cyclin D1 (CCND1) expression to aid in the diagnosis of mantle cell lymphoma (MCL). Howe et al (Clin Chem. 2004 January; 50(1):80-7) used real-time quantitative RT-PCR to evaluate cyclin D1 mRNA expression and found that quantitative RT-PCR for cyclin D1 mRNA normalized to CD19 mRNA can be used in the diagnosis of MCL in blood, marrow, and tissue. Alternatively, patients with breast cancer could be selected for treatment with a CDK inhibitor using diagnostic tests outline above. Tumour cells commonly over-express cyclin D and it has been shown that cyclin D is over-expressed in breast cancer. Therefore breast cancer may in particular be treated with a CDK inhibitor as provided herein.

In addition, the cancer may be analysed for INK4a and RB loss of function, and cyclin D1 or CDK4 overexpression or CDK4 mutation. RB loss and mutations inactivating $p16^{INK4a}$ function or hypermethylation of $p16^{INK4a}$ occur in many tumour types. Cyclin D1 is amplified in 40% of head and neck, over-expressed in 50% of breast cancers and 90% of mantle cell lymphomas. p16 is deleted in 60% of non-small lung carcinomas and in 40% of pancreatic cancers. CDK4 is amplified in 20% of sarcomas and in 10% of gliomas. Events resulting in RB or $p16^{INK4a}$ inactivation through mutation, deletion, or epigenetic silencing, or in the overexpression of cyclin D1 or CDK4 can be identified by the techniques outlined herein. Tumours with up-regulation, in particular over-expression of cyclin D or CDK4 or loss of INK4a or RB function may be particularly sensitive to CDK inhibitors. Thus, the patient may be subjected to a diagnostic test to detect a marker characteristic of over-expression of cyclin D or CDK4 or loss of INK4a or RB function.

Cancers that experience INK4a and RB loss of function and cyclin D1 or CDK4 overexpression, include small cell lung cancer, non-small cell lung cancer, pancreatic cancer, breast cancer, glioblastoma multiforme, T cell ALL and mantle cell lymphoma. Therefore patients with small cell lung cancer, non-small cell lung cancer, pancreatic cancer, breast cancer, glioblastoma multiforme, T cell ALL or mantle cell lymphoma could be selected for treatment with a CDK inhibitor using diagnostic tests outlined above and may in particular be treated with a CDK inhibitor as provided herein.

Patients with specific cancers caused by aberrations in the D-Cyclin-CDK4/6-INK4-Rb pathway could be identified by using the techniques described herein and then treated with a CDK4 inhibitor as provided. Examples of abnormalities that activate or sensitise tumours to CDK4 signal include, receptor activation e.g. Her-2/Neu in breast cancer, ras mutations for example in pancreatic, colorectal or lung cancer, raf mutations for example in melanoma, p16 mutations for example in melanoma, p16 deletions for example in lung cancer, p16 methylation for example in lung cancer or cyclin D overexpression for example in breast cancer. Thus, a patient could be selected for treatment with a compound of the invention using diagnostic tests as outlined herein to identify up-regulation of the D-Cyclin-CDK4/6-INK4-Rb pathway for example by overexpression of cyclin D, mutation of CDK4, mutation or depletion of pRb, deletion of p16-INK4, mutation, deletion or methylation of p16, or by activating events upstream of the CDK4/6 kinase e.g. Ras mutations or Raf mutations or hyperactive or over-expressed receptors such as Her-2/Neu.

CDK4 activation can also occur in tumours with ras or raf mutations or growth factor activation. Therefore, in one embodiment, the patient is selected for treatment with a compound of the invention using the diagnostic test described herein to identify whether the tumour has activated (via mutation or overexpression) ras, raf, EGFR, IGFR, FGFR, cKit, and/or PDGFR.

EXAMPLES

The invention will now be illustrated, but not limited, by reference to the specific embodiments described in the following examples.

In the examples, the following abbreviations are used.
AcOH acetic acid
BOC tert-butyloxycarbonyl
CDI 1,1-carbonyldiimidazole
DMAW90 Solvent mixture: DCM: MeOH, AcOH, $H_2O$ (90: 18:3:2)
DMAW120 Solvent mixture: DCM: MeOH, AcOH, $H_2O$ (120:18:3:2)
DMAW240 Solvent mixture: DCM: MeOH, AcOH, $H_2O$ (240:20:3:2)
DCM dichloromethane
DMF dimethylformamide
DMSO dimethyl sulphoxide
EDC 1-ethyl-3-(3'-dimethylaminopropyl)-carbodiimide
$Et_3N$ triethylamine
EtOAc ethyl acetate
$Et_2O$ diethyl ether
HOAt 1-hydroxyazabenzotriazole
HOBt 1-hydroxybenzotriazole
MeCN acetonitrile
MeOH methanol
P.E. petroleum ether
$SiO_2$ silica
TBTU N,N,N',N'-tetramethyl-O-(benzotriazol-1-yl)uronium tetrafluoroborate
THF tetrahydrofuran The compounds described in the following examples were characterized by liquid chromatography and mass spectroscopy using the systems and operating conditions set out below. Where atoms with different isotopes are present and a single mass is quoted, the mass quoted for the compound is the monoisotopic mass (i.e. $^{35}Cl$; $^{79}Br$ etc.). Several systems were used (described below) and these were equipped and set up to run under closely similar operating conditions. The operating conditions used are also described below.
Agilent 1200SL-6140 LC-MS System—RAPID:
HPLC System: Agilent 1200 series SL
Mass Spec Detector: Agilent 6140 single quadrupole
Second Detector Agilent 1200 MWD SL
Low pH Mobile Phase
Eluent A: 95:5 $H_2O$:$CH_3CN$+0.1% Formic Acid.
Eluent B: $CH_3CN$.
Gradient: 5-95% eluent B over 1.1 minutes.
Flow: 0.9 mL/min.
Column: Waters Acquity HPLC BEH C18; 1.7μ; 2.1×50 mm.
Column T: 50° C.
High pH Mobile Phase
Eluent A: 95:5 10 mM $NH_4HCO_3$+$NH_4OH$:$CH_3CN$ (pH=9.2).

Eluent B: CH$_3$CN.
Gradient: 5-95% eluent B over 1.1 minutes.
Flow: 0.9 mL/min.
Column: Waters Acquity HPLC BEH C18; 1.7µ; 2.1×50 mm.
Column T: 50° C.
Agilent MS Running Conditions:
Capillary voltage: 3000V on ES pos (2700V on ES Neg).
Fragmentor/Gain: 190 on ES pos (160 on ES neg).
Gain: 1
Drying gas flow: 12.0 L/min
Gas Temperature: 345° C.
Nebuliser Pressure: 60 psig
Scan Range: 125-800 amu
Ionisation Mode ElectroSpray Positive-Negative switching.
Mass Directed Purification LC-MS System Preparative LC-MS is a standard and effective method used for the purification of small organic molecules such as the compounds described herein. The methods for the liquid chromatography (LC) and mass spectrometry (MS) can be varied to provide better separation of the crude materials and improved detection of the samples by MS. Optimisation of the preparative gradient LC method will involve varying columns, volatile eluents and modifiers, and gradients. Methods are well known in the art for optimising preparative LCMS methods and then using them to purify compounds. Such methods are described in Rosentreter U, Huber U.; Optimal fraction collecting in preparative LCMS; *J Comb Chem.;* 2004; 6(2), 159-64 and Leister W, Strauss K, Wisnoski D, Zhao Z, Lindsley C., Development of a custom high-throughput preparative liquid chromatography/mass spectrometer platform for the preparative purification and analytical analysis of compound libraries; *J Comb. Chem.;* 2003; 5(3); 322-9.

One such system for purifying compounds via preparative LC-MS is described below although a person skilled in the art will appreciate that alternative systems and methods to those described could be used. In particular, normal phase preparative LC-based methods might be used in place of the reverse phase methods described here. Most preparative LCMS systems utilise reverse phase LC and volatile acidic modifiers, since the approach is very effective for the purification of small molecules and because the eluents are compatible with positive ion electrospray mass spectrometry. Employing other chromatographic solutions e.g. normal phase LC, alternatively buffered mobile phase, basic modifiers etc as outlined in the analytical methods described above could alternatively be used to purify the compounds.

Preparative LC-MS System Description:
Waters Fractionlynx System:
2767 Dual Loop Autosampler/Fraction Collector
2525 preparative pump
CFO (column fluidic organiser) for column selection
RMA (Waters reagent manager) as make up pump
Waters ZQ Mass Spectrometer
Waters 2996 Photo Diode Array detector
Waters ZQ Mass Spectrometer
Software:
Masslynx 4.1
Waters MS Running Conditions:
Capillary voltage: 3.5 kV (3.2 kV on ES Negative)
Cone voltage: 25 V
Source Temperature: 120° C.
Multiplier: 500 V
Scan Range: 125-800 amu
Ionisation Mode ElectroSpray Positive or
  ElectroSpray Negative
Low pH Chromatography:
Phenomenex Synergy MAX-RP, 10µ, 100×21.2 mm
(alternatively used Thermo Hypersil-Keystone HyPurity Aquastar, 5µ, 100×21.2 mm for more polar compounds)
High pH Chromatography:
Waters XBridge C18 5µ 100×19 mm
(alternatively used Phenomenex Gemini, 5µ, 100×21.2 mm)
Eluents:
Low pH chromatography with formic acid:
Solvent A: H$_2$0+0.1% Formic Acid, pH~2.3
Solvent B: CH$_3$CN+0.1% Formic Acid
Low pH Chromatography with Trifluoroacetic Acid:
Solvent A: H$_2$O+0.1% TFA, pH~1.5
Solvent B: CH$_3$CN+0.1% TFA
High pH Chromatography:
Solvent A: H$_2$0+10 mM NH$_4$HCO$_3$+NH4OH, pH=9.2
Solvent B: CH$_3$CN
Make Up Solvent:
MeOH+0.2% Formic Acid (for all chromatography type)
Methods:

According to the analytical trace the most appropriate preparative chromatography type was chosen. A typical routine was to run an analytical LC-MS using the type of chromatography (low or high pH) most suited for compound structure. Once the analytical trace showed good chromatography a suitable preparative method of the same type was chosen. Typical running condition for both low and high pH chromatography methods were:

Flow rate: 24 mL/min
Gradient: Generally all gradients had an initial 0.4 min step with 95% A+5% B.

Then according to analytical trace a 3.6 min gradient was chosen in order to achieve good separation (e.g. from 5% to 50% B for early retaining compounds; from 35% to 80% B for middle retaining compounds and so on)

Wash: 1.2 minute wash step was performed at the end of the gradient
Re-equilibration: 2.1 minutes re-equilibration step was ran to prepare the system for the next run
Make Up flow rate: 1 mL/min Samples were typically dissolved in 100% MeOH or 100% DMSO General Procedures
General Procedure A (SEM Protection)

To the benzimidazole or imidazole substrate in THF (10 vols.), cooled to ° C. under N$_2$, was added the NaH (1.2 mol. eq., 60% dispersion in mineral oil) in portions. After 30 minutes the 2-(trimethylsilyl)ethoxymethyl chloride (1.2 mol eq.) was added and the mixture was stirred overnight at room temperature. The reaction was then quenched with 2M aqueous HCl and then further diluted with EtOAc and water. The product was extracted with EtOAc (×3).

Alternatively, the reaction mixture was quenched with sat. aq. NH$_4$Cl, the THF removed in vacuo, and then the product extracted into CHCl$_3$ (×3).

The combined organic layers were washed with brine and dried (MgSO$_4$). The product was purified by SiO$_2$ chromatography or used directly without further purification where appropriate. Substituted benzimidazoles and imidazoles were typically obtained as a mixture of two regioisomers.

General Procedure B (Boc Protection)

To the amine or heterocycle starting material in THF:H$_2$O (1:1) was added di-tert-butyl dicarbonate (1.5 mol. eq.) followed by 1M aqueous NaOH (3.0 mol. eq). The reaction was stirred at room temperature for an hour. The reaction was then concentrated in vacuo and then diluted with more water. The product was extracted with EtOAc (×3). The combined organic layers were washed with brine and dried (MgSO$_4$). The product was filtered and evaporated to dryness to yield the product.

General Procedure C (Suzuki)

The aryl or heteroaryl bromide (1 mol. eq.), arylboronic acid (or boronic acid pinacol ester) (1.5 mol. eq.), Pd$_2$(dba)$_3$ (0.02 mol. eq.) and S-Phos (0.08 mol. eq.) were added to a microwave reaction tube equipped with a stir bar in air. The flask was evacuated and refilled with nitrogen twice. 1,4-dioxane (20 vol.) and aqueous K$_3$PO$_4$ (2M, 2 mol. eq.) were added by syringe. The tube was sealed and heated in a CEM Discovery microwave at 120° C. for 40 minutes. The mixture was then diluted with H$_2$O/CHCl$_3$, filtered and the aqueous layer was extracted three times with CHCl$_3$ (or CHCl$_3$/$^i$PrOH, 2:1). The combined extracts were dried over (Na$_2$SO$_4$), filtered, and concentrated in vacuo. The residue was then purified by either preparative LCMS or SiO$_2$ chromatography (eluting with dichloromethane/MeOH/NH$_3$ systems, typically dichloromethane/2.0M NH$_3$ in MeOH; 97:3 to 95:5)

General Procedure D (SEM Deprotection)

To a stirred solution of the 2-(trimethylsilyl)ethoxymethyl-protected substrate in MeOH (30-40 vols.), kept at ~15° C. was added, conc. aqueous HCl (2 mL) dropwise. The mixture was stirred at room temperature overnight then concentrated in vacuo. The product was purified by either trituration with Et$_2$O, SiO$_2$ chromatography (eluting with dichloromethane/MeOH/NH$_3$ systems) or preparative LCMS.

General Procedure E (SEM Deprotection)

Whilst being kept at ~15° C. the 2-(trimethylsilyl) ethoxymethyl-protected substrate was dissolved in H$_2$O (3 vols.) and HCl (4M in 1,4-dioxane; 30 vols.). The mixture was stirred at room temperature for 2-3 hours then concentrated to dryness in vacuo. The product was purified by either trituration with Et$_2$O, SiO$_2$ chromatography (eluting with dichloromethane/MeOH/NH$_3$ systems) or preparative LCMS.

General Procedure F (SEM Deprotection)

As for General procedure D, except that the reaction mixture was partitioned between EtOAc and water. The aqueous layer was basified with sat. aqueous NaHCO$_3$ and then extracted with CHCl$_3$/$^i$PrOH (70:30). The organic solution was dried (Na$_2$SO$_4$) and then evaporated in vacuo. The product was purified by either trituration with Et$_2$O, SiO$_2$ chromatography (eluting with dichloromethane/MeOH/NH$_3$ systems) or preparative LCMS.

General Procedure G (Boc Deprotection)

To the BOC-protected substrate was added HCl (4 M in 1,4-dioxane, 0.1 M; 20 vols.) and water (2 vols.). The reaction was stirred at room temperature until complete and then evaporated to dryness to yield the amine as the title compound as the HCl salt. If necessary, the product was further purified by either trituration with Et$_2$O, SiO$_2$ chromatography (eluting with dichloromethane/MeOH/NH$_3$ systems) or preparative LCMS.

General Procedure K (Methanesulfonate Salt Formation)

The substrate was dissolved in THF (20 vols.) to which was added methanesulfonic acid (1M in THF, 1 mol. eq.) while cooling 0° C. The resulting product was collected by filtration. Where the product did not precipitated, the mixture was evaporated to dryness and the product washed with Et$_2$O.

General Purification Methods

Final products were purified by either SiO$_2$ chromatography or mass directed liquid chromatography (LCMS). SiO$_2$ chromatography was typically performed with 1-10% MeOH/dichloromethane or 1-10% MeOH/EtOAc as the mobile phase. For final products with a short retention time, 2M NH$_3$/MeOH was used as the polar eluent. For compounds with higher retention times, EtOAc/hexane was used as the mobile phase. In the case of LCMS, products were isolated as the free base, formate salt or trifluoroacetate salt, depending on the mobile phase employed. Final compounds could be optionally converted to the free base or other salt forms as required.

$^1$H NMR

The $^1$H NMR spectra of final compounds were complex due to the existence of two rotamers. Where possible, signals from each rotamer are quoted separately. Typically, however, signals from different rotamers coincided and therefore were referred to as 'm' (multiplet)

PREPARATION OF INTERMEDIATES

Examples 1 to 47 describe the preparation of synthetic intermediates.

Example 1

1-Dimethylaminomethyl-1H-benzoimidazol-5-ylm-ethyl)-dimethyl-amine

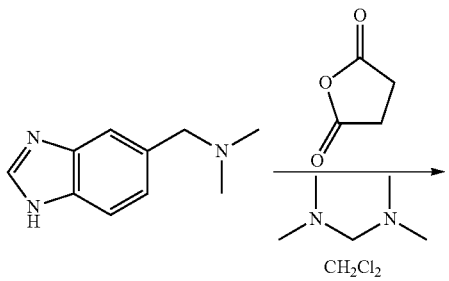

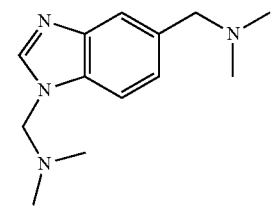

(1H-Benzoimidazol-5-ylmethyl)-dimethyl-amine (500 mg, 2.89 mmol), tetramethyldiaminomethane (324 mg, 3.18 mmol), K$_2$CO$_3$ (438 mg, 3.18 mmol) were stirred in dichloromethane (15 mL) at room temperature. Succinic anhydride (318 mg, 3.18 mmol) was added and stirring continued for an further 1 hour. The mixture was then poured into 15 ml 6N aqueous NaOH and the solution stirred vigorously for 10 min.

The organic layer was isolated and washed with brine, dried (Na$_2$SO$_4$) and concentrated in vacuo to an oil. The oil was dissolved in toluene and filtered. The filtrate was evaporated to dryness, giving the product as a colourless oil (470 mg). $^1$H NMR (400 MHz, CDCl$_3$): 7.92 (1H, s), 7.74 (0.5H, d), 7.70 (0.5H, s), 7.48-7.44 (1H, m), 7.33 (0.5H, dd), 7.23 (0.5H, d), 4.85 (2H, s), 3.57 (2H, d), 2.36 (6H, s), 2.27 (6H, s).

Example 2

Dimethyl-(5-morpholin-4-ylmethyl-benzoimidazol-1-ylmethyl)-amine (as a mixture with the corresponding regiosomer)

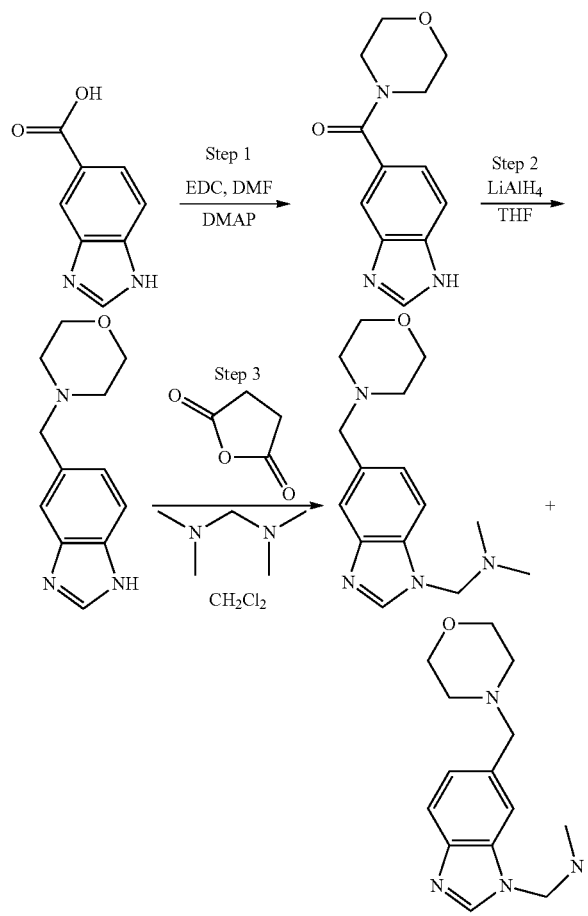

Step 1: To a stirred solution of 1H-benzoimidazole-5-carboxylic acid (10 g, 61.7 mmol), morpholine (7.55 mL, 86.3 mmol), ethyldiisopropylamine (16.1 mL, 92.5 mmol) and 4-dimethylaminopyridine (380 mg, 3.08 mmol) in DMF (60 mL) at room temperature was added EDC (12.4 g, 64.8 mmol) in a single portion. The mixture was stirred at room temperature for 3 days then concentrated in vacuo. The product was purified by recrystallisation from acetonitrile (70 mL), providing (1H-benzoimidazol-5-yl)-morpholin-4-yl-methanone (8.7 g).

Step 2: To a stirred solution of (1H-benzoimidazol-5-yl)-morpholin-4-yl-methanone (1 g, 4.32 mmol) in THF (60 mL) at 0° C. was added LiAlH$_4$ (2M in THF; 4.32 mL, 8.65 mmol) dropwise. The mixture was stirred 0° C. for 2 hours then warmed to room temperature for 2 hours. The mixture was cooled again to 0° C. and then quenched by addition of H$_2$O (0.328 mL), followed by 15% aqueous NaOH solution (0.328 mL) and finally H$_2$O (3×0.328 mL). The mixture was stirred for 1 hour and left to stand overnight. The mixture was diluted with THF, filtered, concentrated in vacuo and purified by SiO2 chromatography to give 5-morpholin-4-ylmethyl-1H-benzoimidazole (838 mg). Step 3 was performed by repeating procedures described for Example 1 then gave the title compound as a mixture of two regioisomers.

Example 3

5,6-Dimethoxy-1-propoxymethyl-1H-benzoimidazole

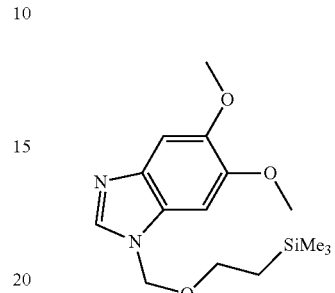

The title compound was prepared by repeating the procedures described in General procedure A (SEM Protection). MS(ESI) m/z 309 (M+H)$^+$

Example 4

(5,6-Dimethoxy-benzoimidazol-1-ylmethyl)-dimethyl-amine

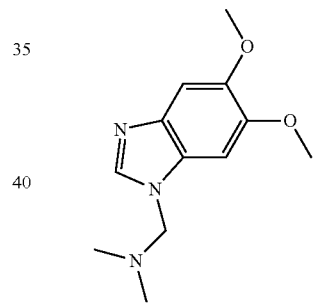

The title compound was prepared by repeating the procedures described for Example 1
$^1$H NMR (400 MHz, CDCl$_3$): 7.81 (1H, s), 7.29 (1H, s), 7.07-6.92 (1H, m), 4.79 (2H, s), 3.96 (6H, s), 2.36 (6H, s).

Example 5

5-(4-Methyl-piperazin-1-ylmethyl)-benzoimidazole-1-carboxylic acid tert-butyl ester (as a mixture with the 6-regioisomer)

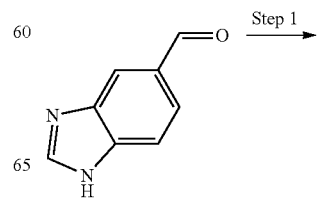

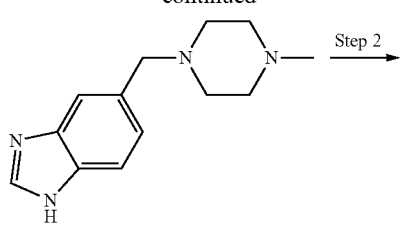

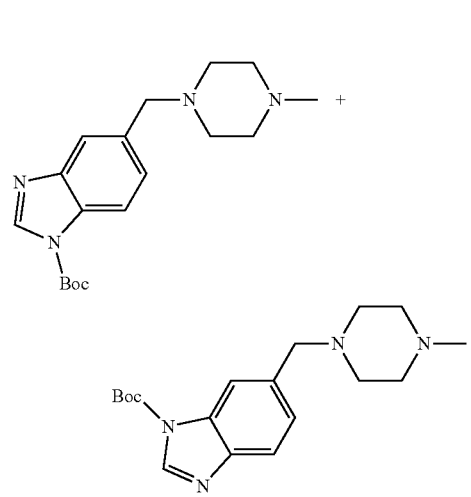

Step 1: 1H-Benzimidazole-5-carbaldehyde (0.50 g, 3.4 mmol), 1-methylpiperazine (0.42 mL, 3.8 mmol) and sodium cyanoborohydride (0.16 mg, 3.8 mmol) in DMF:AcOH (10:1, 10 mL) were stirred overnight at room temperature. The mixture was concentrated in vacuo and then diluted with water and THF (~1:1).

Step 2 was performed, using this solution, by following procedures described in General procedure B (BOC Protection). The title compound was obtained as a mixture of two regioisomers. MS(ESI) m/z 331 (M+H)+.

Example 6

5,7-Difluoro-1-(2-trimethylsilanyl-ethoxymethyl)-1H-benzoimidazole (as a mixture with the corresponding regioisomer)

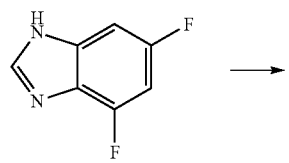

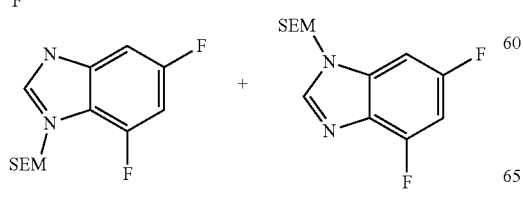

Compound was prepared by following General procedure A (SEM Protection).

Example 7

Imidazol-1-ylmethyl-dimethyl-amine

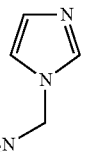

Imidazole (5 g, 73.5 mmol) and dimethylamine hydrochloride (6 g, 73.5 mmol) were stirred in water (12.5 mL) at room temperature. The solution was gradually acidified to pH 5 by the addition of conc. aqueous HCl. A solution of formaldehyde (37% in water; 6.05 mL, 80.8 mmol) was added and the mixture was left to stand for 16 hours. Then it was basified with an excess of 20% KOH solution (~40 mL) and K$_2$CO$_3$ (~6 g) was added to salt out the organics. This mixture was extracted with CHCl$_3$ (3×40 mL) and dried over anhydrous K$_2$CO$_3$. The solution was filtered and the solvent removed under vacuum. The crude (~12 g) was distilled under reduced pressure (bp=63° C. at 0.1 mbar) to yield Imidazol-1-ylmethyl-dimethyl-amine as a colourless oil (6.1 g, 66%). 1H NMR (400 MHz, CDCl$_3$): 7.51 (1H, s), 7.02 (2H, bs), 4.67 (2H, s), 2.29 (6H, s).

Example 8

[1-(1-Dimethylaminomethyl-1H-imidazol-4-ylmethyl)-piperidin-4-yl]-dimethyl-amine

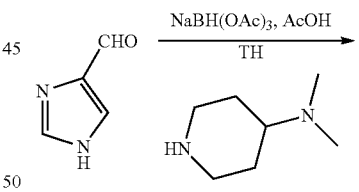

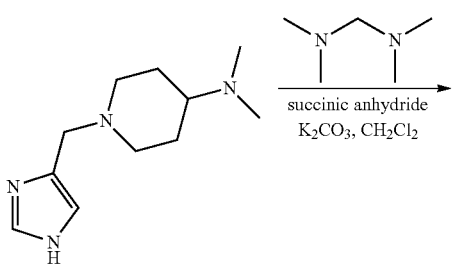

-continued

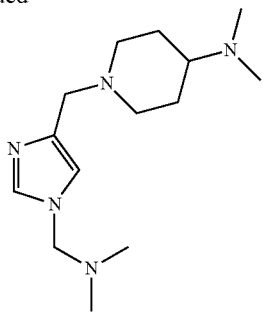

Aldehyde (0.5 g, 1 eq), amine (1.2 eq.), AcOH (1.2 eq.) were stirred in THF (10 ml/mmol) for 2 hours. NaBH(OAc)₃ (4 eq.) was added and stirring continued for 72 hr. Reaction was quenched by addition of excess AcOH/MeOH and stirred for a further 2 hr. Mixture was concentrated in vacuo and passed through an SCX column, eluting with 0.4 M NH₃/MeOH to give product. The crude product was dissolved in AcOEt, filtered and the filtrate evaporated to give the product as a colourless liquid (0.99 g). This was used directly in the next step without further purification.

Repeating procedures described for Example 1 gave the title compound.

Example 9

1-Methyl-4-[1-(2-trimethylsilanyl-ethoxymethyl)-1H-imidazol-4-yl]-1H-pyrazole (as a mixture with the 5-regioisomer)

By following General procedure A (SEM Protection), 4-iodo-1H-imidazole (500 mg, 2.58 mmol) was used to prepare 4-iodo-1-(2-trimethylsilanyl-ethoxymethyl)-1H-imidazole product (462 mg and 305 mg) (as a mixture with the 5-regioisomer).

In a three separate tubes, a suspension of 4-iodo-1-(2-trimethylsilanyl-ethoxymethyl)-1H-imidazole (100 mg, 0.308 mmol), 1-benzyl-4-(4,4,5,5-tetramethyl)-1,3,2-dioxaborolan-2-yl-1H-pyrazole (97 mg, 0.463 mmol) Pd₂(dba)₃ (3.0 mg, 0.003 mmol), 2-dicyclohexylphosphino-2',6'-dimethoxybiphenyl (5.0 mg, 0.012 mmol) in 2M aqueous K₃PO₄ (2 mol. eq.; 0.30 mL) and 1,4-dioxane (0.6 mL) was degassed with nitrogen. Each tube was heated in a microwave reactor at 80° C. for 1 hour. The combined reactions were diluted with H₂O and CHCl₃, filtered and extracted into CHCl₃ (×3). The combined extracts were dried (MgSO₄), filtered and concentrated in vacuo. The product was purified by SiO₂ chromatography providing the title compound (as a mixture with the 5-regioisomer) (88 mg).

Example 10

6-(4-Methyl-piperazin-1-yl)-1-(2-trimethylsilanyl-ethoxymethyl)-1H-benzoimidazole (as a mixture with the 5-regioisomer)

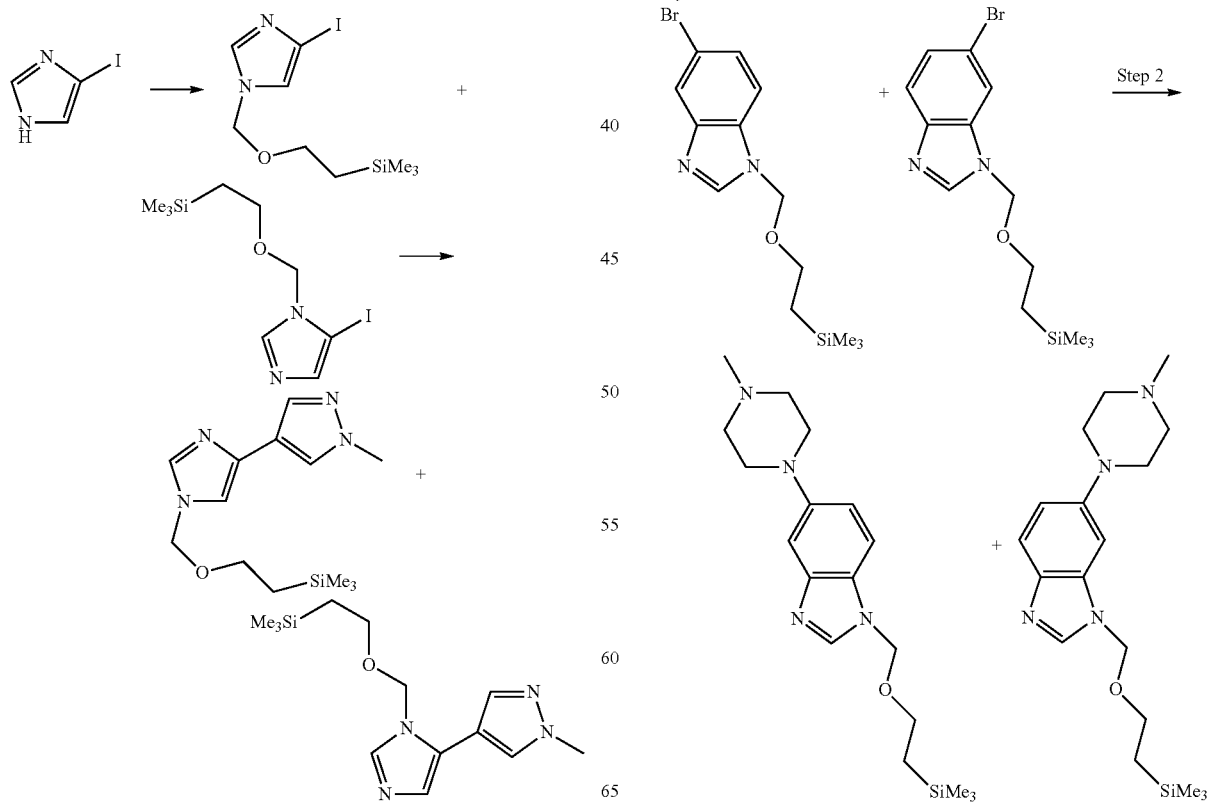

Step 1: By following General procedure A (SEM Protection), 6-bromo-1H-benzoimidazole (3.00 g, 15.2 mmol) was used to give 6-bromo-1-(2-trimethylsilanyl-ethoxymethyl)-1H-benzoimidazole (as a mixture with the 5-regioisomer) (4.47 g).

Step 2. (Buchwald coupling): In a microwave reaction vial a suspension of 6-bromo-1-(2-trimethylsilanyl-ethoxymethyl)-1H-benzoimidazole (500 mg, 1.53 mmol), 1-methyl-piperazine (0.203 mL, 1.83 mmol) $Pd_2(dba)_3$ (0) (14 mg, 0.015 mmol), 2-dicyclohexylphosphino-2',4',6'-triisopropyl-biphenyl (36 mg, 0.076 mmol) and $NaO^tBu$ (206 mg, 2.14 mmol) in 2-methyl-propan-2-ol (1.5 mL) was degassed with nitrogen. The reaction was heated in a microwave reaction at 100° C. for 1 hour. The mixture was diluted with $H_2O$, acidified by the addition of 2M aqueous HCl, stirred with EtOAc and then filtered. The EtOAc layer was then extracted with $H_2O$ (×3). The combined aqueous fractions were neutralized with saturated $NaHCO_3$ solution and then extracted with $CHCl_3/^iPrOH$ (2:1) (×3). The combined extracts were dried ($MgSO_4$), filtered and concentrated in vacuo. The product was purified by $SiO_2$ chromatography providing the title compound (387 mg).

Example 11

Dimethyl-{1-[3-(2-trimethylsilanyl-ethoxymethyl)-3H-benzoimidazol-5-yl]-piperidin-4-yl}-amine (as a mixture with the 6-regioisomer)

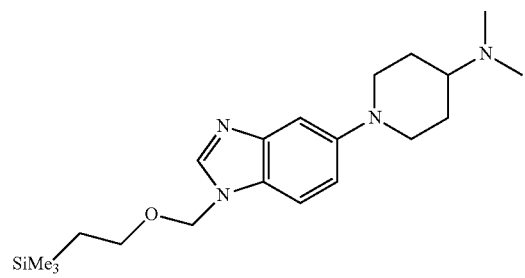

+

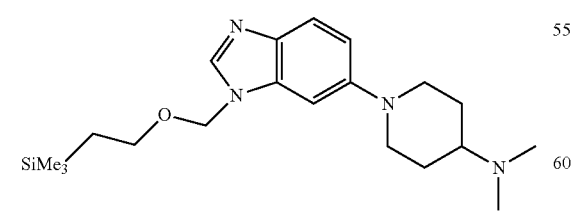

The title compound was prepared by following procedures described for Example 10. $^1H$ NMR (400 MHz, $CDCl_3$): 7.91 (0.5H, s), 7.85 (0.5H, s), 7.68 (0.5H, d), 7.42 (0.5H, d), 7.34 (0.5H, d), 7.11-6.99 (1.5H, m), 5.52-5.46 (2H, m), 3.74 (2H, t), 3.57-3.45 (2H, m), 2.87-2.70 (2H, m), 2.70-2.53 (1H, m), 2.49 (6H, s), 2.17-2.06 (2H, m), 1.90-1.74 (2H, m), 0.97-0.84 (2H, m), −0.04 (9H, s).

Example 12

4-[1-(2-Trimethylsilanyl-ethoxymethyl)-1H-benzoimidazol-5-yl]-piperazine-1-carboxylic acid-tert-butyl ester (as a mixture with the 6-regioisomer)

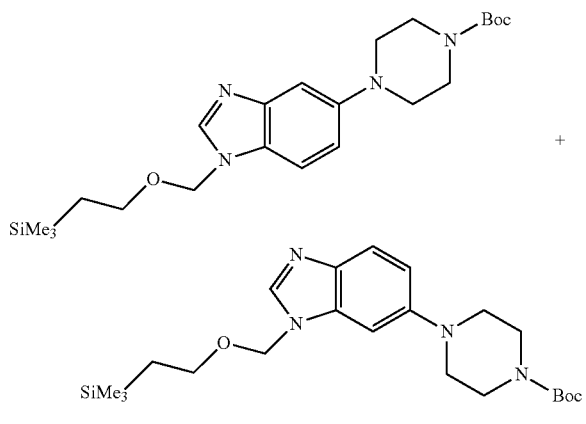

The title compound was obtained by following the procedures described in Example 10. MS(ESI) m/z 433.2 $(M+H)^+$ Example 13

{1-[1-(2-Trimethylsilanyl-ethoxymethyl)-1H-benzoimidazol-5-yl]-pyrrolidin-3-yl}-carbamic acid tert-butyl ester (as a mixture with the 6-regioisomer)

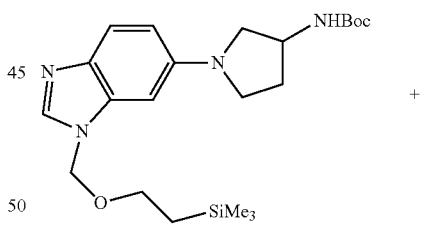

+

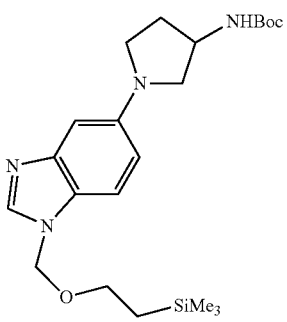

The title compound was obtained by following the procedures described in Example 10. MS(ESI) m/z 433.2 (M+H)⁺

Example 14

4-[1-(2-Silanyl-ethoxymethyl)-1H-benzoimidazol-5-yl]-[1,4]diazepane-1-carboxylic acid tert-butyl ester (as a mixture with the 6-regioisomer)

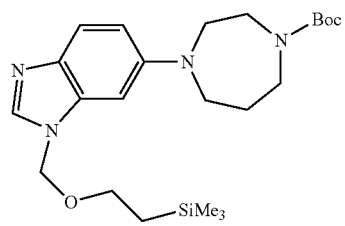

+

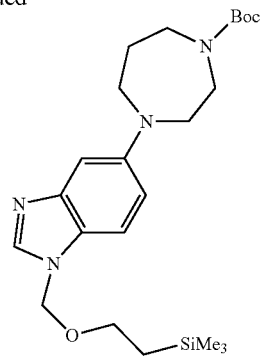

The title compound was obtained by following the procedures described in Example 10. MS(ESI) m/z 447.2 (M+H)⁺

Example 15

(1-Dimethylaminomethyl-1H-benzoimidazol-4-ylmethyl)-dimethyl-amine (as a mixture with the 7-regioisomer)

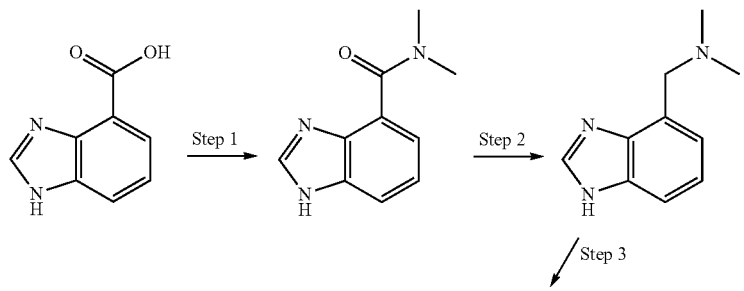

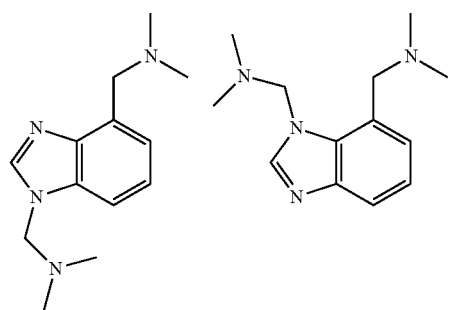

Step 1: To a stirred solution of 1H-benzoimidazole-4-carboxylic acid hydrochloride (1 g, 5.04 mmol), dimethylamine (2M in THF; 3.78 mL, 7.55 mmol) and ethyldiisopropylamine (3.51 mL, 20.1 mmol) in DMF (5.0 mL) at room temperature was added O-benzotriazole-N,N,N',N'-tetramethyl-uronium-hexafluoro-phosphate (1.95 g, 5.14 mmol) in a single portion. The mixture was stirred at room temperature overnight then concentrated in vacuo. The product was purified by SiO$_2$ chromatography followed by trituration with Et$_2$O providing 1H-benzoimidazole-4-carboxylic acid dimethylamide (730 mg).

Step 2 and 3: Title compound was prepared by repeating procedures described for Example 2, step 2.

Example 16

4-(2-Trimethylsilanyl-ethoxymethoxy)-1-(2-trimethylsilanyl-ethoxymethyl)-1H-benzoimidazole (as a mixture with the 7-regioisomer)

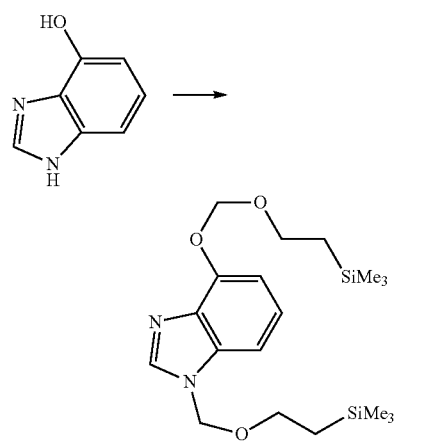

To a stirred suspension of 1H-benzoimidazol-4-ol (440 mg, 3.28 mmol) in THF (13 mL) at room temperature was added NaH (60% dispersion in mineral oil; 276 mg, 6.89 mmol) in 3 portions over 15 min. The mixture was stirred at room temperature for 1.5 hours before it was heated to 65° C. for 30 min. The THF was removed and replaced with DMF (10 mL) and the mixture was warmed to 65° C. for 30 min. The mixture was cooled to 10° C., 2-(trimethylsilyl)ethoxymethyl chloride (1.19 mL, 6.72 mmol) was added dropwise and the mixture was stirred at room temperature overnight. H$_2$O and Et$_2$O were added, the mixture was filtered and the phases separated. The aqueous phase was extracted into Et$_2$O (×3), dried (MgSO$_4$) and concentrated in vacuo. The product was purified by SiO$_2$ chromatography and followed by trituration with Et$_2$O to provide the title compound (177 mg).

Example 17

Methyl-{1-[1-(2-trimethylsilanyl-ethoxymethyl)-1H-benzoimidazol-4-yl]-ethyl}-carbamic acid tert-butyl ester and methyl-{1-[3-(2-trimethylsilanyl-ethoxymethyl)-3H-benzoimidazol-4-yl]-ethyl}-carbamic acid tert-butyl ester Step 1

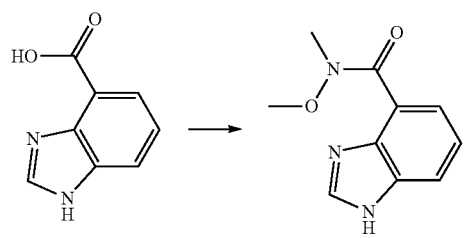

To a stirred solution of 1H-benzoimidazole-4-carboxylic acid hydrochloride (2.0 g, 10.1 mmol), N,O-dimethylhydroxylamine hydrochloride (1.47 g, 15.1 mmol) and ethyldiisopropylamine (7.02 mL, 40.3 mmol) in DMF (10 mL) at room temperature was added O-benzotriazole-N,N,N',N'-tetramethyl-uronium-hexafluoro-phosphate (3.90 g, 10.3 mmol) in a single portion. The mixture was stirred at room temperature overnight then concentrated in vacuo. Purification by SiO$_2$ chromatography followed by trituration with EtOAc provided 1H-benzoimidazole-4-carboxylic acid methoxy-methyl-amide (945 mg).

Step 2

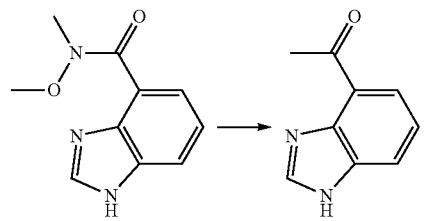

To a stirred solution of 1H-benzoimidazole-4-carboxylic acid methoxy-methyl-amide (742 mg, 3.62 mmol) in THF (36 mL) at −78° C. was added MeLi (1.6M; 2.49 mL, 3.98 mmol) dropwise. The mixture was stirred at −78° C. for 2 hours before an additional 1.0 mol. eq. MeLi (2.3 mL) was added dropwise. The mixture was stirred at −78° C. for a further 2 hours before saturated aqueous NH$_4$Cl solution was added and the mixture warmed to room temperature. Enough water was added to dissolve all solids and the phases were separated. The aqueous phase was extracted into CHCl$_3$ (×3), dried and concentrated in vacuo to give a white solid. Trituration with EtOAc (5 mL) followed by collection by filtration and washing with 4:1 Et₂O/EtOAc (5 mL) provided 1-(1H-benzoimidazol-4-yl)-ethanone (487 mg).

Step 3

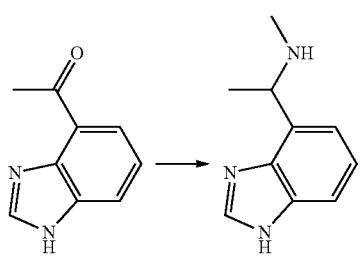

A solution of 1-(1H-benzoimidazol-4-yl)ethanone (72 mg, 0.449 mmol), methylamine (2M in THF; 2.25 mL, 4.50 mmol) and HCl in 1,4-dioxane (4M; 0.337 mL, 1.35 mmol) in MeOH (2.7 mL) was stirred at room temperature for 3 days before it was cooled to 0° C. and NaBH₄ (20 mg, 0.539 mmol) was added in a single portion. The mixture was stirred at room temperature overnight before it was diluted with MeOH, stirred for 1 hour and concentrated in vacuo. The residue was purified by SiO₂ chromatography providing [1-(1H-benzoimidazol-4-yl)-ethyl]-methyl-amine (46 mg).

Step 4

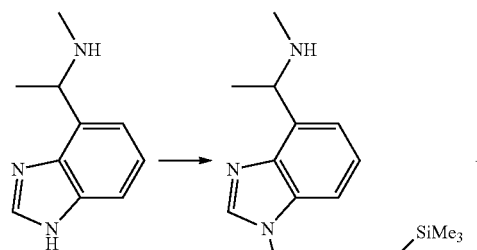

By following General procedure A (SEM Protection), [1-(1H-benzoimidazol-4-yl)-ethyl]-methyl-amine (167 mg, 1.25 mmol) was used to give the SEM-protected product (222 mg) (as a mixture of two regioisomers).

Step 5

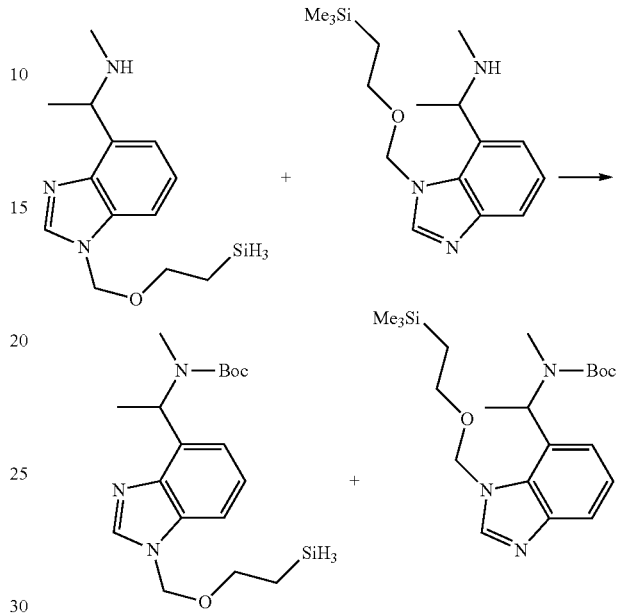

By following General procedure B (BOC Protection), the title compound was obtained (220 mg, 0.727 mmol).

Example 18

[2-(1-Diethoxymethyl-1H-benzoimidazol-5-yloxy)-ethyl]-dimethyl-amine (as a mixture with the 6-regioisomer)

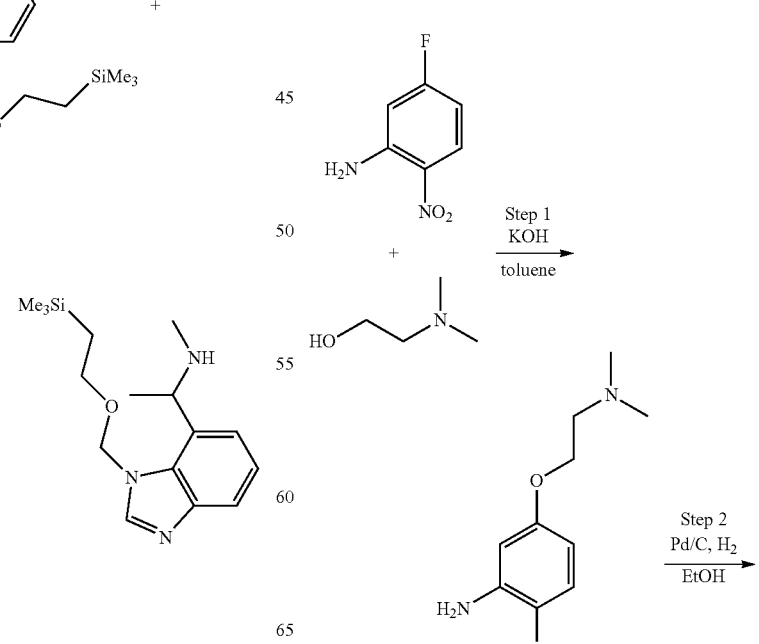

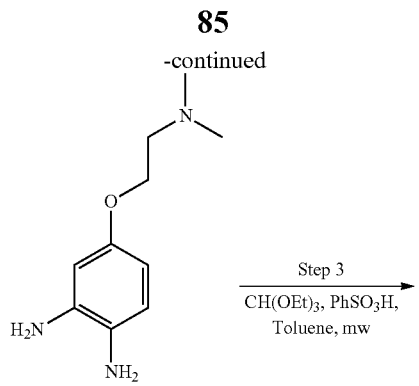

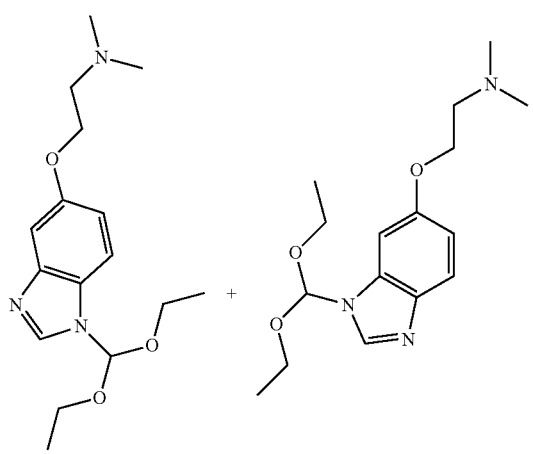

Step 1: 3-Fluoro-6-nitroaniline (0.7 g, 4.48 mmol) and N,N-dimethylethanolamine (1.34 mL, 13.45 mmol) were dissolved in toluene (5 mL). This solution was cooled at 0° C. and finely ground KOH (1.258 g, 22.4 mmol) was added to the stirring mixture. The reaction mixture was stirred for 16 hours at room temperature, diluted with $H_2O$ (30 mL) and then extracted with $CHCl_3$ (3×25 mL). The combined organics were dried ($Na_2SO_4$), filtered and the solvent was removed in vacuo. Purification by $SiO_2$ chromatography (0% to 10% 2.0M $NH_3$ in MeOH/dichloromethane) gave 5-(2-dimethylamino-ethoxy)-2-nitro-phenylamine as a dark oil (0.665 g, 90%). MS(ESI) m/z 226.0 $(M+H)^+$ Step 2: 5-(2-Dimethylamino-ethoxy)-2-nitro-phenylamine (0.85 g, 3.77 mmol) was dissolved in EtOH and shaken under an atmosphere of $H_2$ for 6 hours. The catalyst was removed by filtration. Evaporation in vacuo gave 4-(2-Dimethylamino-ethoxy)-benzene-1,2-diamine as a dark yellow oil (0.665 g, 90%). MS(ESI) m/z 196.0 $(M+H)^+$ Step 3: Starting from 4-(2-dimethylamino-ethoxy)-benzene-1,2-diamine (0.36 g, 1.84 mmol), the title compound was obtained as a mixture of two regioisomers by following procedures described for Example 102 (method 1) step 3. Except that the reaction was heated in a microwave oven for 30 minutes at 120° C. to reach completion. The solvent was then completely removed under vacuum and the product used directly without further purification. MS(ESI) m/z 206.0 (M —$CH(OEt)_2)^+$.

Example 19

1-Diethoxymethyl-5-(2,2-dimethyl-[1,3]dioxolan-4-ylmethoxy)-1H-benzoimidazole

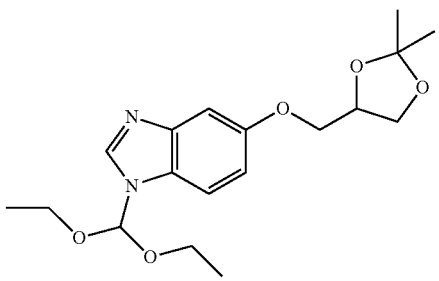 [SMILES: CCOC(OCC)n1cnc2cc(OCC3COC(C)(C)O3)ccc21]

Compound was prepared by repeating procedures described for Example 18. MS(ESI) m/z 249.0 (M —CH$(OEt)_2)^+$.

Example 20

4-[(3H-Benzoimidazole-5-carbonyl)-amino]-piperidine-1-carboxylic acid tert-butyl ester (as a mixture with the 6-regioisomer)

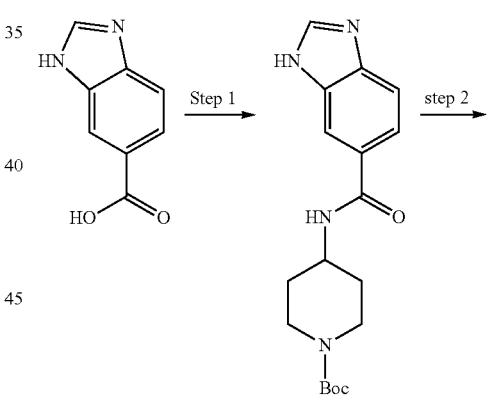

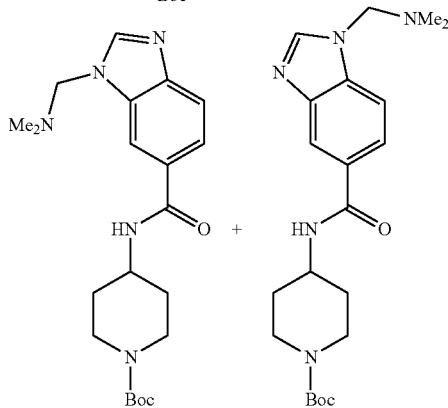

Step 1 (Amide Coupling): 5-Benzimidazole carboxylic acid (0.50 g, 3.1 mmol), EDC.HCl (0.72 g, 3.7 mmol) and HOBt (0.58 mg, 3.7 mmol) in dichloromethane (11 mL) was stirred at room temperature for 10 minutes. 4-Amino-piperidine-1-carboxylic acid tert-butyl ester (0.70 g, 3.4 mmol) and DIPEA (0.59 ml, 3.4 mmol) were added and the mixture was stirred for 3 hours. The mixture was then partitioned between EtOAc and sat. aqueous $Na_2CO_3$. The layers were separated and the aqueous layer was extracted with EtOAc (×3). The combined organic layers were washed with water, brine and dried ($MgSO_4$). The solvent was evaporated in vacuo to give 3H-benzoimidazole-5-carboxylic acid (1-methyl-piperidin-4-yl)-amide.

Step 2: The title compound was then obtained by repeating procedures described for Example 1. MS(ESI) m/z 343 $(M-H)^+$

Example 21

4-(3-Dimethylaminomethyl-3H-benzoimidazole-5-carbonyl)-piperazine-1-carboxylic acid tert-butyl ester (as a mixture with the 6-regioisomer)

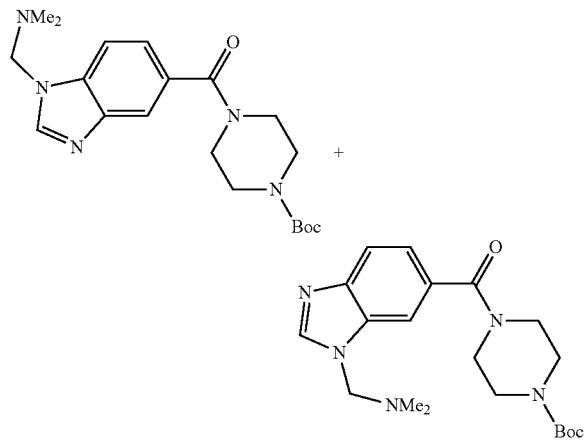

The compound was prepared by repeating procedures described for Example 20.

Example 22

5'-[(tert-butoxycarbonyl-ethyl-amino)-methyl]-4'-methyl-[2,3']bipyridinyl-4-carboxylic acid methyl ester

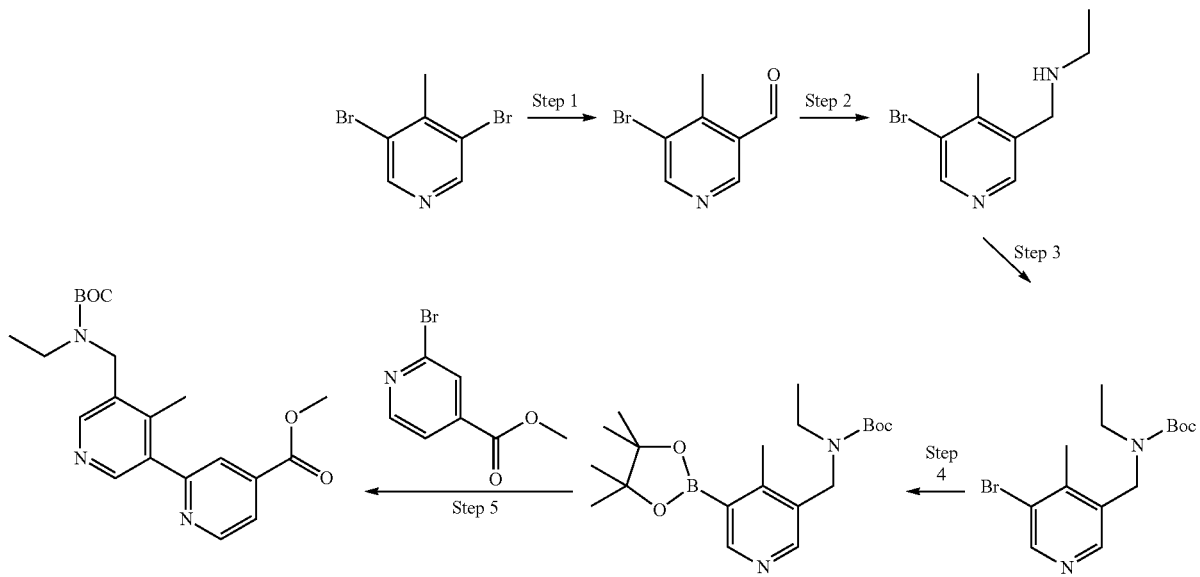

Step 1: 2,6-Dibromotoluene (9.8 g, 39 mmol) in THF (300 mL) was stirred under $N_2$ and was then cooled to −100° C. (ether/liquid $N_2$). n-BuLi (16.4 mL, 41 mmol, 2.5 M in hexane) was then added drop wise and after stirring for 5 minutes DMF (4.5 mL, 58.6 mmol) was added. The reaction was stirred for a further 20 minutes and then for an hour at −78° C. The reaction was quenched with saturated aqueous $NH_4Cl$ and allowed to warm up to room temperature. The reaction was diluted with water and the pH adjusted to pH 7-8 with sat. aqueous $NaHCO_3$. The mixture was evaporated in vacuo to remove the THF, and the product was then extracted with $Et_2O$ (×3). The combined organic layers were washed with brine and dried ($MgSO_4$). The product was filtered and evaporated on vacuo to give 5-bromo-4-methyl-pyridine-3-carbaldehyde as a colourless solid which was used without further purification.

Step 2. To the 5-bromo-4-methyl-pyridine-3-carbaldehyde (6.7 g, 16.9 mmol) in dry MeOH (150 mL) at room temperature, was added ethylamine (51 mL, 101 mmol; 2 M solution in MeOH) over approx 30 minutes. The mixture was allowed to stir for another 30 minutes in order to allow imine formation.

To a solution of $NaCNBH_3$ (0.80 g, 18.5 mmol) in MeOH (30 mL) was added anhydrous $ZnCl_2$ (1.2 g, 9.1 mmol), at room temperature and the mixture stirred for 20 minutes. The resulting $NaCNBH_3/ZnCl_2$ solution was then added drop wise to the pre-formed imine solution. The combined mixture was then acidified with HCl (4 M in 1,4-dioxane) to pH 4 and stirred overnight at room temperature. The reaction was evaporated to dryness and partitioned between water and EtOAc. The aqueous layer was adjusted to pH ~9 with $NaHCO_3$ (sat., aq.) and then extracted with EtOAc (×3). The combined organic layers were washed with water, brine, dried (MgSO₄) and then evaporated to dryness. Purification by SiO₂ chromatography have (5-bromo-4-methyl-pyridin-3-yl-methyl)-ethyl-amine.

Step 3: Compound was prepared by following General procedure B (BOC Protection)

Step 4: To (5-bromo-4-methyl-pyridin-3-ylmethyl)-ethyl-carbamic acid tert-butyl ester (8.0 g, 19 mmol.) was added the bis(pinacolato)diboron (7.4 g, 29 mmol), KOAc (5.7 g, 58 mmol) and anhydrous DMSO (30 mL), under N₂. The mixture was degassed and then the [1,1'-bis(diphenylphosphino)ferrocene]dichloropalladium(II) (0.71 g, 0.97 mmol) was added. The reaction was heated to 100° C. until complete. The reaction was worked up by adding water and extracting with diethyl ether (×5). The combined organic layers were washed with water, brine, dried (MgSO₄) and then evaporated to dryness. Purification by SiO₂ chromatography gave ethyl-[4-methyl-5-(4,4,5,5-tetramethyl-[1,3,2]dioxaborolan-2-yl)-pyridin-3-ylmethyl]-carbamic acid tert-butyl ester (3.3 g).

Step 5: Ethyl-[4-methyl-5-(4,4,5,5-tetramethyl-[1,3,2]dioxaborolan-2-yl)-pyridin-3-ylmethyl]-carbamic acid tert-butyl ester (1.5 g, 5.1 mmol) and 2-bromo-isonicotinic acid methyl ester (1.3 g, 6.1 mmol) were suspended in 1,4-dioxane (25 mL). To the mixture was added K₃PO₄.3H₂O (0.90 g, 4.52 mmol, 1 M in water). The reaction was degassed with N₂ and PdCl₂(PPh₃)₂ (72 mg, 0.1 mmol) was added. The reaction was heated to 60° C. for 3 hours. The mixture was then diluted with water and neutralised to pH 7. The mixture was concentrated in vacuo, to remove organic solvent, and then partitioned between water and EtOAc. The aqueous layer was extracted with EtOAc (×3). The combined organic layers were washed with water, brine, dried (MgSO₄) and then evaporated to dryness. Purification by SiO₂ chromatography gave the title compound (1.36 g). m/z 386 (M+H)⁺

Example 23

2-Isoquinolin-4-yl-isonicotinic acid methyl ester

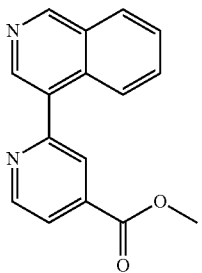 [SMILES: COC(=O)c1ccnc(-c2cncc3ccccc23)c1]

To 2-bromonicotinic acid methyl ester (30 g, 111 mmol), isoquinoline-4-boronic acid (20 g, 92.6 mmol), 1,4-dioxane (770 mL) and 3M aqueous K₃PO4 (35 mL, 105 mmol) were stirred together. The vessel was evacuated and flushed with nitrogen several times to remove oxygen. PdCl₂(PPh₃)₂ (1.62 g, 1.85 mmol) was added and the vessel and the stirred mixture was heated at 70° C. overnight. The mixture was then cooled, concentrated in vacuo to 50% of original volume and filtered. The filtrate was concentrated in vacuo and the resulting residue stirred in butylmethylether (220 mL). The mixture was then filtered to remove solid. The filtrate was cooled in an ice bath and stirred for 1 hour after which time the product precipitated as a white solid. The product was collected and dried to give isoquinolin-4-yl-isonicotinic acid methyl ester (4.97 g, 16%) (combined from two crops) [M+H]⁺:264.7.

Example 24

5'-[(tert-Butoxycarbonyl-ethyl-amino)-methyl]-[2,3']bipyridinyl-4-carboxylic acid methyl ester

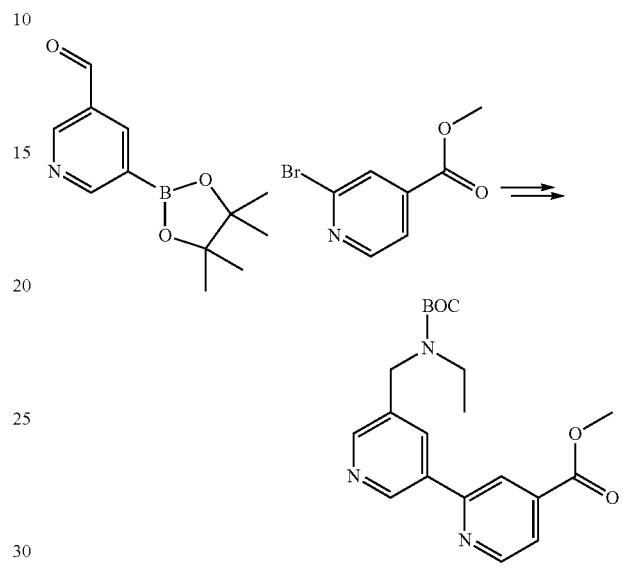

By repeating procedures described for Example 23, 2-bromonicotinic acid methyl ester and 5-formyl pyridine-3-boronic acid pinacol ester were used to give 5'-formyl-[2,3']bipyridinyl-4-carboxylic acid methyl ester.

The title compound was then obtained by repeating procedures described for Example 22 step 2 (reductive amination) followed by General procedure B (BOC Protection) MS(ESI) m/z 372 (M+H)⁺

Example 25

Method 1

2-Bromo-N-methoxy-N-methyl-isonicotinamide

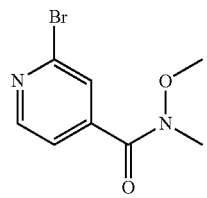

2-Bromo-isonicotinic acid (0.5 g, 2.47 mmol) was dissolved in dry THF (10 mL). 2-Chloro-4,6-dimethoxy[1,3,5]triazine (0.77 g, 4.4 mmol) and diisopropylethylamine (0.96 g, 0.74 mmol) were added and the solution was stirred for 1 hour after which N,O-dimethyl hydroxylamine hydrochloride (0.241 g, 2.47 mmol) was added. The mixture was stirred for a further 16 hours at room temperature and then diluted with water (15 mL). The aqueous mixture was then extracted with EtOAc (3×10 mL). The combined organics were washed successively with a saturated aqueous Na₂CO₃, 1N aqueous HCl and then brine. The organic phase was dried (Na₂SO₄) and then evaporated to dryness. Purification by SiO₂ chromatography (eluting with EtOAc/hexane; 2:1) gave a product which was then suspended in Et₂O. The insoluble material was removed by filtration and the filtrate was evaporated in vacuo to give 2-bromo-N-methoxy-N-methyl-isonicotinamide (0.342 g, 56%). MS(ESI) m/z 244.9 (M+H)⁺

Example 25

Method 2

To 2-bromoisonicotinic acid, (25.2 g, 124 mmol), HOBt (20.2 g, 149 mmol) and O,N-dimethyl-hydroxylamine hydrochloride (14.6 g, 149 mmol) in DMF (150 mL) at 0° C., was added diisopropylethyalamine (26.0 mL, 149 mmol). EDC (28.6 g, 149 mmol) was then added and the mixture stirred at room temperature for 1 hour. The mixture was then poured into ice cold water (500 mL) and the resulting solution extracted with EtOAc (3×150 mL). The combined organic fraction was were washed with water (2×200 mL), 0.5 M HCl (200 mL), sat. NaHCO₃ solution, brine (200 mL) and then dried (MgSO₄). The solvent was evaporated in vacuo to give 2-bromo-N-methoxy-N-methyl-isonicotinamide (23 g, 75%)

The following six compounds were prepared by repeating procedures described for Example 25 method 1

| Ex. | Structure | MS(ESI) m/z |
|---|---|---|
| 26 | 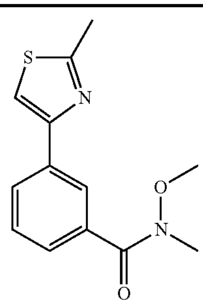 | 263.1 [M + H]⁺ |
| 27 | 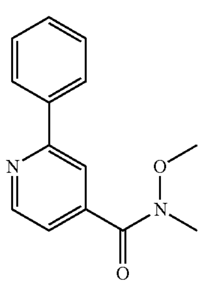 [SMILES: CON(C)C(=O)c1ccnc(-c2ccccc2)c1] | 243.1 [M + H]⁺. |
| 28 | 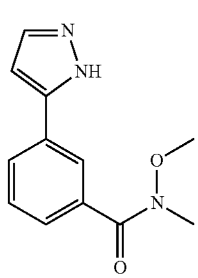 [SMILES: CON(C)C(=O)c1cccc(-c2ccn[nH]2)c1] | 232.1 [M + H]⁺ |
| 29 | | 248.0 [M + H]⁺ |
| 30 | | 325.9 [M + H]⁺ |
| 31 | | 200.0 [M + H]⁺ |

Example 26

N-Methoxy-N-methyl-3-(2-methyl-thiazol-4-yl)-benzamide

Example 27

N-Methoxy-N-methyl-2-phenyl-isonicotinamide

Example 28

N-Methoxy-N-methyl-3-(2H-pyrazol-3-yl)-benzamide

Example 29

Example
N-Methoxy-N-methyl-3-thiophen-2-yl-benzamide

Example 30

3-Chloro-5-iodo-N-methoxy-N-methyl-benzamide

Example 31

3-Chloro-N-methoxy-N-methyl-benzamide

Example 32

2-(2,3-Difluoro-6-methoxy-phenyl)-N-methoxy-N-methyl-isonicotinamide

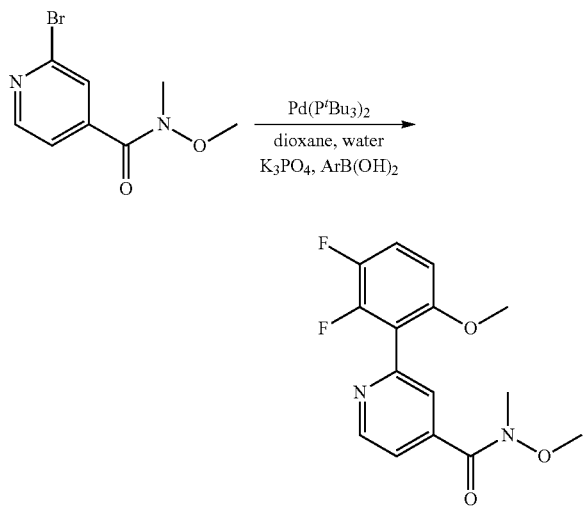

A flask containing 2-bromo-N-methoxy-N-methyl-isonicotinamide (Example 25, using method 2) (3.0 g, 12.2 mmol) 2,3-difluoro-6-methoxyphenylboronic acid (4.6 g, 24.4 mmol)) and 2M aqueous $K_3PO_4$ (15 mL, 30.6 mmol) in 1,4-dioxane (40 mL) was successively evacuated and flushed with nitrogen. $Pd(P^tBu_3)_2$ (268 mg, 0.48 mmol) was then added and the mixture heated at 90° C. for 2 hours. The mixture was cooled, concentrated in vacuo and then partitioned between EtOAc and sat. aqueous $NaHCO_3$ solution. The organic layer was washed with brine, dried ($MgSO_4$) and concentrated in vacuo. Purification by $SiO_2$ chromatography (eluting with 30-100% EtOAc/hexane) gave the title compound (0.856 g, 23%). MS(ESI) m/z 309 $(M+H)^+$ The following compounds were prepared by repeating procedures described for Example 32. Additional comments with regard to methods are highlighted where appropriate

| Ex. | structure | | Additional comments |
|---|---|---|---|
| 33 | 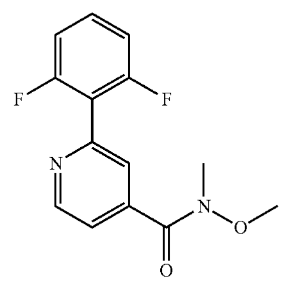 [SMILES: CON(C)C(=O)c1ccnc(-c2c(F)cccc2F)c1] | 2-(2,6-Difluoro-phenyl)-N-methoxy-N-methyl-isonicotinamide | |
| 34 | 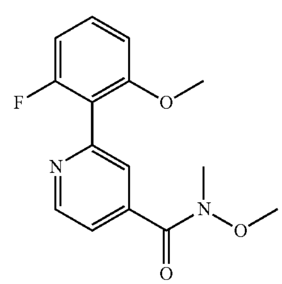 [SMILES: COc1cccc(F)c1-c1cc(C(=O)N(C)OC)ccn1] | 2-(2-Fluoro-6-methoxy-phenyl)-N-methoxy-N-methyl-isonicotinamide | |
| 35 | 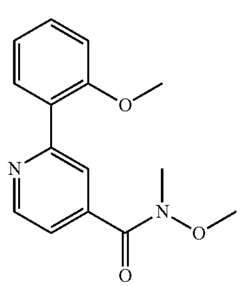 [SMILES: COc1ccccc1-c1cc(C(=O)N(C)OC)ccn1] | N-Methoxy-2-(2-methoxy-phenyl)-N-methyl-isonicotinamide | used $Pd_2(dba)_3$ instead of $Pd(P^tBu_3)_2$ for Example 35 |

| Ex. | structure | | Additional comments |
|---|---|---|---|
| 36 | 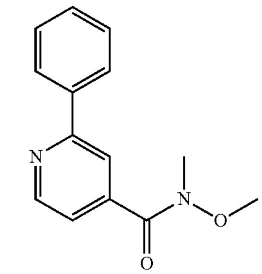 [SMILES: CON(C)C(=O)c1ccnc(-c2ccccc2)c1] | N-Methoxy-N-methyl-2-phenyl-isonicotinamide | |
| 37 | 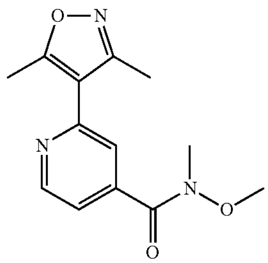 | 2-(3,5-Dimethyl-isoxazol-4-yl)-N-methoxy-N-methyl-isonicotinamide | used Pd$_2$(dba)$_3$ instead of Pd(P$^t$Bu$_3$)$_2$ for Example 37 |

Example 38

N-Methoxy-N-methyl-2-(4-tributylsilanyloxymethyl-phenyl)-isonicotinamide

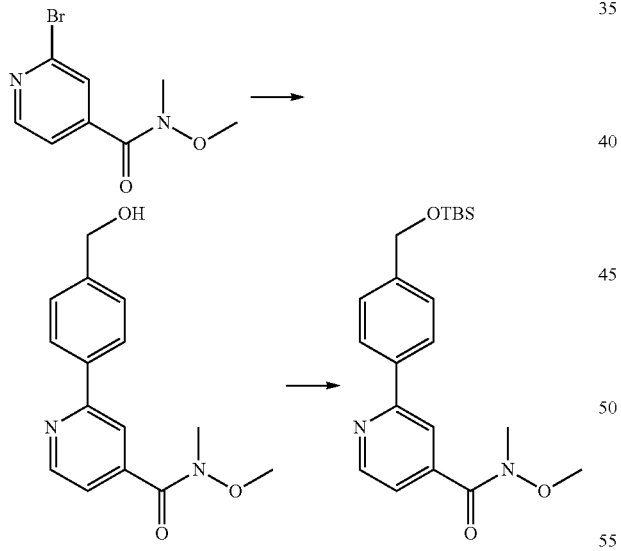

Step 1

By following procedures described in Example 32, starting from 2-bromo-N-methoxy-N-methyl-isonicotinamide and 4-hydroxymethyl phenyl boronic acid [but using Pd$_2$(dba)$_3$ instead of Pd(P$^t$Bu$_3$)$_2$], step 1 gave 2-(4-hydroxymethyl-phenyl)-N-methoxy-N-methyl-isonicotinamide.

To a solution of 2-(4-hydroxymethyl-phenyl)-N-methoxy-N-methyl-isonicotinamide (206 mg, 0.76 mmol) in dichloromethane (1.5 mL) was added imidazole (57 mg, 0.83 mmol) and TBSCl (126 mg, 0.83 mmol). After stirring for 5 hours, the mixture was partitioned between dichloromethane and water. The organic layer was dried (MgSO$_4$), evaporated and the residue purified by SiO$_2$ chromatography (eluting with 30-60% EtOAc/hexanes) to give the title compound (264 mg).

Example 39

6-Chloro-2'-methoxy-biphenyl-3-carboxylic acid methoxy-methyl-amide

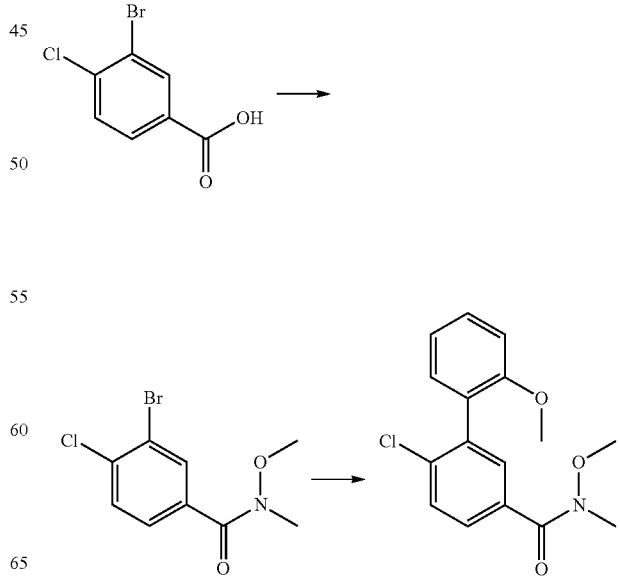

Step 1

By following procedures described for Example 17 step 1, 3-bromo-4-chloro-benzoic acid (5.0 g, 21.2 mmol) was used to give 3-bromo-4-chloro-N-methoxy-N-methyl-benzamide (5.86 g).

Step 2

The title compound was prepared by repeating the procedure described for Examples 38 but using Pd(PPh₃)₄ instead of Pd(P$^t$Bu₃)₂ and 2M Na₂CO₃ instead of 2M K₃PO₄.

Example 40

6-Cyano-2'-methoxy-biphenyl-3-carboxylic acid methyl ester

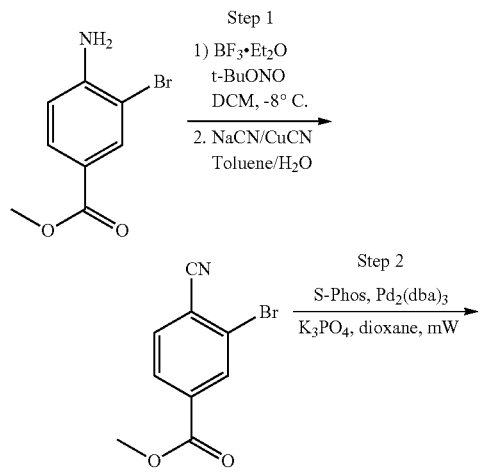

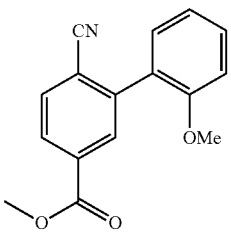

Step 1: Methyl 4-amino-3-bromo benzoate (0.5 g, 2.17 mmol) was dissolved in dry dichloromethane (5 mL) and the solution was cooled to −10° C. A solution of BF₃·Et₂O (0.41 ml, 3.26 mmol) followed by tert-butyl nitrite (0.32 mL, 2.72 mmol) was added dropwise to the mixture. The very dense solution was allowed to reach room temperature and was then diluted with hexanes (10 mL). The resulting solid was collected by filtration and washed again with hexanes. This was rapidly transferred in a flask containing a solution of NaCN (0.32 g, 6.52 mmol) and CuCN (0.233 g, 2.61 mmol) in H₂O/toluene (2:1; 3 mL) at 5° C. and stirred at this temperature for 30 min. The mixture was then allowed to reach room temperature and finally it was heated at 60° C. for a further 25 min. The solution was then cooled to room temperature and then partitioned between water (15 mL) and EtOAc (15 mL). The organic phase was washed with brine, dried (Na₂SO₄) and solvent was removed in vacuo. Recrystallisation from hexanes/EtOAc gave 3-bromo-4-cyano-benzoic acid methylester as a grey solid (0.213 g, 41%). ¹H NMR (400 MHz, d₆-Acetone): 8.35 (1H, d), 8.17 (1H, dd), 8.05 (1H, d), 3.97 (3H, s).

Step 2: By following procedures described in General procedure C (Suzuki), 3-bromo-4-cyano-benzoic acid methyl-ester (0.205 g, 0.85 mmol) and 2-methoxy phenyl boronic acid (0.156 g, 1.02 mmol) were used to obtain the title compound (0.170 g, 62%), following SiO₂ chromatography (hexanes/EtOAc=6:1). MS(ESI) m/z 268.0 (M+H)⁺

Example 41

3-{5-[(tert-Butoxycarbonyl-ethyl-amino)-methyl]-pyridin-3-yl}-4-cyano-benzoic acid methyl ester

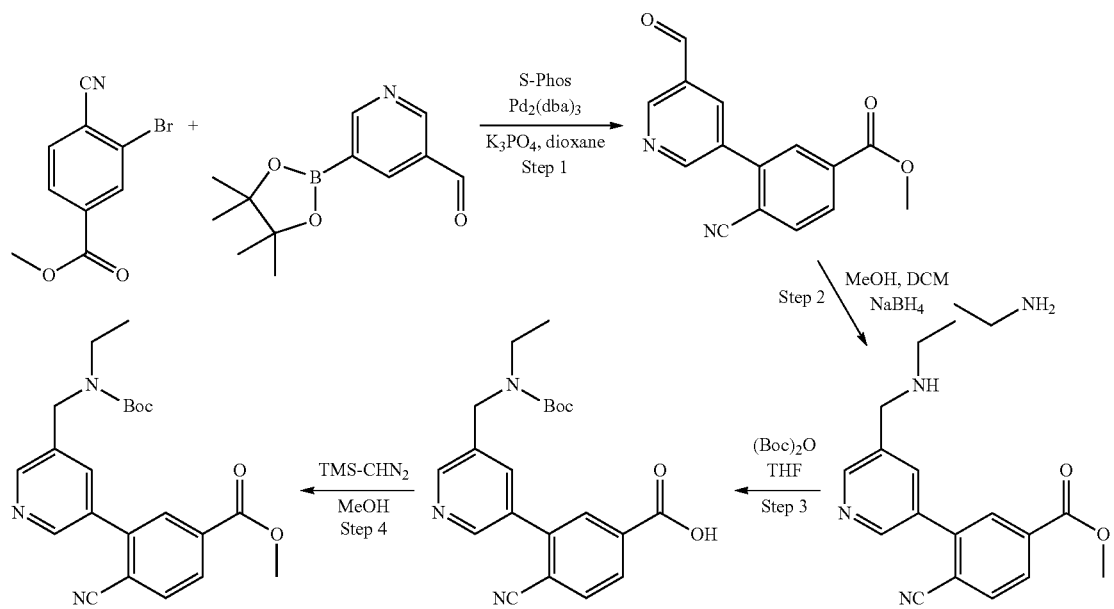

Step 1: By following the general procedure for General procedure C (Suzuki), 3-bromo-4-cyano-benzoic acid methylester (0.5 g, 2.08 mmol) and 5-formyl pyridine-3-pinacol borane (0.583 g, 2.5 mmol) were used to give 4-cyano-3-(5-formyl-pyridin-3-yl)-benzoic acid methyl ester (0.455 g, 80%). MS(ESI) m/z 267.0 (M+H)⁺.

Step 2: 4-Cyano-3-(5-formyl-pyridin-3-yl)-benzoic acid methyl ester (0.445 g, 1.67 mmol) was suspended in MeOH/dichloromethane (1:1; 8 mL) and a solution of ethylamine (2M in MeOH, 1.25 mL, 2.51 mmol) was added. The mixture was stirred for 16 hours at room temperature. The mixture was then was cooled to 0° C. and NaBH₄ (76 mg, 2.01 mmol) was added in portions over 10 minutes. After allowing the mixture to warm to room temperature over 2 h, the reaction was quenched with 1 mL of water. The solution was concentrated in vacuo to ⅓ of its original volume and then it was partitioned between H₂O and EtOAc. The aqueous phase was extracted with EtOAc (×2) and the combined organics were dried (Na₂SO₄) filtered and the solvent removed in vacuo to give 4-cyano-3-(5-ethylaminomethyl-pyridin-3-yl)benzoic acid methyl ester as a yellow oil (0.353 g, 72%). MS(ESI) m/z 296.0 (M+H)⁺.

Step 3 and 4: By following General procedure B (BOC Protection), 4-cyano-3-(5-ethylaminomethyl-pyridin-3-yl)-benzoic acid methyl ester (0.334 g, 1.13 mmol) was used to give 3-{5-[(tert-butoxycarbonyl-ethyl-amino)-methyl]-pyridin-3-yl}-4-cyano-benzoic acid in quantitative yield. Esterification with TMS-diazomethane in MeOH gave the title compound (97 mg, 30%). MS(ESI) m/z 396.0 (M+H)⁺.

Example 42

2-(2,6-Difluoro-phenyl)-pyridine-4-carbaldehyde

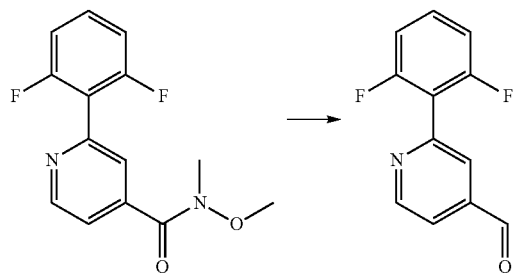 [SMILES: CON(C)C(=O)c1ccnc(-c2c(F)cccc2F)c1 ; O=Cc1ccnc(-c2c(F)cccc2F)c1]

To a stirred solution of (2-(2,6-difluoro-phenyl)-N-methoxy-N-methyl-isonicotinamide (Example 33) (268 mg, 0.963 mmol) in toluene (1.2 mL) at −78° C. was added DIBAL (1M in toluene; 1.01 mL, 1.01 mmol) dropwise. The mixture was stirred −78° C. for 2 hours then warmed to 0° C. and the reaction was quenched by the addition of 1M aqueous HCl. The mixture was neutralized using saturated aqueous NaHCO₃ solution and then extracted into CHCl₃ (×3). The combined extracts were dried (MgSO₄), filtered and concentrated in vacuo. The product was purified by SiO₂ chromatography providing the title compound (127 mg).

Example 43

2-(2-Fluoro-6-methoxy-phenyl)-pyridine-4-carbaldehyde

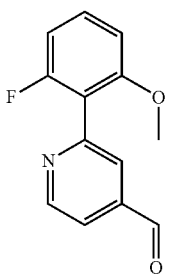

Compound was prepared by repeating procedures described for Example 42.

Example 44

6'-Fluoro-2'-methoxy-biphenyl-3-carbaldehyde

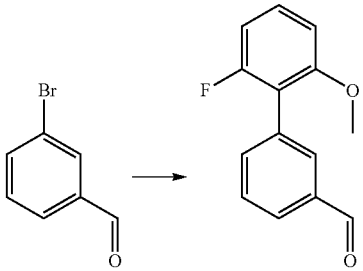 [SMILES: O=Cc1cccc(Br)c1 ; COc1cccc(F)c1-c1cccc(C=O)c1]

Compound was prepared by repeating procedures described for Example 32.

Examples 45-47

Were prepared by following General procedure C (Suzuki) starting from 4-cyano-3-(4,4,5,5-tetramethyl-[1,3,2]dioxaborolan-2-yl)-benzoic acid methyl ester and the appropriate heteroaryl bromide.

| Example | 45 | 46 | 47 |
|---|---|---|---|
| Structure | | | |
| Name | 4-Cyano-3-isoquinolin-4-yl-benzoic acid methyl ester | 4-Cyano-3-(3,5-dimethyl-1H-pyrazol-4-yl)-benzoic acid methyl ester | 4-Cyano-3-pyridin-3-yl-benzoic acid methyl ester |

Examples 48 to 51

Examples 48 to 51 describe the preparation of compounds of the formula (I).

Example 48

[2-(2,6-Difluoro-phenyl)-pyridin-4-yl]-[5-(1-methyl-1H-pyrazol-4-yl)-1H-imidazol-2-yl]-methanone

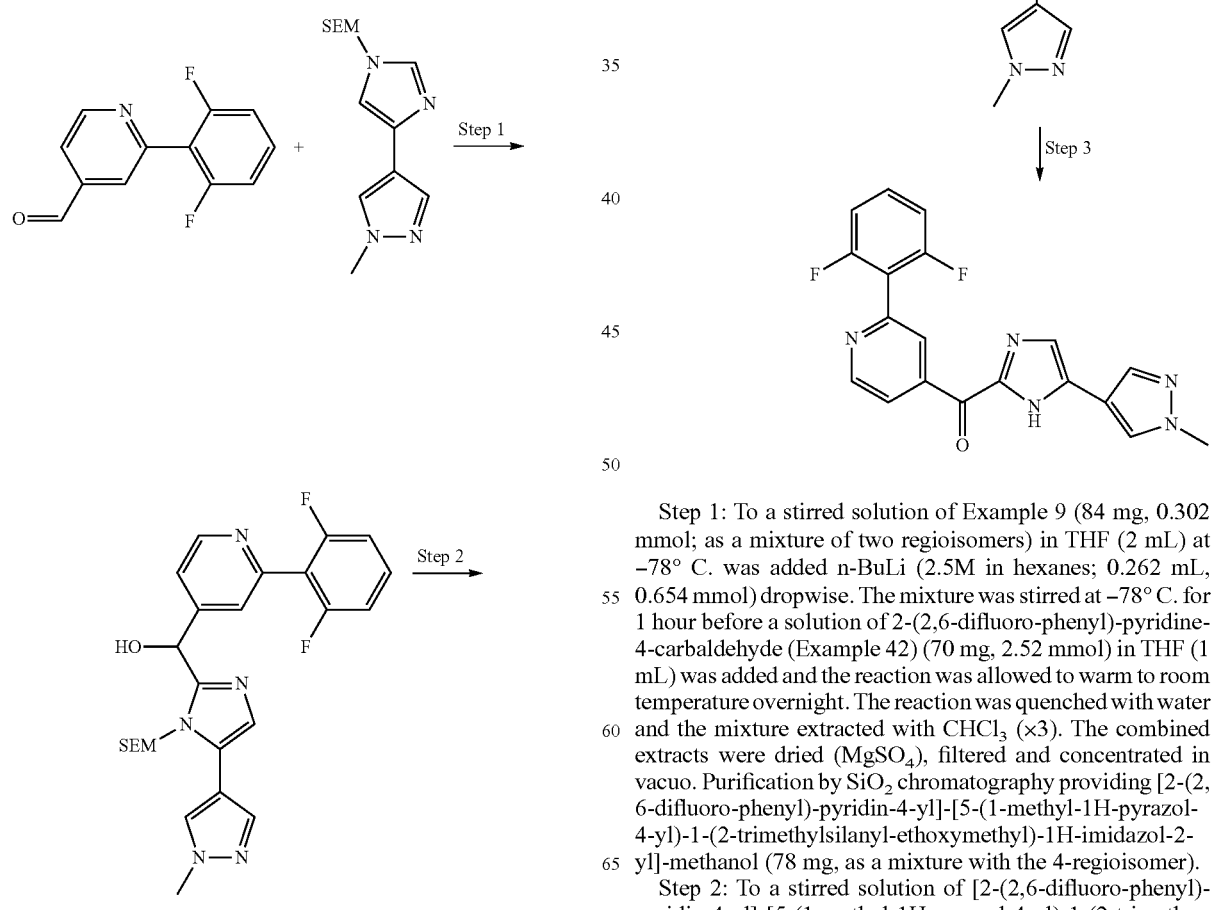

Step 1: To a stirred solution of Example 9 (84 mg, 0.302 mmol; as a mixture of two regioisomers) in THF (2 mL) at −78° C. was added n-BuLi (2.5M in hexanes; 0.262 mL, 0.654 mmol) dropwise. The mixture was stirred at −78° C. for 1 hour before a solution of 2-(2,6-difluoro-phenyl)-pyridine-4-carbaldehyde (Example 42) (70 mg, 2.52 mmol) in THF (1 mL) was added and the reaction was allowed to warm to room temperature overnight. The reaction was quenched with water and the mixture extracted with CHCl₃ (×3). The combined extracts were dried (MgSO₄), filtered and concentrated in vacuo. Purification by SiO₂ chromatography providing [2-(2,6-difluoro-phenyl)-pyridin-4-yl]-[5-(1-methyl-1H-pyrazol-4-yl)-1-(2-trimethylsilanyl-ethoxymethyl)-1H-imidazol-2-yl]-methanol (78 mg, as a mixture with the 4-regioisomer).

Step 2: To a stirred solution of [2-(2,6-difluoro-phenyl)-pyridin-4-yl]-[5-(1-methyl-1H-pyrazol-4-yl)-1-(2-trimethylsilanyl-ethoxymethyl)-1H-imidazol-2-yl]methanol (78 mg, 0.157 mmol, as a mixture of two regioisomers) in dichloromethane (3 mL) at room temperature was added manganese dioxide (273 mg, 3.14 mmol). The mixture was stirred at room temperature overnight before it was filtered and concentrated in vacuo. Purification by SiO$_2$ chromatography provided [2-(2,6-difluoro-phenyl)-pyridin-4-yl]-[5-(1-methyl-1H-pyrazol-4-yl)-1-(2 trimethylsilanyl-ethoxymethyl)-1H-imidazol-2-yl]-methanone (75 mg, as a mixture of two regioisomers).

Step 3: Title compound was prepared by following General procedure D (SEM deprotection)

The following compounds were prepared by following procedures described for Example 48. Additional comments with regard to methods and purification are highlighted where appropriate.

| Example | Structure | Additional comments | NMR | MS (ESI) |
|---|---|---|---|---|
| 48 | 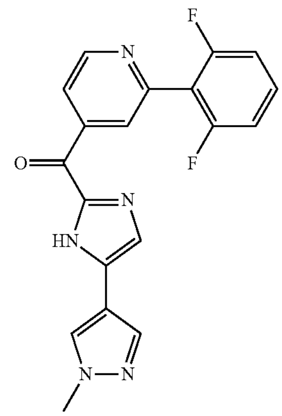 [SMILES: Cn1cc(-c2cnc(C(=O)c3ccnc(-c4c(F)cccc4F)c3)[nH]2)cn1] | Described above | $^1$H NMR (400 MHz, Me-d$_3$-OD): CDCl$_3$): 9.02 (1H, d), 8.70-8.39 (2H, m), 7.88-7.69 (2H, m), 7.47-7.37 (2H, m), 7.12-7.02 (2H, m), 3.99 (3H, s). | 366 [M + H]$^+$ |
| 49 | 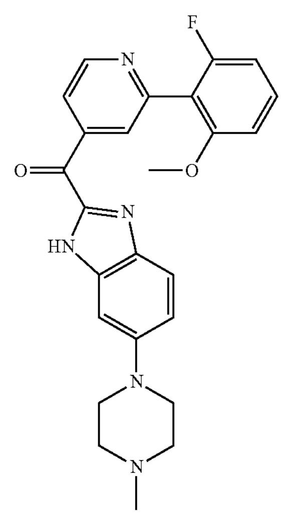 [SMILES: COc1cccc(F)c1-c1cc(C(=O)c2nc3ccc(N4CCN(C)CC4)cc3[nH]2)ccn1] | Starting with: example 43 and example 10. Step 2: purified by prep. LCMS. Step 3. product triturated with Et$_2$O/hexanes. | $^1$H NMR (400 MHz, CDCl$_3$): 9.09-8.97 (1.0H, m), 8.55-8.43 (2.0H, m), 7.88-7.78 (0.8H, m), 7.56-7.47 (0.2H, m), 7.45-7.33 (1.3H, m), 7.26-7.21 (0.2H, m), 7.13 (0.8H, dd), 6.94 (0.7H, d), 6.91-6.81 (2.1H, m), 3.85-3.79 (3.0H, m), 3.50-3.37 (4.0H, m), 3.01-2.49 (7.0H, m). Mixture of rotamers. | 446 [M + H]$^+$ |

-continued

| Example | Structure | Additional comments | NMR | MS (ESI) |
|---|---|---|---|---|
| 50 | 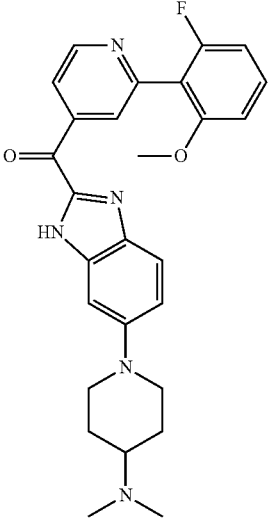 [SMILES: COc1cccc(F)c1-c1cc(C(=O)c2nc3ccc(N4CCC(N(C)C)CC4)cc3[nH]2)ccn1] | Starting with example 43 and example 11. Step 2: no purification Step 3: final product purified by prep. LCMS. | $^1$H NMR (400 MHz, CDCl$_3$): 9.07-8.97 (1.0H, m), 8.55-8.42 (2.0H, m), 7.85-7.76 (0.8H, m), 7.50 (0.2H, d), 7.44-7.34 (1.3H, m), 7.27-7.17 (0.2H, m), 7.14 (0.7H, dd), 6.92 (0.7H, d), 6.90-6.78 (2.1H, m), 3.88 (1.7H, d), 3.82 (3.0H, s), 3.78 (0.3H, d), 2.94-2.47 (9.0H, m), 2.24-2.09 (2.0H, m), 1.94-1.74 (2.0H, m). Mixture of rotamers. | 474 [M + H]$^+$ |
| 51 | 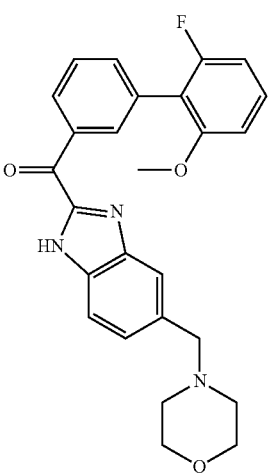 [SMILES: COc1cccc(F)c1-c1cccc(C(=O)c2nc3cc(CN4CCOCC4)ccc3[nH]2)c1] | Starting with example 44 and example 2. Final product purified by SiO$_2$ chromatography. | $^1$H NMR (400 MHz, CDCl$_3$): 8.81 (1H, dq), 8.69 (1H, dd), 7.97-7.88 (1H, m), 7.74 (1H, dd), 7.65 (1H, t), 7.62-7.30 (3H, m), 6.90-6.79 (2H, m), 3.83 (3H, s), 3.81-3.52 (6H, m), 2.76-2.30 (4H, m).. | 446 [M + H]$^+$ |

Example 49

[2-(2-Fluoro-6-methoxy-phenyl)-pyridin-4-yl]-[6-(4-methyl-piperazin-1-yl)-1H-benzoimidazol-2-yl]-methanone

Example 50

[6-(4-Dimethylamino-piperidin-1-yl)-1H-benzoimidazol-2-yl]-[2-(2-fluoro-6-methoxy-phenyl)-pyridin-4-yl]-methanone

Example 51

(6'-Fluoro-2'-methoxy-biphenyl-3-yl)-(5-morpholin-4-ylmethyl-1H-benzoimidazol-2-yl)-methanone

General Procedure H (nBuLi Metallation)

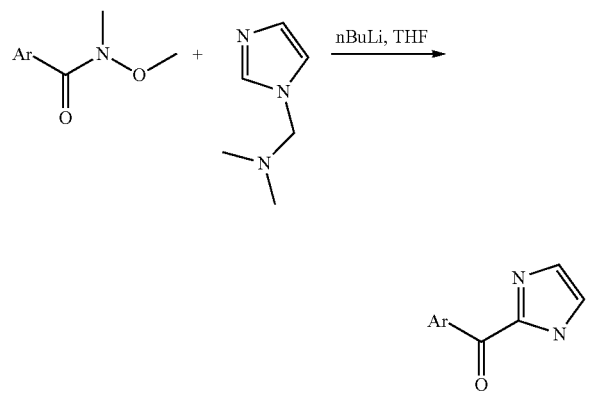

To a stirred solution of the imidazol-1-ylmethyl-dimethyl-amine (1 mol. eq.) in THF (20 vol.) at −78° C. was added n-BuLi (1 mol. eq; 2.5M solution in hexane). After 1 hour at −78° C., the appropriate N-methoxy-N-methyl-amide (1.05 mol. eq.) was added dropwise as a solution in THF (10 vol.) and the mixture allowed to warm to room temperature. After a further 3 hours, the reaction was worked up.

2M aqueous HCl (20 vol.) was added and stirring continued for a further 2 hours. The organic solvent was removed in vacuo. The solution was neutralised with sat. aq. NaHCO$_3$, diluted with water and then extracted with CHCl$_3$ (×3). The combined organic layers were dried (Na$_2$SO$_4$), filtered and the solvent removed in vacuo. Purification by SiO$_2$ chromatography (dichloromethane/EtOAc; 4:1) provided the product.

Examples 52 to 58

The following were prepared by following procedures described for General procedure H (nBuLi metallation A). Additional comments with regard to methods and purification highlighted where appropriate.

Examples 52 to 54 in the table below describe the preparation of synthetic intermediates. Examples 55 to 58 describe the preparation of compounds of the formula (I).

| Example | Structure | Additional comments | $^1$H NMR | LC/MS |
|---------|-----------|---------------------|-----------|-------|
| 52 | 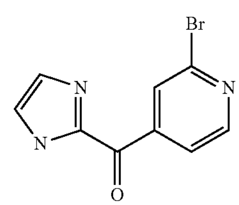 [SMILES: O=C(c1ccnc(Br)c1)c1ncc[nH]1] | Starting with Example 7 (0.158 g, 1.27 mmol) and Example 25 (from method 1) (0.326 g, 1.33 mmol). Gave product 0.143 g, 45%). | | 252.0 [M + H]$^+$ |
| 53 | 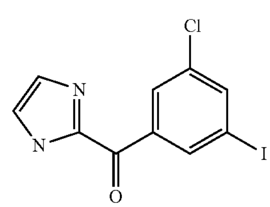 [SMILES: O=C(c1cc(Cl)cc(I)c1)c1ncc[nH]1] | Starting with Example 7 and Example 30 | | 332.8 [M + H]$^+$ |
| 54 | 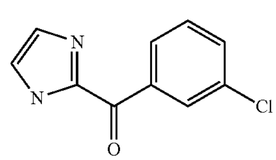 [SMILES: O=C(c1cccc(Cl)c1)c1ncc[nH]1] | Starting with Example 7 and Example 31 | | 206.9 [M + H]$^+$ |

-continued

| Example | Structure | Additional comments | ¹H NMR | LC/MS |
|---|---|---|---|---|
| 55 | (2-methylthiazol-4-yl phenyl imidazol-2-yl ketone) | Starting with Example 7 and Example 26 | 1H-NMR (400 MHz, d$_6$-Acetone): 12.78-12.11 (1H, bs), 9.16 (1H, t), 8.76-8.67 (1H, m), 8.31-8.22 (1H, m), 7.89-7.80 (1H, m), 7.62 (1H, t), 7.54 (1H, s), 7.36 (1H, s), 2.78 (3H, s). | 270.0 [M + H]⁺ |
| 56 | (2-phenylpyridin-4-yl imidazol-2-yl ketone) | Starting with Example 7 and Example 27. Product precipitated from the work up mixture following concentration in vacuo. Product was collected and triturated with Et$_2$O | 1H NMR (400 MHz, d$_6$-Acetone): 13.01-12.05 (1H, m), 8.98 (1H, s), 8.92 (1H, d), 8.34 (1H, dd), 8.26-8.16 (2H, m), 7.63 (1H, bs), 7.59-7.53 (2H, m), 7.53-7.46 (1H, m), 7.42 (1H, bs). | 250.1 [M + H]⁺ |
| 57 | (3-(1H-pyrazol-3-yl)phenyl imidazol-2-yl ketone) | Starting with example 7 and Example 28. Product purified by trituration with Et$_2$O | 1H NMR (400 MHz, d$_6$-Acetone): 12.50-12.33 (1H, m), 9.08 (1H, s), 8.68 (1H, d), 8.14 (1H, d), 7.86 (1H, d), 7.65-7.51 (2H, m), 7.36 (1H, s), 6.80 (1H, d). | 239.0 [M + H]⁺ |
| 58 | (3-(thiophen-3-yl)phenyl imidazol-2-yl ketone) | Starting with Example 7 and Example 29. | 1H NMR (400 MHz, d6-Acetone): 12.52-12.30 (1H, m), 8.99 (1H, t), 8.65-8.56 (1H, m), 8.05-7.96 (1H, m), 7.86 (1H, dd), 7.68-7.56 (3H, m), 7.45 (2H, s). | 255.0 [M + H]⁺ |

111

Example 52

(2-Bromo-pyridin-4-yl)-(1H-imidazol-2-yl)-methanone

Example 53

(3-Chloro-5-iodo-phenyl)-(1H-imidazol-2-yl)-methanone

Example 54

(3-Chloro-phenyl)-(1H-imidazol-2-yl)-methanone

Example 55

(1H-Imidazol-2-yl)-[3-(2-methyl-thiazol-4-yl)-phenyl]-methanone

Example 56

(1H-Imidazol-2-yl)-(2-phenyl-pyridin-4-yl)-methanone

Example 57

(1H-Imidazol-2-yl)-[3-(2H-pyrazol-3-yl)-phenyl]-methanone

Example 58

(1H-Imidazol-2-yl)-(3-thiophen-3-yl-phenyl)-methanone

Examples 59 to 101

Examples 59 to 101 below describe the preparation of compounds of the formula (I).

Example 59

[2-(4-Hydroxymethyl-phenyl)-pyridin-4-yl]-(1H-imidazol-2-yl)-methanone

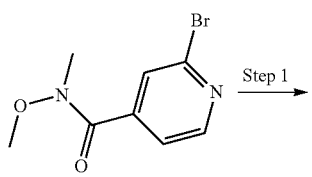

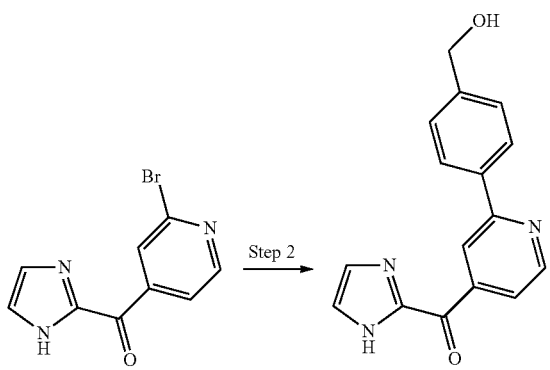

Step 1: By following General procedure H (n-BuLi metallation), 2-bromo-N-methoxy-N-methyl-isonicotinamide (Example 25, method 1) (0.326 g, 1.33 mmol) was used to prepare (2-bromo-pyridin-4-yl)-(1H-imidazol-2-yl)-methanone (0.143 g, 45%).

Step 2: 2-Bromo-pyridin-4-yl)-(1H-imidazol-2-yl)-methanone (60 mg, 0.24 mmol) and 4-methanol-phenyl boronic acid (47 mg, 0.31 mmol) were added in a microwave tube and dissolved in a mixture EtOH/Toluene (1:1; 0.9 mL. A solution of $K_2CO_3$ (197 mg, 1.43 mmol) in MeOH/$H_2O$ (1:1, 1 mL) was added to the tube followed by the Pd(P($^t$Bu)$_3$)$_2$ (2.4 mg, 0.0046 mmol). The tube was sealed, purged with nitrogen and the mixture was heated at 85° C. for 2 h in a microwave reactor. The solution was diluted with EtOAc (10 mL) and filtered. The EtOAc solution was washed with water (10 mL), brine (10 mL) and finally dried ($Na_2SO_4$). The solution was filtered and the solvent removed in vacuo. The crude material was purified by $SiO_2$ chromatography (EtOAc/Hexanes; 2:1 to 3:1) and then triturated 3 times with $Et_2O$ to give the title compound as a white solid (4 mg, 6%). MS(ESI) m/z 279.2 (M+H)$^+$. $^1$H NMR (400 MHz, Me-d$_3$-OD): 8.84 (1H, d), 8.67 (1H, s), 8.16-8.01 (3H, m), 7.54 (2H, d), 7.45 (2H, s), 4.71 (2H, s).

Example 60

(1H-Imidazol-2-yl)-[2-(3-methoxy-phenyl)-pyridin-4-yl]-methanone

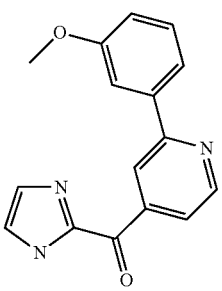 [SMILES: COc1cccc(-c2cc(C(=O)c3ncc[nH]3)ccn2)c1]

Compound was prepared by repeating procedures described for Example 59. MS(ESI) m/z 280.1 (M+H)$^+$. $^1$H NMR (400 MHz, CDCl$_3$): 8.97 (1H, d), 8.87 (1H, s), 8.42

(1H, d), 7.75 (1H, s), 7.68 (1H, d), 7.46 (1H, d), 7.44-7.36 (2H, m), 7.05 (1H, dd), 3.94 (3H, s).

Example 61

(3-Chloro-5-thiophen-3-yl-phenyl)-(1H-imidazol-2-yl)-methanone

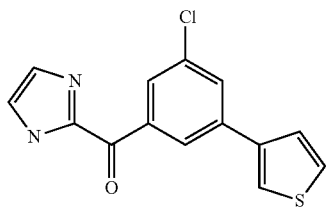 [SMILES: O=C(c1cc(Cl)cc(-c2ccsc2)c1)c1ncc[nH]1]

Starting from Example 53, the title compound was prepared by repeating procedures described for Example 59, step 2) followed by final trituration with MeOH. MS(ESI) m/z 288.9 (M+H)+. 1HNMR (400 MHz, DMSO-d6): 13.61 (1H, s), 8.63 (1H, s), 8.48 (1H, s), 8.11 (2H, s), 7.72 (1H, dd), 7.69-7.63 (1H, m), 7.59 (1H, s), 7.36 (1H, s).

Example 62

(3'-Amino-biphenyl-3-yl)-(1H-imidazol-2-yl)-methanone

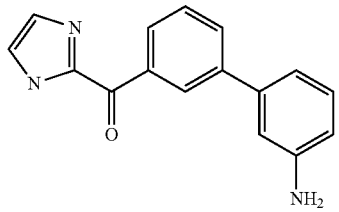 [SMILES: Nc1cccc(-c2cccc(C(=O)c3ncc[nH]3)c2)c1]

Starting from Example 54, the title compound was prepared by repeating procedures described for General procedure C (Suzuki) except Pd(OAc)$_2$ was used in place of Pd$_2$(dba)$_3$ and K$_2$CO$_3$ was used in place of K$_3$PO$_4$. EtOAc was used in place of CHCl$_3$ during the work up. MS(ESI) m/z 264.0 (M+H)+. 1H NMR (400 MHz, d6-Acetone): 12.40 (1H, bs), 8.90 (1H, t), 8.68-8.59 (1H, m), 7.92-7.84 (1H, m), 7.61 (1H, t), 7.52 (1H, s), 7.36 (1H, s), 7.20 (1H, t), 7.05 (1H, t), 6.96 (1H, d), 6.73 (1H, dd), 4.78 (2H, s).

Example 63

(3-Chloro-5-thiazol-4-yl-phenyl)-(1H-imidazol-2-yl)-methanone

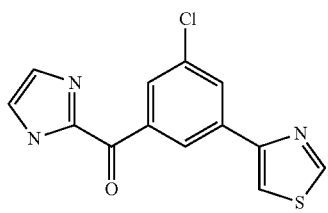 [SMILES: O=C(c1cc(Cl)cc(-c2cscn2)c1)c1ncc[nH]1]

A solution of Example 53 (50 mg, 0.15 mmol) in 1,4-dioxane (3 mL) was stirred in a microwave reaction tube. 4-Tributylstannanyl-thiazole (62 mg, 0.165 mmol) followed by Pd(PPh$_3$)$_4$ (10 mg, 8.6 µmol) was added to the stirred mixture. The tube was sealed and the reaction was heated at 120° C. for 30 mins. The mixture was then diluted with EtOAc (20 mL) and washed with brine. The organic phase was then dried over Na$_2$SO$_4$, filtered and the solvent evaporated. The crude was triturated in dichloromethane and the collected precipitate was purified further by SiO$_2$ chromatography (Hexanes/EtOAc; 9:1 to 2:1) to give the title compound as a beige solid (10 mg, 23%). MS(ESI) m/z 289.9 (M+H)+. 1H NMR (400 MHz, DMSO-d6): 13.62 (1H, s), 9.28 (1H, d), 8.97 (1H, t), 8.58 (1H, t), 8.46 (1H, d), 8.34 (1H, t), 7.58 (1H, s), 7.39 (1H, s).

Example 64

(3,5-Di-thiophen-3-yl-phenyl)-(1H-imidazol-2-yl)-methanone

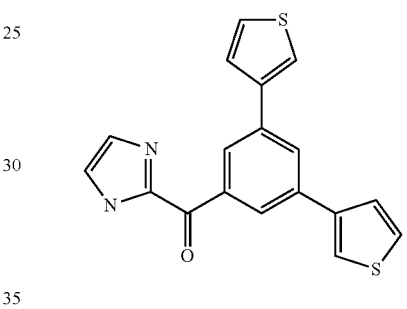

Starting from Example 61, the title compound was prepared by repeating procedures described for Example 62. Product was purified by preparative LCMS. MS(ESI) m/z 337.2 (M+H)+. 1H NMR (400 MHz, d6-Acetone): 12.70-12.20 (1H, m), 8.91 (2H, d), 8.33 (1H, t), 7.97 (2H, dd), 7.71 (2H, dd), 7.66 (2H, dd), 7.55 (1H, s), 7.40 (1H, s).

Example 65

(1H-Imidazol-2-yl)-[3-(1-methyl-1H-pyrazol-3-yl)-5-thiophen-3-yl-phenyl]-methanone

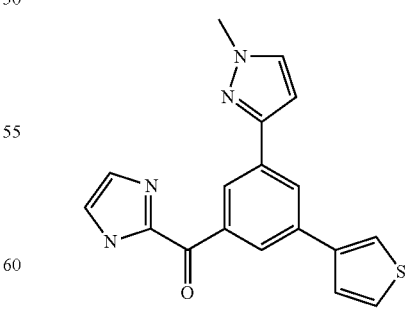

Starting from Example 61, the title compound was prepared by repeating procedures described for Example 59. MS(ESI) m/z 335.0 (M+H)+. 1H NMR (400 MHz, d6-Acetone): 12.79-12.16 (1H, m), 8.92 (1H, t), 8.81 (1H, t), 8.13

(1H, t), 7.99 (1H, dd), 7.71 (1H, dd), 7.69-7.60 (1H, m), 7.58 (1H, s), 7.50 (1H, d), 7.43-7.33 (1H, s), 6.53 (1H, d), 4.02 (3H, s).

General Procedure I (nBuLi Metallation)

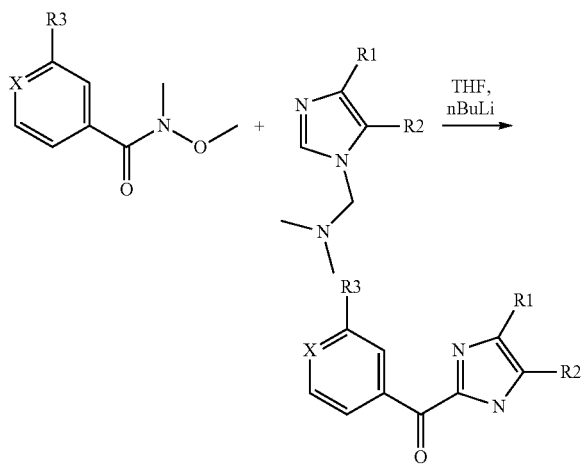

To a stirred solution of the dimethylaminomethyl protected heterocycle (1 mol. eq.) in THF (20 vol.) at −78° C. was added n-BuLi (1 mol. eq; 2.5M solution in hexane). After 1 hour at −78° C., the appropriate N-methoxy-N-methyl-amide (1.05 mol. eq.) was added dropwise as a solution in THF (10 vol.) and then the mixture was allowed to warm to room temperature. After a further 3 hours, the reaction was complete.

2M aqueous HCl (20 vol.) was added and stirring continued for a further 2 hours. The mixture was then partitioned between $CHCl_3$ and water. The organic layer was dried ($MgSO_4$), concentrated in vacuo and the product purified by $SiO_2$ chromatography eluting with 0-10% MeOH/dichloromethane. For compounds with lower retention time the mobile phase contained 0-1% conc. aqueous ammonia.

The following analogs were prepared according to the procedures described for General procedure I (nBuLi metallation). Additional comments with regard to methods and purification are highlighted where appropriate.

| Example | Structure | Additional comments | $^1$H NMR | MS(ESI) m/z |
|---|---|---|---|---|
| 66 | 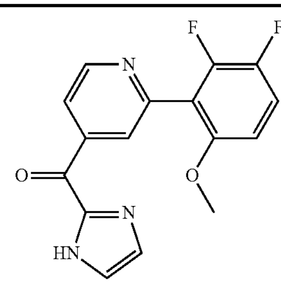 | Starting with Example 7 and Example 32. | $^1$H NMR (400 MHz, $CDCl_3$): 10.66 (1H, s), 9.00 (1H, d), 8.55-8.41 (2H, m), 7.44 (1H, s), 7.36 (1H, s), 7.21 (1H, q), 6.76-6.68 (1H, m), 3.79 (3H, s) | 316.2 (M + H)$^+$ |
| 67 | 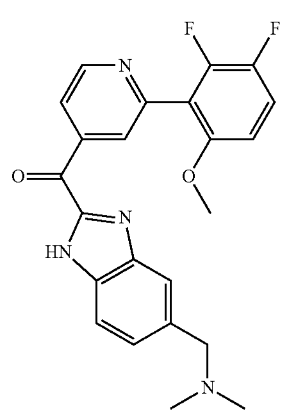 [SMILES: COc1ccc(F)c(F)c1-c1cc(C(=O)c2nc3cc(CN(C)C)ccc3[nH]2)ccn1] | Starting with example 1 and Example 32. | $^1$H NMR (400 MHz, $CDCl_3$): 10.60 (1H, br), 9.04 (1H, d), 8.60-8.50 (2H, m), 7.95-7.83 (1H, m), 7.58-7.48 (1.4H, m), 7.39 (0.6H, d), 7.21 (1H, q), 6.78-6.68 (1H, m), 3.80 (3H, s), 3.61 (2H, s), 2.31 (6H, s). | 423 [M + H]$^+$ |

| Example | Structure | Additional comments | ¹H NMR | MS(ESI) m/z |
|---|---|---|---|---|
| 68 | 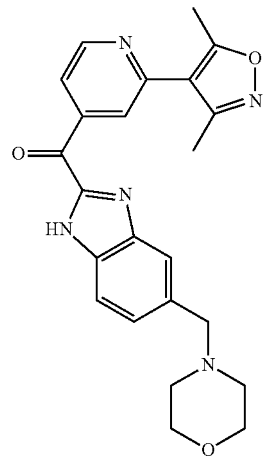 [SMILES: Cc1noc(C)c1-c1cc(C(=O)c2nc3cc(CN4CCOCC4)ccc3[nH]2)ccn1] | Starting with Example 37 and Example 2. Purified by preparative LCMS. | ¹H NMR (400 MHz, Me-d₃-OD): 8.93 (0.9H, d), 8.64 (0.1H, d), 8.61 (0.8H, s), 8.57 (0.1H, s), 8.20 (0.9H, dd), 7.82 (0.2H, s), 7.80-7.69 (1.6H, m), 7.67 (0.2H, dd), 7.58-7.43 (1.2H, m), 7.26 (0.1H, d), 3.76-3.61 (6.0H, m), 2.68 (2.6H, s), 2.58-2.43 (7H, m), 2.36 (0.4H, s). Mixture of rotamers. | 418 [M + H]⁺ |
| 69 | 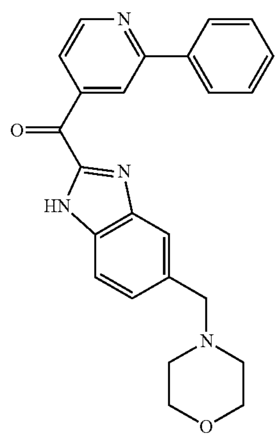 [SMILES: O=C(c1ccnc(-c2ccccc2)c1)c1nc2cc(CN3CCOCC3)ccc2[nH]1] | Starting with Example 36 and Example 2. Purified by preparative LCMS. | ¹H NMR (400 MHz, Me-d₃-OD): 8.90 (0.9H, d), 8.78 (0.9H, s), 8.63-8.55 (0.1H, m), 8.26 (0.9H, dd), 8.22 (0.1H, s), 8.10 (1.7H, d), 7.96 (0.3H, d), 7.82-7.68 (1.7H, m), 7.65 (0.2H, dd), 7.61-7.42 (4.1H, m), 7.26 (0.1H, d), 3.76-3.61 (6.0H, m), 2.60-2.42 (4.0H, m). Mixture of rotamers. | 399 [M + H]⁺ |
| 70 | 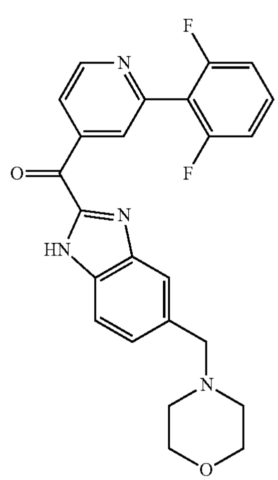 [SMILES: O=C(c1ccnc(-c2c(F)cccc2F)c1)c1nc2cc(CN3CCOCC3)ccc2[nH]1] | Starting with Example 33 and Example 2. Purified by preparative LCMS | ¹H NMR (400 MHz, CDCl₃): 9.06 (1H, d), 8.63 (1H, d), 8.60-8.54 (1H, m), 7.93 (1H, d), 7.71-7.36 (3H, m), 7.12-7.04 (2H, m), 3.89-3.60 (6H, m), 2.87-2.22 (4H, m). | 435 [M + H]⁺ |

| Example | Structure | Additional comments | ¹H NMR | MS(ESI) m/z |
|---|---|---|---|---|
| 71 | 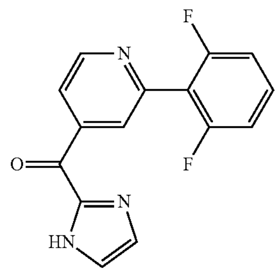 [SMILES: O=C(c1ccnc(-c2c(F)cccc2F)c1)c1ncc[nH]1] | Starting with Example 33 and Example 7. | ¹H NMR (400 MHz, Me-d₃-OD): 8.91 (1H, d), 8.41 (1H, s), 8.34 (1H, dd), 7.63-7.31 (3H, m), 7.22-7.12 (2H, m). | 286 [M + H]⁺ |
| 72 | 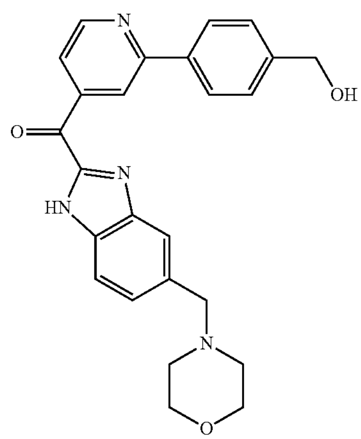 [SMILES: O=C(c1ccnc(-c2ccc(CO)cc2)c1)c1nc2cc(CN3CCOCC3)ccc2[nH]1] | Starting with Example 38 and Example 2. Purified by preparative LCMS | ¹H NMR (400 MHz, Me-d₃-OD): 8.89 (0.8H, d), 8.78 (0.8H, s), 8.62-8.55 (0.1H, m), 8.25 (0.8H, dd), 8.22 (0.1H, s), 8.09 (1.7H, d), 7.95 (0.3H, d), 7.85-7.66 (1.7H, m), 7.64 (0.2H, dd), 7.59-7.41 (3.1H, m), 7.26 (0.1H, d), 4.72 (1.7H, s), 4.69 (0.3H, s), 3.78-3.60 (6.0H, m), 2.59-2.43 (4H, m). Mixture of rotamers. | 429 [M + H]⁺ |
| 73 | 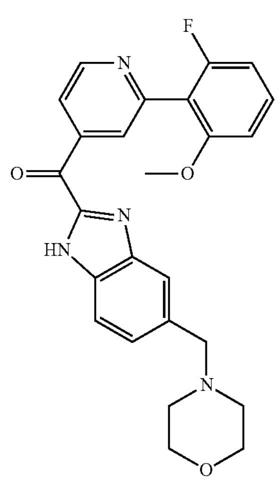 [SMILES: COc1cccc(F)c1-c1cc(C(=O)c2nc3cc(CN4CCOCC4)ccc3[nH]2)ccn1] | Starting with Example 34 and Example 2. | ¹H NMR (400 MHz, CDCl₃): 9.03 (1H, d), 8.58-8.46 (2H, m), 7.93 (1H, d), 7.75-7.32 (3H, m), 6.92-6.80 (2H, m), 3.99-3.56 (9H, m), 2.99-2.22 (4H, m). | 447 [M + H]⁺ |

| Example | Structure | Additional comments | ¹H NMR | MS(ESI) m/z |
| --- | --- | --- | --- | --- |
| 74 | 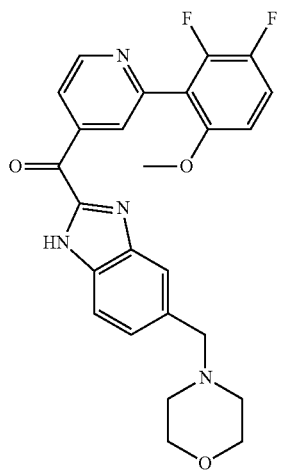 [SMILES: COc1ccc(F)c(F)c1-c1cc(C(=O)c2nc3cc(CN4CCOCC4)ccc3[nH]2)ccn1] | Starting with Example 32 and Example 2. Purified by preparative LCMS. | ¹H NMR (400 MHz, CDCl₃): 9.04 (1H, d), 8.60-8.49 (2H, m), 8.01-7.89 (1H, m), 7.78-7.38 (2H, m), 7.22 (1H, q), 6.74 (1H, dt), 4.00-3.56 (9H, m), 3.04-2.21 (4H, m). | 465 [M + H]⁺ |
| 75 | 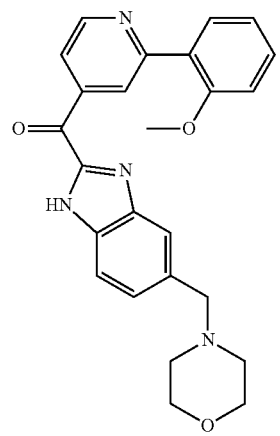 [SMILES: COc1ccccc1-c1cc(C(=O)c2nc3cc(CN4CCOCC4)ccc3[nH]2)ccn1] | Starting with Example 35 and Example 2. Purified by preparative LCMS. | ¹H NMR (400 MHz, CDCl₃): 9.02-8.93 (2H, m), 8.38 (1H, ddd), 7.96-7.85 (2H, m), 7.68-7.38 (3H, m), 7.14 (1H, t), 7.07 (1H, d), 3.95 (3H, s), 3.88-3.57 (6H, m), 2.72-2.36 (4H, m). | 429 [M + H]⁺ |

| Example | Structure | Additional comments | ¹H NMR | MS(ESI) m/z |
|---|---|---|---|---|
| 76 | 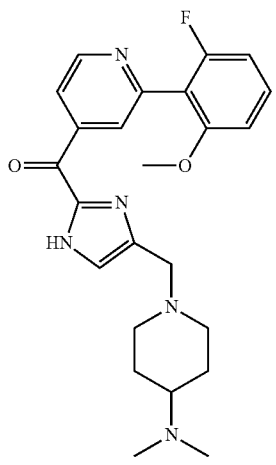 [SMILES: COc1cccc(F)c1-c1cc(C(=O)c2nc(CN3CCC(N(C)C)CC3)c[nH]2)ccn1] | Starting with Example 34 and Example 8. Purified by preparative LCMS. | ¹H NMR (400 MHz, CDCl₃): 8.96 (1H, d), 8.50-8.35 (2H, m), 7.36 (1H, q), 7.21 (1H, s), 6.89-6.78 (2H, m), 3.81 (3H, s), 3.69-3.56 (2H, m), 3.15-2.87 (2H, m), 2.33 (6H, s), 2.28-2.07 (3H, m), 1.91-1.79 (2H, m), 1.68-1.51 (2H, m). | 438 [M + H]⁺ |
| 77 | 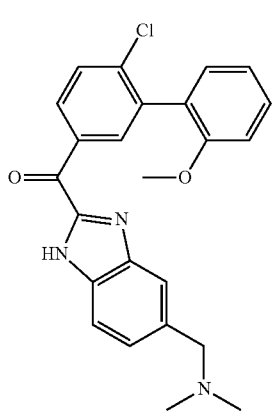 [SMILES: COc1ccccc1-c1cc(C(=O)c2nc3cc(CN(C)C)ccc3[nH]2)ccc1Cl] | Starting with Example 39 and Example 1. Purified by preparative LCMS. | ¹H NMR (400 MHz, CDCl₃): 8.75 (1H, d), 8.57 (2H, d), 7.91 (1H, s), 7.77 (1H, s), 7.66 (1H, d), 7.52-7.39 (2H, m), 7.34-7.24 (1H, m), 7.14-6.99 (2H, m), 4.90 (1H, s), 4.08 (2H, s), 3.82 (3H, s), 2.62 (6H, s). | 420 [M + H]⁺ |

Example 66

[2-(2,3-Difluoro-6-methoxy-phenyl)-pyridin-4-yl]-(1H-imidazol-2-yl)-methanone

Example 67

[2-(2,3-Difluoro-6-methoxy-phenyl)-pyridin-4-yl]-(5-dimethylaminomethyl-1H-benzoimidazol-2-yl)-methanone

Example 68

[2-(3,5-Dimethyl-isoxazol-4-yl)-pyridin-4-yl]-(5-morpholin-4-ylmethyl-1H-benzoimidazol-2-yl)-methanone

Example 69

(5-Morpholin-4-ylmethyl-1H-benzoimidazol-2-yl)-(2-phenyl-pyridin-4-yl)-methanone

Example 70

[2-(2,6-Difluoro-phenyl)-pyridin-4-yl]-(5-morpholin-4-ylmethyl-1H-benzoimidazol-2-yl)-methanone

Example 71

[2-(2,6-Difluoro-phenyl)-pyridin-4-yl]-(1H-imidazol-2-yl)-methanone

Example 72

[2-(4-Hydroxymethyl-phenyl)-pyridin-4-yl]-(5-morpholin-4-ylmethyl-1H-benzoimidazol-2-yl)-methanone

Example 73

[2-(2-Fluoro-6-methoxy-phenyl)-pyridin-4-yl]-(5-morpholin-4-ylmethyl-1H-benzoimidazol-2-yl)-methanone

Example 74

[2-(2,3-Difluoro-6-methoxy-phenyl)-pyridin-4-yl]-(5-morpholin-4-ylmethyl-1H-benzoimidazol-2-yl)-methanone

Example 75

[2-(2-Methoxy-phenyl)-pyridin-4-yl]-(5-morpholin-4-ylmethyl-1H-benzoimidazol-2-yl)-methanone

Example 76

[4-(4-Dimethylamino-piperidin-1-ylmethyl)-1H-imidazol-2-yl]-[2-(2-fluoro-6-methoxy-phenyl)-pyridin-4-yl]-methanone

Example 77

(6-Chloro-2'-methoxy-biphenyl-3-yl)-(5-dimethylaminomethyl-1H-benzoimidazol-2-yl)-methanone

Example 78

[2-(2-Fluoro-6-methoxy-phenyl)-1-oxy-pyridin-4-yl]-[5-(4-oxy-morpholin-4-ylmethyl)-1H-benzoimidazol-2-yl]-methanone

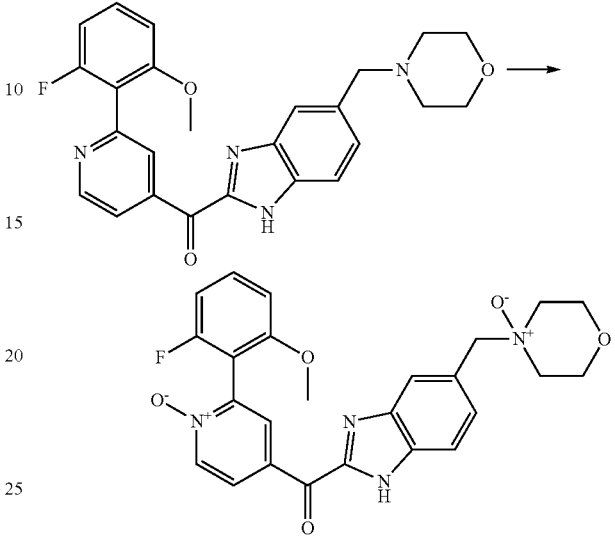

To a stirred solution of [2-(2-fluoro-6-methoxy-phenyl)-pyridin-4-yl]-(5-morpholin-4-ylmethyl-1H-benzoimidazol-2-yl)-methanone (Example 73) (110 mg, 0.246 mmol) in dichloromethane (5 mL) at 0° C. was added meta-chloroperoxybenzoic acid (75%; 125 mg, 0.524 mmol) in portions. The mixture was warmed to room temperature and stirred overnight before additional meta-chloroperoxybenzoic acid (0.5 mol. eq.) was added at 0° C. and the mixture was stirred at room temperature for 6 hours. The mixture was neutralized by the addition of saturated aqueous $NaHCO_3$ solution and extracted into $CHCl_3$ (×3). The combined extracts were dried ($MgSO_4$), filtered and concentrated in vacuo. The product was purified by preparative LCMS providing the title compound (48 mg). MS(ESI) m/z 479 (M+H)[+]. $^1$H NMR (400 MHz, DMSO-$d_6$): 8.69 (1H, dd), 8.67-8.61 (1H, m), 8.59 (1H, d), 8.25 (1H, s), 8.10-7.50 (4H, m), 7.06 (1H, d), 6.99 (1H, t), 4.75 (2H, s), 4.03 (2H, br t), 3.84-3.72 (5H, m), 3.64-3.52 (3H, m), 3.06 (2H, br d).

General Procedure J (LDA Metallation)

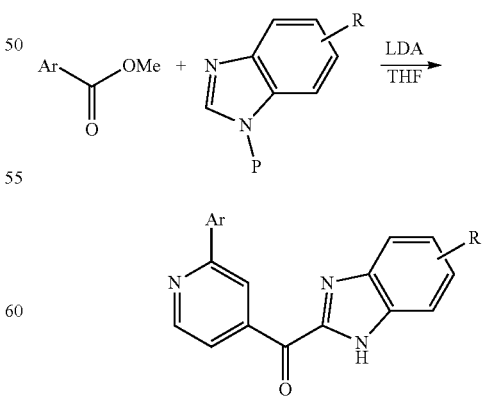

P = $CH_2NMe_2$, SEM, CH(OEt)$_2$ or Boc

P=$CH_2NMe_2$, SEM, CH(OEt)$_2$ or Boc

To a stirred solution of benzimidazole (1 mol. eq.) and methyl ester (1 mol. eq.) in THF (30 vols.) at −78° C. was added LDA (2M solution in THF, 1 to 2 mol. eq.) dropwise. The mixture was stirred at −78° C. for 1-2 hours and was then quenched using work up method A, B, C or D described below.

Work up Method A: To the reaction mixture, at −78° C., was added 2M aqueous HCl. The mixture was allowed to warm to room temperature and stirred for 1 hour. THF was evaporated in vacuo and the remaining aqueous solution was washed with Et$_2$O. The aqueous layer was neutralised by the addition of saturated aqueous NaHCO$_3$ and then extracted with CHCl$_3$ (×3). The combined organic extracts were dried (MgSO$_4$), filtered and concentrated in vacuo. Subsequent purification by preparative LCMS gave the products.

Work up Method B: To the reaction mixture, at −78° C., was added sat. aqueous NH$_4$Cl. The mixture was then allowed to warm to room temperature. The mixture was then diluted with 2M aqueous HCl (20 vols.) and allowed to stir overnight at room temperature. The pH was adjusted to pH 7-8 and the products were extracted with CHCl$_3$: $^i$PrOH (3:1; ×3). The combined organic layers were washed with water, brine and dried (MgSO$_4$). The solution was filtered and the solvent removed in vacuo. Purification by either SiO$_2$ chromatography (mobile phase; EtOAc/2.0M NH$_3$ in MeOH; 95:5 to 90:10, or dichloromethane/2.0M NH$_3$ in MeOH; 95:2 to 90:5) or preparative LCMS to give the product.

Work up method C: To the reaction mixture, at −78° C. was added sat. aqueous NH$_4$Cl. The mixture was then allowed to warm to room temperature. The products were extracted with EtOAc (×3). The combined organic layers were washed with water, brine and dried (MgSO$_4$). The products were filtered and evaporated to dryness in vacuo. Purification by either SiO$_2$ chromatography (mobile phase; EtOAc/2.0M NH$_3$ in MeOH; 95:5 to 90:10 or dichloromethane/2.0M NH$_3$ in MeOH; 95:2 to 90:5) or preparative LCMS to gave the product.

Work up method D: To the reaction mixture, at −78° C. was added water and EtOAc. The EtOAc layer was concentrated and purified by SiO$_2$ chromatography or preparative LCMS.

The following compounds were prepared according to General procedure J (LDA metallation) and work up A. Additional comments with regard to synthetic procedures, deprotection of final products and purification are highlighted where appropriate

| Example | Structure | Additional comments | $^1$H NMR | MS(ESI) m/z |
|---|---|---|---|---|
| 79-A | 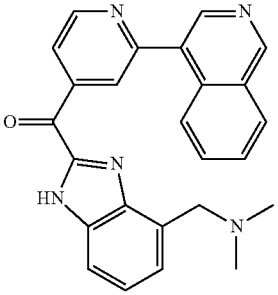 [SMILES: CN(C)Cc1cccc2[nH]c(C(=O)c3ccnc(-c4cncc5ccccc45)c3)nc12] | Starting with Example 23 and Example 15. Purification: prep. LCMS Product obtained as the formate salt. | $^1$H NMR (400 MHz, DMSO-d$_6$): 9.47 (1H, d), 9.12 (1H, dd), 8.95-8.72 (2H, m), 8.41-8.32 (2H, m), 8.29 (1H, d), 8.18 (1H, br s), 7.90 (1H, ddd), 7.80 (1H, ddd), 7.64 (1H, s), 7.44-7.29 (2H, m), 3.87 (2H, s), 2.20 (6H, s). | 408 [M + H]$^+$ |
| 79-B | 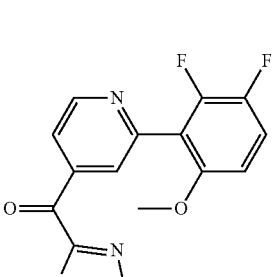 | Starting with Example 32 and Example 15. Purification: The crude material was heated in MeOH/1M HCl cooled and collected by filtration providing the HCl salt. | $^1$H NMR (400 MHz, DMSO-d$_6$): 8.99 (1H, d), 8.64-8.27 (2H, m), 7.89-7.25 (4H, m), 7.03 (1H, ddd), 3.85 (2H, br s), 3.78 (3H, s), 2.20 (6H, s). | 423 [M + H]$^+$ |

-continued

| Example | Structure | Additional comments | $^1$H NMR | MS(ESI) m/z |
|---|---|---|---|---|
| 80 | 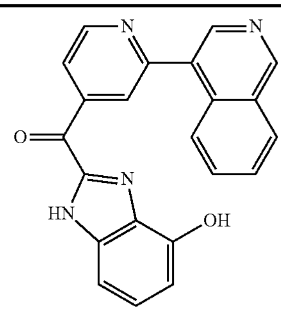 | Starting with Example 23 and Example 16. SEM deprotection: General procedure D. Purification: prep. LCMS. General procedure K to afford the methanesulfonate salt. | $^1$H NMR (400 MHz, DMSO-d$_6$): 9.73 (0.6H, s), 9.61 (0.4H, s), 9.14 (0.6H, d), 8.93 (0.4H, d), 8.88 (0.6H, s), 8.74-8.69 (1.0H, m), 8.52-8.45 (1.8H, m), 8.39 (0.4H, d), 8.28 (0.4H, d), 8.15-8.03 (1.0H, m), 7.95 (1.0H, dd), 7.87 (0.4H, dd), 7.80 (0.4H, d), 7.30 (0.4H, dd), 7.22 (0.6H, dd), 7.14 (0.4H, d), 7.08 (0.6H, d), 6.86 (0.4H, d), 6.70 (0.6H, d), 3.40 (1.0H, s), 2.32 (4.0H, s). Mixture of rotamers. | 367 [M + H]$^+$ |
| 81 | 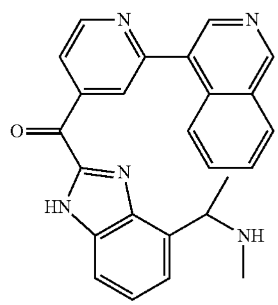 [SMILES: CNC(C)c1cccc2[nH]c(C(=O)c3ccnc(-c4cncc5ccccc45)c3)nc12] | Starting with Example 23 and Example 17. Deprotection: General procedure D. Purification: prep. LCMS providing the product as the trifluoroacetate salt. | $^1$H NMR (400 MHz, D$_2$O): 9.68 (0.9H, s), 9.65 (0.1H, s), 9.02 (0.9H, d), 8.79 (0.1H, d), 8.66 (0.9H, s), 8.58 (0.1H, s), 8.54-8.40 (2.8H, m), 8.40-8.28 (0.1H, m), 8.24 (0.9H, d), 8.15 (0.9H, dd), 8.09-7.99 (1.2H, m), 7.77 (0.9H, d), 7.65 (0.1H, d), 7.54 (1.0H, dd), 7.47 (0.9H, d), 7.42 (0.1H, dd), 7.37 (0.1H, d), 4.92 (1.0H, q), 2.53 (2.6H, s), 2.51 (0.4H, s), 1.75 (2.6H, d), 1.68 (0.4H, d). Mixture of rotamers. | 408 [M + H]$^+$ |
| 82 | 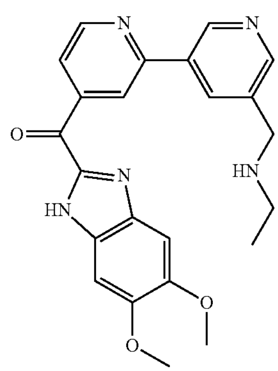 [SMILES: CCNCc1cncc(-c2cc(C(=O)c3nc4cc(OC)c(OC)cc4[nH]3)ccn2)c1] | Starting with Example 3 and Example 24. Deprotection: General procedure D. Purification: prep. LCMS providing the product as the formate salt. | $^1$H NMR (400 MHz, DMSO-d$_6$): 9.21 (1H, d), 8.99 (1H, dd), 8.80 (1H, dd), 8.66 (1H, d), 8.51 (1H, dd), 8.33 (1H, dd), 8.25 (2H, s), 7.20 (2H, s), 3.92 (2H, s), 3.86 (6H, s), 2.67 (2H, q), 1.10 (3H, t) | 418 [M + H]$^+$ |
| 83 | 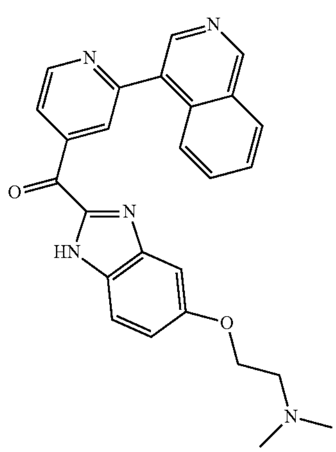 [SMILES: CN(C)CCOc1ccc2[nH]c(C(=O)c3ccnc(-c4cncc5ccccc45)c3)nc2c1] | Starting with Example 18 and Example 23. Following chromatography, trituration with Et$_2$O/EtOAc gave the product. | $^1$H NMR (400 MHz, Me-d3-OD): 9.38 (1H, s), 9.04 (1H, d), 8.70 (2H, s), 8.41 (1H, d), 8.26 (2H, d), 7.89 (1H, t), 7.85-7.74 (1H, m), 7.69 (1H, d), 7.17 (1H, s), 7.10 (1H, d), 4.21 (2H, t), 2.86 (2H, t), 2.41 (6H, s). | 438.2 [M + H]$^+$ |

The following compounds were prepared according to General procedure J (LDA metallation) and work up B. Additional comments with regard to synthetic procedures, deprotection of final products and purification are highlighted where appropriate.

| Example | Structure | Additional comments | ¹H NMR | MS(ESI) m/z |
|---|---|---|---|---|
| 84 | 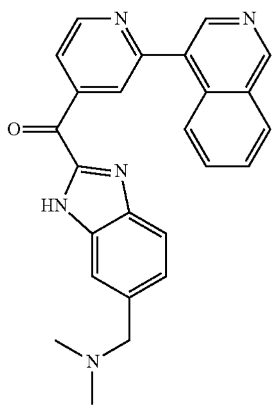 [SMILES: CN(C)Cc1ccc2nc(C(=O)c3ccnc(-c4cncc5ccccc45)c3)[nH]c2c1] | Starting with Example 23 and Example 1. Purification: by trituration with Et₂O. | ¹H NMR (400 MHz, DMSO-d₆): 13.89 (1H, br s), 9.47 (1H, s), 9.13 (1H, d), 8.76 (1H, s), 8.75-8.76 (1H, m), 8.41-8.33 (2H, m), 8.29 (1H, d), 8.03-7.35 (5H, m), 4.18 (2H, br s), 3.30 (6H, s). | 408 [M + H]⁺ |
| 85 | 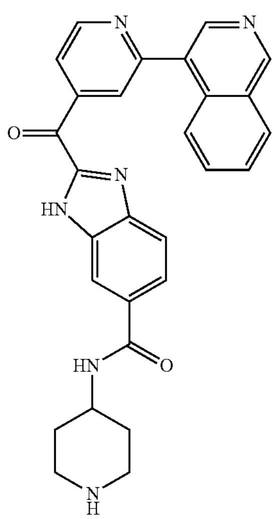 [SMILES: O=C(NC1CCNCC1)c1ccc2nc(C(=O)c3ccnc(-c4cncc5ccccc45)c3)[nH]c2c1] | Starting with Example 23 and Example 20. Purification: prep LCMS to give the product as the formate salt | ¹H NMR (400 MHz, Me-d₃-OD): 9.42-8.43 (4H, m), 8.37 (3H, s), 8.32-7.70 (7H, m), 4.28-4.12 (1H, m), 3.57-3.44 (2H, m), 3.23-3.13 (2H, m), 2.36-2.14 (2H, m), 2.00-1.78 (2H, m). | 477 [M + H]⁺ |
| 86 | 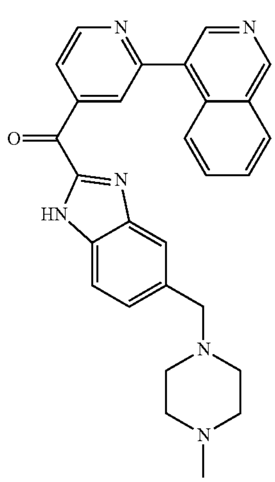 [SMILES: CN1CCN(Cc2ccc3[nH]c(C(=O)c4ccnc(-c5cncc6ccccc56)c4)nc3c2)CC1] | Starting from Example 23 and Example 5. Deprotection: general procedure G. Purification: prep. LCMS to give the product as the formate salt | ¹H NMR (400 MHz, Me-d₃-OD): 9.40-9.33 (1H, m), 9.06 (1H, d), 8.75-8.96 (1.5H, s), 8.47 (1H, s), 8.42 (0.5H, d), 8.29-7.24 (7H, m), 3.79, 3.77 (2H, 2 x s), 3.01 (4H, br s), 2.86-2.60 (7H, m). | 463 [M + H]⁺ |

| Example | Structure | Additional comments | ¹H NMR | MS(ESI) m/z |
|---|---|---|---|---|
| 87 | 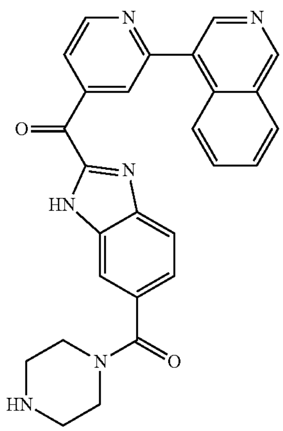 [SMILES: O=C(c1ccnc(-c2cncc3ccccc23)c1)c1nc2ccc(C(=O)N3CCNCC3)cc2[nH]1] | Starting with Example 23 and Example 21. Deprotection: general procedure G. Purification: prep. LCMS to give the product as the formate salt | ¹H NMR (400 MHz, DMSO-d$_6$): 9.47 (1H, s), 9.12 (1H, d), 8.76 (1H, s), 8.67 (1H, s), 8.42-8.33 (2H, m), 8.29 (1H, d), 7.90 (1H, t), 7.86-7.72 (3H, m), 7.40 (1H, d), 3.47 (4H, s), 2.71 (4H, s). | 463 [M + H]⁺ |
| 88 | 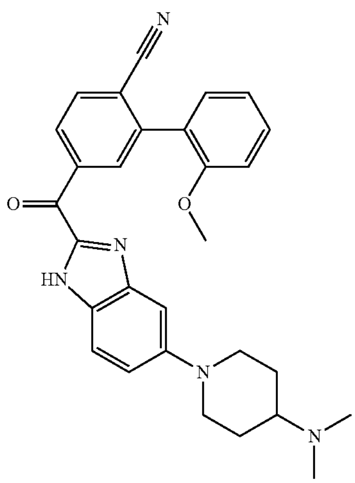 [SMILES: COc1ccccc1-c1cc(C(=O)c2nc3cc(N4CCC(N(C)C)CC4)ccc3[nH]2)ccc1C#N] | Starting with Example 11 and Example 40. Reaction was quenched with NaHCO$_3$ (sat., aq.) instead of NH$_4$Cl. Deprotection: General procedure D. Purification: prep. LCMS, providing the product as the trifluoroacetate salt. | ¹H NMR (400 MHz, DMSO-d$_6$): 9.50 (1H, s), 8.62 (1H, dd), 8.52 (1H, d), 8.14 (1H, d), 7.67 (1H, d), 7.57-7.48 (1H, m), 7.38 (1H, dd), 7.29-7.17 (2H, m), 7.14 (1H, t), 7.00 (1H, s), 3.90 (2H, d), 3.82 (3H, s), 3.38-3.29 (1H, m), 2.86-2.72 (8H, m), 2.10 (2H, d), 1.81-1.68 (2H, m). | 480.2 [M + H]⁺ |
| 89 | 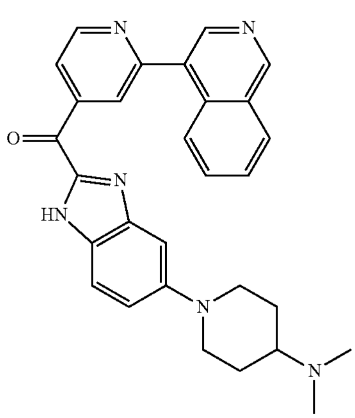 [SMILES: CN(C)C1CCN(c2ccc3[nH]c(C(=O)c4ccnc(-c5cncc6ccccc56)c4)nc3c2)CC1] | Starting with Example 11 and Example 23. Reaction was quenched with NaHCO$_3$ (sat., aq.) instead of NH$_4$Cl. Deprotection: General procedure D giving the product as the HCl salt | ¹H NMR (400 MHz, CDCl$_3$): 10.80-10.44 (1H, m), 9.39 (1H, s), 9.10 (1H, d), 8.83 (1H, s), 8.77 (1H, d), 8.54 (1H, d), 8.35 (1H, d), 8.11 (1H, d), 7.84-7.75 (2H, m), 7.70 (1H, t), 7.50 (0.2H, d), 7.38 (0.2H, s), 7.16 (0.8H, dd), 6.92 (0.8H, s), 3.86 (1.7H, d), 3.76 (0.3H, d), 2.94-2.78 (2H, m), 2.51-2.36 (7H, m), 2.04 (2H, d), 1.80-1.69 (2H, m). | 477.2 [M + H]⁺ |

| Example | Structure | Additional comments | ¹H NMR | MS(ESI) m/z |
|---|---|---|---|---|
| 90 | 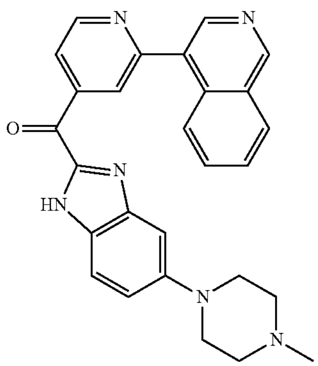 | Starting with Example 10 and Example 23. Reaction was quenched with NaHCO₃ (sat., aq.) instead of NH₄Cl. Deprotection: General procedure D. Purification: by trituration with Et₂O. | ¹H NMR (400 MHz, Me-d₃-OD): 9.38 (1H, s), 9.03 (1H, d), 8.69 (2H, d), 8.39 (1H, d), 8.26 (2H, d), 7.94-7.85 (1H, m) 7.85-7.75 (1H, m), 7.67 (1H, d), 7.23 (1H, d), 7.07 (1H, s), 3.35 (4H, s), 2.68 (4H, s ), 2.43-2.37 (3H, m). | 579.2 [M + H]⁺ |
| 91 | 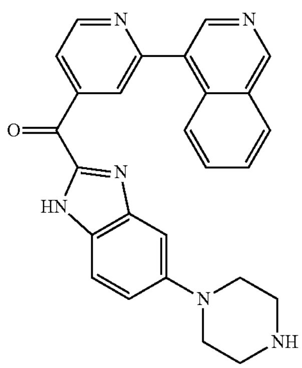 [SMILES: O=C(c1ccnc(-c2cncc3ccccc23)c1)c1nc2cc(N3CCNCC3)ccc2[nH]1] | Starting with Example 12 and Example 23. Reaction was quenched with NaHCO₃ (sat., aq.) instead of NH₄Cl. Deprotection: General procedure D. | ¹H NMR (400 MHz, Me-d₃-OD): 9.37 (1H, s), 9.02 (1H, d), 8.68 (2H, d), 8.38 (1H, d), 8.25 (2H, d), 7.88 (1H, t), 7.79 (1H, t), 7.66 (1H, d), 7.22 (1H, d), 7.07 (1H, s), 3.23 (4H, d), 3.03 (4H, s). | 435.0 [M + H]⁺ |
| 92 | 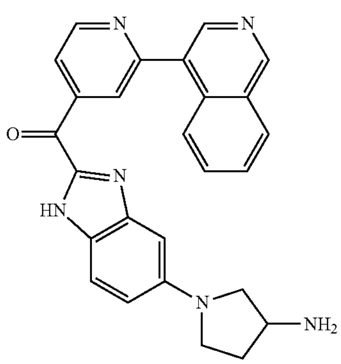 [SMILES: NC1CCN(c2ccc3[nH]c(C(=O)c4ccnc(-c5cncc6ccccc56)c4)nc3c2)C1] | Starting with Example 13 and Example 23 but quenching the reaction with NaHCO₃ (sat., aq.) instead of NH₄Cl. Deprotection: general procedure F. | ¹H NMR (400 MHz, DMSO-d₆): 9.45 (1H, s), 9.07 (1H, d), 8.74 (1H, s), 8.64 (1H, s), 8.39-8.24 (3H, m), 7.94-7.84 (1H, m), 7.79 (1H, t), 7.65 (1H, d), 6.78 (1H, d), 6.41 (1H , s), 3.66-3.54 (1H, m), 3.53-3.39 (3H, m), 2.98 (1H, dd), 2.17-2.05 (1H, m), 1.75 (1H, dd). | 435.0 [M + H]⁺ |
| 93 | 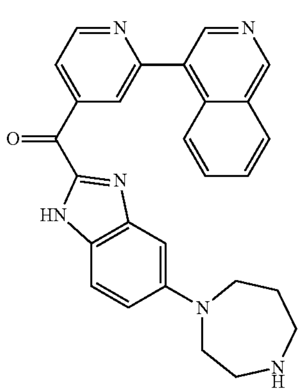 [SMILES: O=C(c1ccnc(-c2cncc3ccccc23)c1)c1nc2cc(N3CCCNCC3)ccc2[nH]1] | Starting with Example 23 and Example 14. Reaction was quenched with NaHCO₃ (sat., aq.) instead of NH₄Cl. Deprotection: general procedure F | ¹H NMR (400 MHz, DMSO-d₆): 9.46 (1H, s), 9.07 (1H, d), 8.74 (1H, s), 8.64 (1H, s), 8.34 (2H, d), 8.28 (1H, d), 7.89 (1H, t), 7.80 (1H, t), 7.64 (1H, d), 6.98 (1H, d), 6.60 (1H, s), 3.62 (2H, s), 3.54 (2H, s), 2.90 (2H, s), 2.65 (2H, s), 1.82 (2H, s). | 449.0 [M + H]⁺ |

The following compounds were prepared according to General procedure J (LDA metallation) and work up C. Additional comments with regard to synthetic procedures, deprotection of final products and purification are highlighted where appropriate.

| Example | Structure | Additional comments | ¹H NMR | MS(ESI) m/z |
|---|---|---|---|---|
| 94 | 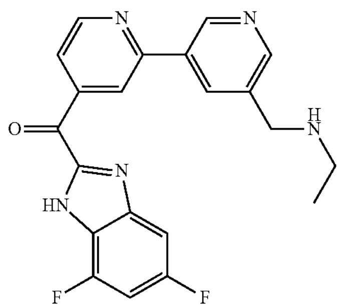 [SMILES: CCNCc1cncc(-c2cc(C(=O)c3nc4cc(F)cc(F)c4[nH]3)ccn2)c1] | Starting with Example 6 and Example 24. Deprotection: General method D. Product isolated as the HCl salt. | ¹H NMR (400 MHz, Me-d$_3$-OD): 9.66-9.62 (0.5H, m), 9.55-9.48 (0.5H, m), 9.34-9.23 (1H, m), 9.09 (0.5H, d), 9.07-8.95 (1.5H, m), 8.89-8.85 (0.5H, d), 8.61-8.53 (1H, m), 8.09-7.83 (0.5H, m), 7.43-7.13 (1.5H, m), 7.08 (0.5H, dt), 4.57, 4.53 (2H, 2 x s), 3.31-3.23 (2H, m), 1.43 (3H, t). Mixture of rotamers. | 394 [M + H]⁺ |
| 95 | 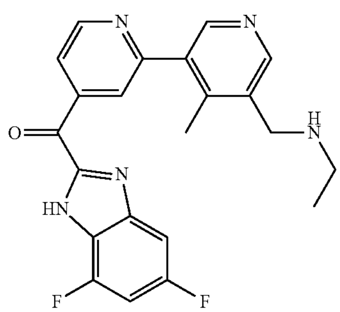 [SMILES: CCNCc1cncc(-c2cc(C(=O)c3nc4cc(F)cc(F)c4[nH]3)ccn2)c1C] | Starting with Example 6 and Example 22. Deprotection: General method D. Product isolated as the HCl salt. | ¹H NMR (400 MHz, Me-d$_3$-OD): 9.17-8.84 (2.5H, m), 8.77 (0.4H, s), 8.55-8.52 (0.4H, m), 8.19-8.12 (0.4H, m), 8.04-8.01 (0.4H, m), 7.70-7.25 (2.5H, m), 7.06 (0.4H, dt), 4.68, 4.60, 4.54 (2H, 3 x s), 3.40-3.43 (2H, m), 2.82, 2.78, 2.68 (3H, 3 x s), 1.49-1.44 (3H, m). Mixture of rotamers. | 408 [M + H]⁺ |
| 96 | 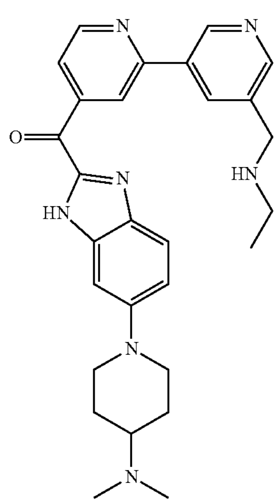 [SMILES: CCNCc1cncc(-c2cc(C(=O)c3nc4ccc(N5CCC(N(C)C)CC5)cc4[nH]3)ccn2)c1] | Starting with Example 11 and Example 24. Deprotection: General method D. Purification: prep. LCMS to give the product as the formate salt | ¹H NMR (400 MHz, Me-d$_3$-OD): 9.37 (0.8H, d), 8.99 (0.8H, d), 8.85 (0.8, s), 8.81-8.76 (0.8, m), 8.76-8.70 (0.8, m), 8.48 (2.4, br s), 8.34 (0.8H, d), 7.71 (0.8H, br d), 7.27 (0.8, br d), 4.37 (2H, s), 3.97 (2H, br d), 3.18 (2H, q), 2.96-2.83 (8H, m), 2.22 (2H, br d), 1.97-1.85 (2H, m), 1.38 (3H, t). | 484 [M + H]⁺ |

Example 79-A (4-Dimethylaminomethyl-1H-benzoimidazol-2-yl)-(2-isoquinolin-4-yl-pyridin-4-yl)-methanone (formate salt)

Example 79-B

[2-(2,3-Difluoro-6-methoxy-phenyl)-pyridin-4-yl]-(4-dimethylaminomethyl-1H-benzoimidazol-2-yl)-methanone (hydrochloride salt)

Example 80

(4-Hydroxy-1H-benzoimidazol-2-yl)-(2-isoquinolin-4-yl-pyridin-4-yl)-methanone (methanesulfonate salt)

Example 81

(2-Isoquinolin-4-yl-pyridin-4-yl)-[4-(1-methylamino-ethyl)-1H-benzoimidazol-2-yl]-methanone (trifluoroacetate salt)

Example 82

(5,6-Dimethoxy-1H-benzoimidazol-2-yl)-(5'-ethylaminomethyl-[2,3']bipyridinyl-4-yl)-methanone (formate salt)

Example 83

[5-(2-Dimethylamino-ethoxy)-1H-benzoimidazol-2-yl]-(2-isoquinolin-4-yl-pyridin-4-yl)-methanone

Example 84

(6-Dimethylaminomethyl-1H-benzoimidazol-2-yl)-(2-isoquinolin-4-yl-pyridin-4-yl)-methanone

Example 85

2-(2-Isoquinolin-4-yl-pyridine-4-carbonyl)-3H-benzoimidazole-5-carboxylic acid piperidin-4-ylamide (formate salt)

Example 86

(2-Isoquinolin-4-yl-pyridin-4-yl)-[5-(4-methyl-piperazin-1-ylmethyl)-1H-benzoimidazol-2-yl]-methanone (formate salt)

Example 87

(2-Isoquinolin-4-yl-pyridin-4-yl)-[6-(piperazine-1-carbonyl)-1H-benzoimidazol-2-yl]-methanone (formate salt)

Example 88

5-[5-(4-Dimethylamino-piperidin-1-yl)-1H-benzoimidazole-2-carbonyl]-2'-methoxy-biphenyl-2-carbonitrile (trifluoroaceteate salt)

Example 89

[5-(4-Dimethylamino-piperidin-1-yl)-1H-benzoimidazol-2-yl]-(2-isoquinolin-4-yl-pyridin-4-yl)-methanone (hydrochloride salt)

Example 90

(2-Isoquinolin-4-yl-pyridin-4-yl)-[5-(4-methyl-piperazin-1-yl)-1H-benzoimidazol-2-yl]-methanone

Example 91

(2-Isoquinolin-4-yl-pyridin-4-yl)-(5-piperazin-1-yl-1H-benzoimidazol-2-yl)-methanone

Example 92

[5-(3-Amino-pyrrolidin-1-yl)-1H-benzoimidazol-2-yl]-(2-isoquinolin-4-yl-pyridin-4-yl)-methanone

Example 93

(5-[1,4]Diazepan-1-yl-1H-benzoimidazol-2-yl)-(2-isoquinolin-4-yl-pyridin-4-yl)-methanone

Example 94

(5,7-Difluoro-1H-benzoimidazol-2-yl)-(5'-ethylaminomethyl-[2,3']bipyridinyl-4-yl)-methanone (hydrochloride salt)

Example 95

(5,7-Difluoro-1H-benzoimidazol-2-yl)-(5'-ethylaminomethyl-4'-methyl-[2,3']bipyridinyl-4-yl)-methanone (hydrochloride salt)

Example 96

[6-(4-Dimethylamino-piperidin-1-yl)-1H-benzoimidazol-2-yl]-(5'-ethylaminomethyl-[2,3']bipyridinyl-4-yl)-methanone (formate salt)

Example 97

(2-Isoquinolin-4-yl-pyridin-4-yl)-[6-(4-methyl-piperazine-1-carbonyl)-1H-benzoimidazol-2-yl]methanone

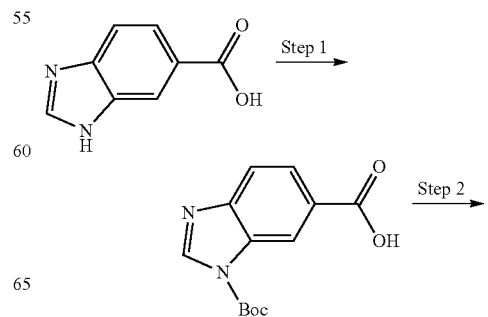

141

-continued

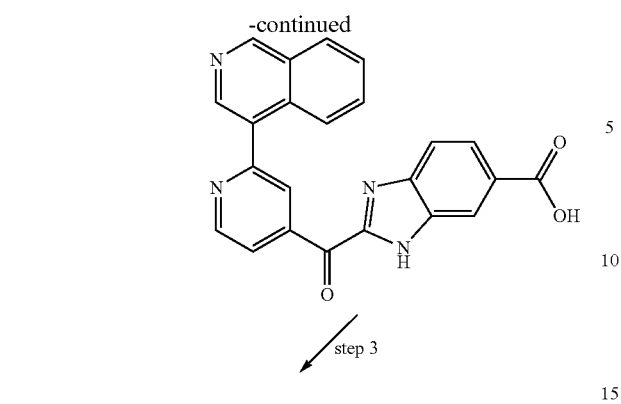

↓ step 3

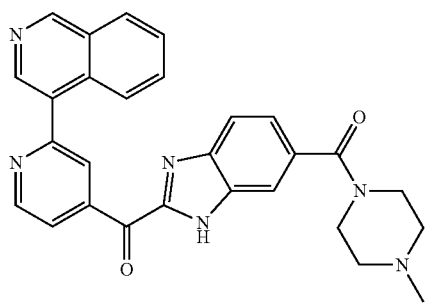

Step 1 was performed following General procedure B (BOC Protection).

Step 2 was performed following General procedure J (LDA metallation) and work up C.

Step 3: Final EDC coupling with N-methylpiperazine, following procedures described from Example 20, gave the title compound. MS(ESI) m/z 477 (M+H)+. 1H NMR (400 MHz, DMSO-d6): 13.84 (1H, br s), 9.47 (1H, s), 9.13 (1H, d), 8.76 (1H, s), 8.68 (1H, s), 8.39 (1H, d), 8.35 (1H, d), 8.29 (1H, d), 7.99-7.67 (4H, m), 7.42 (1H, br s), 3.53 (4H, br s), 2.33 (4H, br s), 2.21 (3H, s).

Example 98

[5-(2,3-Dihydroxy-propoxy)-1H-benzoimidazol-2-yl]-(2-isoquinolin-4-yl-pyridin-4-yl)-methanone

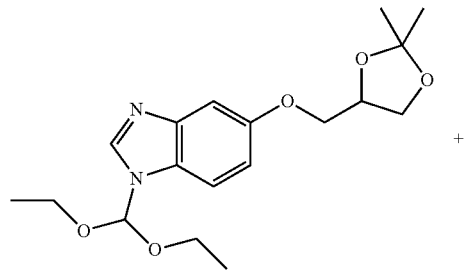

+

142

-continued

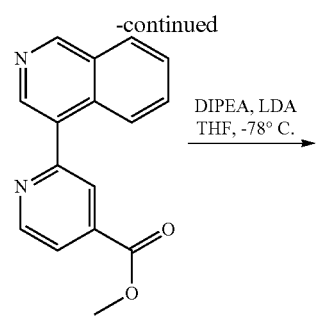

Example 19 (0.55 g, 1.57 mmol) and Example 23 (0.562 g, 2.13 mmol) were reacted according to General procedure J (LDA metallation). The mixture was quenched with cold water and then extracted with dichloromethane. The dichloromethane fraction was washed with brine, dried (Na2SO4) and evaporated to dryness. The product was dissolved in 1,4-dioxane/H2O/MeOH (1:1:1; 6 mL) and then HCl (4M in 1,4-dioxane; 6 mL) was added. After stirring for 2 hours at room temperature, the mixture was evaporated to dryness. Purification by SiO2 chromatography (dichloromethane/2M NH3 in MeOH; 5% to 12%) gave a crude product. This was dissolved in CHCl3 and washed with water. The CHCl3 layer was then evaporated to give the title compound. MS(ESI) m/z 441.0 (M+H)+. 1H NMR (400 MHz, Me-d3-OD): 9.38 (1H, s), 9.05 (1H, d), 8.70 (2H, d), 8.41 (1H, d), 8.26 (2H, d), 7.95-7.86 (1H, m), 7.86-7.78 (1H, m), 7.70 (1H, d), 7.18 (1H, s), 7.11 (1H, d), 4.21-4.12 (1H, m), 4.12-4.01 (2H, m), 3.78-3.68 (2H, m).

Example 99

2-(2-Isoquinolin-4-yl-pyridine-4-carbonyl)-3H-benzoimidazole-5-carboxylic acid (1-methyl-piperidin-4-yl)-amide (formate salt)

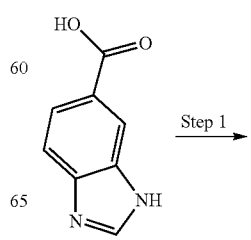

Step 1 →

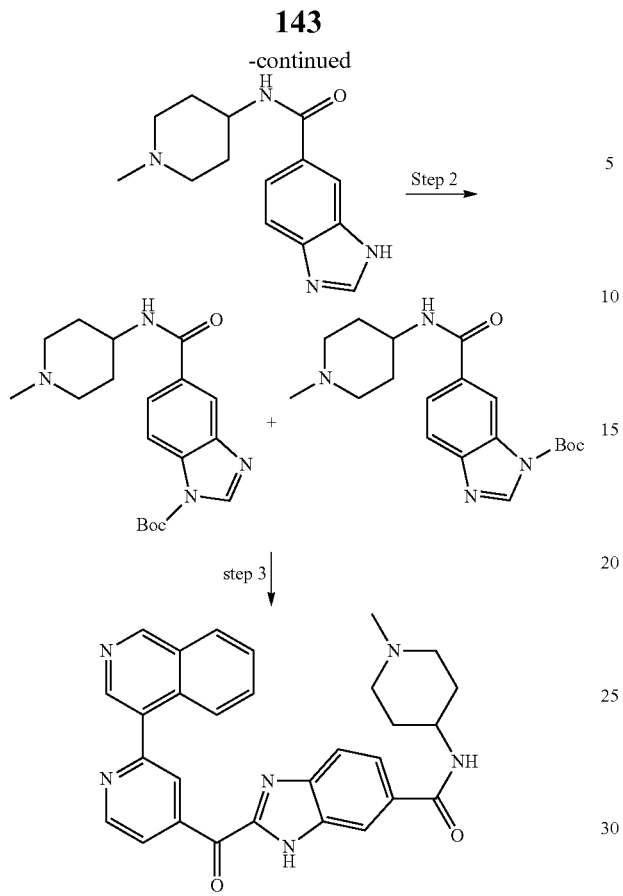

Step 1 was performed following procedures describe for Example 20.

Step 2: Boc protection was performed according to General procedure B (BOC Protection).

Step 3. Following General procedure J (LDA metallation) and work up C and then purification by preparative LCMS gave the product which was triturated with EtOAc to provide the title compound as the formate salt. MS(ESI) m/z 491 (M+H)$^+$. $^1$H NMR (400 MHz, DMSO-d$_6$): 9.47 (1H, s), 9.12 (1H, d), 8.79-8.72 (2H, m), 8.49-8.20 (4H, m), 8.16 (1H, s), 7.98-7.73 (4H, m), 3.91-3.68 (1H, m), 2.93-2.75 (2H, m), 2.23 (3H, s), 2.10-2.02 (2H, m), 1.84-1.76 (2H, m), 1.68-1.58 (2H, m).

Example 100

2-(2-Isoquinolin-4-yl-pyridine-4-carbonyl)-3H-benzoimidazole-5-carboxylic acid methyl-piperidin-4-yl amide

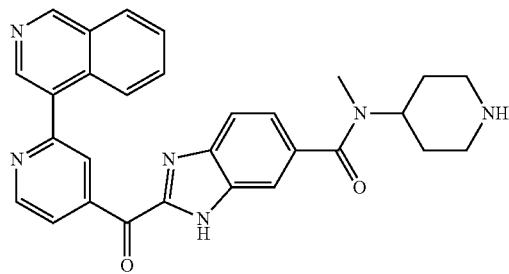 [SMILES: CN(C(=O)c1ccc2nc(C(=O)c3ccnc(-c4cncc5ccccc45)c3)[nH]c2c1)C1CCNCC1]

Starting with 4-methylamino-piperidine-1-carboxylic acid tert-butyl ester, the title compound was prepared by repeating procedures described for Example 99. The product was purified by preparative LCMS. MS(ESI) m/z 491 (M+H)$^+$. $^1$H NMR (400 MHz, DMSO-d$_6$): 9.50-9.36 (1H, m), 9.17-9.05 (1H, m), 8.91-8.58 (2H, m), 8.45-8.06 (3H, m), 7.96-7.24 (5H, m), 3.38-3.25 (3H, s), 3.07-2.75 (5H, m), 1.78-1.46 (4H, m).

Example 101

4-(5,6-Dimethoxy-1H-benzoimidazole-2-carbonyl)-2-(5-ethylaminomethyl-pyridin-3-yl)-benzonitrile (methanesulfonate salt)

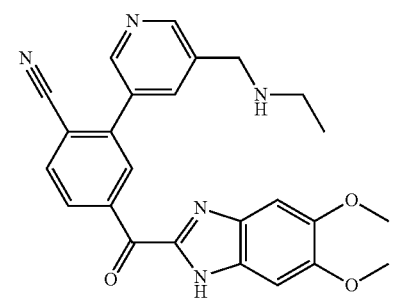 [SMILES: CCNCc1cncc(-c2cc(C(=O)c3nc4cc(OC)c(OC)cc4[nH]3)ccc2C#N)c1]

Example 4 and Example 41 were used as starting materials. Compound was prepared by repeating procedures described for General procedure J (LDA metallation) but using an alternative work up procedure. 4M HCl in 1,4-dioxane (6 mL) was added to the quenched reaction at room temperature and stirring continued for 4 hours. The organic solvent was evaporated in vacuo and the remaining aqueous solution was neutralised with sat. aqueous NaHCO$_3$. This was washed once with diethyl ether (10 mL) and extracted with CHCl$_3$/$^i$P-rOH=70:30 (3×10 mL). The CHCl$_3$ organic phase was dried (Na$_2$SO$_4$) and evaporated to dryness. Trituration with MeOH provided the title compound as a the free base. This was suspended in dichloromethane (4 mL) and methansulfonic acid (0.15M in THF was added to the suspension. After 1 hour the solvent was removed under vacuum to give the title compound as the methanesulfonate salt (37 mg, 31%). MS(ESI) m/z 442.0 (M+H)$^+$. $^1$H NMR (400 MHz, Me-d$_3$-OD): 9.01 (1H, d), 8.86 (1H, d), 8.70 (1H, s), 8.65 (1H, dd), 8.32 (1H, d), 8.16 (1H, d), 7.20 (2H, s), 4.44 (2H, s), 4.00-3.93 (7H, m), 3.24 (2H, q), 2.71 (3H, s), 1.40 (3H, t).

Example 102

Method 1 (Synthetic Intermediate)

(2-Bromo-pyridin-4-yl)-[5-(4-dimethylamino-piperidin-1-yl)-1-(2-trimethylsilanyl-ethoxymethyl)-1H-benzoimidazol-2-yl]-methanone (as a mixture with the 6-regioisomer)

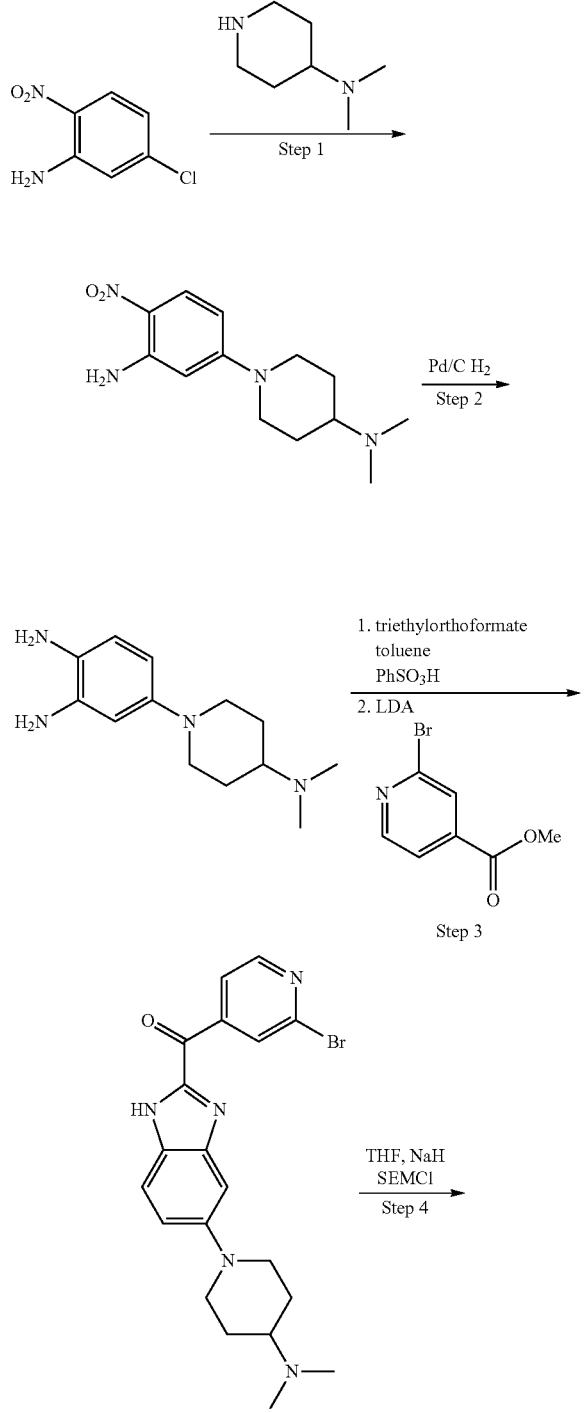

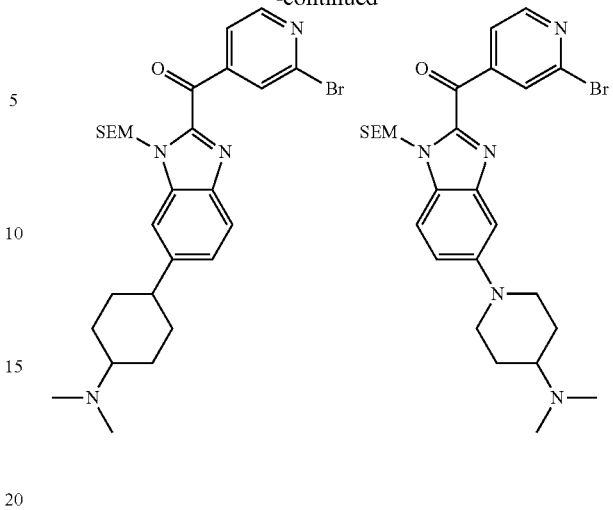

Step 1: To 5-chloro-2-nitroaniline (16.9 mmol) in DMF (56 mL) was added 4-(dimethylamino)piperidine (18.5 mmol) and $K_2CO_3$ (18.5 mmol). The reaction was stirred at 140° C. overnight after which another further 9.2 mmol of the amine was added. Stirring at 140° C. was continued for a further 5 hours. The mixture was allowed to cool and then the precipitate was collected by filtration. The precipitate was washed with EtOAc and then the combined filtrates were evaporated to dryness. The residue suspended in water and the resulting precipitate collected by filtration. The product was washed with water and then dried to give a [1-(3-amino-4-nitro-phenyl)-piperidin-4-yl]-dimethyl-amine as a brown/orange solid (3.9 g).

Step 2: To [1-(3-amino-4-nitro-phenyl)piperidin-4-yl]-dimethyl-amine (3.8 g, 14.4 mmol) was added Pd/C (300 mg) in EtOH (205 mL). The flask was shaken under $H_2$ atmosphere for 6 hours. The catalyst was removed by filtration and the filtrate evaporated to dryness to give 4-(4-dimethylamino-piperidin-1-yl)benzene-1,2-diamine which was used directly in the next step.

Step 3: A mixture of 4-(4-dimethylamino-piperidin-1-yl)-benzene-1,2-diamine (3.5 g, 14.9 mmol), triethyl orthoformate (10.0 ml, 59.7 mmol), benzenesulfonic acid (83 mg, 0.52 mmol) in toluene (30 mL) was heated at reflux, under $N_2$, overnight. Approximately half the volume of the toluene added was then distilled off. The same quantity of anhydrous toluene was re-added. Again this quantity of solvent was distilled off. The mixture was allowed to cool to room temperature.

To the mixture was then added the DIPEA (3.1 mL, 1.2 mmol), THF (~20 mL) and 2-bromo-isonicotinic acid methyl ester (4.2 mmol, 19.4 mmol) under $N_2$. The reaction was cooled to −78° C. and LDA (9.7 ml, 19.4 mmol) was added slowly. The mixture was stirred for another 2 hours at −78° C. and quenched at this temperature with water. The reaction was allowed to warm up to room temperature. The reaction was concentrated in vacuo. The aqueous mixture was then acidified with aqueous HCl (2M; approx ⅓ volume), left for 1 hour and then basified with sat. aqueous $NaHCO_3$. The product was extracted with EtOAc (×4). The combined organic layers were washed with brine and dried over MgSO₄. The product was filtered and evaporated to dryness in vacuo. The residue was stirred with Et₂O and the resulting precipitate was collected by filtration and washed Et₂O. The product was dried in vacuo to give the product (6 g).

Step 4: (2-Bromo-pyridin-4-yl)-[5-(4-dimethylamino-piperidin-1-yl)-1H-benzoimidazol-2-yl]-methanone (11.9 g, 27.8 mmol) was dissolved in 200 mL of dry THF. This solution was cooled at 0° C. and NaH 60% dispersion (1.34 g, 33.3 mmol) was added in portions. The mixture stirred at 0° C. for 30 minutes and then the 2-(trimethylsilyl)ethoxymethyl chloride (5.56 g, 33.3 mmol) was added dropwise. The mixture was allowed to warm at room temperature while stirring overnight. 2M Aqueous HCl (300 mL) was carefully added and then the aqueous mixture was washed with EtOAc (3×100 mL). The aqueous phase was then neutralised with saturated aqueous NaHCO₃ and then extracted with CHCl₃/ⁱPrOH (3:1; 3×250 mL). The combined CHCl₃/i-PrOH fractions were dried (Na₂SO₄) and then evaporated to dryness. Purification by SiO₂ chromatography (dichloromethane/NH₃ 2.0M in MeOH; 98:2 to 90:10) gave the title compound as a dark red oil (11.2 g, yield 72%; as a mixture of two regioisomers). MS(ESI) m/z 558, 560.2 (M+H)⁺.

Examples 103 to 124

Examples 103 to 124 describe the preparation of compounds of the formula (I).

Example 103

[2-(2,3-Difluoro-6-methoxy-phenyl)-pyridin-4-yl]-[5-(4-dimethylamino-piperidin-1-yl)-1H-benzoimidazol-2-yl]-methanone

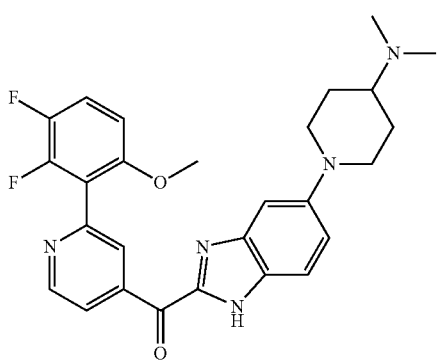 [SMILES: COc1ccc(F)c(F)c1-c1cc(C(=O)c2nc3cc(N4CCC(N(C)C)CC4)ccc3[nH]2)ccn1]

Example 102, method 1 (0.9 g, 1.61 mmol) was used as starting material. The title compound (0.24 g, 24%) was prepared by following procedures described in Example 32 followed by General procedure F (SEM deprotection). MS(ESI) m/z 492.2 (M+H)⁺. ¹H NMR (400 MHz, CDCl₃): 9.02 (1H, d), 8.57-8.52 (1H, m), 8.50 (1H, d), 7.80 (0.8H, d), 7.52-7.46 (0.2H, m), 7.39 (0.2H, s), 7.21 (1H, q), 7.16 (0.8H, dd), 6.91 (1H, d), 6.77-6.70 (1H, m), 3.86 (2H, d), 3.80 (3H, s), 2.93-2.76 (2H, m), 2.43 (7H, d), 2.05 (2H, d), 1.83-1.73 (2H, m).

Example 104

[5-(4-Isopropyl-piperazin-1-yl)-1H-benzoimidazol-2-yl]-(2-isoquinolin-4-yl-pyridin-4-yl)-methanone

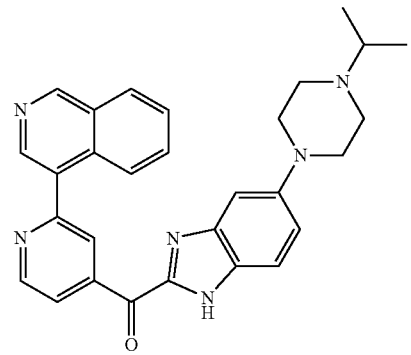 [SMILES: CC(C)N1CCN(c2ccc3[nH]c(C(=O)c4ccnc(-c5cncc6ccccc56)c4)nc3c2)CC1]

Example 91 (83 mg, 0.19 mmol) was added to a screw cap vial and dissolved in 1,2-dichloroethane/MeOH (1:1; 2 mL). Acetone (40 μl, 0.54 mmol) and glacial acetic acid (20 μl, 0.38 mmol) were added to the vial followed by NaBH(OAc)₃ (61 mg, 0.29 mmol). The reaction was heated at 37° C. for 4 hours and then quenched with 1M aqueous NaOH (4 mL). The mixture was diluted with water and then extracted with CHCl₃/ⁱPrOH (3:1; 3×5 mL). The combined organic fractions were dried (Na₂SO₄) and then evaporated to dryness. Purification by SiO₂ chromatography (dichloromethane/NH₃ 2.0M in MeOH; 2% to 8%) to give the title compound as a red solid (18 mg, 20%). MS(ESI) m/z 477.2 (M+H)⁺. ¹H NMR (400 MHz, Me-d₃-OD): 9.38 (1H, s), 9.04 (1H, d), 8.69 (2H, d), 8.43-8.35 (1H, m), 8.26 (2H, d), 7.94-7.85 (1H, m), 7.85-7.75 (1H, m), 7.68 (1H, d), 7.24 (1H, d), 7.07 (1H, s), 3.31-3.28 (4H, m), 2.84-2.75 (5H, m), 1.16 (6H, d).

General Procedure L (Suzuki)

The heteroaryl bromide (1 mol. eq.), aryl or heteroarylboronic acid (or boronic acid pinacol ester) (2.0 mol. eq.), Pd (PPh₃)₄ (0.1 mol. eq.) and solid K₃PO₄ (3 mol. eq.) were added to a microwave reaction tube equipped with a stir bar. A mixture solvent of DME:toluene:MeOH (4:4:1, to make 0.1M solution) was added afterwards. The microwave tube was sealed and degassed. It was heated in a microwave reactor at 100° C. or higher for 10 plus minutes upon different substrates. The mixture was then diluted with H₂O/CHCl₃, filtered and the aqueous layer was extracted three times with CHCl₃ (or CHCl₃/ⁱPrOH, 2:1). The combined extracts were dried (Na₂SO₄), filtered, and concentrated in vacuo. The residue was then purified by SiO₂ chromatography (eluting with EtOAc/Heptane system).

General Procedure M (Suzuki)

The aryl or heteroaryl bromide (1 mol. eq.), aryl or heteroarylboronic acid (or boronic acid pinacol ester) (2.0 mol. eq.) and Pd (PPh₃)₄ (0.1 mol. eq.) were added to a microwave reaction tube equipped with a stir bar. A mixture solvent of DME:toluene:EtOH=4:4:1 (to make a 0.1M solution) and aqueous K₃PO₄ (2M, 4 mol. eq.) were added. The microwave tube was sealed and degassed. It was heated in a microwave reactor at 120° C. or higher for at least 40 minutes depending on the substrate used. The mixture was then diluted with H₂O/CHCl₃, filtered and the aqueous layer was extracted three times with CHCl₃ (or CHCl₃/ⁱPrOH, 2:1). The combined extracts were dried over (Na₂SO₄), filtered, and concentrated in vacuo. The residue was then purified by either preparative HPLC or SiO₂ chromatography (eluting with dichloromethane/MeOH/NH₃ systems) to give the product.

General Procedure N (BOC Deprotection)

To the BOC-protected substrate was added TFA:dichloromethane (1:1, 0.1M). The reaction was stirred at room temperature for 1 hour until complete and then evaporated to dryness to yield the crude amine. Purification by reparative HPLC then gave the product. This method was also used for SEM deprotection in certain cases.

Example 105-A

4-{4-[6-(4-dimethylamino-piperidin-1-yl)-1H-benzoimidazole-2-carbonyl]-4'-methyl[2,3']bipyridinyl-6'-yl}piperazine-1-carboxylic acid tert-butyl ester and Example 105-B

[6-(4-Dimethylamino-piperidin-1-yl)-1H-benzoimidazol-2-yl]-(4'-methyl-6'-piperazin-1-yl-[2,3']bipyridinyl-4-yl)-methanone

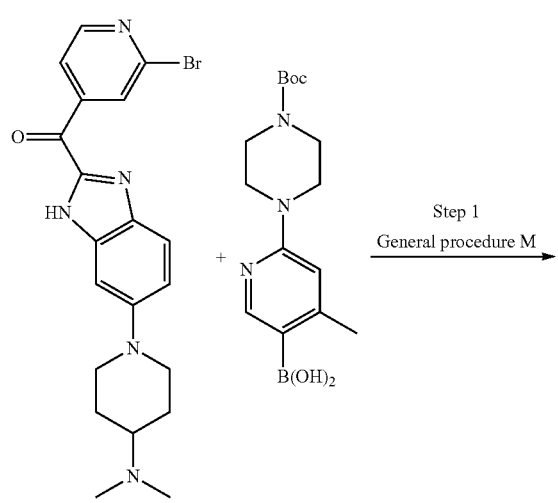

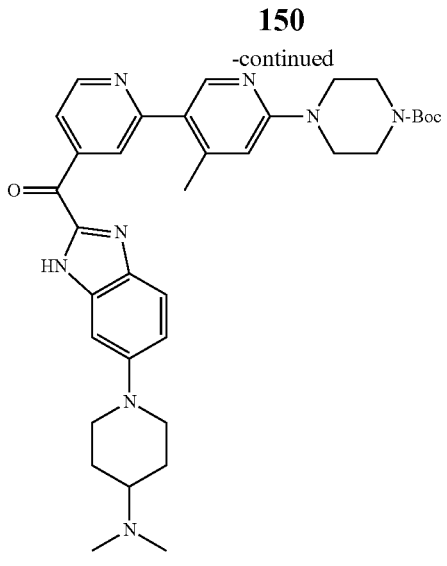

Example 105-A (as a mixture with the corresponding 5-substituted benzimidazole regioisomer)

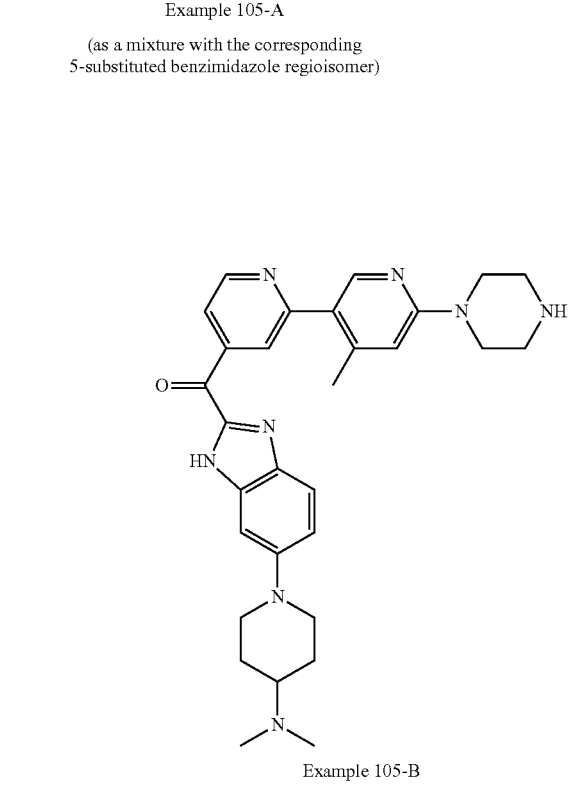

Example 105-B

The product from Example 102 (Method 1, Step 3) (0.23 mmol) was used as starting material. Step 1 was performed according General procedure M (Suzuki), giving Example 105-A. Step 2 was performed by following General procedure N (BOC deprotection) to afford the Example 105-B (61 mg, 50%). MS(ESI) m/z 525.3107 (M+H)⁺. ¹H NMR (400 MHz, DMSO-d₆): 8.90 (1H, d), 8.43 (1H, s), 8.25 (1H, s), 8.14 (1H, d), 7.64 (1H, s), 7.19 (1H, d), 6.78 (1H, s), 3.80-3.74 (2H, m), 3.50-3.45 (4H, m), 2.80-2.75 (4H, m), 2.74-2.65 (2H, m), 2.41 (3H, s), 2.20 (6H, s), 1.90-1.85 (2H, m), 1.55-1.50 (2H, m).

The following compounds were prepared in an analogous fashion to Example 105-A starting with the appropriate boronic acid (or pinacol ester).

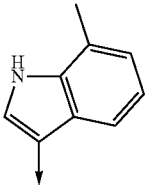

| Example | Ar | Yield | ¹H NMR/additional comments | HRMS m/z |
|---|---|---|---|---|
| 106 | 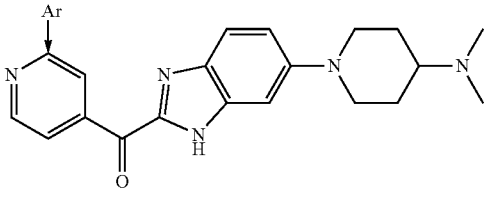 | 38 mg, 35% | ¹H NMR (400 MHz, DMSO-d₆): 13.28 (1H, bs), 11.65 (1H, s), 8.87 (1H, d), 8.76 (1H, s), 8.38 (1H, d), 8.20 (1H, d), 8.03 (1H, d), 7.74-7.80 (1H, m), 7.20 (1H, m), 7.15-7.03 (2H, m), 6.93 (1H, s), 3.77-3.85 (2H, m), 2.86-2.76 (2H, m), 2.57 (3H, s), 2.32-2.27 1H, m), 2.25 (6H, s), 1.96-1.88 (2H, m), 1.63-1.51 (2H, m). | 479.2545 (M + H)⁺ |
| 107 | 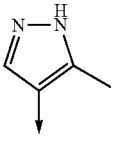 | 39 mg, 40% | ¹H NMR (400 MHz, DMSO-d₆): 13.21 (1H, s), 12.87 (1H, d), 8.80 (1H, d), 8.48 (1H, s), 8.30 (1H, s), 8.02 (1H, d), 7.68 (1H, d), 7.19 (1H, d), 6.87 (1H, s), 3.75-3.70 (2H, m), 2.76-2.70 (2H, m), 2.51 (3H, s), 2.21 (6H, s), 1.90-1.86 (2H, m), 1.53-1.51 (2H, m). | 430.2350 (M + H)⁺ |
| 108 | 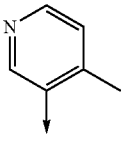 | 60 mg, 60% | ¹H NMR (400 MHz, DMSO-d₆): 13.32 (1H, s), 8.99 (1H, d), 8.65 (1H, s), 8.53 (1H, d), 8.30 (1H, d), 7.66 (1H, d), 7.42 (1H, d), 7.18 (1H, d), 6.86 (1H, s), 3.75-3.70 (2H, m), 2.80-2.75 (2H, m), 2.51 (3H, s), 2.21 (6H, s), 1.90-1.85 (2H, m), 1.55-1.50 (2H, m). | 441.2403 (M + H)⁺ |
| 109 | 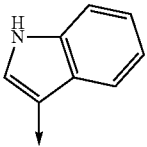 | 35 mg, 25% | Starting from 1-(phenylsulfonyl)-3-indoleboronic acid. Final deprotection: MeOH/K₂CO₃/ 80° C. for 40 minutes | 465.2400 (M + H)⁺ |

| Example | Ar | HRMS m/z |
|---|---|---|
| 110 | 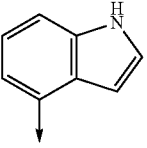 | 465.2401 (M + H)⁺ |
| 111 | 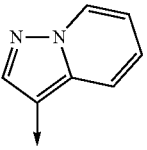 | 466.2357 (M + H)⁺ |
| 112 | 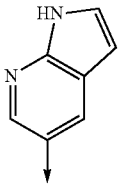 | 466.2354 (M + H)⁺ |

| | | |
|---|---|---|
| 113 | 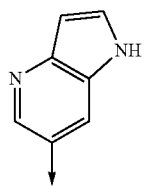 | 466.2354 (M + H)⁺ |
| 114 | 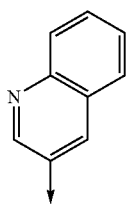 | 477.2391 (M + H)⁺ |
| 115 | 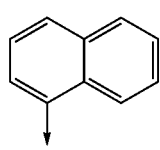 | 476.2444 (M + H)⁺ |
| 116 | 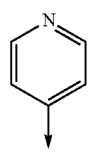 | 427.2267 (M + H)⁺ |
| 117 | 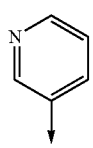 | 427.2243 (M + H)⁺ |
| 118 | 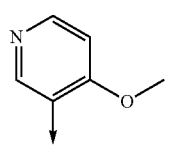 | 457.2346 (M + H)⁺ |

-continued
| 119 | 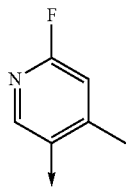 | 459.2308 (M + H)+ |
| --- | --- | --- |
| 120 | 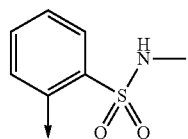 | 519.2175 (M + H)+ |
| 121 | 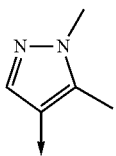 | 444.2513 (M + H)+ |
| 122 | 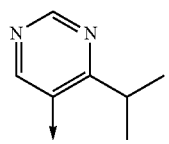 | 470.2680 (M + H)+ |
| 123 | 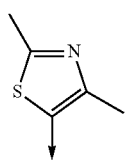 | 461.2106 (M + H)+ |
| 124 | 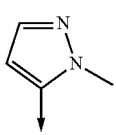 | 430.2348 (M + H)+ |

Example 106

[6-(4-Dimethylamino-piperidin-1-yl)-1H-benzoimidazol-2-yl]-[2-(7-methyl-1H-indol-3-yl)-pyridin-4-yl]-methanone

Example 107

[6-(4-Dimethylamino-piperidin-1-yl)-1H-benzoimidazol-2-yl]-[2-(5-methyl-1H-pyrazol-4-yl)-pyridin-4-yl]-methanone

Example 108

[6-(4-Dimethylamino-piperidin-1-yl)-1H-benzoimidazol-2-yl]-(4'-methyl-[2,3']bipyridinyl-4-yl)-methanone

Example 109

[6-(4-Dimethylamino-piperidin-1-yl)-1H-benzoimidazol-2-yl]-[2-(1H-indol-3-yl)-pyridin-4-yl]-methanone

Example 110

[6-(4-Dimethylamino-piperidin-1-yl)-1H-benzoimidazol-2-yl]-[2-(1H-indol-4-yl)-pyridin-4-yl]-methanone

Example 111

[6-(4-Dimethylamino-piperidin-1-yl)-1H-benzoimidazol-2-yl]-(2-pyrazolo[1,5-a]pyridin-3-yl-pyridin-4-yl)-methanone (methaneulfonate salt)

Example 112

[6-(4-Dimethylamino-piperidin-1-yl)-1H-benzoimidazol-2-yl]-[2-(1H-pyrrolo[2,3-b]pyridin-5-yl)-pyridin-4-yl]-methanone

Example 113

[6-(4-Dimethylamino-piperidin-1-yl)-1H-benzoimidazol-2-yl]-[2-(1H-pyrrolo[3,2-b]pyridin-6-yl)-pyridin-4-yl]-methanone

Example 114

[6-(4-Dimethylamino-piperidin-1-yl)-1H-benzoimidazol-2-yl]-(2-quinolin-3-yl-pyridin-4-yl)-methanone

Example 115

[6-(4-Dimethylamino-piperidin-1-yl)-1H-benzoimidazol-2-yl]-(2-naphthalen-1-yl-pyridin-4-yl)-methanone

Example 116

[2,4']Bipyridinyl-4-yl-[6-(4-dimethylamino-piperidin-1-yl)-1H-benzoimidazol-2-yl]-methanone

Example 117

[2,3']Bipyridinyl-4-yl-[6-(4-dimethylamino-piperidin-1-yl)-1H-benzoimidazol-2-yl]-methanone

Example 118

[6-(4-Dimethylamino-piperidin-1-yl)-1H-benzoimidazol-2-yl]-(4'-methoxy-[2,3']bipyridinyl-4-yl)-methanone

Example 119

[6-(4-Dimethylamino-piperidin-1-yl)-1H-benzoimidazol-2-yl]-(6'-fluoro-4'-methyl-[2,3']bipyridinyl-4-yl)-methanone

Example 120

2-{4-[6-(4-Dimethylamino-piperidin-1-yl)-1H-benzoimidazole-2-carbonyl]-pyridin-2-yl}-N-methyl-benzenesulfonamide

Example 121

[6-(4-Dimethylamino-piperidin-1-yl)-1H-benzoimidazol-2-yl]-[2-(1,5-dimethyl-1H-pyrazol-4-yl)-pyridin-4-yl]-methanone

Example 122

[6-(4-Dimethylamino-piperidin-1-yl)-1H-benzoimidazol-2-yl]-[2-(4-isopropyl-pyrimidin-5-yl)-pyridin-4-yl]-methanone

Example 123

[6-(4-Dimethylamino-piperidin-1-yl)-1H-benzoimidazol-2-yl]-[2-(2,4-dimethyl-thiazol-5-yl)-pyridin-4-yl]-methanone

Example 124

[6-(4-Dimethylamino-piperidin-1-yl)-1H-benzoimidazol-2-yl]-[2-(2-methyl-2H-pyrazol-3-yl)-pyridin-4-yl]-methanone

Example 102

Method 2 (Synthetic Intermediate)

(2-Bromo-pyridin-4-yl)-[5-(4-dimethylamino-piperidin-1-yl)-1-(2-trimethylsilanyl-ethoxymethyl)-1H-benzoimidazol-2-yl]-methanone (as a mixture with the 6-regioisomer)

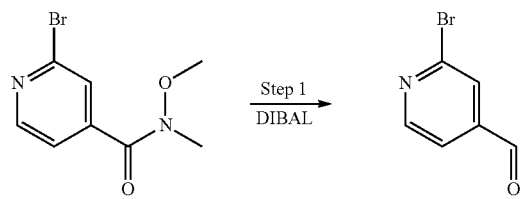
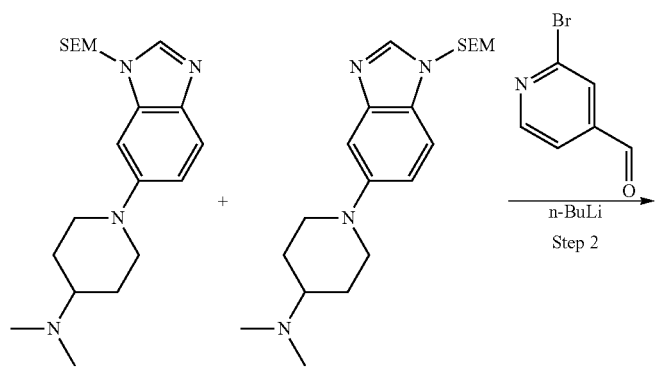
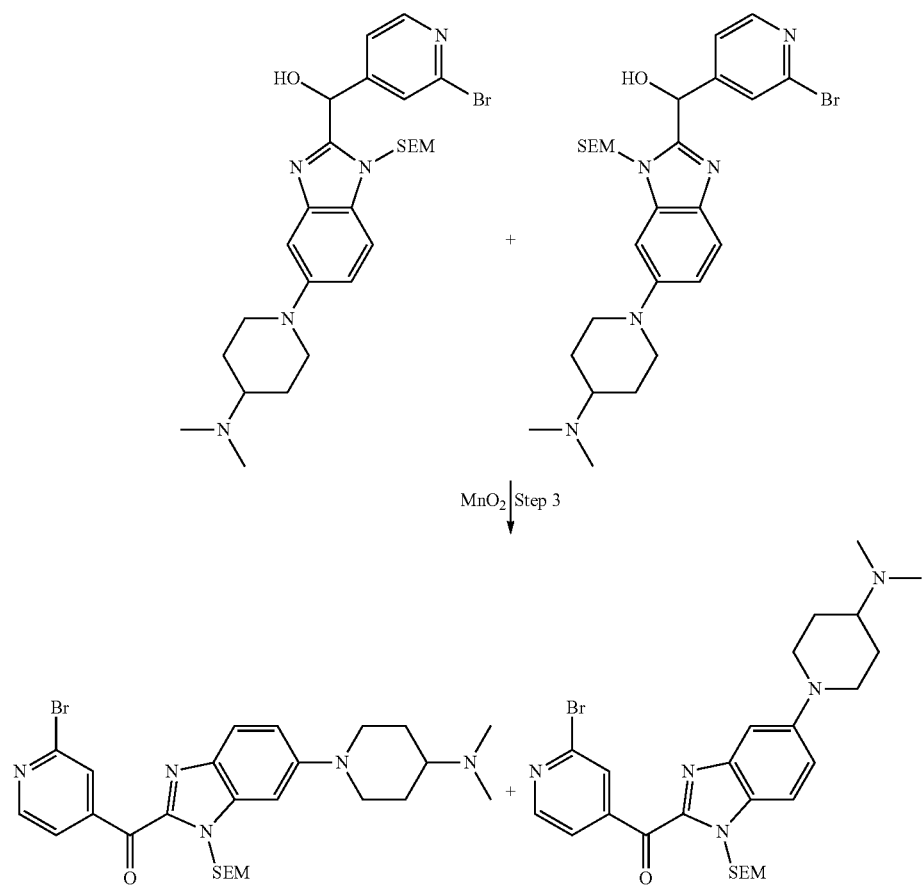

Starting with Example 25, Step 1 was performed by following procedures describe for Example 42. Step 2 and Step 3 were performed by following procedures describe for Example 48.

Examples 125 to 140

Examples 125 to 140 describe the preparation of compounds of the formula (I).

Starting from Example 102 (method 2), the following were prepared according to General procedures C (Suzuki) by coupling with the appropriate boronic acid or ester. Deprotection using General procedures D, E or F followed by purification gave the final products.

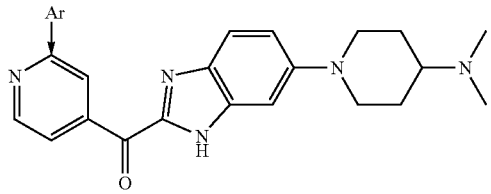

| Example | Structure: Ar = | Additional comments | NMR | LC/MS |
|---|---|---|---|---|
| 125 | F-phenyl-OMe | Deprotection: General procedure D. | ¹H NMR (400 MHz, CDCl₃): 9.48-9.29 (2.0H, m), 8.86-8.80 (0.2H, m), 8.77 (0.8H, dd), 8.22 (0.8H, d), 8.10 (1.0H, dd), 7.91 (0.2H, d), 7.80 (0.2H, s), 7.63-7.47 (2.0H, m), 7.41 (1.0H, dd), 7.33 (0.8H, d), 4.34 (3.0H, s), 4.28 (1.6H, br d), 4.18 (0.4H, br d), 3.35-3.20 (2.0H, m), 3.01-2.77 (7.0H, m), 2.54-2.43 (2.0H, m), 2.26-2.12 (2.0H, m). Mixture of rotamers. | 474 [M + H]⁺ |
| 126 | dimethylpyrazole N-Me | Deprotection: General procedure E. Product isolated as the HCl salt. | ¹H NMR (400 MHz, DMSO-d₆): 8.91 (0.2H, dd), 8.78 (0.8H, d), 8.53 (0.2H, s), 8.12 (0.2H, dd), 7.88 (0.8H, br s), 7.84-7.77 (0.8H, m), 7.75 (0.2H, d), 7.60 (0.8H, d), 7.39 (1.0H, br d), 7.15 (1.0H, br s), 3.92-3.79 (2.0H, m), 3.77 (0.6H, s), 3.75 (2.4H, s), 3.73-3.65 (0.5H, m), 3.54-3.44 (0.5H, m), 3.42-3.27 (1.0H, m), 2.92-2.80 (1.0H, m), 2.76 (1.4H, d), 2.72 (4.6H, d), 2.39 (2.3H, s), 2.37 (0.7H, s), 2.29 (0.5H, s), 2.28 (2.5H, s), 2.24-2.13 (2.0H, m), 2.04-1.77 (2.0H, m). Mixture of rotamers. | 458 [M + H]⁺ |
| 127 | piperidinyl-phenyl | Deprotection: General procedure E. Purification: prep. LCMS giving the product as the TFA salt. | ¹H NMR (400 MHz, Me-d₃-OD): 8.94-8.86 (0.6H, m), 8.72 (0.2H, d), 8.69 (0.5H, d), 8.45 (0.5H, s), 8.37 (0.2H, s), 8.34 (0.3H, dd), 8.28-8.18 (0.7H, m), 8.13 (0.4H, d), 8.09 (0.9H, d), 7.84 (0.5H, dd), 7.77-7.70 (0.5H, m), 7.68-7.59 (1.4H, m), 7.55 (0.4H, d), 7.50 (0.9H, d), 7.38 (0.7H, dd), 7.31 (0.3H, dd), 7.23-7.14 (1.0H, m), 4.04-3.89 (2.0H, m), 3.72-3.55 (4.0H, m), 3.48-3.36 (1.0H, m), 3.02-2.84 (8.0H, m), 2.30-2.16 (2.0H, m), 2.03-1.75 (8.0H, m). Mixture of rotamers. | 509 [M + H]⁺ |

-continued

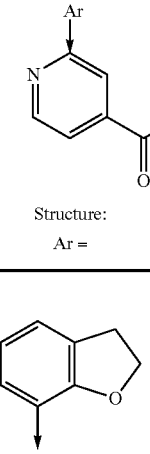

| Example | Structure: Ar = | Additional comments | NMR | LC/MS |
|---|---|---|---|---|
| 128 | 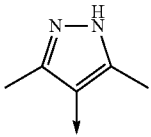 | Deprotection: General procedure E. Product isolated as the HCl salt. | $^1$H NMR (400 MHz, Me-d$_3$-OD): 8.94-8.87 (1.0H, m), 8.85 (0.8H, d), 8.80 (0.2H, d), 8.27 (0.8H, dd), 8.21 (0.2H, dd), 7.77-7.68 (2.0H, m), 7.59 (1.0H, d), 7.55-7.43 (1.0H, m), 7.40 (0.2H, s), 7.36 (0.8H, s), 7.18 (1.0H, t), 4.90-4.81 (2.0H, m), 3.98 (2.0H, br d), 3.55-3.47 (1.0H, m), 3.40 (2.0H, t), 3.14-3.01 (2.0H, m), 2.94 (6.0H, s), 2.28 (2.0H, br d), 2.06-1.92 (2.0H, m). Mixture of rotamers. | 468 [M + H]$^+$ |
| 129 | 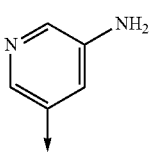 | Deprotection: General procedures E. Product isolated as the formate salt. | $^1$H NMR (400 MHz, D$_2$O): 8.45 (1H, d), 8.40 (1H, s), 7.51 (1H, d), 7.46 (1H, s), 7.26 (1H, d), 6.91 (1H, d), 6.80 (1H, s), 3.57 (2H, br d), 3.24 (1H, br t), 2.83 (6H, s), 2.56 (2H, br t), 2.15 (6H, s), 2.10 (2H, br d), 1.77-1.60 (2H, m). | 444 [M + H]$^+$ |
| 130 | | Deprotection: General procedures E. Product isolated as the HCl salt. | $^1$H NMR (400 MHz, D$_2$O/DMSO-d$_6$): 8.92 (1H, d), 8.50 (2H, s), 8.47 (1H, s), 8.23-8.10 (2H, m), 7.84-7.70 (2H, m), 7.34 (1H, d), 7.24 (1H, s), 3.91 (2H, br d), 3.28-3.12 (1H, m), 2.88 (2H, br t), 2.78 (6H, s), 2.21 (2H, br d), 1.89-1.74 (2H, m). | 442 [M + H]$^+$ |
| 131 | 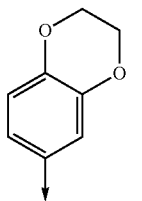 | Deprotection: General procedure F. | $^1$H NMR (400 MHz, CDCl$_3$): 8.90 (1H, t), 8.75-8.70 (1H, m), 8.38-8.33 (1H, m), 7.82 (1H, d), 7.70 (1H, d), 7.65 (1H, dd), 7.48 (0.2H, s), 7.42 (0.2H, s), 7.17 (0.8H, dd), 7.01 (1H, d), 6.91 (0.8H, d), 4.34 (4H, s), 3.84 (2H, d), 2.92-2.75 (2H, m), 2.40 (7H, d), 2.03 (2H, d), 1.80-1.67 (2H, m). | 484.2 [M + H]$^+$ |

Example 125

[6-(4-Dimethylamino-piperidin-1-yl)-1H-benzoimidazol-2-yl]-[2-(5-fluoro-2-methoxy-phenyl)-pyridin-4-yl]-methanone

Example 126

[6-(4-Dimethylamino-piperidin-1-yl)-1H-benzoimidazol-2-yl]-[2-(1,3,5-trimethyl-1H-pyrazol-4-yl)-pyridin-4-yl]-methanone

Example 127

[6-(4-Dimethylamino-piperidin-1-yl)-1H-benzoimidazol-2-yl]-[2-(4-piperidin-1-yl-phenyl)-pyridin-4-yl]-methanone (trifluoroacetate salt)

Example 128

[2-(2,3-Dihydro-benzofuran-7-yl)-pyridin-4-yl]-[6-(4-dimethylamino-piperidin-1-yl)-1H-benzoimidazol-2-yl]-methanone (hydrochloride salt)

Example 129

[6-(4-Dimethylamino-piperidin-1-yl)-1H-benzoimidazol-2-yl]-[2-(3,5-dimethyl-1H-pyrazol-4-yl)-pyridin-4-yl]-methanone (formate salt)

Example 130

(5'-Amino-[2,3']bipyridinyl-4-yl)-[6-(4-dimethylamino-piperidin-1-yl)-1H-benzoimidazol-2-yl]-methanone (formate salt)

Example 131

[2-(2,3-Dihydro-benzo[1,4]dioxin-6-yl)-pyridin-4-yl]-[6-(4-dimethylamino-piperidin-1-yl)-1H-benzoimidazol-2-yl]-methanone

Example 132

[6-(4-Dimethylamino-piperidin-1-yl)-7-fluoro-1H-benzoimidazol-2-yl]-(2-isoquinolin-4-yl-pyridin-4-yl)-methanone (trifluoroacetate salt)

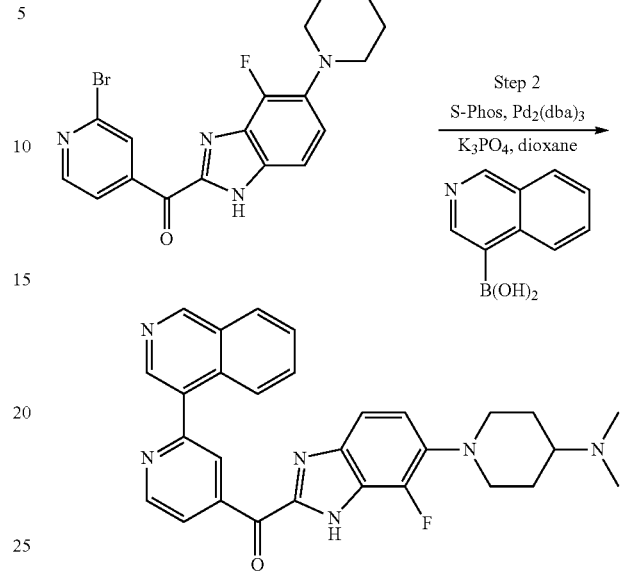

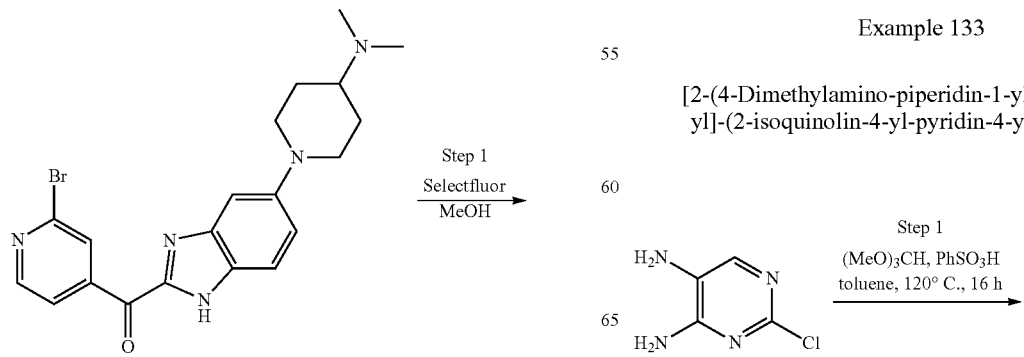

Step 1: Example 102 (method 2) (0.5 g, 1.17 mmol) was dissolved in MeOH (10 mL) in a screw cap vial and the mixture was cooled at −10° C. 1-Chloromethyl-4-fluoro-1,4-diazoniabicyclo[2.2.2]octane bis(tetrafluoroborate) (Selectfluor™) (0.62 g, 1.75 mmol) was added to the vessel which was then sealed and heated at 40° C. for 2 hours. After cooling to room temperature further Selectfluor™ (0.414 g, 1.17 mmol) was added and the reaction heated again at 40° C. for 3 hours. The mixture was filtered and then the filtrate was partitioned between 10% aqueous $NaHCO_3$ and EtOAc. The organic phase was washed with brine, dried ($MgSO_4$) and evaporated to dryness. Purification by $SiO_2$ chromatography (dichloromethane/2.0M $NH_3$ in MeOH; 3% to 5%) gave (2-Bromo-pyridin-4-yl)-[5-(4-dimethylamino-piperidin-1-yl)-4-fluoro-1H-benzoimidazol-2-yl]-methanone (81 mg, 15%). MS(ESI) m/z 447.7 $(M+H)^+$.

Step 2: Was performed according to General procedure C (Suzuki). The product was purified by prep. LCMS to give the title compound as the trifluoroacetate salt. MS(ESI) m/z 495.2 $(M+H)^+$. $^1$H NMR (400 MHz, Me-$d_3$-OD): 9.66 (1H, s), 9.12 (1H, d), 8.82 (2H, d), 8.54-8.44 (3H, m), 8.14 (1H, t), 7.99 (1H, t), 7.50 (1H, d), 7.36-7.26 (1H, m), 3.62 (2H, d), 3.41-3.35 (1H, m), 3.03-2.95 (8H, m), 2.23 (2H, d), 2.06-1.91 (2H, m).

Example 133

[2-(4-Dimethylamino-piperidin-1-yl)-9H-purin-8-yl]-(2-isoquinolin-4-yl-pyridin-4-yl)-methanone -continued

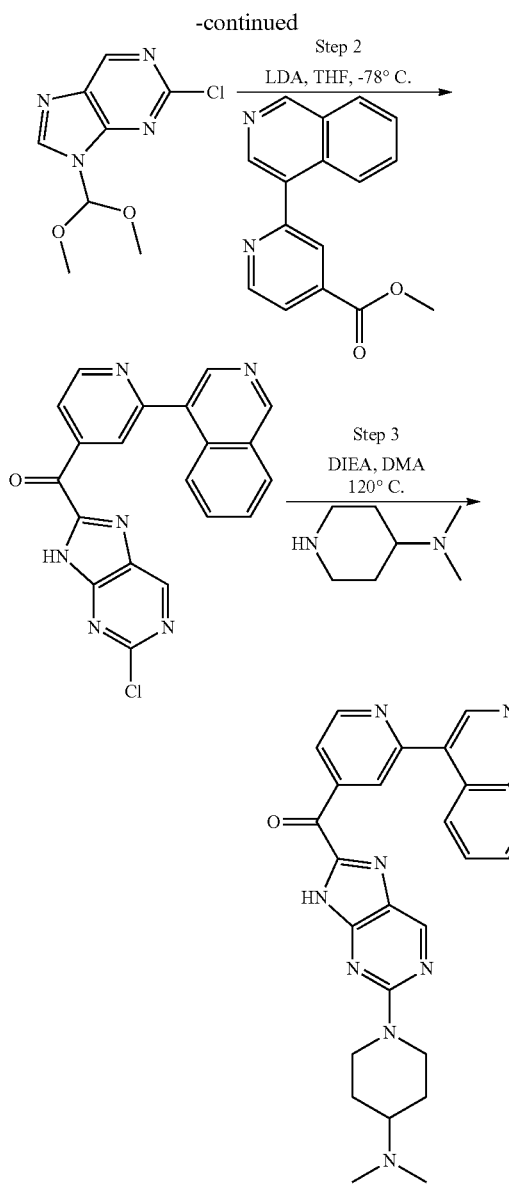

Step 1: A toluene suspension of 2-chloro-pyrimidine 4,5-diamine (289 mg, 2.0 mmol), trimethylorthoformate (1.9 g, 18 mmol) and benzenesulfonic acid (14 mg, 0.08 mmol) was heated at reflux overnight. The reaction was cooled and diisopropylethylamine (28 □l, 0.08 mmol) was added. The mixture was evaporated to dryness and the 2-chloro-9-dimethoxymethyl-9H-purine was used without further purification.

Step 2: Using the product from Step 1 and 2-isoquinolin-4-yl-isonicotinic acid methyl ester (Example 23) (528 mg, 2.0 mmol), Step 2 was performed using General procedure J (LDA metallation) followed by work up method D. A precipitate formed during the work up which was collected by filtration and washed with EtOAc to give (2-chloro-9H-purin-8-yl)-(2-isoquinolin-4-yl-pyridin-4-yl)-methanone as a brown solid. This was used without further purification Step 3: To a 0.5 mL DMA solution of crude (2-chloro-9H-purin-8-yl)-(2-isoquinolin-4-yl-pyridin-4-yl)-methanone (60 mg, 0.155 mmol) was added dimethyl-piperidin-4-yl-amine (199 mg, 1.55 mmol) and DIEA (270 µl, 1.55 mmol). The mixture was heated to 120° C. for 1 hour. The mixture was then cooled and evaporated to dryness. Purification by preparative LCMS gave the title compound. HRMS m/z 479.2329 (M+H)$^+$.

Example 134

(2-[1,4]-Diazepan-1-yl-9H-purin-8-yl)-(2-isoquinolin-4-yl-pyridin-4-yl)-methanone

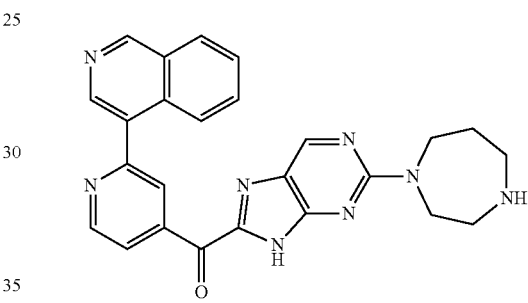

Compound was prepared by following procedures described for Example 133. [1,4]-Diazepan-1-carboxylic acid tert-butyl ester was used instead of dimethyl-piperidin-4-yl-amine. Deprotection [General Procedure N (Boc deprotection)] and final purification by preparative LCMS gave the title compound. HRMS: m/z 451.1993 (M+H)$^+$. $^1$H NMR (400 MHz, DMSO-d$_6$): 9.36 (1H, s), 9.00 (1H, dd), 8.59 (1H, m), 8.34-8.27 (2H, m), 8.19 (1H, d), 8.11 (1H, d), 7.99 (1H, d), 7.67-7.79 (2H, m), 3.60 (4H, m), 2.63 (2H, m), 2.47 (2H, m), 1.51 (2H, m).

Example 135

[5-(4-Dimethylamino-piperidin-1-yl)-3H-imidazo[4,5-b]pyridin-2-yl]-(2-isoquinolin-4-yl-pyridin-4-yl)-methanone

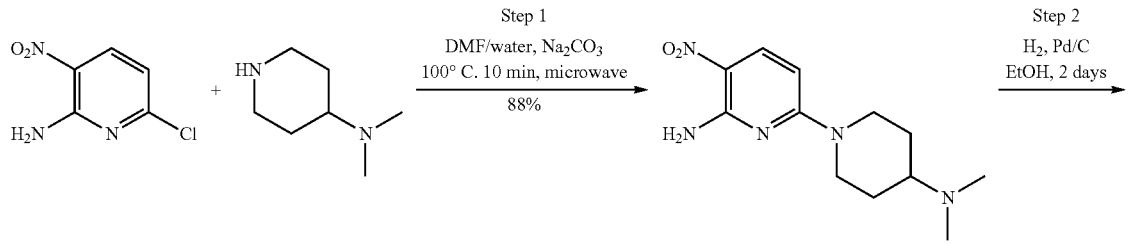

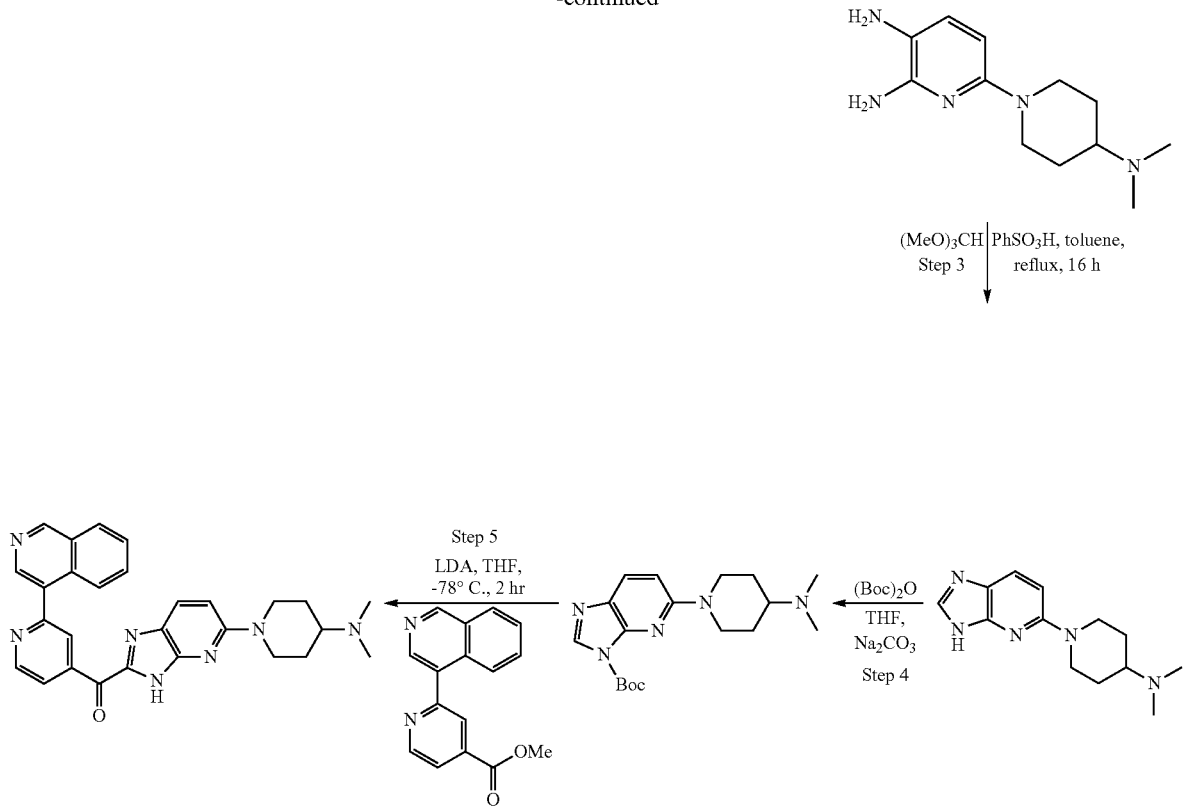

Step 1: A solution of 6-chloro-3-nitro-pyridine-2-yl-amine (7 g, 40.6 mmol), dimethylpiperidine-4-yl-amine (5.7 g, 44.5 mmol), $K_2CO_3$ (6.39 g, 60.9 mmol) and DMF/water (4:1, 100 mL) was heated at 100° C. for 10 minutes in microwave reactor. After cooling, water was added and the resulting precipitate was collected by filtration and dried to give 6-(4-dimethylamino-piperidin-1-yl)-3-nitro-pyridin-2-yl-amine (9.48 g, 88%) as a yellow solid. $^1$H NMR (400 MHz, $CD_2Cl_2$) δ: 1.48 (m, 2H), 1.72 (m, 2H), 2.28 (s, 6H), 2.42 (m, 1H), 3.01 (m, 2H), 4.50 (m, 2H), 6.16 (d, J=9.54 Hz, 1H), 8.14 (d, J=9.54 Hz, 1H). HRMS: m/z 266.1628 [M+H]$^+$.

Step 2: A mixture of 6-(4-dimethylamino-piperidin-1-yl)-3-nitro-pyridin-2-yl-amine (4 g, 15.1 mmol), 5% Pd/C (0.8 g), and EtOH (200 mL) was shaken under $H_2$ for 2 days. The solution was filtered and filtrate was concentrated to afford 6-(4-dimethylamino-piperidin-1-yl)-pyridin-2,4-yl-diamine (~4 g, ~100%) as a dark green solid. $^1$H NMR (400 MHz, $CD_2Cl_2$) δ:1.51 (m, 2H), 1.90 (m, 2H), 2.31 (s, 6H), 2.65 (m, 2H), 2.90 (br, 2H), 3.71 (m, 1H), 4.15 (m, 2H), 4.25 (br, 2H), 6.00 (d, J=8.53 Hz, 1H), 6.90 (d, J=8.03 Hz, 1H). MS(ESI) m/z 236 [M+H]$^+$.

Step 3: A solution of 6-(4-dimethylamino-piperidin-1-yl)-pyridin-2,4-yl-diamine (4 g, 17.5 mmol), trimethylorthoformate (12.6 g, 119.1 mmol), benzenesulfonic acid (0.110 g, 0.1 mmol) and methanol (100 mL) was heated at reflux overnight. The cooled mixture was then acidified to pH~3 with 2N HCl and stirred at room temperature for 1 hour. The solution was basified with $NaHCO_3$ and concentrated to afford crude [1-(3H-imidazo[4,5-b]pyridin-5-yl)-piperidin-4-yl]-dimethyl-amine (~4.0 g, ~100%) as a dark green solid. $^1$H NMR (400 MHz, $CD_2Cl_2$) δ 1.61 (m, 2H), 1.98 (m, 2H), 2.34 (s, 6H), 2.45 (m, 1H), 2.90 (m, 2H), 4.38 (m, 2H), 6.73 (d, J=9.03 Hz, 1H), 7.82 (d, J=9.03 Hz, 1H) 7.88 (s, 1H). MS(ESI) m/z 246[M+H]$^+$.

Step 4: A solution of [1-(3H-imidazo[4,5-b]pyridin-5-yl)-piperidin-4-yl]-dimethyl-amine (4 g, 16.3 mmol), di-tert-butyl dicarbonate (4.3 g, 19.6 mmol), $NaHCO_3$ (5.1 g, 48.9 mmol) and tetrahydrofuran/water (2:1, 80 mL) was stirred at room temperature overnight. The mixture was then diluted with water and extracted with EtOAc. The EtOAc layer was concentrated in vacuo and the residue purified by $SiO_2$ chromatography ($CH_2Cl_2$/MeOH, 5%-10%) to afford 5-(4-dimethylamino-piperidin-1-yl)-imidazo[4,5-b]pyridine-3-carboxylic acid tert-butyl ester (4.2 g, 75%) as a dark green solid. $^1$H NMR (400 MHz, $CD_2Cl_2$) δ 1.54 (m, 2H), 1.69 (s, 9H), 1.93 (m, 2H), 2.32 (s, 6H), 2.39 (m, 1H), 2.90 (m, 2H), 4.40 (m, 2H), 6.81 (d, J=9.03 Hz, 1H), 8.05 (d, J=9.03 Hz, 1H) 8.45 (s, 1H). MS(ESI) m/z 346[M+H]$^+$.

Step 5: Using the product from Step 4 (100 mg, 0.29 mmol) and 2-isoquinolin-4-yl-isonicotinic acid methyl ester (Example 23) (77 mg, 0.29 mmol) as starting materials, Step 5 was performed using General procedure J (LDA metallation), followed by work up method D, to afford the title compound (22 mg, 16%) as a yellow solid. $^1$H NMR (400 MHz, $CD_3OD$) δ 1.38 (m, 2H), 1.89 (m, 2H), 2.22 (s, 6H), 2.38 (m, 1H), 2.88 (m, 2H), 4.51 (m, 2H), 6.93 (d, J=9.54 Hz, 1H), 7.68 (m, 1H), 7.79 (m, 2H), 8.15 (m, 2H), 8.26 (d, J=5.02 Hz, 1H), 8.54 (s, 1H), 8.59 (s, 1H), 8.91 (d, J=5.02 Hz, 1H), 9.27, (s, 1H). HR-MS: m/z 478.2378 [M+H]+.

Example 136

[5-(4-Dimethylamino-piperidin-1-yl)-3H-imidazo[4,5-b]pyridin-2-yl]-[2-(1,3,5-trimethyl-1H-pyrazol-4-yl)-pyridin-4-yl]-methanone

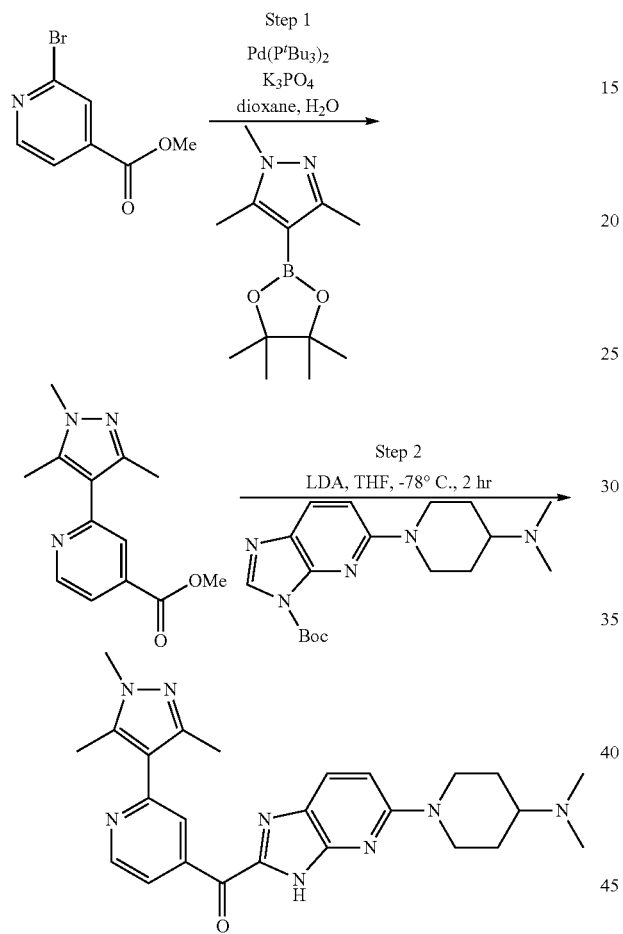

Step 1: To a microwave reactor tube was added 2-bromo-isonicotinic acid methyl ester (150 mg, 0.69 mmol), 1,3,5-trimethyl-4-(4,4,5,5-tetramethyl-[1,3,2]dioxaborolan-2-yl)-1H-pyrazole (197 mg, 0.83 mmol) and Pd$_2$(P$^t$Bu$_3$)$_2$ (14 mg, 0.028 mmol) and 1,4-dioxane (2 mL). The mixture was degassed and then 2M aqueous K$_3$PO$_4$ (0.46 mL, 1.4 mmol) was added. The mixture was heated in a microwave reactor at 80° C. for 1 hour. The cooled mixture was partitioned between CHCl$_3$ and water. The organic layer was isolated and the product purified by SiO$_2$ chromatography (0-15% MeOH in EtOAc) to give 2-(1,3,5-trimethyl-1H-pyrazol-4-yl-isonicotinic acid methyl ester (68 mg, 21%) as a yellow gum. MS(ESI) m/z 246 [M+H]+.

Step 2: A mixture of 5-(4-dimethylamino-piperidin-1-yl)-imidazo[4,5-b]pyridin-3-carboxylic acid tert-butyl ester (Step 1) (50 mg, 0.145 mmole), 2-(1,3,5-trimethyl-1H-pyrazol-4-yl-isonicotinic acid methyl ester (35 mg, 0.145 mmole), and tetrahydrofuran (3 ml) was cooled to −78° C. and reacted in accordance with General procedure J (LDA metallation), followed by work up method D. Thus, lithium diisopropylamide (2N, 0.15 ml, 0.30 mmole) was added slowly to the mixture which was stirred at −78° C. for 2 hours and then quenched with water. Solvent was removed and crude product was purified by using HPLC to afford [5-(4-dimethylamino-piperidin-1-yl)-3H-imidazo[4,5-b]pyridin-2-yl]-[2-(1,3,5-trimethyl-1H-pyrazol-4-yl)-pyridin-4-yl]-methanone (3 mg, 4.5%) as a yellow solid. 1H NMR (400 MHz, CD$_3$OD) δ 1.57 (m, 2H), 1.99 (m, 2H), 2.33 (s, 6H), 2.35 (s, 3H), 2.43 (s, 3H), 2.90 (m, 2H), 3.14 (m, 1H), 3.81 (s, 3H), 4.49 (m, 2H), 6.90 (d, J=9.03 Hz, 1H), 7.85 (d, J=9.03 Hz, 1H), 7.95 (d, J=5.02 Hz, 1H), 8.11 (s, 1H), 8.78 (d, J=5.02 Hz, 1H). MS(ESI) m/z 459 [M+1].

Example 137

4-[6-(4-Dimethylamino-piperidin-1-yl)-1H-benzoimidazole-2-carbonyl]-2-isoquinolin-4-yl-benzonitrile

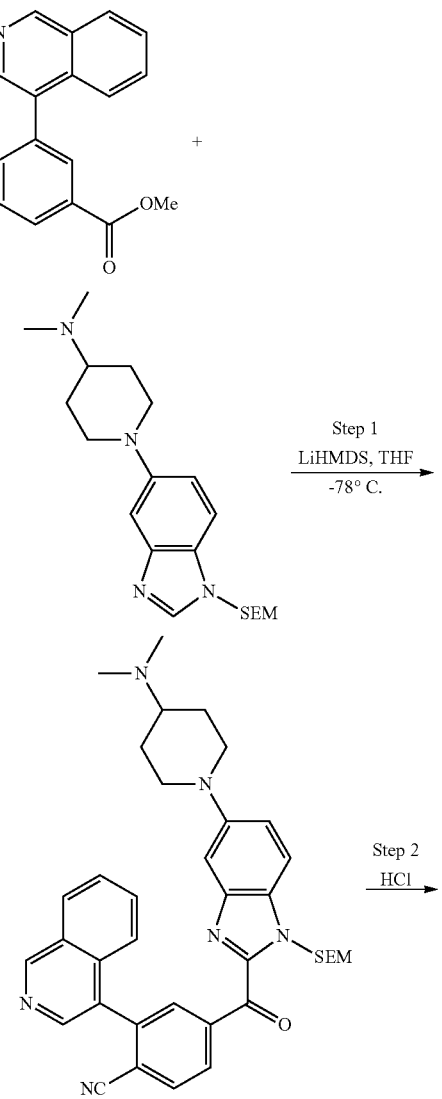

-continued

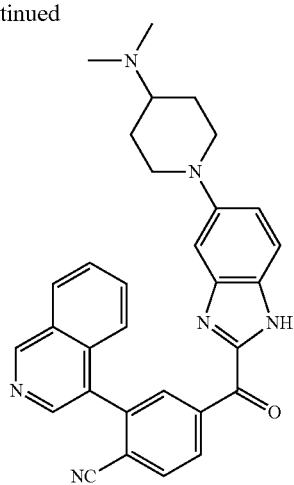

Step 1: Example 11 (2 mmol) in THF (3 mL) was added to 6 mol. eq. of LiHMDS in THF (4.1 mL 1M LiHMDS+10 mL THF) cooled at −78° C. Cooling was removed and stirring was continued for 5 minutes until the mixture became dark in color. The mixture was cooled again to −78° C. for 5 minutes prior to addition of 4-cyano-3-isoquinolin-4-yl-benzoic acid methyl ester (Example 45, 1 mol. eq) dissolved in 5 mL THF. The mixture was then allowed to warm to room temperature over 30 minutes. The mixture was diluted with sat. aq. NH$_4$Cl solution and extracted into dichloromethane (3×). The organic fraction was dried (Na$_2$SO$_4$/MgSO$_4$) and concentrated. Purification by SiO$_2$ chromatography (0-25% MeOH in dichloromethane) gave the product.

Step 2: Deprotection using General procedure D (SEM deprotection) gave the title compound (12 mg, 18%). MS(ESI) m/z 501.3 (M+H)$^+$. $^1$H NMR (400 MHz, DMSO-d$_6$): 9.51 (1H, s), 8.76 (1H, dd), 8.66 (2H, d), 8.33 (2H, dd), 7.90-7.86 (2H, m), 7.82 (1H, d), 7.71 (1H, d), 7.14 (1H, d), 6.90 (1H, s), 3.75-3.70 (2H, m), 2.75-2.72 (2H, m), 2.51 (6H, s), 1.90-1.84 (2H, m), 1.55-1.50 (2H, m).

The following examples were prepared by following procedures described for Example 137, using the appropriate heteroaryl bromides.

| Example | Structure | Additional comments | MS(ESI) m/z |
|---|---|---|---|
| 138 | 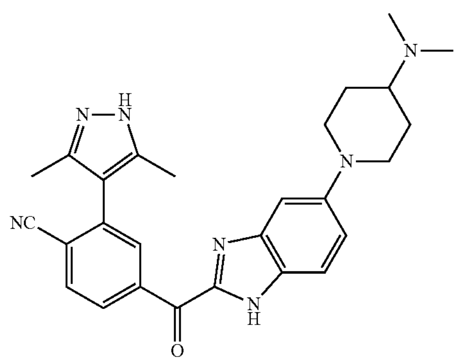 [SMILES: Cc1n[nH]c(C)c1-c1cc(C(=O)c2nc3cc(N4CCC(N(C)C)CC4)ccc3[nH]2)ccc1C#N] | Starting from Example 46. Yield = 2 mg, 2% | 468.3 (M + H)$^+$ |
| 139 | 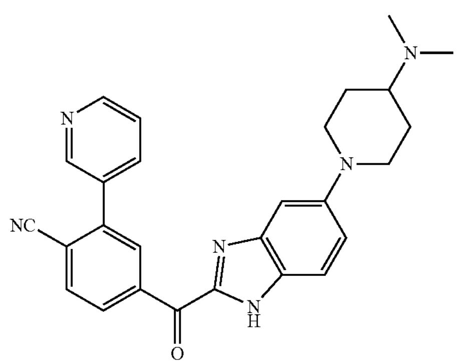 [SMILES: CN(C)C1CCN(c2ccc3[nH]c(C(=O)c4ccc(C#N)c(-c5cccnc5)c4)nc3c2)CC1] | Starting from Example 47. Yield = 7 mg, 6% | 451.3 (M + H)$^+$ |

Example 138
4-[5-(4-Dimethylamino-piperidin-1-yl)-1H-benzoimidazole-2-carbonyl]-2-(3,5-dimethyl-1H-pyrazol-4-yl)-benzonitrile
Example 139
4-[5-(4-Dimethylamino-piperidin-1-yl)-1H-benzoimidazole-2-carbonyl]-2-pyridin-3-yl-benzonitrile
Example 140
4-[5-(4-Dimethylamino-piperidin-1-yl)-3H-imidazo[4,5-b]pyridine-2-carbonyl]-2-(1H-pyrrolo[2,3-c]pyridin-4-yl)-benzonitrile
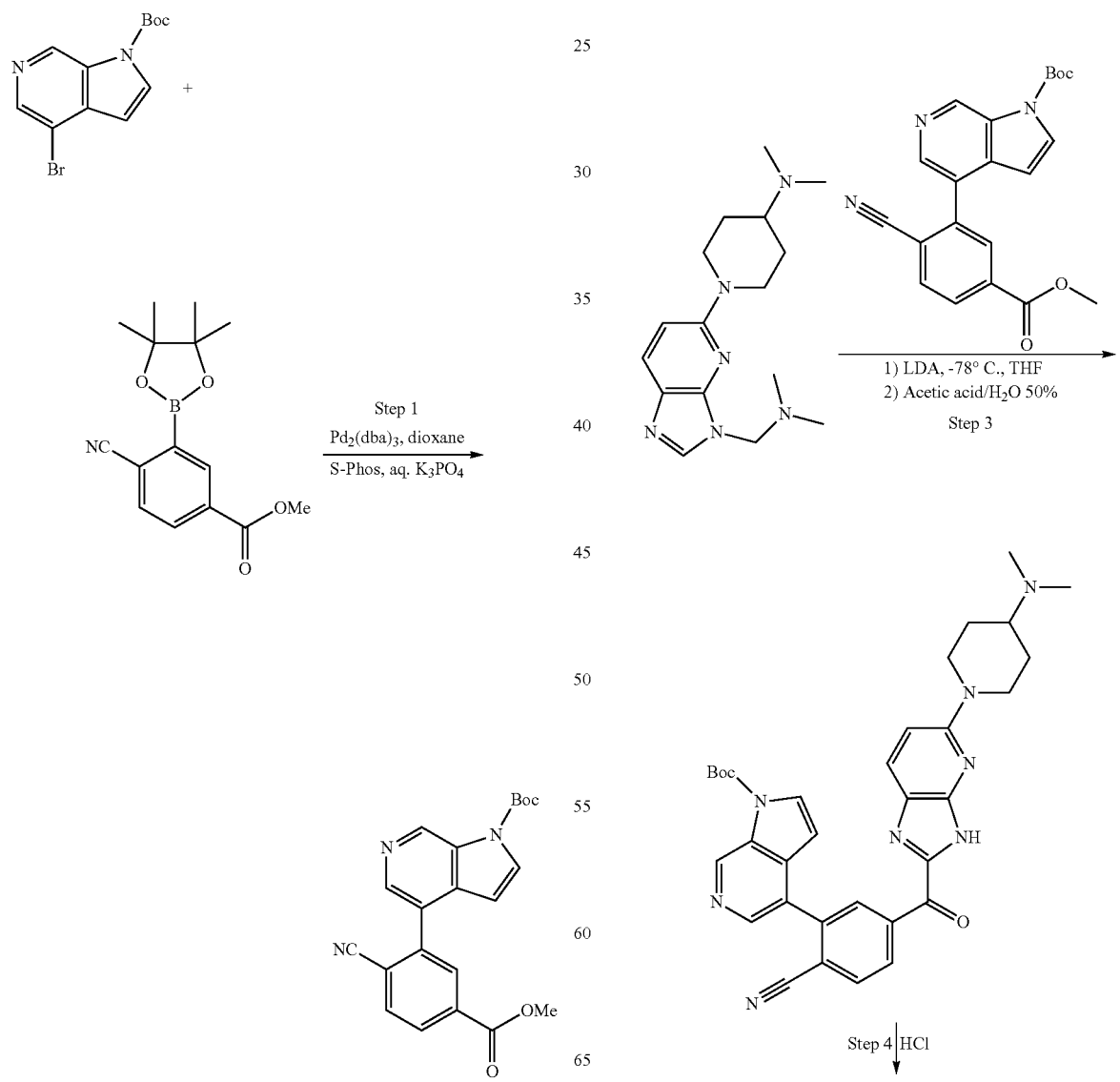

-continued

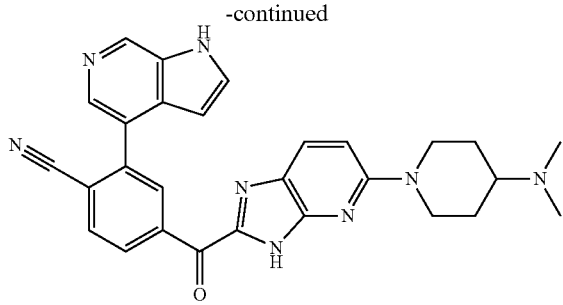

Step 1: Using 4-bromo-pyrrolo[2,3-c]pyridine-1-carboxylic acid tert-butyl ester (synthesized based on US 2005/0090529 A1, p82) (1 mol. eq.) and 4-cyano-3-(4,4,5,5-tetramethyl-[1,3,2]dioxaborolan-2-yl)-benzoic acid methyl ester (2.0 mol. eq.) a starting materials, the reaction was performed using General procedure L (Suzuki) to give 4-(2-cyano-5-methoxycarbonyl-phenyl)-pyrrolo[2,3-c]pyridine-1-carboxylic acid tert-butyl ester. MS(ESI) m/z 378.4 (M+H)+.

Step 2: Using [1-(3H-imidazo[4,5-b]pyridin-5-yl)-piperidin-4-yl]-dimethyl-amine [Example 135 (step 3], the reaction was performed by following procedures described in Example 1 to give [1-(3-dimethylaminomethyl-3H-imidazo[4,5-b]pyridin-5-yl)-piperidin-4-yl]-dimethyl-amine.

Step 3: To a solution of dimethylaminomethyl protected imidazole (2 mol eq,) in THF (0.5M), cooled to −78° C., was slowly added 2M LDA (3.5 mol eq). After 5 min, the reaction mixture was treated with a solution of 4-(2-cyano-5-methoxycarbonyl-phenyl)-pyrrolo[2,3-c]pyridine-1-carboxylic acid tert-butyl ester (Step 1) (1 mol eq,) in THF (1 vols.) at −78° C. After 5 min, the reaction mixture was quenched with 50% acetic acid in water (0.25 vols.) at −78° C. The mixture was allowed to warm to room temperature and concentrated to remove most THF. The residue was diluted with EtOAc (200 mL) and basified with aqueous ammonium hydroxide until pH>8. The organic layer was washed with brine, dried (MgSO4) and concentrated in vacuo. The residue was then purified by either preparative HPLC or SiO2 chromatography (eluting with dichloromethane/MeOH/NH3 systems).

Step 4: Deprotection using General procedure N (BOC deprotection) to gave the title compound (33%). HRMS m/z 491.2305 (M+H)+. 1H NMR (400 MHz, DMSO-d6): 13.5 (1H, bs), 11.98 (1H, s), 8.90 (1H, s), 8.74 (1H, d), 8.52 (1H, d), 8.32 (1H, s), 8.23 (1H, d), 7.95 (1H, d), 7.78 (1H, m), 7.02 (1H, d), 6.64 (1H, d), 4.43 (2H, d), 2.90-2.99 (2H, m), 2.30-2.39 (1H, m), 2.18 (6H, s), 1.84 (2H, d), 1.41-1.31 (2H, m).

Example 141

Synthetic Intermediate

4-Cyano-3-[1,6]naphthyridin-8-yl-benzoic acid methyl ester

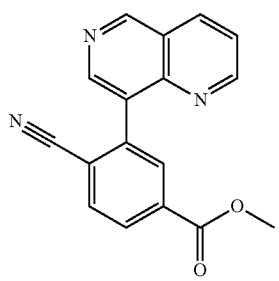 [SMILES: COC(=O)c1ccc(C#N)c(-c2cncc3cccnc23)c1]

Using, 8-bromo-[1,6]naphthyridine (1 mol. eq.) and 4-cyano-3-(4,4,5,5-tetramethyl-[1,3,2]dioxaborolan-2-yl)-benzoic acid methyl ester (2.0 mol. eq.) as starting materials, the product was prepared using General procedure L (Suzuki) to give the title compound. MS(ESI) m/z 290.1 (M+H)+.

Example 142

Synthetic Intermediate

4-Cyano-3-[3,5-dimethyl-1-(2-trimethylsilanyl-ethoxymethyl)-1H-pyrazol-4-yl]-benzoic acid methyl ester

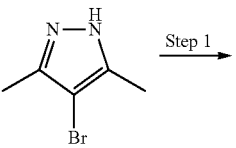

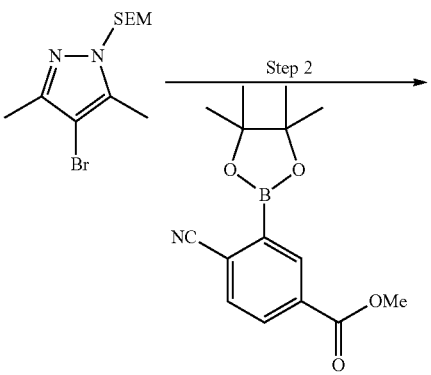

-continued

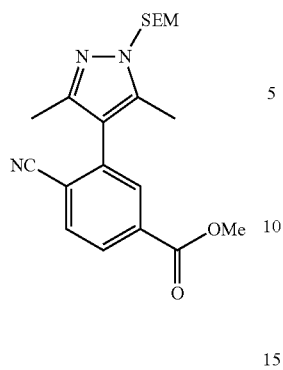

Step 1: To a stirring suspension of 4-bromo-3,5-dimethyl-1H-pyrazole (3.5 g, 20 mmol) and $Cs_2CO_3$ (13 g, 40 mmol) in 40 mL DMA was added (2-chloromethoxy-ethyl)-trimethyl-silane (5.3 mL, 30 mmol) at room temperature. The resulting mixture was stirred for 1 hour and was diluted with 100 mL EtOAc. The organic layer was washed with brine, dried ($Na_2SO_4$), filtered, and concentrated in vacuo. The residue was then purified by $SiO_2$ chromatography (eluting with EtOAc/Heptane system) to give 4-bromo-3,5-dimethyl-1-(2-trimethylsilanyl-ethoxymethyl)-1H-pyrazole 6.1 g (100%). MS(ESI) m/z 307.3 (M+H)⁺. Step 2 was performed using General procedure L (Suzuki) to give the product. MS(ESI) m/z 386.4 (M+H)⁺.

Example 143

Synthetic Intermediate

[1-(3-Dimethylaminomethyl-3H-benzoimidazol-5-yl)-piperidin-4-yl]-dimethyl-amine

Starting from 5-chloro-2-nitro-phenylamine, the product was prepared by following procedures described in Example 135 (Steps 1-3) and Example 1.

Examples 144 to 171

Examples 144 to 171 describe the preparation of compounds of the formula (I).

The Examples in the table below (Examples 144 to 147) were prepared by following procedures described for Example 140. Deprotection using General procedure N was used as appropriate.

| Example | Structure: | Additional comments | HRMS m/z |
| --- | --- | --- | --- |
| 144 | | Starting from Example 140 (Step 1) and Example 143 | 490.2353 (M + H)⁺. |
| 145 | | Starting from Example 141 and Example 143. | 502.2370 (M + H)⁺. |

| Example | Structure: | Additional comments | HRMS m/z |
|---|---|---|---|
| 146 | | Starting from Example 141 and Example 140 (Step 2) | 503.2303 (M + H)⁺. |
| 147 | | Starting from Example 142 and Example 140 (Step 2) Deprotection: General procedure N | 469.2477 (M + H)⁺. |

Example 144

4-[6-(4-Dimethylamino-piperidin-1-yl)-1H-benzoimidazole-2-carbonyl]-2-(1H-pyrrolo[2,3-c]pyridin-4-yl)-benzonitrile Example 145

4-[6-(4-Dimethylamino-piperidin-1-yl)-1H-benzoimidazole-2-carbonyl]-2-[1,6]naphthyridin-8-yl-benzonitrile Example 146

4-[5-(4-Dimethylamino-piperidin-1-yl)-3H-imidazo[4,5-b]pyridine-2-carbonyl]-2-[1,6]naphthyridin-8-yl-benzonitrile Example 147

4-[5-(4-Dimethylamino-piperidin-1-yl)-3H-imidazo[4,5-b]pyridine-2-carbonyl]-2-(3,5-dimethyl-1H-pyrazol-4-yl)-benzonitrile (for alternative synthesis of this compound, see Example 168)

Example 148

[5-(4-dimethylamino-piperidin-1-yl)-3H-imidazo[4,5-b]pyridin-2-yl]-[2-(2,3-difloro-6-methoxy-phenyl)-pyridin-4-yl]-methanone

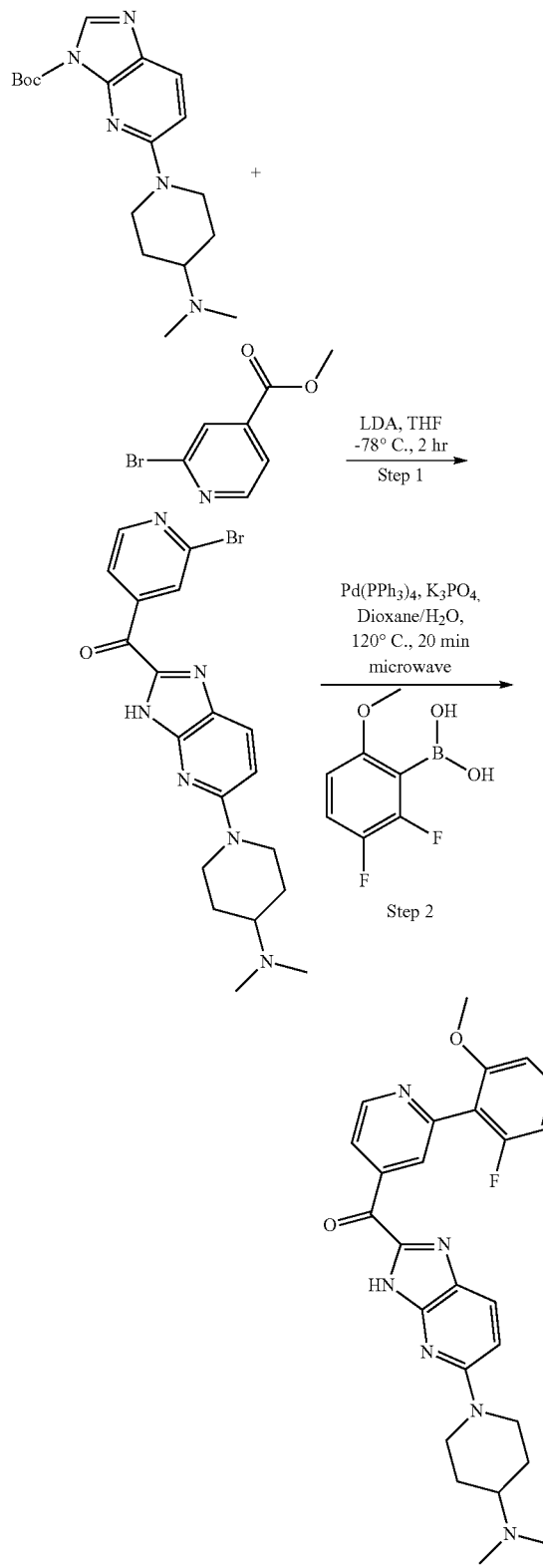

Step 1: Starting with 5-(4-dimethylamino-piperidin-1-yl)-imidazo[4,5-b]pyridine-3-carboxylic acid tert-butyl ester [Example 135, Step 4 (Step 4)] (711 mg, 2.05 mmol) and methyl-2-bromo-isonicotinate (445 mg, 2.05 mmol), the reaction was performed by following General procedure J (LDA metallation) followed by work up method D. Purification by $SiO_2$ chromatography ($CH_2Cl_2$/MeOH) gave [5-(4-dimethylamino-piperidin-1-yl)-3H-imidazo[4,5-b]pyridin-2-yl]-[2-bromo-pyridin-4-yl]-methanone (350 mg, 40%). $^1$H NMR (400 MHz, $CD_3OD$) δ 1.43 (m, 2H), 1.93 (m, 2H), 2.26 (s, 6H), 2.47 (m, 1H), 2.87 (m, 2H), 4.53 (m, 2H), 6.95 (d, J=9.54 Hz, 1H), 7.83 (d, J=9.03 Hz, 1H), 8.14 (d, 5.03 Hz, 1H), 8.42 (s, 1H), 8.47 (d, J=5.02 Hz, 1H). MS(ESI) m/z 430 [M+H]$^+$.

Step 2: Starting with the product from Step 1 (30 mg, 0.07 mmol), the reaction was performed using General procedure C (Suzuki), except that Pd(PPh$_3$)$_4$ was used in place of Pd$_2$(dba)$_3$/S-Phos and EtOAc was used in the aqueous work up instead of CHCl$_3$. Purification by preparative LCMS gave the title compound (3 mg, 8.7%). $^1$H NMR (400 MHz, $CD_3OD$) δ 1.51 (m, 2H), 1.98 (m, 2H), 2.28 (s, 3H), 2.31 (s, 6H), 2.48 (m, 1H), 2.94 (m, 2H), 4.58 (m, 2H), 6.93 (d, J=9.54 Hz, 1H), 7.01 (d, J=9.03 Hz, 1H), 7.37 (m, 1H), 7.89 (d, J=9.03 Hz, 1H), 8.30 (d, 5.52 Hz, 1H), 8.36 (s, 1H), 8.85 (d, J=5.52 Hz, 1H). HR-MS m/z 493.2159 [M+1].

Example 149

[6-(4-dimethylamino-piperidin-1-yl)-1H-benzoimidazol-2-yl]-[2-(5-methyl-imidazol-1-yl)-pyridin-4-yl]-methanone (hydrochloride salt)

Example 150

[6-(4-Dimethylamino-piperidin-1-yl)-1H-benzoimidazol-2-yl]-[2-(4-methyl-imidazol-1-yl)-pyridin-4-yl]-methanone (hydrochloride salt)

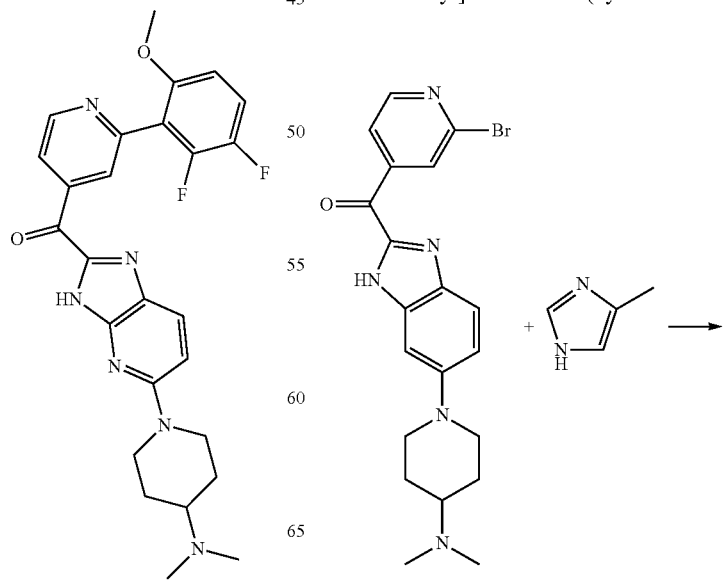

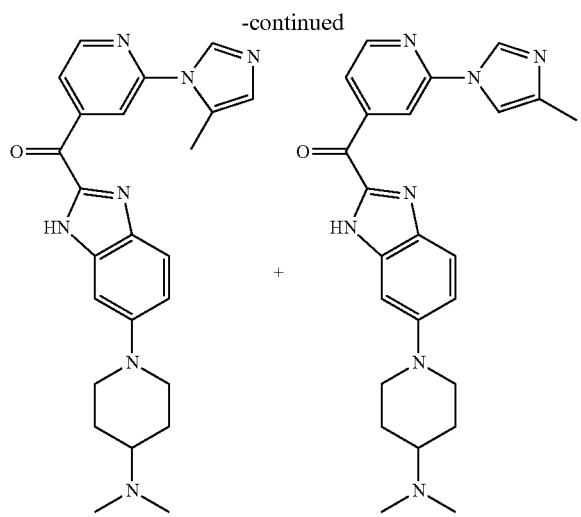

A suspension of starting material (taken from Example 102, Step 3) [method 2] (200 mg, 0.467 mmol), 4-methyl-1H-imidazole (96 mg, 1.17 mmol), CuI (9.0 mg, 0.047 mmol), trans-1,2-bis(methylamino)cyclohexane (27 mg, 0.187 mmol) and Cs$_2$CO$_3$ (533 mg, 1.64 mmol) in DMF (1 mL) under N$_2$ was heated at 110° C. for 16 hours. The mixture was then diluted with CHCl$_3$/$^i$PrOH (2:1), filtered and concentrated in vacuo. Purification by preparative LCMS afforded the two regioisomeric products. Treatment of the two products with HCl (1M in 1,4-dioxane) afforded the title compounds as hydrochloride salts.

[6-(4-Dimethylamino-piperidin-1-yl)-1H-benzoimidazol-2-yl]-[2-(4-methyl-imidazol-1-yl)-pyridin-4-yl]-methanone (93 mg)

MS(ESI) m/z 430 (M+H)$^+$. $^1$H NMR (400 MHz, D$_2$O): 9.47 (0.6H, s), 9.37 (0.4H, s), 8.86 (0.6H, d), 8.64 (0.4H, d), 8.45 (0.6H, s), 8.31 (0.6H, d), 8.14 (0.4H, s), 7.98 (0.6H, s), 7.94-7.87 (1.4H, m), 7.81 (0.6H, s), 7.74 (0.4H, d), 7.58 (0.6H, dd), 7.53 (0.4H, s), 7.47 (0.4H, dd), 4.00 (1.1H, br d), 3.91 (0.9H, br d), 3.73-3.63 (0.7H, m), 3.59-3.47 (1.4H, m), 3.22 (0.9H, br t), 2.96 (3.4H, s), 2.92 (2.6H, s), 2.50-2.40 (4.1 H, m), 2.35 (0.9H, br d), 2.24-2.10 (1.1H, m), 2.10-1.93 (0.9H, m). Mixture of rotamers.

[6-(4-Dimethylamino-piperidin-1-yl)-1H-benzoimidazol-2-yl]-[2-(5-methyl-imidazol-1-yl)-pyridin-4-yl]-methanone (32 mg)

MS(ESI) m/z 430 (M+H)$^+$. $^1$H NMR (400 MHz, D$_2$O): 9.15 (0.6H, s), 9.02 (0.4H, s), 8.90 (0.6H, d), 8.68 (0.4H, d), 8.37 (1.2H, d), 8.01 (0.4H, d), 7.96 (0.4H, d), 7.83 (0.6H, d), 7.68 (0.4H, d), 7.64 (0.6H, s), 7.47 (1.0H, d), 7.44-7.34 (1.4H, m), 3.93 (1.2H, br d), 3.86 (0.8H, br d), 3.64-3.46 (1.2H, m), 3.33 (1.2H, br t), 3.16 (0.8H, br t), 2.91 (3.6H, s), 2.87 (2.4H, s), 2.45-2.25 (5.0H, m), 2.14-1.90 (2.0H, m). Mixture of rotamers.

Example 151

[6-(4-Dimethylamino-piperidin-1-yl)-1H-benzoimidazol-2-yl]-[2-(2-methyl-benzoimidazol-1-yl)-pyridin-4-yl]-methanone

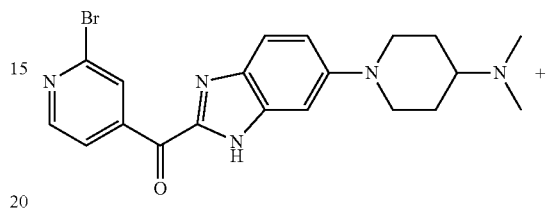

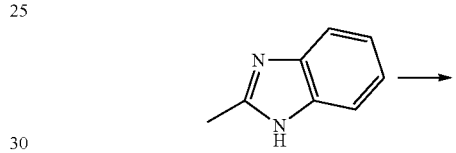

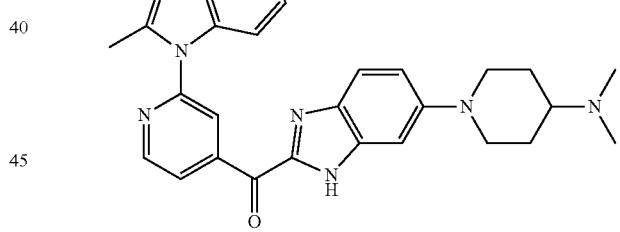

A mixture of (2-bromo-pyridin-4-yl)-[6-(4-dimethylamino-piperidin-1-yl)-1H-benzoimidazol-2-yl]-methanone (0.46 mmol, 1.0 mol eq.) [Example 102 (Method 1, Step 3)], 2-methyl benzimidazole (0.56 mmol, 1.2 mol eq), CuI (0.047 mmol, 0.5 mol eq.), (1R,2R)—N,N'-dimethyl-cyclohexane-1,2-diamine (0.093 mmol, 0.2 mol eq.) in 2 mL of DMF was heated at 130° C. for 48 h under nitrogen. The reaction was diluted with 50 mL EtOAc and 50 mL brine. The organic layer was separated and dried over Na$_2$SO$_4$, filtered and evaporated to dryness. HPLC purification gave the title compound (31 mg, 14%). HRMS m/z 480.2502 (M+H)$^+$. $^1$H NMR (400 MHz, DMSO-d$_6$): 8.96 (1H, d), 8.65 (1H, s), 8.30 (1H, d), 7.74-7.63 (3H, m), 7.31-7.29 (2H, m), 7.17 (1H, d), 6.93 (1H, s), 4.16 (1H, bs), 3.77-3.74 (2H, m), 2.80-2.71 (2H, m), 2.70 (3H, s), 2.20 (6H, s), 1.89-1.85 (2H, m), 1.57-1.48 (2H, m).

The following compounds were prepared in an analogous fashion to Example 151. Example 102 [Method 1, Step 3] was used as starting material.

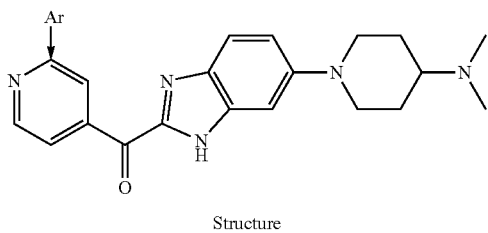
Structure

| Example | Ar | HRMS m/z |
|---|---|---|
| 152 | 2,5-dimethyl-imidazol-1-yl | 444.2515 (M + H)+. |
| 153 | 2,4-dimethyl-imidazol-1-yl | 444.2520 (M + H)+. |
| 154 | imidazo[4,5-c]pyridin-3-yl (as a 1:1 mixture with Example 155) | 467.2305 (M + H)+ |
| 155 | imidazo[4,5-c]pyridin-1-yl (as a 1:1 mixture with Example 154) | 467.2305 (M + H)+ |
| 156 | imidazo[4,5-b]pyridin-3-yl | 467.2300 (M + H)+. |
| 157 | imidazo[4,5-b]pyridin-1-yl | 467.2300 (M + H)+. |
| 158 | benzoimidazol-1-yl | 466.2350 (M + H)+. |

Example 152

[6-(4-Dimethylamino-piperidin-1-yl)-1H-benzoimidazol-2-yl]-[2-(2,5-dimethyl-imidazol-1-yl)-pyridin-4-yl]-methanone Example 153

[6-(4-Dimethylamino-piperidin-1-yl)-1H-benzoimidazol-2-yl]-[2-(2,4-dimethyl-imidazol-1-yl)-pyridin-4-yl]-methanone Example 154

[6-(4-Dimethylamino-piperidin-1-yl)-1H-benzoimidazol-2-yl]-(2-imidazo[4,5-c]pyridin-3-yl-pyridin-4-yl)-methanone Example 155

[6-(4-Dimethylamino-piperidin-1-yl)-1H-benzoimidazol-2-yl]-(2-imidazo[4,5-c]pyridin-1-yl-pyridin-4-yl)-methanone Example 156

[6-(4-Dimethylamino-piperidin-1-yl)-1H-benzoimidazol-2-yl]-(2-imidazo[4,5-b]pyridin-3-yl-pyridin-4-yl)-methanone Example 157

[6-(4-Dimethylamino-piperidin-1-yl)-1H-benzoimidazol-2-yl]-(2-imidazo[4,5-b]pyridin-1-yl-pyridin-4-yl)-methanone Example 158

(2-Benzoimidazol-1-yl-pyridin-4-yl)-[6-(4-dimethylamino-piperidin-1-yl)-1H-benzoimidazol-2-yl]-methanone Example 159

[5-(2,3-Difluoro-6-methoxy-phenyl)-pyridin-3-yl]-(5-dimethylaminomethyl-1H-benzoimidazol-2-yl)-methanone Compound was prepared by following procedures for the synthesis of Example 67, starting from 5-bromo-nicotinic acid instead of 2-bromo-isonicotinic acid. MS(ESI) m/z 423 (M+H)+. $^1$H NMR (400 MHz, CDCl$_3$): 10.86 (1H, br), 9.89 (1H, s), 9.10-9.00 (1H, m), 8.94 (1H, s), 7.94-7.82 (1H, m), 7.61-7.46 (1.5H, m), 7.38 (0.5H, d), 7.22 (1H, q), 6.80-6.70 (1H, m), 3.82 (3H, s), 3.62 (2H, s), 2.32 (6H, s).

Example 160

4-[5-(Pyrrolidin-3-yloxy)-3H-imidazo[4,5-b]pyridine-2-carbonyl]-2-(1,3,5-trimethyl-1H-pyrazol-4-yl)-benzonitrile

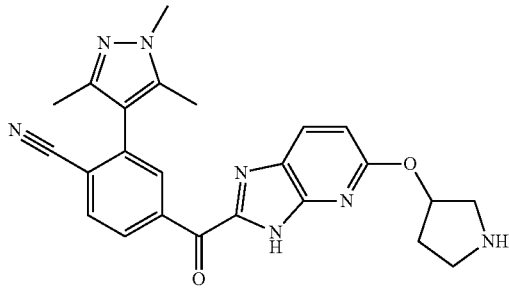 [SMILES: Cc1nn(C)c(C)c1-c1cc(C(=O)c2nc3ccc(OC4CCNC4)nc3[nH]2)ccc1C#N]

HRMS (m/z): calculated 442.1991, observed 442.2009.

The title compound was prepared from 3-(3H-imidazo[4,5-b]pyridin-5-yloxy)-pyrrolidine-1-carboxylic acid tert-butyl ester (see below) using lithiation/acylation methods analogous those described above.

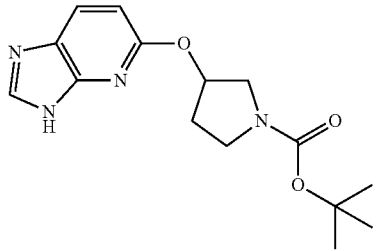 [SMILES: CC(C)(C)OC(=O)N1CCC(Oc2ccc3nc[nH]c3n2)C1]

Example 161

4-[5-(4-Dimethylamino-piperidin-1-yl)-3H-imidazo[4,5-b]pyridine-2-carbonyl]-2-(1,3,5-trimethyl-1H-pyrazol-4-yl)-benzamide

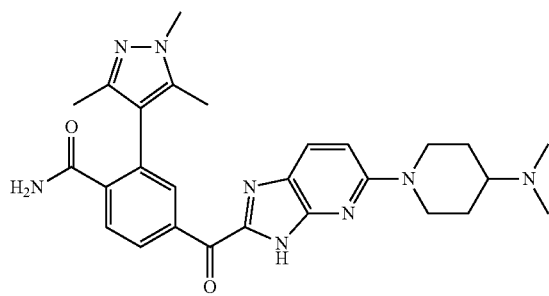 [SMILES: Cc1nn(C)c(C)c1-c1cc(C(=O)c2nc3ccc(N4CCC(N(C)C)CC4)nc3[nH]2)ccc1C(N)=O]

Step 1

3-(1,3,5-Trimethyl-1H-pyrazol-4-yl)-terephthalamic acid methyl ester

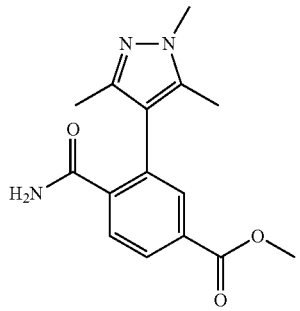 [SMILES: COC(=O)c1ccc(C(N)=O)c(-c2c(C)nn(C)c2C)c1]

Following General procedure L (Suzuki) and leaving the crude mixture at room temperature for 3 d, using 4-bromo-1,3,5-trimethyl-1H-pyrazole and 4-cyano-3-(4,4,5,5-tetramethyl-[1,3,2]dioxaborolan-2-yl)-benzoic acid methyl ester to give 4-cyano-3-[3,5-dimethyl-1-(2-trimethylsilanyl-ethoxymethyl)-1H-pyrazol-4-yl]-benzoic acid methyl ester. MS(ESI) m/z 288.1 (M+H)⁺.

Step 2

4-[5-(4-Dimethylamino-piperidin-1-yl)-3H-imidazo[4,5-b]pyridine-2-carbonyl]-2-(1,3,5-trimethyl-1H-pyrazol-4-yl)-benzamide

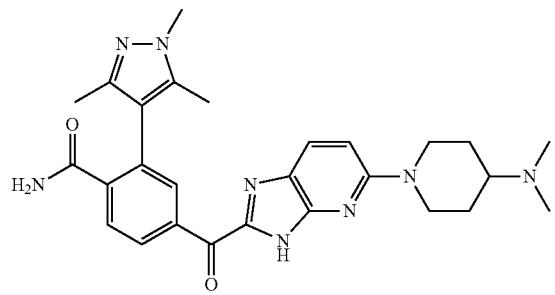 [SMILES: Cc1nn(C)c(C)c1-c1cc(C(=O)c2nc3ccc(N4CCC(N(C)C)CC4)nc3[nH]2)ccc1C(N)=O]

Following General procedure P (LDA metallation, ketone formation and in situ deprotection) using 3-(1,3,5-Trimethyl-1H-pyrazol-4-yl)-terephthalamic acid methyl ester and [1-(3-dimethylaminomethyl-3H-imidazo[4,5-b]pyridin-5-yl)-piperidin-4-yl]-dimethyl-amine to give 4-[5-(4-dimethylamino-piperidin-1-yl)-3H-imidazo[4,5-b]pyridine-2-carbonyl]-2-(1,3,5-trimethyl-1H-pyrazol-4-yl)-benzonitrile. (84%). HRMS m/z 501.2721 (M+H)⁺.

Example 162

4-[5-(4-Dimethylamino-piperidin-1-yl)-3H-imidazo[4,5-b]pyridine-2-carbonyl]-N,N-dimethyl-2-(1,3,5-trimethyl-1H-pyrazol-4-yl)-benzamide

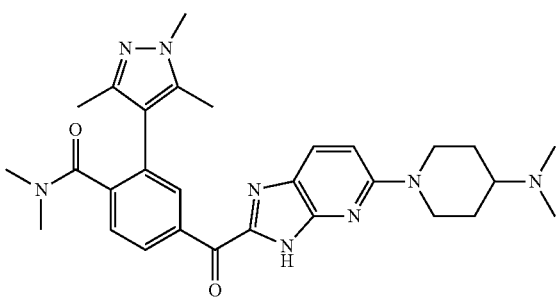

191

Step 1

N,N-Dimethyl-3-(1,3,5-trimethyl-1H-pyrazol-4-yl)-terephthalamic acid methyl ester

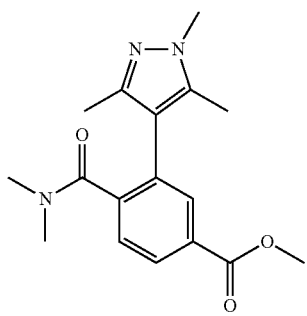

To a cooled (0° C.) suspension of NaH (60%, 10 mg, 3.5 equiv) in THF was added 4-bromo-1,3,5-trimethyl-1H-pyrazole and 4-cyano-3-(4,4,5,5-tetramethyl-[1,3,2]dioxaborolan-2-yl)-benzoic acid methyl ester (20 mg, 0.07 mmol) and the resulting mixture was treated with MeI (50 mg, 5 equiv). The reaction mixture was stirred at room temperature for 1 h, quenched with 50% AcOH in water, and extracted with EtOAc. Combined organics were dried over $Na_2SO_4$, filtered, concentrated and purified by column chromatography (MeOH/$CH_2Cl_2$) to give N,N-Dimethyl-3-(1,3,5-trimethyl-1H-pyrazol-4-yl)-terephthalamic acid methyl ester. MS(ESI) m/z 316.2 $(M+H)^+$.

Step 2

4-[5-(4-Dimethylamino-piperidin-1-yl)-3H-imidazo[4,5-b]pyridine-2-carbonyl]-N,N-dimethyl-2-(1,3,5-trimethyl-1H-pyrazol-4-yl)-benzamide

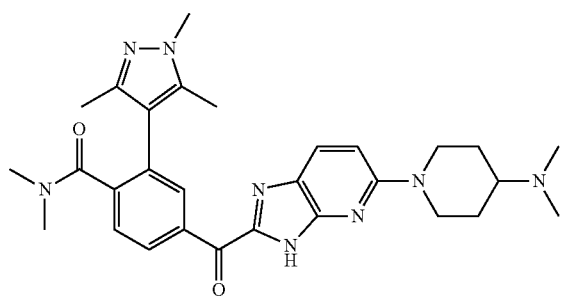

Following General procedure P (LDA metallation, ketone formation and in situ deprotection) using N,N-Dimethyl-3-(1,3,5-trimethyl-1H-pyrazol-4-yl)-terephthalamic acid methyl ester and [1-(3-dimethylaminomethyl-3H-imidazo[4,5-b]pyridin-5-yl)-piperidin-4-yl]-dimethyl-amine to give 4-[5-(4-dimethylamino-piperidin-1-yl)-3H-imidazo[4,5-b]pyridine-2-carbonyl]-2-(1,3,5-trimethyl-1H-pyrazol-4-yl)-benzonitrile. (84%). HRMS m/z 529.3036 $(M+H)^+$.

Example 163

(5-[1,4]Diazepan-1-yl-3H-imidazo[4,5-b]pyridine-2-yl)-(2-isoquinolin-4-yl-pyridin-4-yl)-methanone

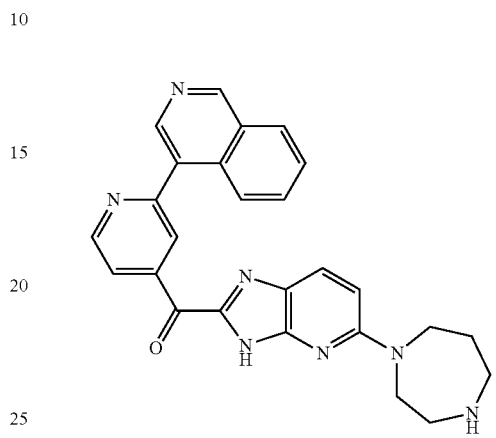

Synthetic scheme

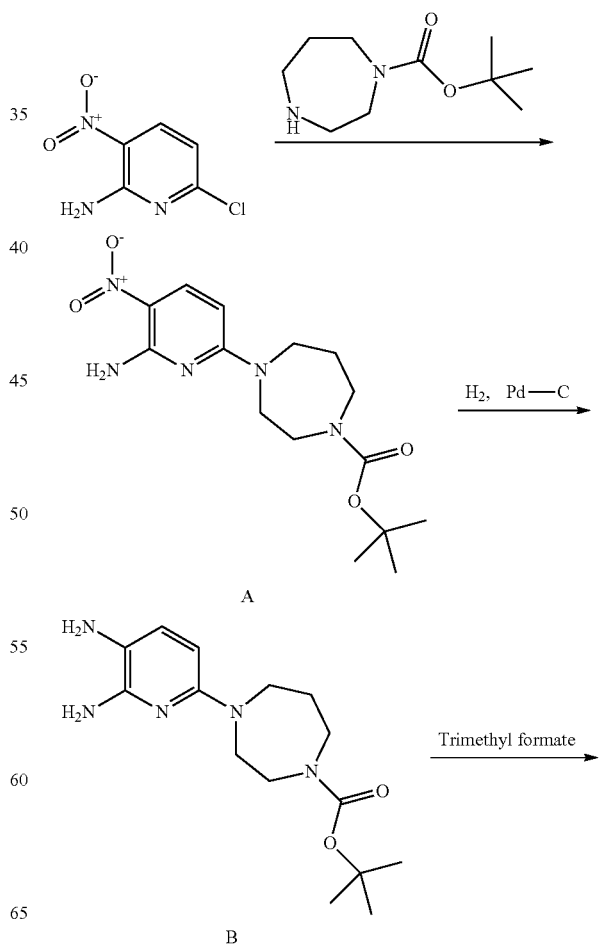

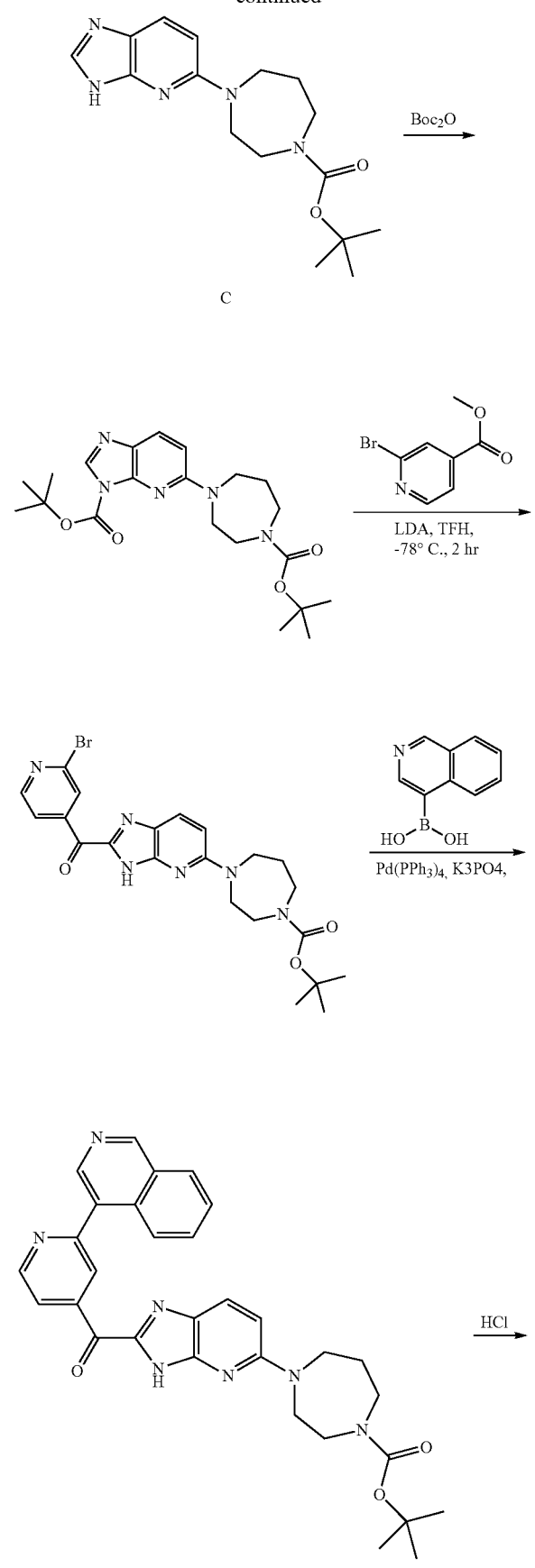

5-(4-tert-butoxycarbonyl-[1,4]diazepam-1-yl)-imidazo[4,5-b]pyridine-3-carboxylic acid tert-butyl ester The title compound was synthesized using a procedure identical to the one described in the steps 1-4 in Example 160 with the exception that N-tert-butoxycarbonyl homopiperazine was used in the place of dimethyl piperidine-4-yl-amine in the first step. The characterization data for the intermediates A, B and C is shown below.

4-(6-Amino-5-nitro-pyridin-2-yl)-[1,4]diazepane-1-carboxylic acid tert-butyl ester 6-(4-dimethylamino-piperidin-1-yl)-3-nitro-pyridin-2-yl-amine (Intermediate A)

$^1$H NMR (400 MHz, CDCl$_3$) δ 1.41 and 1.44 (two singlets due to rotamers, 9H), 1.92 (m, 2H), 3.41 (m, 2H), 3.56 (m, 2H), 3.85 (m, 6H), 6.02 (d, J=8.00 Hz, 1H), 8.19 (d, J=8.00 Hz, 1H). MS: m/z 338.4 [M+1].

4-(5,6-Diamino-pyridin-2-yl)-[1,4]diazepane-1-carboxylic acid tert-butyl ester (Intermediate B)

$^1$H NMR (400 MHz, CDCl$_3$) δ 1.41 and 1.45 (two singlets due to rotamers, 9H), 1.93 (m, 2H), 2.80 (br s, 2H), 3.20 (m, 2H), 3.29 (m, 6H), 4.20 (br s, 2H), 5.81 (d, J=8.00 Hz, 1H), 6.85 (d, J=8.00 Hz, 1H). MS: m/z 308.3 [M+1].

4-(3H-Imidazo[4,5-b]pyridin-5-yl)-[1,4]diazepane-1-carboxylic acid tert-butyl ester (Intermediate C)

$^1$H NMR (400 MHz, CDCl$_3$) δ 1.35 and 1.39 (two singlets due to rotamers, 9H), 1.99 (m, 2H), 3.24 (m, 2H), 3.45-3.86 (m, 7H), 6.54 (d, J=8.00 Hz, 1H), 7.84 (d, J=8.00 Hz, 1H), 7.85 (s, 1H). MS: m/z 318.3 [M+1].

Step 1

[4-[2-(2-Bromo-pyridine-4-carbonyl)-3H-imidazo[4,5-b]pyridine-5-yl]-[1,4]diazepane-1-carboxylic acid tert-butyl ester The mixture of 5-(4-tert-butoxycarbonyl-[1,4]diazepam-1-yl)-imidazo[4,5-b]pyridine-3-carboxylic acid tert-butyl ester (600 mg, 1.44 mmole), methyl-2-bromo-isonicotinate (310 mg, 1.43 mmole), and tetrahydrofuran (5 ml) was cooled to −78° C. Lithium diisopropylamide (2N, 1.43 ml, 2.87 mmole) was added slowly. Reaction mixture was stirred at −78° C. for 2 hours. Reaction was quenched with water and extracted with EtOAc. EtOAc layer was concentrated and crude product was purified by using silica gel chromatography, eluting with 0% to 40% of EtOAc in $CH_2Cl_2$ to afford [4-[2-(2-bromo-pyridine-4-carbonyl)-3H-imidazo[4,5-b]pyridine-5-yl]-[1,4]diazepane-1-carboxylic acid tert-butyl ester (130 mg, 18%). 1H NMR (400 MHz, $CD_2Cl_2$) δ 1.31 (s, 9H), 1.89 (m, 2H), 3.21 (m, 2H), 3.52 (m, 2H), 3.66 (m, 2H), 3.80 (m, 2H), 6.67 (d, J=9.54 Hz, 1H), 7.87 (d, J=9.03 Hz, 1H), 8.27 (d, J=5.03 Hz, 1H), 8.09 (d, J=5.02 Hz, 1H), 8.55 (s, 1H). MS(ESI) m/z 502 [M+1].

Step 2

[4-[2-(2-Isoquinolin-4-yl-pyridine-4-carbonyl)-3H-imidazo[4,5-b]pyridine-5-yl]-[1,4]diazepane-1-carboxylic acid tert-butyl ester

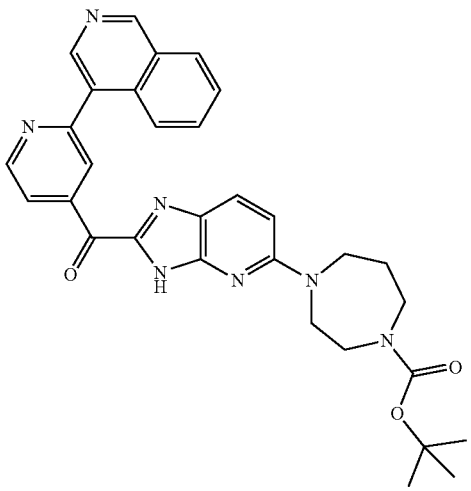 [SMILES: CC(C)(C)OC(=O)N1CCCN(c2ccc3nc(C(=O)c4ccnc(-c5cncc6ccccc56)c4)[nH]c3n2)CC1]

The mixture of [4-[2-(2-bromo-pyridine-4-carbonyl)-3H-imidazo[4,5-b]pyridine-5-yl]-[1,4]diazepane-1-carboxylic acid tert-butyl ester (40 mg, 0.08 mmole), 2-isoquinoline boronic acid (13.8 mg, 0.08 mmole), $Pd(Ph_3)_4$ (27.6 mg, 0.24 mmole), 2 molar of $K_3PO_4$ aqueous (0.08 ml, 0.16 mmole), and dioxane (3.0 ml) was degassed and heated to 120° C. for 20 minutes in microwave. Reaction solution was diluted with water and extracted with EtOAc. EtOAc layer was concentrated. Residue was purified by using silica gel chromatography, eluting with 50% to 100% of EtOAc in $CH_2Cl_2$ to afford [4-[2-(2-isoquinolin-4-yl-pyridine-4-carbonyl)-3H-imidazo[4,5-b]pyridine-5-yl]-[1,4]diazepane-1-carboxylic acid tert-butyl ester (15 mg, 34%). 1H NMR (400 MHz, $CD_2Cl_2$) δ 1.27 (d, 9H), 1.89 (m, 2H), 325 (m, 2H), 3.51 (m, 2H), 3.66 (m, 2H), 3.78 (m, 2H), 6.65 (d, J=9.03 Hz, 1H), 7.61 (t, J=7.53 Hz, J=7.53 Hz, 1H), 7.69 (t, J=7.53 Hz, J=7.53 Hz, 1H), 7.84 (d, J=9.03 Hz, 1H), 8.03 (d, J=8.03 Hz, 1H), 8.27 (d, J=8.03 Hz, 1H), 8.39 (d, J=4.52 Hz, 1H), 8.66 (s, 1H), 8.71 (s, 1H), 8.95 (d, J=5.02 Hz, 1H), 9.28 (s, 1H). HR-MS m/z 550.2570 [M+1].

Step 3

(5-[1,4]Diazepan-1-yl-3H-imidazo[4,5-b]pyridine-2-yl)-(2-isoquinolin-4-yl-pyridin-4-yl)-methanone

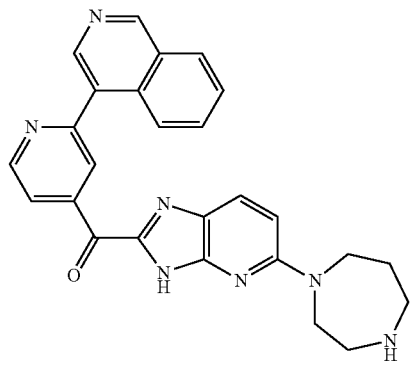 [SMILES: O=C(c1ccnc(-c2cncc3ccccc23)c1)c1nc2ccc(N3CCCNCC3)nc2[nH]1]

The mixture of 4-[2-(2-Isoquinolin-4-yl-pyridine-4-carbonyl)-3H-imidazo[4.5-b]pyridine-5-yl]-[1,4]diazepane-1-carboxylic acid tert-butyl ester (15 mg, 0.03 mmole) and 2 molar HCl in ether (1 ml) was stirred at room temperature for 2 hours. Solvent was removed. Residue was washed with ethyl ether a few times to afford (5-[1,4]diazepan-1-yl-3H-imidazo[4,5-b]pyridine-2-yl)-(2-isoquinolin-4-yl-pyridin-4-yl)-methanone (6 mg, 49%) as a yellow solid. 1H NMR (400 MHz, $CD_3OD$) δ 2.26 (m, 2H), 3.34 (m, 2H), 3.48 (m, 2H), 3.89 (m, 2H), 4.15 (m, 2H), 7.16 (m, 1H), 7.95 (m, 1H), 8.20 (m, 3H), 8.41-9.16 (m, 5H), 9.93 (d, J=6.53 Hz, 1H). HR-MS m/z 450.2033 [M+1].

Example 164

(2-Isoquinolin-4-yl-pyridin-4-yl)-5-piperazin-1-yl-3H-imidazo[4,5-b]pyridin-2-yl)-methanone

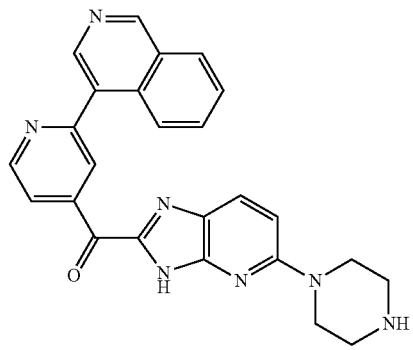 [SMILES: O=C(c1ccnc(-c2cncc3ccccc23)c1)c1nc2ccc(N3CCNCC3)nc2[nH]1]

Synthetic scheme

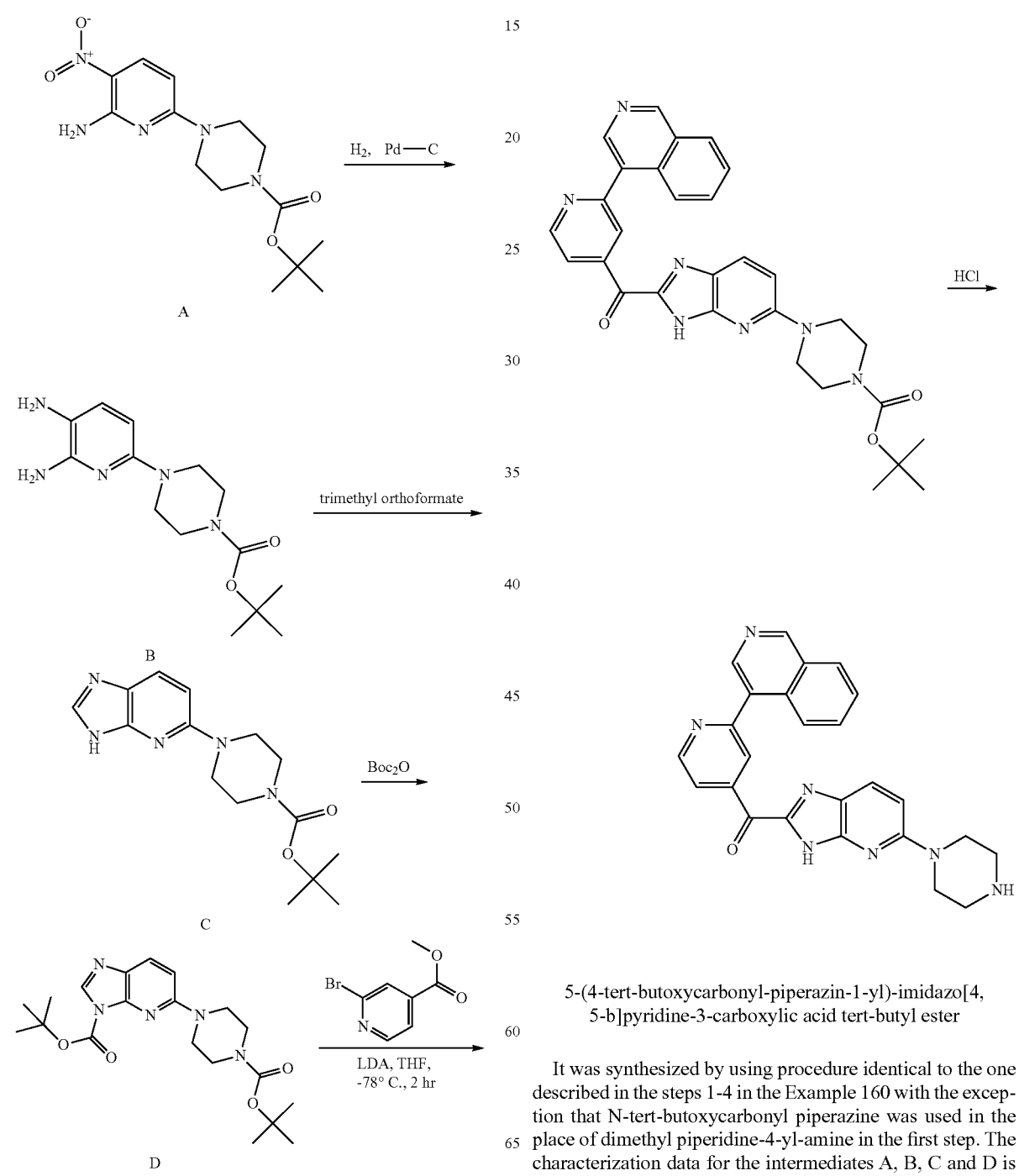

5-(4-tert-butoxycarbonyl-piperazin-1-yl)-imidazo[4,5-b]pyridine-3-carboxylic acid tert-butyl ester It was synthesized by using procedure identical to the one described in the steps 1-4 in the Example 160 with the exception that N-tert-butoxycarbonyl piperazine was used in the place of dimethyl piperidine-4-yl-amine in the first step. The characterization data for the intermediates A, B, C and D is shown below.

4-(6-Amino-5-nitro-pyridin-2-yl)piperazine-1-carboxylic acid tert-butyl ester (Intermediate A)

¹H NMR (400 MHz, CDCl₃) δ 1.49 (s, 9H), 3.52 (m, 4H), 3.72 (m, 4H), 6.08 (d, J=9.00 Hz, 1H), 8.27 (d, J=9.00 Hz, 1H). MS: m/z 324.2 [M+1].

4-(5,6-Diamino-pyridin-2-yl)-piperazine-1-carboxylic acid tert-butyl ester (Intermediate B)

¹H NMR (400 MHz, CDCl₃) δ 1.47 (s, 9H), 2.84 (br s, 2H), 3.29 (m, 4H), 3.52 (m, 4H), 4.23 (br s, 2H), 5.97 (d, J=9.00 Hz, 1H), 6.82 (d, J=9.00 Hz, 1H). MS: m/z 294.5 [M+1].

4-(3H-Imidazo[4,5-b]pyridin-5-yl)-piperazine-1-carboxylic acid tert-butyl ester (Intermediate C)

¹H NMR (400 MHz, CDCl₃) δ 1.50 (s, 9H), 3.59 (m, 9H), 6.69 (d, J=9.00 Hz, 1H), 7.91 (d, J=9.00 Hz, 1H), 7.96 (s, 1H). MS: m/z 304.4 [M+1].

5-(4-tert-Butoxycarbonyl-piperazin-1-yl)-imidazo[4,5-b]pyridine-3-carboxylic acid tert-butyl ester (Intermediate D)

¹H NMR (400 MHz, CDCl₃) δ 1.49 (s, 9H), 1.69 (s, 9H), 3.61 (m, 8H), 6.74 (d, J=9.00 Hz, 1H), 8.06 (d, J=9.00 Hz, 1H), 8.47 (s, 1H). MS: m/z 404.3 [M+1].

Step 1

4-[2-(2-Bromo-pyridine-4-carbonyl)-3H-imidazo[4,5-b]pyridine-5-yl]-piperazine-1-carboxylic acid tert-butyl ester

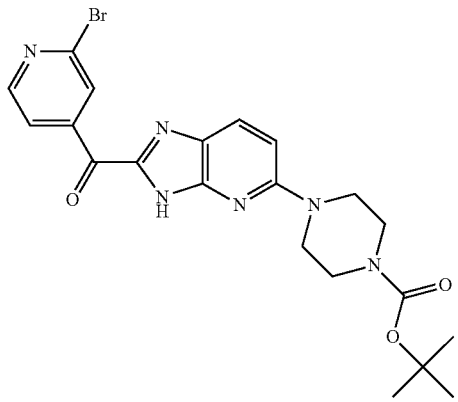 [SMILES: CC(C)(C)OC(=O)N1CCN(c2ccc3nc(C(=O)c4ccnc(Br)c4)[nH]c3n2)CC1]

The mixture of 5-(4-tert-butoxycarbonyl-piperazin-1-yl)-imidazo[4,5-b]pyridine-3-carboxylic acid tert-butyl ester (600 mg, 1.49 mmole), methyl-2-bromo-isonicotinate (321 mg, 1.49 mmole), and tetrahydrofuran (5 ml) was cooled to −78° C. Lithium diisopropylamide (2N, 2.23 ml, 4.46 mmole) was added slowly. Reaction mixture was stirred at −78° C. for 2 hours. Reaction was quenched with water and extracted with EtOAc. EtOAc layer was concentrated and crude product was purified by using silica gel chromatography, eluting with 0% to 40% of EtOAc in CH₂Cl₂ to afford 4-[2-(2-bromo-pyridine-4-carbonyl)-3H-imidazo[4,5-b]pyridine-5-yl]-piperazine-1-carboxylic acid tert-butyl ester (120 mg, 16.6%). 1H NMR (400 MHz, CD₂Cl₂) δ 1.58 (s, 9H), 3.59 (m, 4H), 3.74 (m, 4H), 6.89 (d, J=9.03 Hz, 1H), 8.03 (d, J=9.03 Hz, 1H), 8.39 (d, J=5.03 Hz, 1H), 8.61 (d, J=5.02 Hz, 1H), 8.67 (s, 1H). MS(ESI) m/z 488 [M+1].

Step 2

4-[2-(2-Isoquinolin-4-yl-pyridine-4-carbonyl)-3H-imidazo[4,5-b]pyridine-5-yl-piperazine-1-carboxylic acid tert-butyl ester

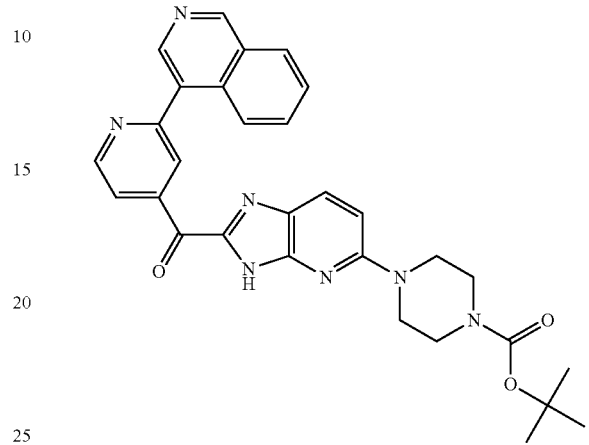

The mixture of 4-[2-(2-bromo-pyridine-4-carbonyl)-3H-imidazo[4,5-b]pyridine-5-yl]-piperazine-1-carboxylic acid tert-butyl ester (44 mg, 0.08 mmole), 2-isoquinoline boronic acid (14.2 mg, 0.08 mmole), Pd(Ph₃)₄ (28.4 mg, 0.24 mmole), 2 molar of K₃PO₄ aqueous (0.08 ml, 0.16 mmole), and dioxane (3.0 ml) was degassed and heated to 120° C. for 20 minutes in microwave. Reaction solution was diluted with water and extracted with EtOAc. EtOAc layer was concentrated. Residue was purified by using silica gel chromatography, eluting with 50% to 100% of EtOAc in CH₂Cl₂ to afford 4-[2-(2-isoquinolin-4-yl-pyridine-4-carbonyl)-3H-imidazo[4.5-b]pyridine-5-yl-piperazine-1-carboxylic acid tert-butyl ester (20 mg, 45.5%). 1H NMR (400 MHz, CD₂Cl₂) δ 1.56 (s, 9H), 3.59 (m, 4H), 3.73 (m, 4H), 6.88 (d, J=9.54 Hz, 1H), 7.90 (m, 1H), 8.01 (d, J=9.04 Hz, 2H), 8.31 (d, J=8.53 Hz, 1H), 8.54 (m, 2H), 8.79 (s, 1H), 8.88 (s, 1H), 9.12 (d, J=5.52 Hz, 1H), 9.47 (s, 1H). HR-MS m/z 536.2414 [M+1].

Step 3

(2-Isoquinolin-4-yl-pyridin-4-yl)-5-piperazin-1-yl-3H-imidazo[4,5-b]pyridin-2-yl)-methanone

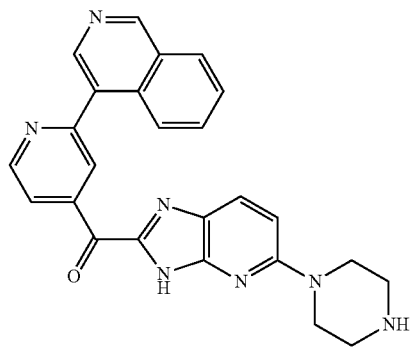 [SMILES: O=C(c1ccnc(-c2cncc3ccccc23)c1)c1nc2ccc(N3CCNCC3)nc2[nH]1]

The mixture of 4-[2-(2-isoquinolin-4-yl-pyridine-4-carbonyl)-3H-imidazo[4.5-b]pyridine-5-yl-piperazine-1-carboxylic acid tert-butyl ester (18 mg, 0.034 mmole) and 2 molar HCl in ether (1 ml) was stirred at room temperature for 2 hours. Solvent was removed. Residue was washed with ethyl ether a few times to afford (2-isoquinolin-4-yl-pyridin-4-yl)-5-piperazin-1-yl-3H-imidazo[4,5-b]pyridin-2-yl)-methanone (10 mg, 68%) as a yellow solid. 1H NMR (400 MHz, DMSO) δ 3.22 (s, 4H), 3.87 (s, 4H), 7.12 (m, 1H), 7.84 (m, 1H), 7.94 (m, 1H), 8.10 (br, 1H), 8.34 (d, J=8.03 Hz, 1H), 8.61 (s=, 1H), 8.78 (br, 1H), 9.10 (s, 1H), 9.16 (br, 1H), 9.56 (br, 1H). HR-MS m/z 436.1884 [M+1].

Example 165

4-[5-(4-Dimethylamino-piperidin-1-yl)-3H-imidazo[4,5-b]pyridine-2-carbonyl]-2-isoquinolin-4-yl-benzonitrile

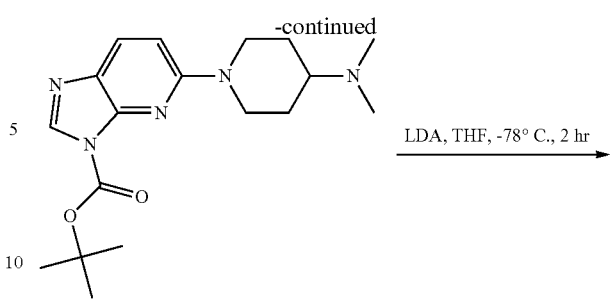

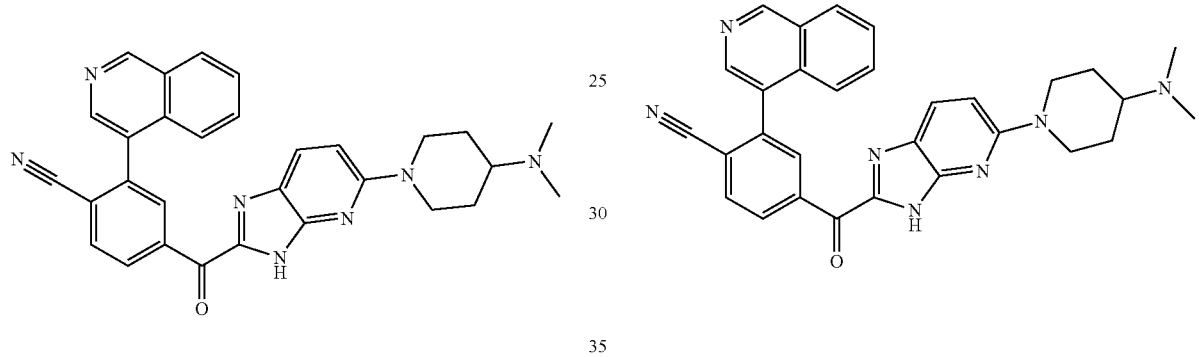

Step 1

4-Cyano-3-isoquinolin-4-yl-benzoic acid methyl ester

Synthetic scheme

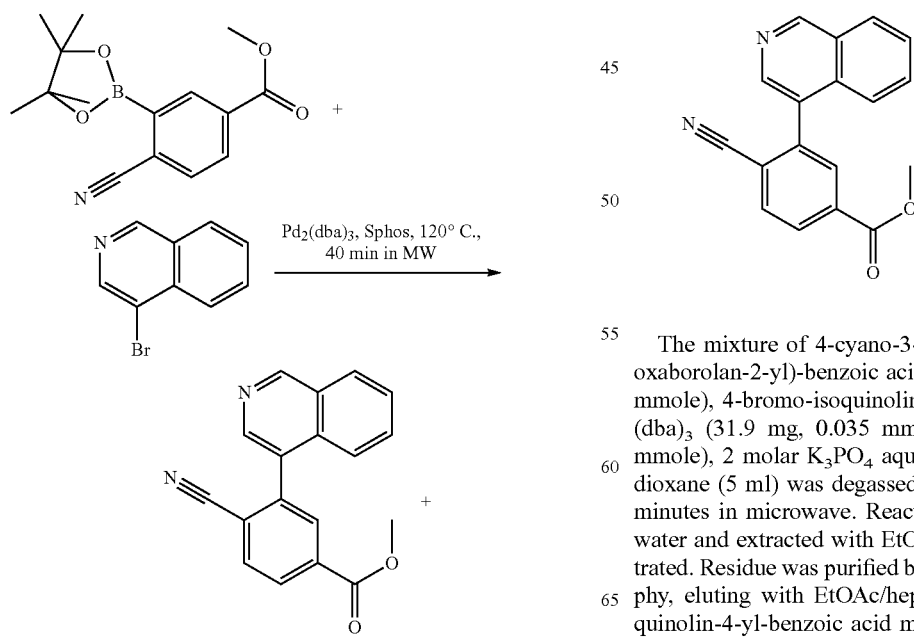

The mixture of 4-cyano-3-(4,4,5,5-tetramethyl-[1,3,2]dioxaborolan-2-yl)-benzoic acid methyl ester (100 mg, 0.348 mmole), 4-bromo-isoquinoline (80 mg, 0.383 mmole), Pd$_2$(dba)$_3$ (31.9 mg, 0.035 mmole), Sphos (28.6 mg, 0.070 mmole), 2 molar K$_3$PO$_4$ aqueous (0.4 ml, 0.8 mmole) and dioxane (5 ml) was degassed and heated to 120° C. for 40 minutes in microwave. Reaction solution was diluted with water and extracted with EtOAc. EtOAc layer was concentrated. Residue was purified by using silica gel chromatography, eluting with EtOAc/heptane to afford 4-cyano-3-isoquinolin-4-yl-benzoic acid methyl ester (60 mg, 60%). 1H NMR (400 MHz, CD$_2$Cl$_2$) δ 3.88 (s, 3H), 7.45 (d, J=8.03 Hz, 1H), 7.65 (m, 2H), 7.90 (m, 1H), 8.06 (d, J=8.53 Hz, 1H), 8.15 (m, 2H), 8.42 (s, 1H), 9.29 (s, 1H). HR-MS m/z 289.0979 [M+1].

Step 2

4-[5-(4-Dimethylamino-piperidin-1-yl)-3H-imidazo[4,5-b]pyridine-2-carbonyl]-2-isoquinolin-4-yl-benzonitrile

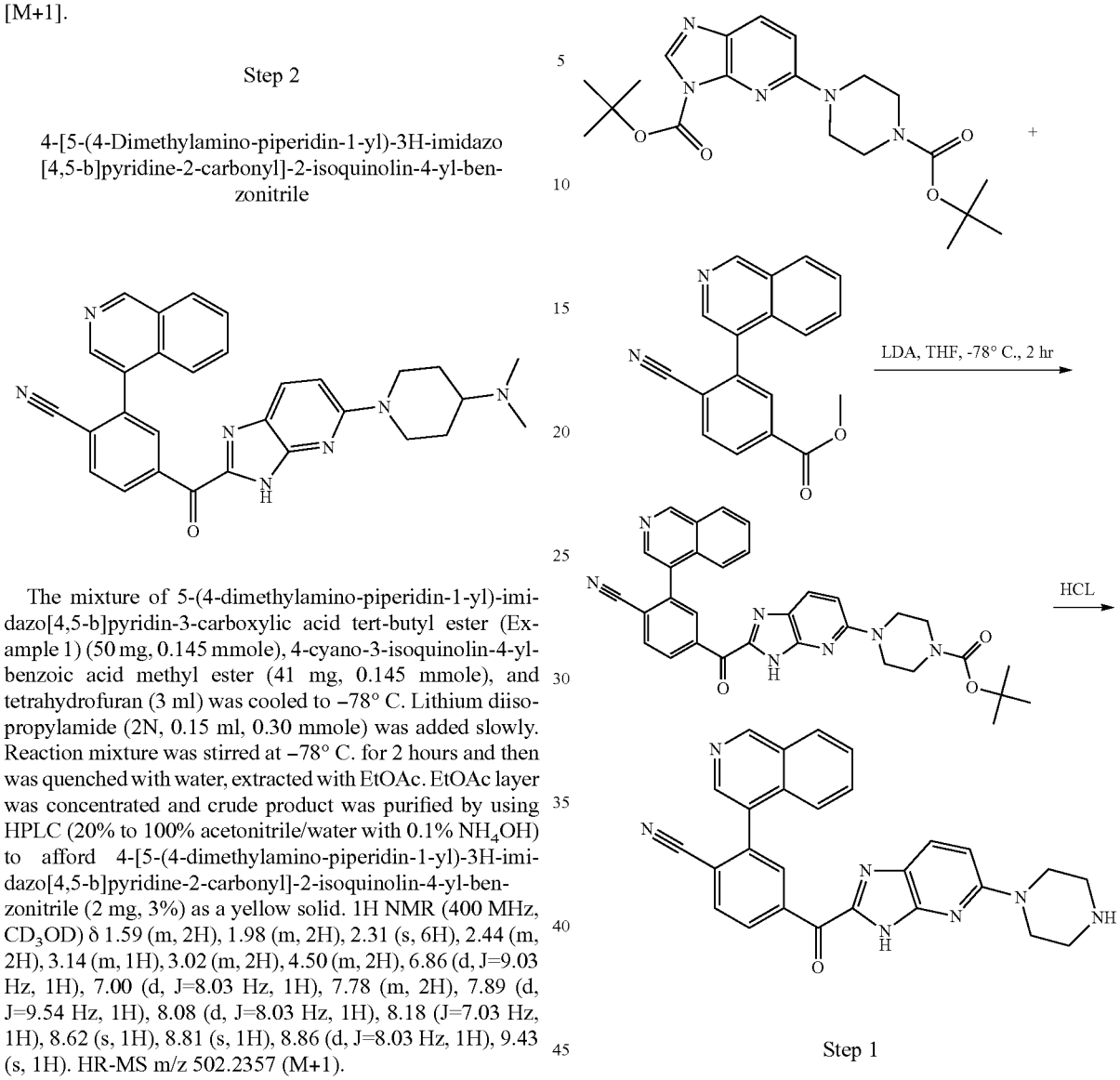

The mixture of 5-(4-dimethylamino-piperidin-1-yl)-imidazo[4,5-b]pyridin-3-carboxylic acid tert-butyl ester (Example 1) (50 mg, 0.145 mmole), 4-cyano-3-isoquinolin-4-yl-benzoic acid methyl ester (41 mg, 0.145 mmole), and tetrahydrofuran (3 ml) was cooled to −78° C. Lithium diisopropylamide (2N, 0.15 ml, 0.30 mmole) was added slowly. Reaction mixture was stirred at −78° C. for 2 hours and then was quenched with water, extracted with EtOAc. EtOAc layer was concentrated and crude product was purified by using HPLC (20% to 100% acetonitrile/water with 0.1% NH$_4$OH) to afford 4-[5-(4-dimethylamino-piperidin-1-yl)-3H-imidazo[4,5-b]pyridine-2-carbonyl]-2-isoquinolin-4-yl-benzonitrile (2 mg, 3%) as a yellow solid. 1H NMR (400 MHz, CD$_3$OD) δ 1.59 (m, 2H), 1.98 (m, 2H), 2.31 (s, 6H), 2.44 (m, 2H), 3.14 (m, 1H), 3.02 (m, 2H), 4.50 (m, 2H), 6.86 (d, J=9.03 Hz, 1H), 7.00 (d, J=8.03 Hz, 1H), 7.78 (m, 2H), 7.89 (d, J=9.54 Hz, 1H), 8.08 (d, J=8.03 Hz, 1H), 8.18 (J=7.03 Hz, 1H), 8.62 (s, 1H), 8.81 (s, 1H), 8.86 (d, J=8.03 Hz, 1H), 9.43 (s, 1H). HR-MS m/z 502.2357 (M+1).

Example 166

2-Isoquinolin-4-yl-4-(5-piperazin-1-yl-3H-imidazo[4,5-b]pyridine-2-carbonyl)-benzonitrile

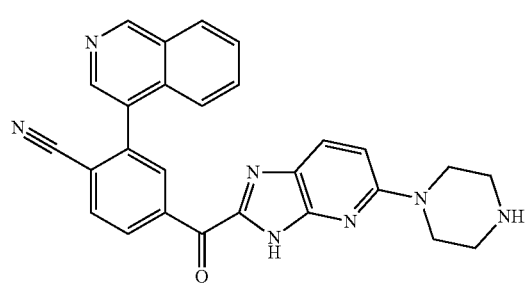 [SMILES: N#Cc1ccc(C(=O)c2nc3ccc(N4CCNCC4)nc3[nH]2)cc1-c1cncc2ccccc12]

Synthetic scheme

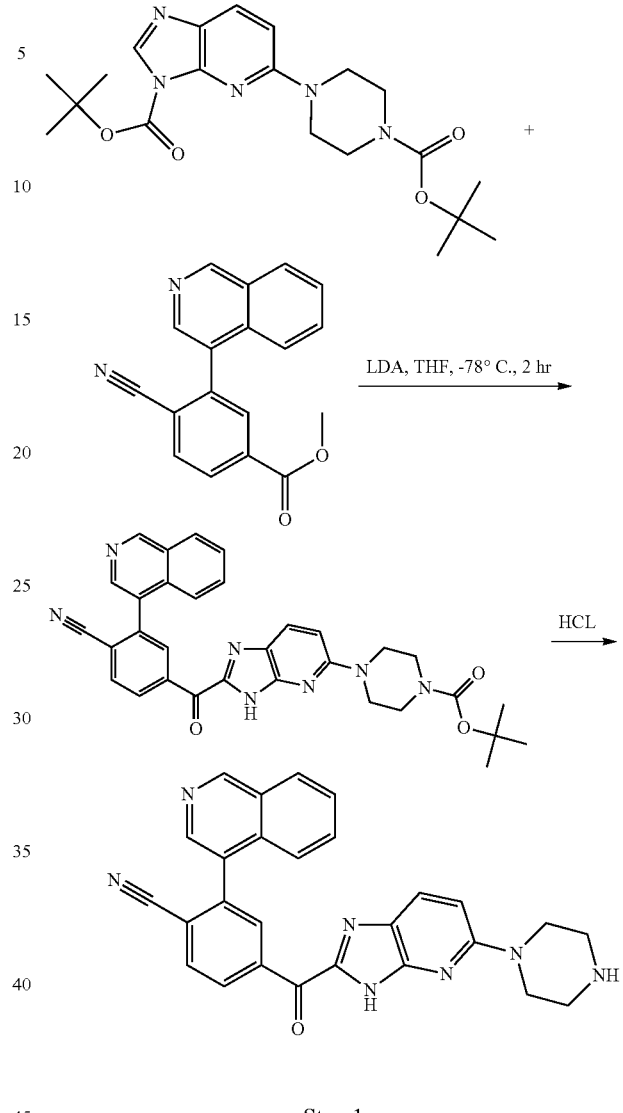

Step 1

4-[2-(4-Cyano-3-isoquinolin-4-yl-benzoyl)-3H-imidazo[4,5-b]pyridine-5-yl]piperazine-1-carboxylic acid tert-butyl ester

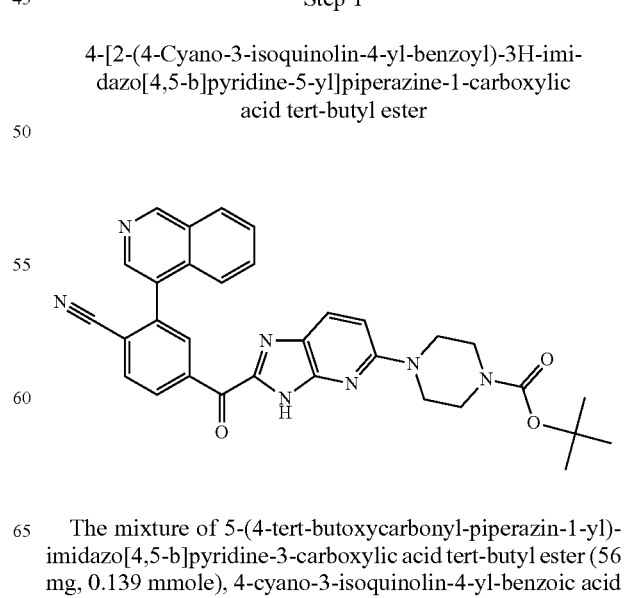

The mixture of 5-(4-tert-butoxycarbonyl-piperazin-1-yl)-imidazo[4,5-b]pyridine-3-carboxylic acid tert-butyl ester (56 mg, 0.139 mmole), 4-cyano-3-isoquinolin-4-yl-benzoic acid methyl ester (40 mg, 0.139 mmole), and tetrahydrofuran (2 ml) was cooled to −78° C. Lithium diisopropylamide (2N, 0.14 ml, 0.28 mmole) was added slowly. Reaction mixture was stirred at −78° C. for 2 hours and then was quenched with water, extracted with EtOAc. EtOAc layer was concentrated and crude product was purified by using silica gel chromatography, eluting with 20% to 100% EtOAc in heptane to afford 4-[2-(4-cyano-3-isoquinolin-4-yl-benzoyl)-3H-imidazo[4,5-b]pyridine-5-yl]piperazine-1-carboxylic acid tert-butyl ester (18 mg, 23%) as a yellow solid. 1H NMR (400 MHz, CD$_2$Cl$_2$) δ 1.60 (s, 9H), 3.57 (m, 4H), 3.71 (m, 4H), 6.85 (d, J=9.03 Hz, 1H), 7.70 (d, J=7.53 Hz, 1H), 7.78 (m, 2H), 7.95 (d, J=9.03 Hz, 1H), 8.09 (d, J=8.03 Hz, 1H), 8.19 (d, J=8.03 Hz, 1H), 8.62 (s, 1H), 8.84 (s, 1H), 8.89 (d, J=8.53 Hz, 1H), 9.43 (s, 1H), 10.28 (s, 1H). HR-MS m/z 560.2406 (M+1).

4-[2-(4-cyano-3-isoquinolin-4-yl-benzoyl)-3H-imidazo[4,5-b]pyridine-5-yl]piperazine-1-carboxylic acid tert-butyl ester solution (16 mg, 0.029 mmole) in 2 M HCl ethylether (2 ml) was stirred at room temperature for 1 hour. Solvent was removed. Solid was washed with ether for three times and purified by using HPLC (20% to 100% acetonitrile in water with 0.1% NH$_4$OH) to afford product (4.6 mg, 25%) as a yellow solid. 1H NMR (400 MHz, CD$_2$Cl$_2$) δ 2.86 (m, 4H), 3.55 (m, 4H), 6.73 (d, J=9.03 Hz, 1H), 7.59 (d, J=8.03 Hz, 1H), 7.66 (m, 2H), 8.00 (d, J=9.03 Hz, 1H), 7.97 (d, J=8.03 Hz, 1H), 8.07 (d, J=8.03 Hz, 1H), 8.50 (s, 1H), 8.72 (s, 1H), 8.77 (d, J=8.03 Hz, 1H), 9.31 (s, 1H). HR-MS m/z 460.1896 (M+1).

Step 2

2-Isoquinolin-4-yl-4-(5-piperazin-1-yl-3H-imidazo[4,5-b]pyridine-2-carbonyl)-benzonitrile Example 167

[5-(4-Dimethylamino-piperidin-1-yl)-3H-imidazo[4,5-b]pyridine-2-yl]-[2-(3,5-dimethyl-1H-pyrazol-4-yl)-pyridin-4-yl]-methanone

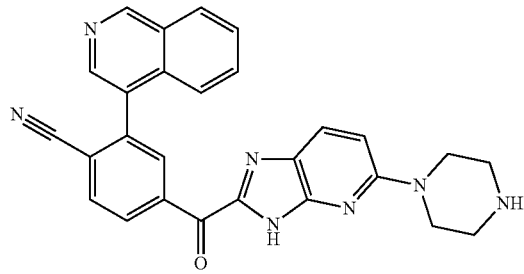 [SMILES: N#Cc1ccc(C(=O)c2nc3ccc(N4CCNCC4)nc3[nH]2)cc1-c1cncc2ccccc12]

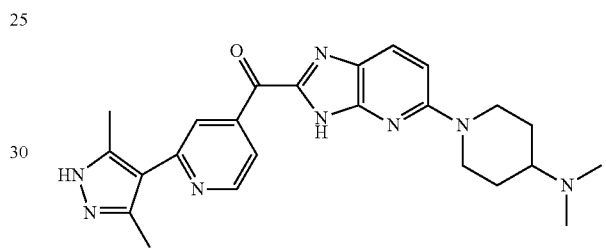

Synthetic scheme

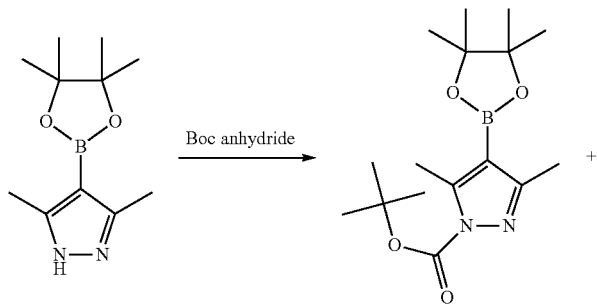

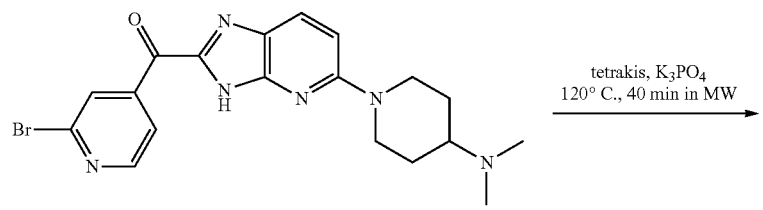

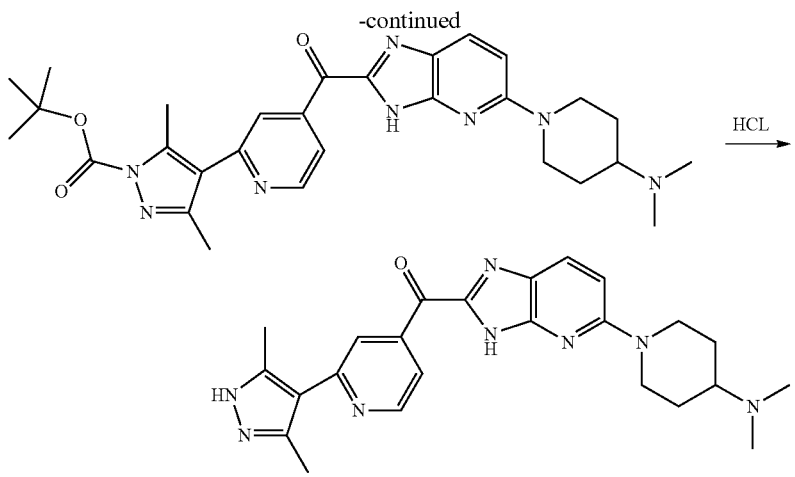

Step 1

3,5-Dimethyl-4-(4,4,5,5-tetramethyl-[1,3,2]dioxaborolan-2-yl)-pyrazole-1-carboxylic acid tert-butyl ester

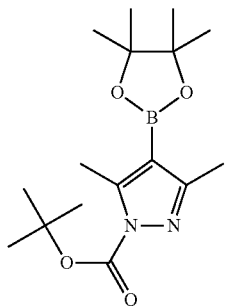 [SMILES: Cc1nn(C(=O)OC(C)(C)C)c(C)c1B1OC(C)(C)C(C)(C)O1]

The mixture of 3,5-dimethyl-4-(4,4,5,5-tetramethyl-[1,3,2]dioxaborolan-2-yl)-pyrazole 91 g, 4.5 mmole), di-tert-butyl dicarbonate (1.18 g, 5.40 mmole), 2 mole of $Na_2CO_3$ aqueous (4.5 ml, 9.01 mmole) and dioxane (30 ml) was stirred overnight. Reaction solution was diluted with water and extracted with EtOAc. EtOAc layer was concentrated. Residue was purified by using chromatograph eluting with 20% to 50% EtOAc in heptane to afford 3,5-dimethyl-4-(4,4,5,5-tetramethyl-[1,3,2]dioxaborolan-2-yl)-pyrazole-1-carboxylic acid tert-butyl ester. 1H NMR (400 MHz, $CD_2Cl_2$) δ 1.33 (s, 9H), 1.52 (s, 6H), 1.66 (s, 6H), 2.34 (s, 3H), 2.67 (s, 3H). HR-MS m/z 323.2132 (M+1).

Step 2

4-{4-[5-(4-Dimethylamino-piperidin-1-yl)-3H-imidazo[4,5-b]pyridine-2-carbonyl]pyridi-2-yl}-3,5-dimethyl-pyrazole-1-carboxylic acid tert-butyl ester

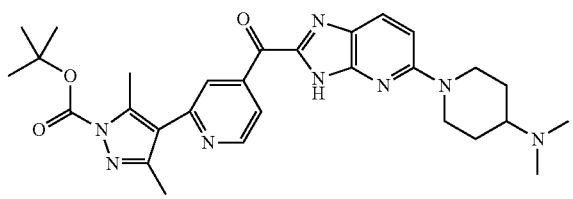 [SMILES: Cc1nn(C(=O)OC(C)(C)C)c(C)c1-c1cc(C(=O)c2nc3ccc(N4CCC(N(C)C)CC4)nc3[nH]2)ccn1]

The mixture of [5-(4-dimethylamino-piperidin-1-yl)-3H-imidazo[4,5-b]pyridin-2-yl]-[2-bromo-pyridin-4-yl]-methanone (Example 162) (50 mg, 0.12 mmole), 3,5-dimethyl-4-(4,4,5,5-tetramethyl-[1,3,2]dioxaborolan-2-yl)-pyrazole-1-carboxylic acid tert-butyl ester. (37.5 mg, 0.12 mmole), $Pd(Ph_3)_4$ (27 mg, 0.023 mmole), 2 molar of $K_3PO_4$ aqueous (0.1 ml, 0.23 mmole), and dioxane (3.0 ml) was degassed and heated to 120° C. for 40 minutes in microwave. Reaction solution was diluted with water and extracted with EtOAc. EtOAc layer was concentrated. Residue was purified by using HPLC (20% to 40% of acetonitrile in water with 0.1% $NH_4OH$) to afford 4-{4-[5-(4-dimethylamino-piperidin-1-yl)-3H-imidazo[4,5-b]pyridine-2-carbonyl]pyridi-2-yl}-3,5-dimethyl-pyrazole-1-carboxylic acid tert-butyl ester (20 mg, 31.5%). 1H NMR (400 MHz, $CD_2Cl_2$) δ 1.68 (s, 9H), 1.90 (m, 2H), 2.05 (m, 2H), 2.44 (s, 6H), 2.74 (m, 1H), 2.77 (s, 6H), 4.16 (m, 2H), 4.56 (m, 2H), 6.90 (d, J=9.54 Hz, 1H), 7.96 (d, J=9.03 Hz, 1H), 8.25 (dd, J=5.02 Hz, 1H), 8.51 (s, 1H), 8.93 (d, J=5.02 Hz, 1H). MS(ESI) m/z 545 [M+1].

Step 3

[5-(4-Dimethylamino-piperidin-1-yl)-3H-imidazo[4,5-b]pyridine-2-yl]-[2-(3,5-dimethyl-1H-pyrazol-4-yl)-pyridin-4-yl]-methanone

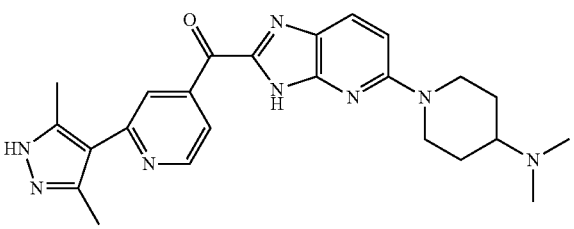 [SMILES: Cc1n[nH]c(C)c1-c1cc(C(=O)c2nc3ccc(N4CCC(N(C)C)CC4)nc3[nH]2)ccn1]

4-{4-[5-(4-dimethylamino-piperidin-1-yl)-3H-imidazo[4,5-b]pyridine-2-carbonyl]pyridi-2-yl}-3,5-dimethyl-pyrazole-1-carboxylic acid tert-butyl ester (20 mg, 0.037 mmole) in 2 molar HCl ethylether (2 ml) was stirred at room temperature for 1 hour. Solvent was removed. Residue was washed with ether for three times and purified by using HPLC (20% to 100% acetonitrile in water with 0.1% $NH_4OH$) to afford [5-(4-dimethylamino-piperidin-1-yl)-3H-imidazo[4,5-b]pyridine-2-yl]-[2-(3,5-dimethyl-1H-pyrazol-4-yl)-pyridin-4-yl]-methanone (4 mg, 25%) as a yellow solid.

1H NMR (400 MHz, $CD_3OD$) δ 1.55 (m, 2H), 1.97 (m, 2H), 2.31 (s, 6H), 2.39 (s, 6H), 2.44 (m, 1H), 2.87 (m, 2H), 4.48 (m, 2H), 6.87 (d, J=9.03 Hz, 1H), 7.83 (d, J=9.03 Hz, 1H), 7.90 (d, J=5.02 Hz, 1H), 8.09 (s, 1H), 8.75 (d, J=5.02 Hz, 1H). HR-MS m/z 445.2484 (M+1).

Example 168

4-[5-(4-Dimethylamino-piperidin-1-yl)-3H-imidazo[4,5-b]pyridine-2-carbonyl]-2-(3,5-dimethyl-1H-pyrazol-4-yl)-benzonitrile (for alternative synthesis of this compound—see Example 147)

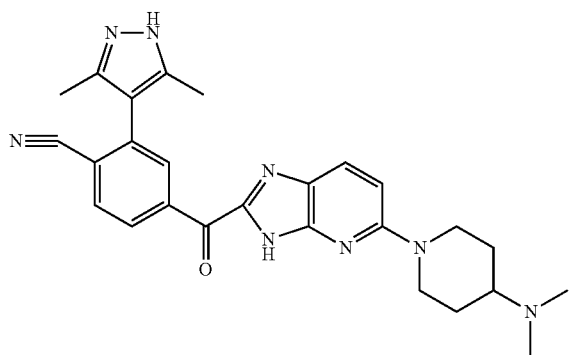 [SMILES: Cc1n[nH]c(C)c1-c1cc(C(=O)c2nc3ccc(N4CCC(N(C)C)CC4)nc3[nH]2)ccc1C#N]

Synthetic scheme

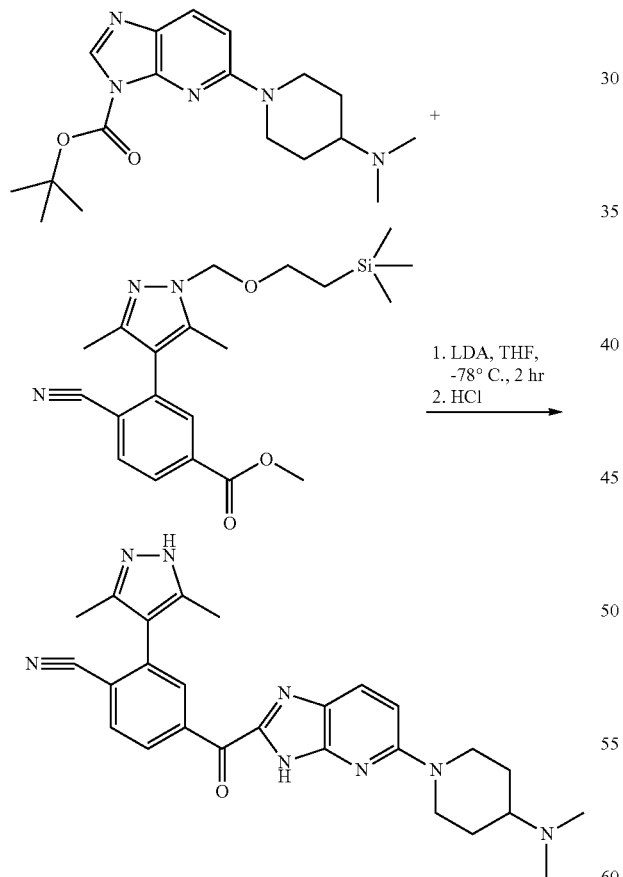

The mixture of 5-(4-dimethylamino-piperidin-1-yl)-imidazo[4,5-b]pyridin-3-carboxylic acid tert-butyl ester (Example 160) (50 mg, 0.145 mmole), 4-cyano-3-[3,5-dimethyl-1-(2-trimethylsilanyl-ethoxymethy)-1H-pyrazole-4-yl]-benzoic acid methyl ester (55.8 mg, 0.145 mmole), and tetrahydrofuran (2 ml) was cooled to −78° C. Lithium diisopropyl amide (2N, 0.22 ml, 0.43 mmole) was added slowly. Reaction mixture was stirred at −78° C. for 2 hours and then was quenched with water, extracted with EtOAc. EtOAc layer was concentrated and crude product was purified by using chromatography, eluting with 20% to 100% MeOH in EtOAc to afford 4-[5-(4-dimethylamino-piperidin-1-yl)3H-imidazo[4,5-b]pyridine-2-carbonyl]-2-[3,5-dimethyl-1-(2-trimethylsilanyl-ethoxymethyl)-1H-pyrazol-4-yl]-benzonitrile (10 mg) as a yellow solid. This yellow solid was suspended in HCl ether solution and sirred overnight. Solvent was removed and crude product was purified by using HPLC (10% to 20% acetonitrile in water with 0.1% of $NH_4OH$) to yield 4-[5-(4-Dimethylamino-piperidin-1-yl)-3H-imidazo[4,5-b]pyridine-2-carbonyl]-[2-(3,5-dimethyl-1H-pyrazol-4-yl)-benzonitrile (2 mg, 25%) as a yellow solid. 1H NMR (400 MHz, $CD_3OD$) δ 1.50 (m, 2H), 1.99 (m, 2H), 2.03 (s, 6H), 2.26 (s, 3H), 2.33 (s, 3H), 2.51 (m, 1H), 2.95 (m, 2H), 4.62 (m, 2H), 7.02 (d, J=9.03 Hz, 1H), 7.89 (d, J=9.03 Hz, 1H), 8.01 (m, 1H), 8.44 (m, 2H). HR-MS m/z 469.2451 (M+1).

Example 169

[2-(3,5-Dimethyl-1H-pyrazol-4-yl)-pyridin-4-yl]-(5-piperazin-1-yl-3H-imidazo[4,5-b]pyridine-2-yl)-methanone Synthetic Scheme

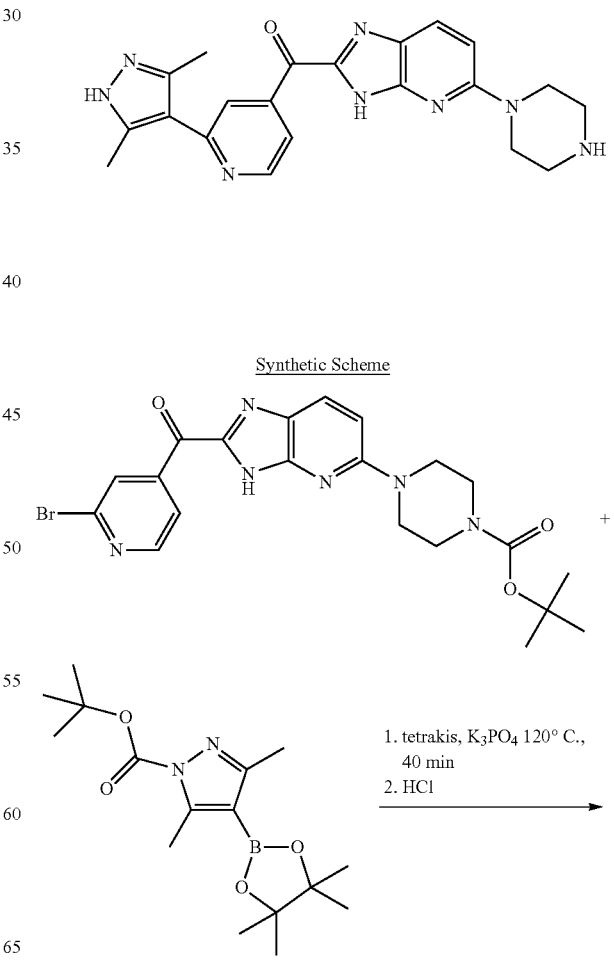

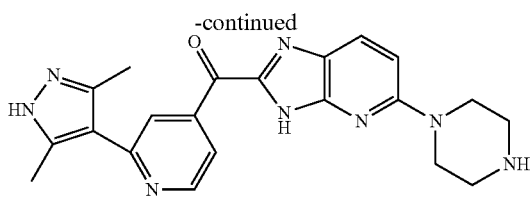

4-{2-[2-(1-tert-Butoxycarbonyl-3,5-dimethyl-1H-pyrazol-4-yl)-pyridine-4-carbonyl]-3H-imidazo[4,5-b]pyridin-5-yl}-piperazine-1-carboxylic acid tert-butyl ester The mixture of [4-[2-(2-bromo-pyridine-4-carbonyl)-3H-imidazo[4,5-b]pyridine-5-yl]-piperazine-1-carboxylic acid tert-butyl ester (Example 164) (100 mg, 0.205 mmole), 3,5-dimethyl-4-(4,4,5,5-tetramethyl-[1,3,2]dioxaborolan-2-yl)-pyrazole-1-carboxylic acid tert-butyl ester (Example 167) (66 mg, 0.205 mmole), Pd(Ph$_3$)$_4$ (23 mg, 0.021 mmole), 2 molar of K$_3$PO$_4$ aqueous (0.21 ml, 0.41 mmole), and dioxane (3.0 ml) was degassed and heated to 120° C. for 40 minutes in microwave. Reaction solution was diluted with water and extracted with EtOAc. EtOAc layer was concentrated to afford 120 mg of crude 4-{2-[2-(1-tert-butoxycarbonyl-3,5-dimethyl-1H-pyrazol-4-yl)-pyridine-4-carbonyl]-3H-imidazo[4,5-b]pyridin-5-yl}-piperazine-1-carboxylic acid tert-butyl ester, which was dissolved in 3 ml of 2 molar HCl ether solution. The acidic solution was stirred for 2 hours, then solvent was removed. Residue was washed with EtOAc and was purified by using HPLC, eluting with 10 to 20% of acetonitrile in water (0.1% of NH$_4$OH) to yield [2-(3,5-Dimethyl-1H-pyrazol-4-yl)-pyridin-4-yl]-(5-piperazin-1-yl-3H-imidazo[4,5-b]pyridine-2-yl)-methanon (20 mg, 24%) as a yellow solid. 1H NMR (400 MHz, CD$_3$OD) δ 2.41 (s, 6H), 2.94 (m, 4H), 3.61 (m, 4H), 6.88 (d, J=9.03 Hz, 1H), 7.87 (d, J=9.03 Hz, 1H), 7.94 (d, J=5.02 Hz, 1H), 8.17 (s, 1H), 8.76 (d, J=5.02 Hz, 1H). HR-MS m/z 403.1981 (M+1).

Example 170

(5-[1,4]Diazepan-1-yl-3H-imidazo[4,5-b]-pyridin-2-yl)-[2-(3,5-dimethyl-1H-pyrazol-4-yl)-pyridin-4-yl]-methanone

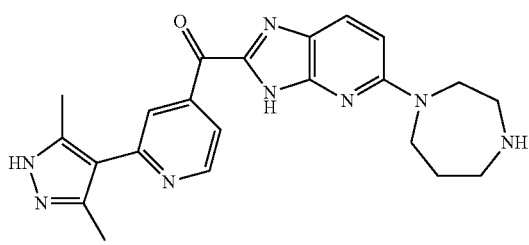 [SMILES: Cc1n[nH]c(C)c1-c1cc(C(=O)c2nc3ccc(N4CCCNCC4)nc3[nH]2)ccn1]

Snythetic scheme

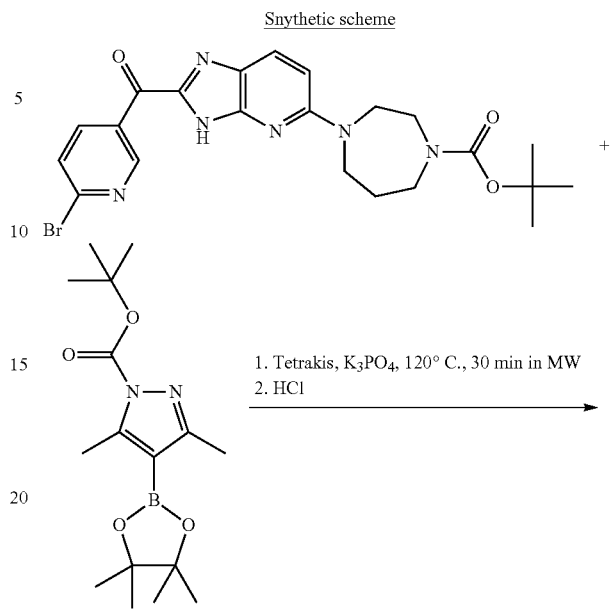

1. Tetrakis, K$_3$PO$_4$, 120° C., 30 min in MW
2. HCl

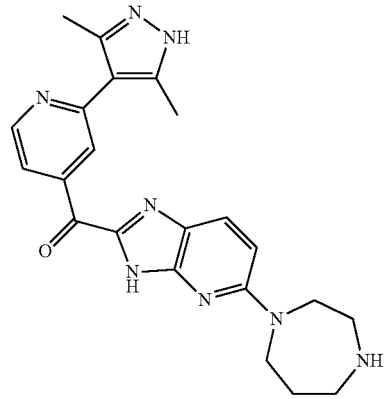

The mixture of [4-[2-(2-bromo-pyridine-4-carbonyl)-3H-imidazo[4,5-b]pyridine-5-yl]-diazepane-1-carboxylic acid tert-butyl ester (Example 163) (58 mg, 0.116 mmole), 3,5-dimethyl-4-(4,4,5,5-tetramethyl-[1,3,2]dioxaborolan-2-yl)-pyrazole-1-carboxylic acid tert-butyl ester (Example 167) (37 mg, 0.116 mmole), Pd(Ph$_3$)$_4$ (13.4 mg, 0.012 mmole), 2 molar of K$_3$PO$_4$ aqueous (0.12 ml, 0.23 mmole), and dioxane (3.0 ml) was degassed and heated to 120° C. for 40 minutes in microwave. Reaction solution was diluted with water and extracted with EtOAc. EtOAc layer was concentrated to afford 40 mg of crude 4-{2-[2-(1-tert-butoxycarbonyl-3,5-dimethyl-1H-pyrazol-4-yl)-pyridine-4-carbonyl]-3H-imidazo[4,5-b]pyridin-5-yl}-[1,4]diazepane-1-carboxylic acid tert-butyl ester, which was dissolved in 2 ml of 2 molar HCl ether solution. The acidic solution was stirred for 2 hours, then solvent was removed. Residue was washed with CH₂Cl₂ and was purified by using HPLC, eluting with 10 to 20% of acetonitrile in water (0.1% of NH₄OH) to yield (5-[1,4]diazepan-1-yl-3H-imidazo[4,5-b]-pyridin-2-yl)-[2-(3,5-dimethyl-1H-pyrazol-4-yl)-pyridin-4-yl]-methanon (7 mg, 42%) as a yellow solid. 1H NMR (400 MHz, CD₃OD) δ 1.98 (m, 1H), 2.04 (m, 1H), 2.40 (m, 1H), 2.79 (m, 1H), 3.01 (m, 1H), 3.64 (m, 1H), 3.84 (m, 5H), 6.78 (m, 1H), 7.83 (d, J=9.03 Hz, 1H), 7.95 (m, 1H), 8.19 (d, J=17.07 Hz, 1H), 8.76 (m, 1H). HR-MS m/z 417.2144 (M+1).

Example 171

(5-[1,4]Diazepan-1-yl-3H-imidazo[4,5-b]-pyridin-2-yl)-[2-(1,3,5-trimethyl-1H-pyrazol-4-yl)-pyridin-4-yl]-methanone

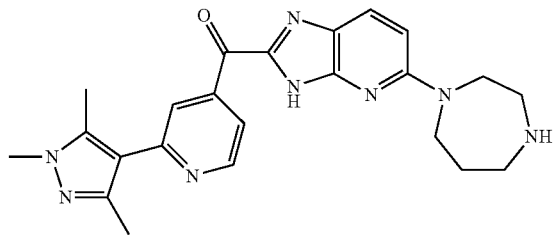 [SMILES: Cc1nn(C)c(C)c1-c1cc(C(=O)c2nc3ccc(N4CCCNCC4)nc3[nH]2)ccn1]

Synthetic scheme

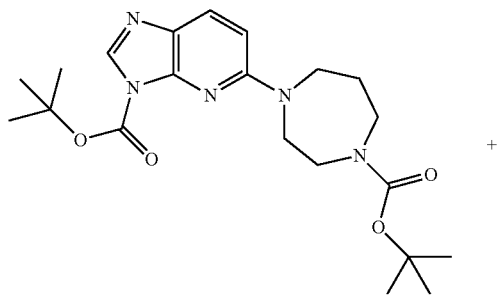

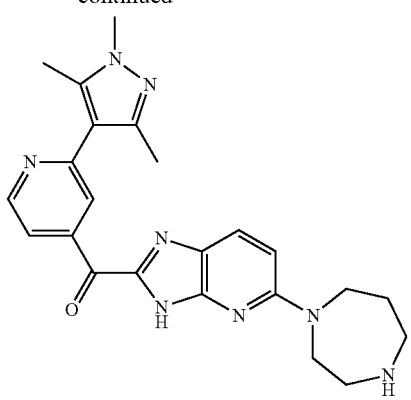

The mixture of 5-(4-tert-butoxycarbonyl-[1,4]diazepam-1-yl)-imidazo[4,5-b]pyridine-3-carboxylic acid tert-butyl ester (100 mg, 0.24 mmole), 2-(1,3,5-trimethyl-1H-pyrazol-4-yl)-isonicotinic acid methyl ester (58.7 mg, 0.24 mmole), and tetrahydrofuran (5 ml) was cooled to −78° C. Lithium diisopropylamide (2N, 0.3 ml, 0.60 mmole) was added slowly. Reaction mixture was stirred at −78° C. for 2 hours. Reaction was quenched with water and extracted with EtOAc. EtOAc layer was concentrated to afford 133 mg of crude 4-{2-[2-1,3,5-trimethyl-1H-pyrazole-4-yl)-pyridine-4-carbonyl]-3H-imidazole[4,5-b]pyridine-5-yl}-[1,4]diazepane-1-carboxylic acid tert-butyl ester, which was dissolved in 2 ml of 2 molar HCl ether solution and was stirred for 2 hours. Solvent was removed. Residue was washed with CH₂Cl₂ and was purified by using HPLC, eluting with 10 to 20% of acetonitrile in water (0.1% of NH₄OH) to yield (5-[1,4]diazepan-1-yl-3H-imidazo[4,5-b]-pyridin-2-yl)-[2-(1,3,5-trimethyl-1H-pyrazol-4-yl)-pyridin-4-yl]-methanon (20 mg, 24%) as a yellow solid. 1H NMR (400 MHz, CD₃OD) δ 1.28 (m, 2H), 1.97 (m, 2H), 2.38 (s, 3H), 2.43 (s, 3H), 2.80 (m, 2H), 3.02 (m, 2H), 3.79 (s, 3H), 3.85 (m, 2H), 6.85 (d, J=9.03 Hz, 1H), 7.86 (d, J=9.54 Hz, 1H), 8.03 (d, J=5.02 Hz, 1H), 8.31 (s, 1H), 8.79 (d, J=5.02 Hz, 1H). HR-MS m/z 431.2296 (M+1).

Example 172

[5-(3-Amino-pyrrolidin-1-yl)-3H-imidazole[4,5-b]pyridine-2-yl]-2-(isoquinolin-4-yl-pyridin-4-yl)-methanone

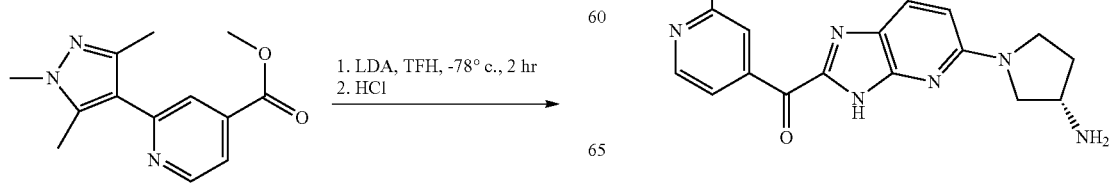

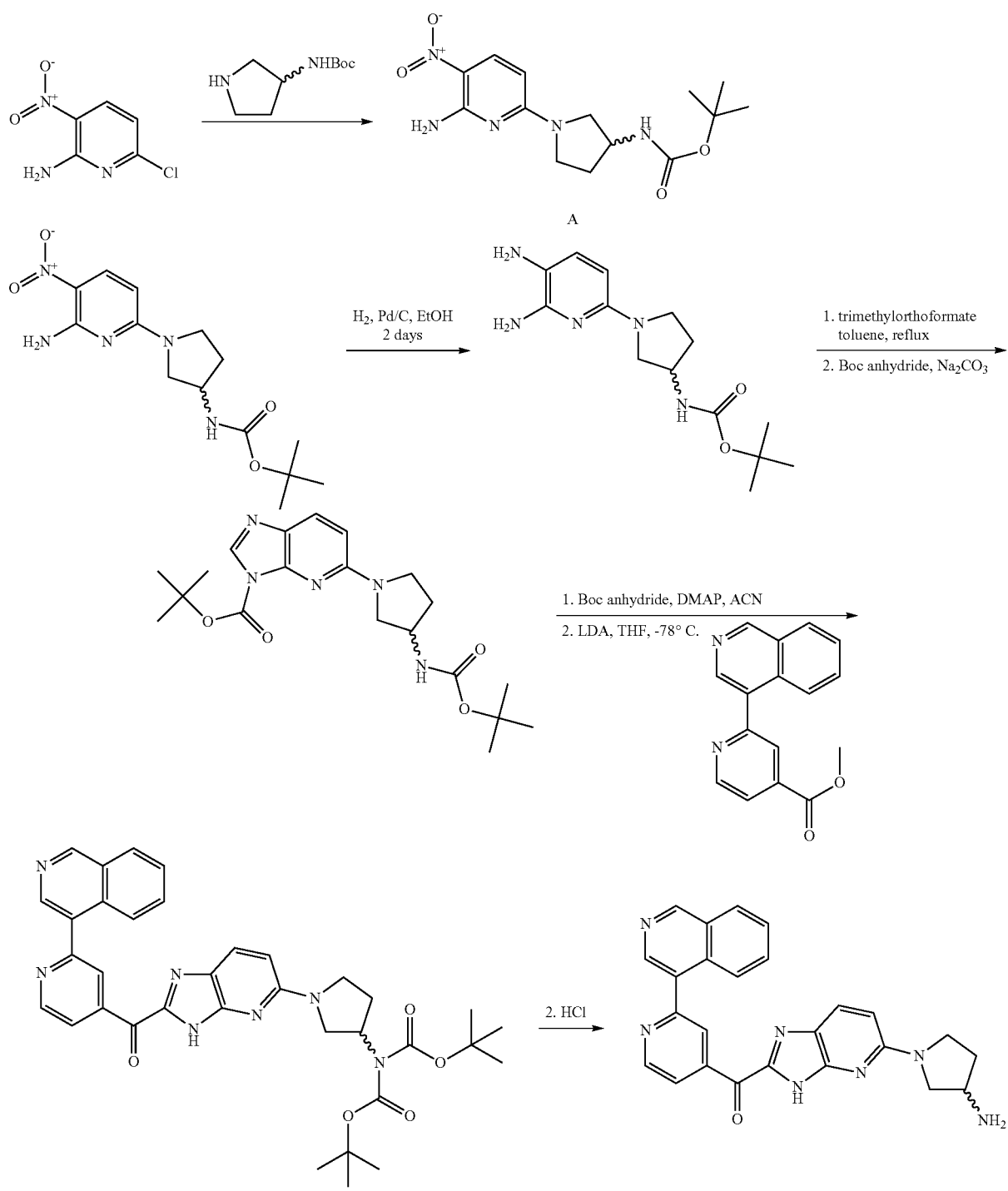
Synthetic scheme
[1-(6-amino-5-nitro-pyridin-2-yl)-pyrrolidin-3-yl]-carbamic acid tert-butyl ester was synthesized from 6-chloro-3-nitro-pyridine-2-yl-amine by using the procedure as described in step 1 in Example 160 with the only change being pyrrolidin-3-yl-carbamic acid tert-butyl ester was used as the amine. The intermediate A had following spectral properties.

¹H NMR (400 MHz, CDCl₃) δ 1.46 (s, 9H), 1.88-2.3 (2 br m, 1H), 3.32-3.90 (br m, 3H), 4.31-4.74 (2 br m, 1H), 5.87 (d, J=9.00 Hz, 1H), 8.17 (d, J=9.00 Hz, 1H). MS: m/z 324.4 [M+1].

Step 1

[1-(5,6-Diamino-pyridin-2-yl)-pyrrolidin-3-yl]-carbamic acid tert-butyl ester

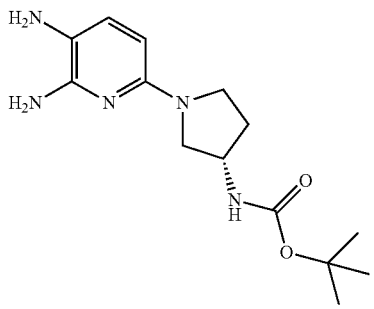 [SMILES: CC(C)(C)OC(=O)N[C@H]1CCN(c2ccc(N)c(N)n2)C1]

The mixture of [1-(6-amino-5-nitro-pyridin-2-yl)-pyrrolidin-3-yl]-carbamic acid tert-butyl ester (2 g, 2.17 mmole), Pd/C (148 mg, 1.23 mmole), and EtOH (100 ml) was shaken under H₂ gas for 2 days. Reaction solution was filtered and filtrate was concentrated to afford [1-(5,6-diamino-pyridin-2-yl)-pyrrolidin-3-yl]-carbamic acid tert-butyl ester (1.8 g, ~100%) as a dark green solid. 1H NMR (400 MHz, CD₃OD) δ 1.17 (m, 1H), 1.44 (s, 9H), 1.86 (m, 16H), 2.18 (m, 12H), 3.14 (m, 1H), 3.42 (m, 1H), 3.59 (m, 1H), 4.505 (m, 1H), 6.67 (d, J=6.53 Hz, 1H), 6.920 (m, 1H). MS(ESI) m/z 294 [M+1].

Step 2

[5-(3-tert-Butoxycarbonylamino-pyrrolidin-1-yl)-imidazo[4,5-b]pyridine-3-carbamic acid tert-butyl ester

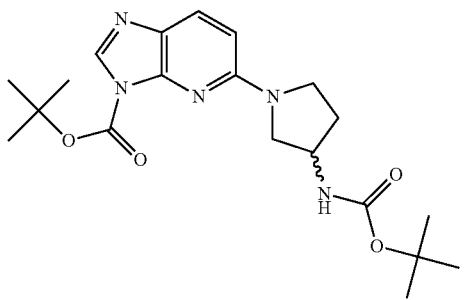 [SMILES: CC(C)(C)OC(=O)NC1CCN(c2ccc3ncn(C(=O)OC(C)(C)C)c3n2)C1]

The solution of [1-(5,6-diamino-pyridin-2-yl)-pyrrolidin-3-yl]-carbamic acid tert-butyl ester (2 g, 6.82 mmole), trimethylorthoformate (3.83 g, 25.9 mmole), benzenesulfonic acid (43 mg, 0.27 mmole) and toluene (100 ml) was heated to reflux overnight. The reaction solution was basified with NaHCO₃ and concentrated to afford crude [1-(3H-imidazo[4,5-b]pyridine-5-yl)-pyrrolin-3-yl]-carbamic acid tert-butyl ester (1.96 g, 94%) as a dark green solid. MS(ESI) m/z 304 [M+1].

The solution of [1-(3H-imidazo[4,5-b]pyridine-5-yl)-pyrrolin-3-yl]-carbamic acid tert-butyl ester (1 g, 3.30 mmole), di-tert-butyl dicarbonate (1.44 g, 6.59 mmole), NaHCO₃ (0.84 g, 9.89 mmole) and tetrahydrofuran/water (3:1, 100 ml) was stirred at room temperature for 2 days. The reaction solution was diluted with water and extracted with EtOAc. EtOAc layer was concentrated. Crude product was purified by using silica gel chromatography (30% EtOAc in CH₂Cl₂ to 100% of EtOAc) to afford [5-(3-tert-butoxy carbonylamino-pyrrolidin-1-yl)-imidazo[4,5-b]pyridine-3-carbamic acid-tert-butyl ester as a green solid (700 mg, 52%). 1H NMR (400 MHz, CD₂Cl₂) δ 1.47 (s, 18H), 2.00 (m, 1H), 2.31 (m, 1H), 3.49 (m, 1H), 4.26 (m, 1H), 4.81 (m, 1H), 6.47 (m, 1H), 8.04 (m, 1H) 8.44 (s, 1H). MS(ESI) m/z 404 [M+1].

Step 3

[5-(3-N,N-Di-tert-butoxycarbonyl-amino-pyrrolidin-1-yl)-3H-imidazole[4,5-b]pyridine-2-yl]-2-(isoquinolin-4-yl-pyridin-4-yl)-methanone

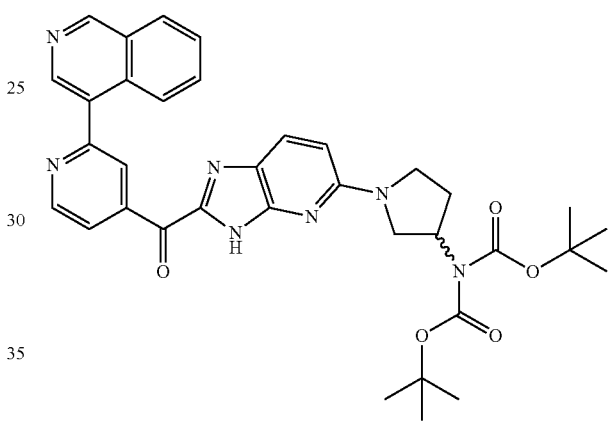

The solution of [5-(3-tert-butoxycarbonylamino-pyrrolidin-1-yl)-imidazo[4,5-b]pyridine-3-carbamic acid-tert-butyl ester (200 mg, 0.50 mmole), di-tert-butyl dicarbonate (1.0 g, 4.96 mmole), DMAP (60.5 mg, 0.50 mmole) and tetrahydrofuran/water (3:1, 50 ml) was stirred at room temperature for 5 days (about 20% of starting material remained). Solvent was removed. Crude product was purified by using silica gel chromatography (heptane, EtOAc in heptane) to afford [5-(3-N,N-di-tert-butoxycarbonyl-amino-pyrrolidin-1-yl)-imidazo[4,5-b]pyridine-3-carbamic acid-tert-butyl ester as a green solid (60 mg, 24%). MS(ESI) m/z 504 [M+1].

The mixture of [5-(3-N,N-di-tert-butoxycarbonyl-amino-pyrrolidin-1-yl)-imidazo[4,5-b]pyridine-3-carbamic acid-tert-butyl ester (35 mg, 0.07 mmole), 2-isoquinolin-4-yl-isonicotinic acid methyl ester (18.4 mg, 0.07 mmole), and tetrahydrofuran (2 ml) was cooled to -78° C. Lithium diisopropylamide (2N, 0.1 ml, 0.18 mmole) was added slowly. Reaction mixture was stirred at -78° C. for 2 hours and then was diluted with water, extracted with EtOAc. EtOAc layer was concentrated and crude product was purified by using HPLC (from 20% to 100% of acetonitrile in water with 0.01% NH₄OH) to afford [5-(3-N,N-di-tert-butoxycarbonyl-amino-pyrrolidin-1-yl)-3H-imidazole[4,5-b]pyridine-2-yl]-2-(isoquinolin-4-yl-pyridin-4-yl)-methanone (20 mg, 45%) as a yellow solid. 1H NMR (400 MHz, CD₂Cl₂) δ 1.36 (m, 1H), 1.52 (s, 18H), 2.37 (m, 1H), 2.46 (m, 1H), 3.55 (m, 1H), 3.85 (m, 1H), 3.92 (m, 1H), 5.02 (m, 1H0, 6.64 (d, J=9.54 Hz, 1H), 8.03 (m, 2H), 8.23 (m, 1H), 8.42 (d, J=8.53 Hz, 1H), 8.57 (d, J=5.02 Hz, 1H), 8.64 (d, J=8.53 Hz, 1H), 8.81 (s, 1H), 8.94 (s, 1H), 9.13 (d, J=5.02 Hz, 1H), 9.54 (s, 1H). MS: m/z 636 [M+1].

Step 4

[5-(3-Amino-pyrrolidin-1-yl)-3H-imidazole[4,5-b]pyridine-2-yl]-2-(isoquinolin-4-yl-pyridin-4-yl)-methanone

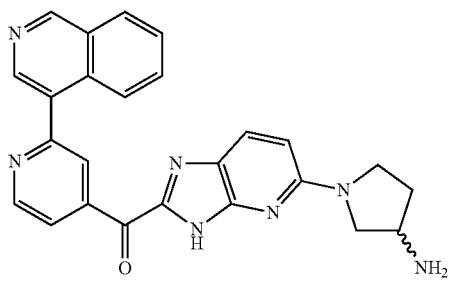 [SMILES: NC1CCN(c2ccc3nc(C(=O)c4ccnc(-c5cncc6ccccc56)c4)[nH]c3n2)C1]

The mixture of [5-(3-N,N-di-tert-butoxycarbonyl-amino-pyrrolidin-1-yl)-3H-imidazole[4,5-b]pyridine-2-yl]-2-(isoquinolin-4-yl-pyridin-4-yl)-methanone (20 mg, 0.03 mmole) and 2 molar HCl in ether (1 ml) was stirred at room temperature for 2 hours. Solvent was removed. Residue was washed with ethyl ether a few times to afford [5-(3-amino-pyrrolidin-1-yl)-3H-imidazole[4,5-b]pyridine-2-yl]-2-(isoquinolin-4-yl-pyridin-4-yl)-methanone (4 mg, 29%) as a yellow solid. 1H NMR (400 MHz, CD$_3$OD) δ 1.32 (m, 1H), 2.29 (m, 1H), 2.56 (m, 1H), 3.16-3.92 (m, 3H), 4.02-4.19 (m, 1H), 6.87-7.10 (dd, J=7.10 Hz, J=88.3 Hz, 1H), 7.91-8.10 (dd, J=9.03 Hz, J=30.12 Hz, 1H), 8.14 (m, 1H), 8.26 (m, 2H), 8.40-8.54 (dd, J=8.53 Hz, J=48.9 Hz, 1H), 8.66 (m, 2H), 8.80-8.89 (m, 1H), 8.95-9.16 (dd, J=5.02 Hz, J=76.8 Hz, 1H), 9.92 (d, J=11.0 Hz, 1H). HR-MS m/z 436.1748 [M+1].

Example 173

4-[5-(4-Dimethylamino-piperidin-1-yl)-3H-imidazo[4,5-b]pyridine-2-carbonyl]-2-(1,3,5-trimethyl-1H-pyrazol-4-yl)-benzonitrile

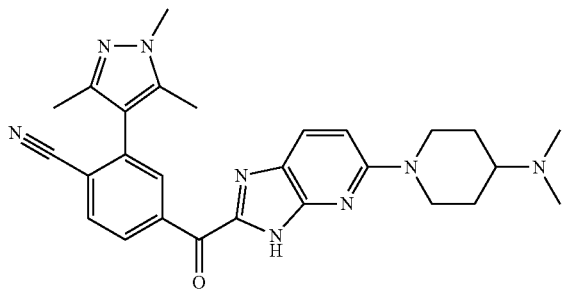 [SMILES: Cc1nn(C)c(C)c1-c1cc(C(=O)c2nc3ccc(N4CCC(N(C)C)CC4)nc3[nH]2)ccc1C#N]

Step 1

4-Cyano-3-(1,3,5-trimethyl-1H-pyrazol-4-yl)-benzoic acid methyl ester

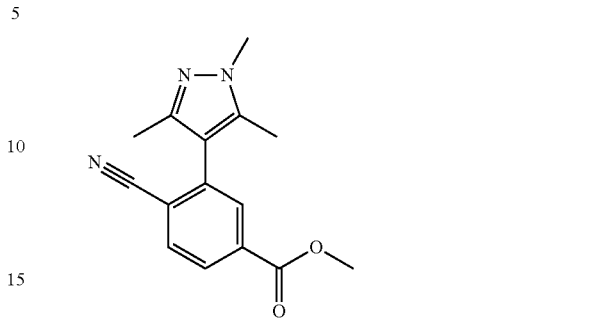

Following General procedure L (Suzuki), using 4-bromo-1,3,5-trimethyl-1H-pyrazole and 4-cyano-3-(4,4,5,5-tetramethyl-[1,3,2]dioxaborolan-2-yl)-benzoic acid methyl ester to give 4-cyano-3-[3,5-dimethyl-1-(2-trimethylsilanyl-ethoxymethyl)-1H-pyrazol-4-yl]-benzoic acid methyl ester. MS(ESI) m/z 270.1 (M+H)$^+$.

Step 2

4-[5-(4-Dimethylamino-piperidin-1-yl)-3H-imidazo[4,5-b]pyridine-2-carbonyl]-2-(1,3,5-trimethyl-1H-pyrazol-4-yl)-benzonitrile

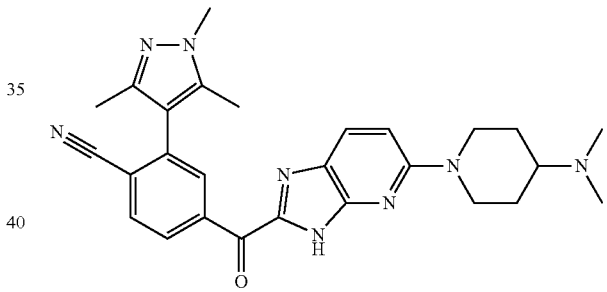

Following General procedure P (LDA metallation, ketone formation and in situ deprotection) using 4-cyano-3-(1,3,5-trimethyl-1H-pyrazol-4-yl)-benzoic acid methyl ester and [1-(3-dimethylaminomethyl-3H-imidazo[4,5-b]pyridin-5-yl)-piperidin-4-yl]-dimethyl-amine to give 4-[5-(4-dimethylamino-piperidin-1-yl)-3H-imidazo[4,5-b]pyridine-2-carbonyl]-2-(1,3,5-trimethyl-1H-pyrazol-4-yl)-benzonitrile. (84%). HRMS m/z 483.2620 (M+H)$^+$.

Example 174

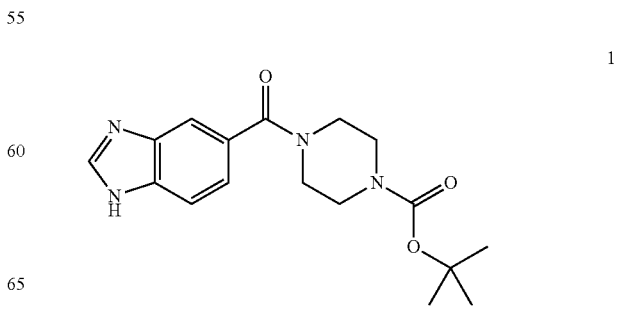

4-(1H-Benzoimidazole-5-carbonyl)-piperazine-1-carboxylic acid tert-butyl ester (1)

In a 250 mL round bottom flask with a stirbar was added Benzimidazole-5-carboxylic acid (2.00 g, 12.3 mmol), Boc-piperazine (2.41 g, 13.0 mmol, 1.05 eq), and Hunig's Base (3.78 mL, 27.1 mmol, 2.2 eq) in DMF (35 mL). After 5 minutes 1-ethyl-3-(3-dimethylaminopropyl)carbodiimide (2.60 g, 13.6 mmol, 1.1 eq) was added portion wise and the dark solution stirred for 2 hr at 23° C. The reaction was diluted with Ethyl Acetate (250 mL) and partitioned between water (50 mL). The layers were separated and the organic washed with water (2×50 mL), brine (30 mL), dried ($Na_2SO_4$), and concentrated to a dark oil. The reaction was purified using Biotage MPLC system (40M column size, 0-20% Methanol/$CH_2Cl_2$ over 35 Column Volumes) giving the desired product as a beige solid (1.45 g, 4.39 mmol, 35.6%). $^1$H NMR (DMSO-$d_6$, 400 MHz) δ 12.6 (s, 1H), δ 8.31 (s, 1H), δ 7.66-7.60 (m, 2H), δ 7.25 (bs, 1H), δ 3.60-3.25 (m, 8H), δ 1.40 (s, 9H); LRMS (m/z): 353 (M+Na), 331 (M+H), 275.

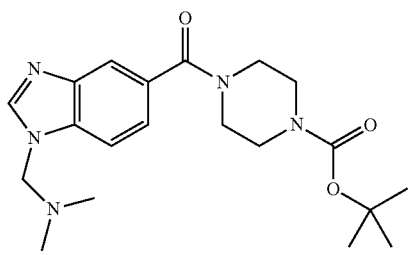

2

4-(1-Dimethylaminomethyl-1H-benzoimidazole-5-carbonyl)-piperazine-1-carboxylic acid tert-butyl ester (2)

To stirring solution of 1 (1.50 g, 4.54 mmol) in dichloromethane (20 mL) was added potassium carbonate (690 mg, 4.99 mmol, 1.1 eq) and succinic anhydride (500 mg, 4.99 mmol, 1.1 eq) at 23° C. Next, N,N,N',N'-tetramethylamino methane (0.68 mL, 4.99 mmol, 1.1 eq) was added dropwise and the suspension stirred at room temperature for 6 hr. The reaction mixture was diluted with dichloromethane (50 mL) and quenched with 20% NaOH (aq) (50 mL). The layers were separated and the organic washed with water, dried over $Na_2SO_4$, and concentrated to an off white solid (1.76 g, 4.74 mmol, 100%). $^1$H NMR (CDCl$_3$, 400 MHz): δ 7.94 (s, 1H), δ 7.79-7.71 (m, 1H), δ 7.60 (s, 0.5H), δ 7.50-7.48 (d, 0.5H), δ 7.38-7.35 (d, 0.5H), δ 7.25-7.22 (d, 0.5H), δ 4.80-4.78 (d, 2H), δ 3.80-3.35 (m, 8H), δ 2.28 (s, 6H), δ 1.41 (s, 9H)

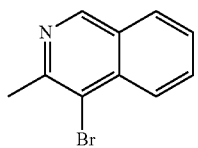

3

4-Bromo-3-methyl-isoquinoline (3)

In a 40 mL screw-top vial with a stirbar was added 3-methyl-isoquinoline (6.00 g, 41.9 mmol) in hydrobromic acid (6 mL), followed by the dropwise addition of bromine (2.2 mL, 42.7 mmol, 1.02 eq). The entire suspension was heated at 100-120° C. for 24 hr. The reaction mix was cooled and diluted with DCM (100 mL) and 1N NaOH added slowly to neutralize the reaction. The organic layer was collected and dried over $Na_2SO_4$ and concentrated to a dark orange oil. The crude reaction was purified using Biotage MPLC system (40M column size, 0-15% Ethyl Acetate/Heptane over 30CV) giving a tan crystalline solid as the desire product (3.48 g, 14.57 mmol, 34.8%). $^1$H NMR (CDCl$_3$, 400 MHz): δ 9.01 (s, 1H), δ 8.12-8.10 (d, 1H), δ 7.87-7.85 (d, 1H), δ7.72-7.68 (dt, 1H), δ 7.54-7.50 (dt, 1H), δ 2.80 (s, 3H); LRMS (m/z): 224, 222 (M+H).

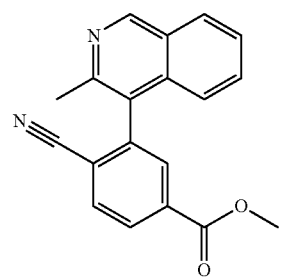

4

4-Cyano-3-(3-methyl-isoquinolin-4-yl)-benzoic acid methyl ester (4)

Into a 40 mL screw-top vial with a stirbar was added 3 (500 mg, 2.25 mmol), 4-cyano-3-(4,4,5,5-tetramethyl-[1,3,2]dioxaborolan-2-yl)-benzoic acid methyl ester (776 mg, 2.70 mmol, 1.2 eq) (prepared according to procedure in *J. Am. Chem. Soc.*, 127, 10539, (2005)), and $K_3PO_4$ (1.004 g, 4.73 mmol. 2.1 eq) in a 10:1 mixture of 1,4-dioxane:$H_2O$ (10 mL/1 mL). To the solution was added bis(di-tert-butyl(4-dimethylaminophenyl)phosphine)dichloropalladium(II) (31.9 mg, 2 mol %), the vial capped and the contents heated to 100° C. for 4 hrs. The reaction was cooled to room temperature and diluted with ethyl acetate (100 mL). The solid was filtered and the filtrate washed with water (2×30 mL), brine, followed by drying over $Na_2SO_4$, and concentrating to a yellow oil. The crude product was purified using Biotage MPLC system (25S column size, 0-30% ethyl acetate/heptane, over 30CV, then 30% isocratic for 10CV) giving white solid as the product (455 mg, 1.51 mmol, 67%). $^1$H NMR (CDCl$_3$, 400 MHz): δ 9.34 (s, 1H), δ 8.30-8.27 (dd, 1H), δ 8.13 (s, 1H), δ 8.08-8.05 (m, 1H), δ 8.00-7.98 (d, 1H), δ 7.64-7.61 (m, 2H), δ 7.17-7.15 (m, 1H), δ 3.99 (s, 1H), δ 2.51 (s, 3H); LRMS (m/z): 303 (M+H)

5

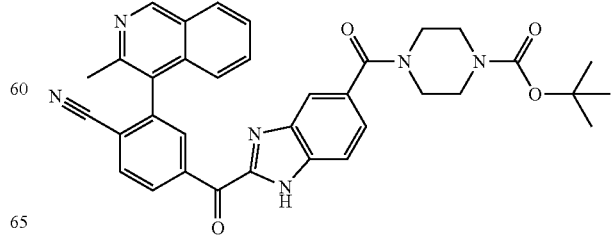

4-{2-[4-Cyano-3-(3-methyl-isoquinolin-4-yl)-benzoyl]-1H-benzoimidazole-5-carbonyl}-piperazine-1-carboxylic acid tert-butyl ester (5)

To a stirring solution of 2 (76 mg, 0.195 mmol) and 4 (62 mg, 0.205 mmol, 1.05 eq) in THF (5 mL) at −78° C. was added freshly prepared 1M LDA dropwise (Prepared from Diisopropylamine and 2.5M n-Butyl Lithium in Hexanes). Upon addition of LDA, an orange color formed and stayed throughout the reaction. After 1.5 hr of stirring at −78° C. the reaction was quenched with 50% aqueous Acetic Acid (5 mL) and the reaction mixture warmed to room temperature. The reaction mixture was diluted with Ethyl Acetate (50 mL) and neutralized using 28-30% Ammonium Hydroxide (aq) until pH~9. The aqueous layer was extracted one additional time with Ethyl Acetate and the combined organics washed with brine, dried ($Na_2SO_4$), and concentrated to a yellow crystalline solid. The crude mixture was purified using Biotage MPLC system (25S column size, 0-10% Methanol/$CH_2Cl_2$ over 70CV), giving title compound as an off white solid (60 mg, 0.100 mmol, 51%). $^1$H NMR (DMSO-$d_6$, 400 MHz): δ 13.9 (s, 1H), δ 9.44 (s, 1H), δ 8.84-8.82 (d, 1H), δ 8.57 (s, 1H), δ 8.39-8.37 (d, 1H), δ 8.27-8.25 (d, 1H), δ 7.90 (bs, 1H), 7.79-7.64 (m, 3H), 7.50-7.35 (m, 1H), δ 7.30-7.28 (d, 1H), δ 3.70-3.30 (m, 8H), δ 2.46 (s, 3H), δ 1.41 (s, 9H); LRMS (m/z): 601 (M+H), 545

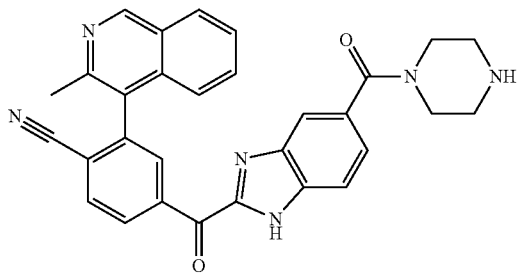

2-(3-Methyl-isoquinolin-4-yl)-4-[5-(piperazine-1-carbonyl)-1H-benzoimidazole-2-carbonyl]-benzonitrile (6)

To a stirring solution of 6 (55 mg, 0.092 mmol) in dry $CH_2Cl_2$ (5 mL) at room temperature was added 4M HCl in Dioxane (0.50 mL, 2.014 mmol, 22 eq). After approximately 30 seconds the solution turned cloudy and a white precipitate began to form. The reaction was stirred an additional 16 hours and then concentrated giving the title compound as a white solid (40 mg, 0.078 mmol, 85%). $^1$H NMR (DMSO-$d_6$, 400 MHz): δ 9.75-9.71 (d, 1H), δ 8.79-8.77 (d, 1H), δ 8.55-8.52 (d, 2H), 68.37-8.35 (d, 1H), δ 8.12-7.96 (m, 2H), δ 7.88-7.81 (m, 2H), δ 7.55-7.49 (m, 2H), δ 3.77 (bs, 4H), δ 3.21 (bs, 4H), δ 2.58 (s, 3H); HRMS (m/z): calculated 501.2039, observed 501.2058.

Example 175

5-[5-(4-Dimethylamino-piperidin-1-yl)-1H-benzoimidazole-2-carbonyl]-2-methoxy-biphenyl-2-carboxylic acid amide

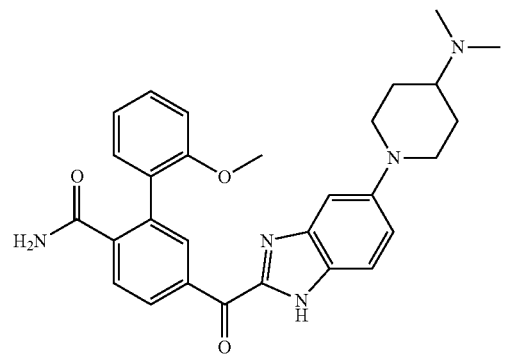 [SMILES: COc1ccccc1-c1cc(C(=O)c2nc3cc(N4CCC(N(C)C)CC4)ccc3[nH]2)ccc1C(N)=O]

Example 88 (50 mg, 0.1 mmol) was dissolved in 2-methoxy ethanol (0.7 mL) in a screw cap vial. An aqueous solution of 2.45M KOH (0.21 mL, 0.52 mmol) was added to the mixture. The vial was sealed and heated at 105° C. for 16 hours. After cooling, the mixture was diluted with sat. aqueous $NaHCO_3$ (10 mL) and then extracted with a mixture of $CHCl_3$/PrOH (3:1; 3×5 mL). The combined organic layers were dried over $Na_2SO_4$, filtered and the solvent was removed in vacuo. Purification by preparative LCMS provided the title compound as a red solid (12 mg, 24%). MS(ESI) m/z 498.2 (M+H)$^+$. $^1$H NMR (400 MHz, DMSO-$d_6$): 13.32 (0.2H, bs), 13.15 (0.8H, s), 8.59-8.51 (1H, m), 8.37 (1H, m), 7.73-7.62 (2H, m), 7.51 (1H, s), 7.46 (0.2H, d), 7.40-7.32 (1H, m), 7.32-7.25 (2H, m), 7.20 (0.2H, s), 7.13 (0.8H, dd), 7.10-6.98 (2H, m), 6.87 (0.8H, s), 3.79-3.65 (5H, m), 2.81-2.63 (2H, m), 2.28-2.14 (7H, m), 1.87 (2H, d), 1.52 (2H, q).

The compounds of Examples 176 to 194 below were prepared by methods described herein or methods analogous thereto.

Example 176

4-[5-(4-Dimethylamino-piperidin-1-yl)-3H-imidazo[4,5-b]pyridine-2-carbonyl]-2-(2-methyl-imidazo[1,2-a]pyridin-3-yl)-benzonitrile

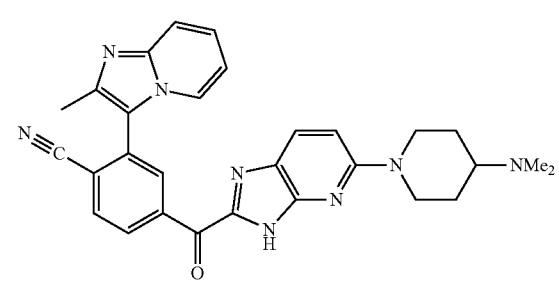 [SMILES: Cc1nc2ccccn2c1-c1cc(C(=O)c2nc3ccc(N4CCC(N(C)C)CC4)nc3[nH]2)ccc1C#N]

Example 177

2-(3,5-Dimethyl-1H-pyrazol-4-yl)-4-[6-(piperazine-1-carbonyl)-1H-benzoimidazole-2-carbonyl]-benzonitrile

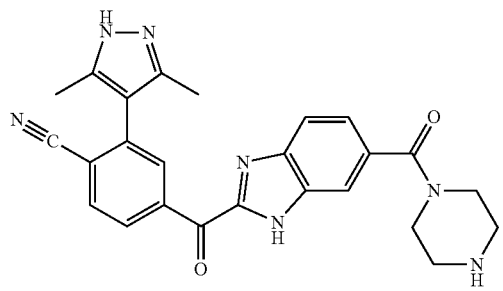 [SMILES: Cc1n[nH]c(C)c1-c1cc(C(=O)c2nc3ccc(C(=O)N4CCNCC4)cc3[nH]2)ccc1C#N]

Example 178

(2-Isoquinolin-4-yl-pyridin-4-yl)-[5-(piperazine-1-carbonyl)-3H-imidazo[4,5-b]pyridin-2-yl]-methanone

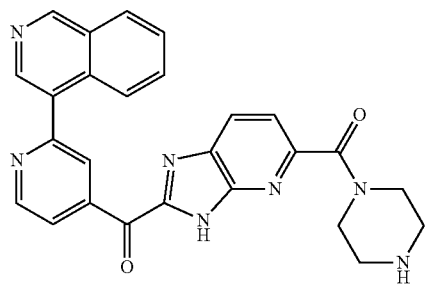 [SMILES: O=C(c1ccnc(-c2cncc3ccccc23)c1)c1nc2ccc(C(=O)N3CCNCC3)nc2[nH]1]

Example 179

4-(5-[1,4']Bipiperidinyl-1'-yl-3H-imidazo[4,5-b]pyridine-2-carbonyl)-2-(3,5-dimethyl-1H-pyrazol-4-yl)-benzonitrile

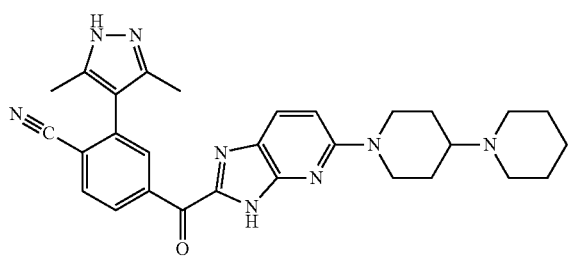 [SMILES: Cc1n[nH]c(C)c1-c1cc(C(=O)c2nc3ccc(N4CCC(N5CCCCC5)CC4)nc3[nH]2)ccc1C#N]

Example 180

2-Isoquinolin-4-yl-4-[6-(piperazine-1-carbonyl)-1H-benzoimidazole-2-carbonyl]-benzonitrile

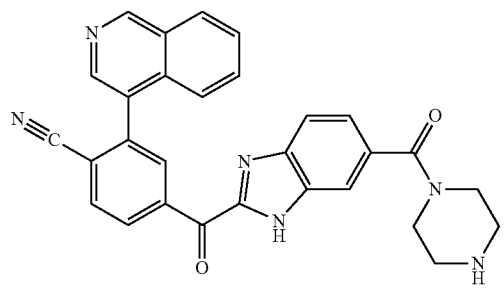 [SMILES: N#Cc1ccc(C(=O)c2nc3ccc(C(=O)N4CCNCC4)cc3[nH]2)cc1-c1cncc2ccccc12]

Example 181

4-(6-Chloro-1H-benzoimidazole-2-carbonyl)-2-[1,6]naphthyridin-8-yl-benzonitrile

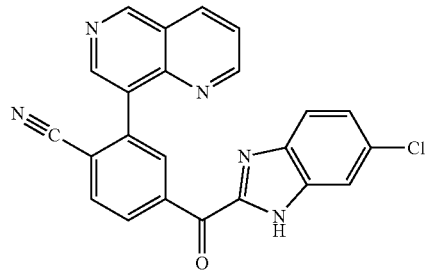 [SMILES: N#Cc1ccc(C(=O)c2nc3ccc(Cl)cc3[nH]2)cc1-c1cncc2cccnc12]

Example 182

(2-Isoquinolin-4-yl-pyridin-4-yl)-[6-(piperazine-1-sulfonyl)-1H-benzoimidazol-2-yl]-methanone

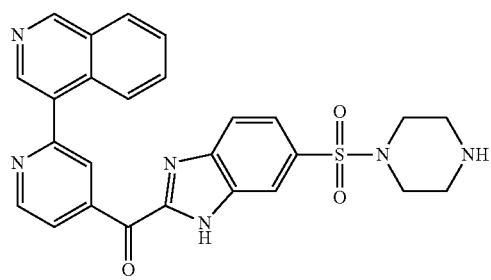 [SMILES: O=C(c1ccnc(-c2cncc3ccccc23)c1)c1nc2ccc(S(=O)(=O)N3CCNCC3)cc2[nH]1]

Example 183

[6-(piperazine-1-carbonyl)-1H-benzoimidazol-2-yl]-[2-(1,3,5-trimethyl-1H-pyrazol-4-yl)-pyridin-4-yl]-methanone

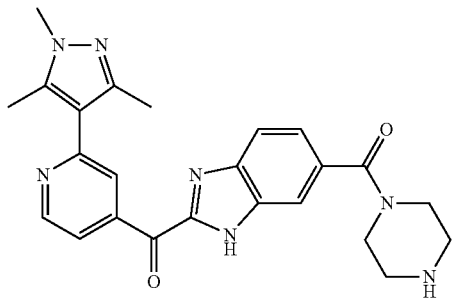 [SMILES: Cc1nn(C)c(C)c1-c1cc(C(=O)c2nc3ccc(C(=O)N4CCNCC4)cc3[nH]2)ccn1]

HRMS m/z 444.2167 (M+H)$^+$.

Example 184

4-[6-(piperazine-1-carbonyl)-1H-benzoimidazole-2-carbonyl]-2-(1,3,5-trimethyl-1H-pyrazol-4-yl)-benzonitrile

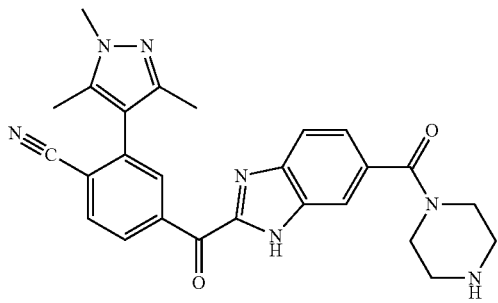 [SMILES: Cc1nn(C)c(C)c1-c1cc(C(=O)c2nc3ccc(C(=O)N4CCNCC4)cc3[nH]2)ccc1C#N]

HRMS m/z 468.2156 (M+H)$^+$.

Example 185

2-(3,5-Dimethyl-1-phenyl-1H-pyrazol-4-yl)-4-[6-(piperazine-1-carbonyl)-1H-benzoimidazole-2-carbonyl]-benzonitrile

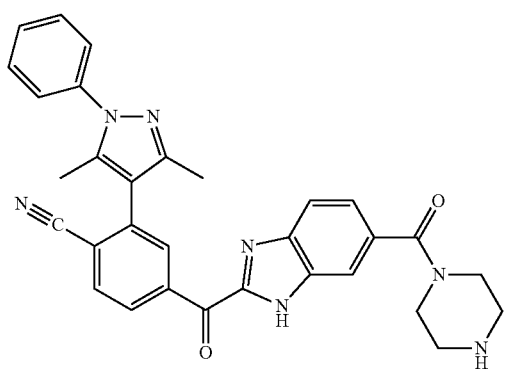 [SMILES: Cc1nn(-c2ccccc2)c(C)c1-c1cc(C(=O)c2nc3ccc(C(=O)N4CCNCC4)cc3[nH]2)ccc1C#N]

HRMS m/z 530.2297 (M+H)$^+$.

Example 186

2-(4-Cyano-3-isoquinolin-4-yl-benzoyl)-3H-benzoimidazole-5-sulfonic acid (2-amino-ethyl)-methyl-amide

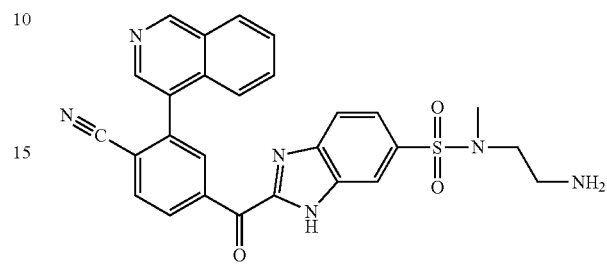

Example 187

2-(3,5-Dimethyl-isoxazol-4-yl)-4-[6-(piperazine-1-carbonyl)-1H-benzoimidazole-2-carbonyl]-benzonitrile

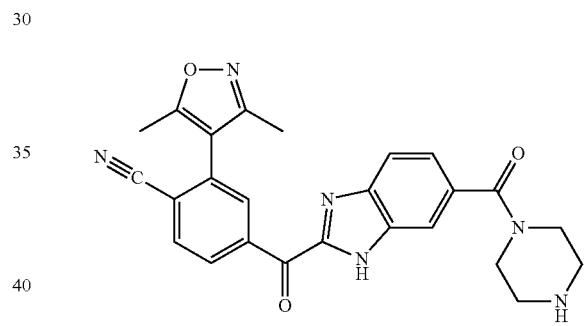

HRMS m/z 455.1842 (M+H)$^+$.

Example 188

6-(4-Dimethylamino-piperidin-1-yl)-1H-benzoimidazol-2-yl]-[3-(3,5-dimethyl-1H-pyrazol-4-yl)-4-fluoro-phenyl]-methanone

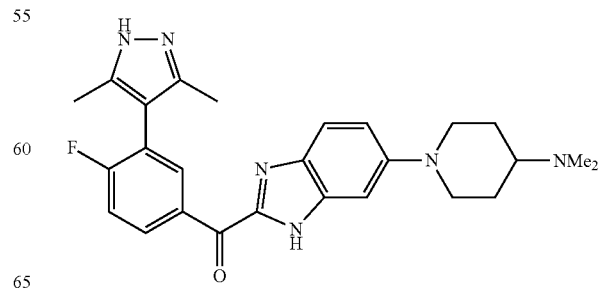

Example 189

4-(5-piperazin-1-yl-3H-imidazo[4,5-b]pyridine-2-carbonyl)-2-(1,3,5-trimethyl-1H-pyrazol-4-yl)-benzonitrile

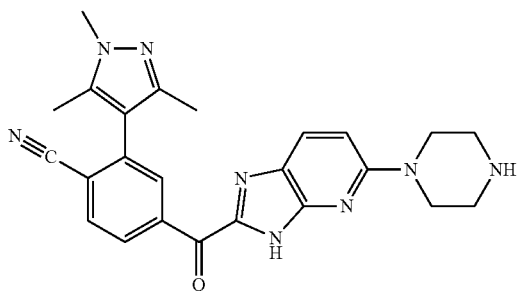 [SMILES: Cc1nn(C)c(C)c1-c1cc(C(=O)c2nc3ccc(N4CCNCC4)nc3[nH]2)ccc1C#N]

Example 190

(5-[1,4']Bipiperidinyl-1'-yl-3H-imidazo[4,5-b]pyridin-2-yl)-(2-isoquinolin-4-yl-pyridin-4-yl)-methanone

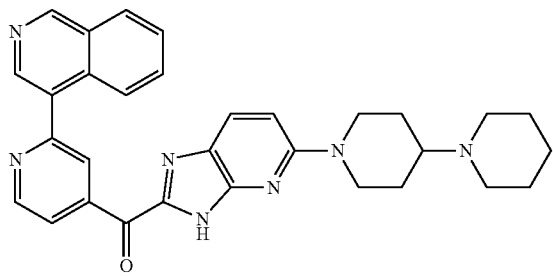 [SMILES: O=C(c1ccnc(-c2cncc3ccccc23)c1)c1nc2ccc(N3CCC(N4CCCCC4)CC3)nc2[nH]1]

Example 191

4-[2-(2-Isoquinolin-4-yl-pyridine-4-carbonyl)-3H-imidazo[4,5-b]pyridin-6-yl]-[1,4]diazepane-1-carboxylic acid tert-butyl ester

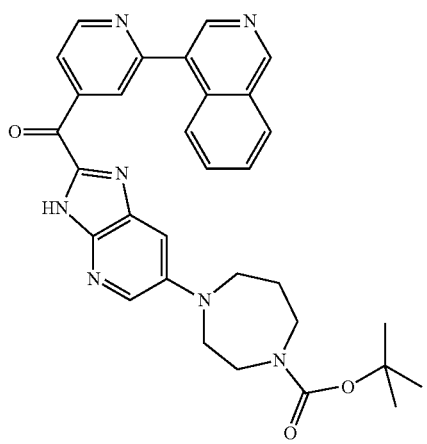 [SMILES: CC(C)(C)OC(=O)N1CCCN(c2cnc3[nH]c(C(=O)c4ccnc(-c5cncc6ccccc56)c4)nc3c2)CC1]

Example 192

[6-(4-Dimethylamino-piperidin-1-yl)-1H-benzoimidazol-2-yl]-(3-isoquinolin-4-yl-4-methoxy-phenyl)-methanone

Step 1

3-Isoquinolin-4-yl-4-methoxy-benzaldehyde

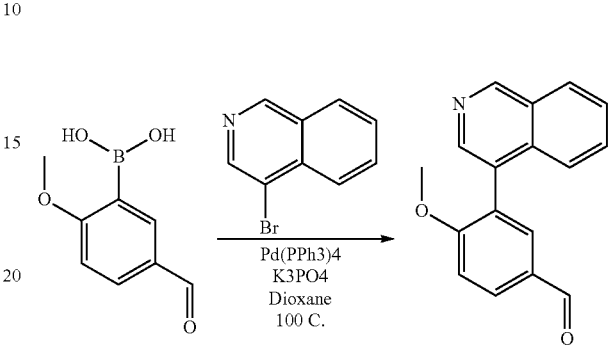

In a 50 mL sealed tube, a mixture of 4-methoxy-benzaldehyde-3-boronic acid (545 mg, 3 mmol), 4-Bromo-isoquinoline (945 mg, 4.5 mmol) and potassium phosphate tribasic (1.27 g, 6 mmol) in dioxane was bubbled with nitrogen gas, then treated with tetrakistriphenylphosphine palladium (347 mg, 0.1 eq). The resulting mixture was heated at 120° C. oil bath for 10 h. The reaction mixture was cooled and filtered through celite, washed with dichloromethane. The filtrate was concentrated and purified by flash chromatography (EtOAc:Heptane) to obtain 3-isoquinolin-4-yl-4-methoxy-benzaldehyde in 97% yield. MS m/z 264.4 (M+H)$^+$.

Step 2

[6-(4-Dimethylamino-piperidin-1-yl)-1H-benzoimidazol-2-yl]-(3-isoquinolin-4-yl-4-methoxy-phenyl)-methanone To a cooled (−78° C.) 1M solution of lithium hexamethyldisilazane (0.88 mL, 0.88 mmol) in THF was added N3,N3-Dimethyl-N1-[3-(2-trimethylsilanyl-ethoxymethyl)-3H-benzoimidazol-5-yl]-pentane-1,3-diamine (82 mg, 0.22 mmol) in 1 mL THF. Solution turned bright orange. After 5 min, the reaction mixture was treated with 3-isoquinolin-4-yl-4-methoxy-benzaldehyde (58 mg, 0.22 mmol) in 1 mL THF. After 20 minutes, the reaction mixture was removed from cold bath, diluted with ethyl acetate and washed with saturated aqueous sodium bicarbonate. The organic phase was dried over Na2SO4, filtered and concentrated in vacuo. The residue was then dissolved in DCM: TFA. After 1 hour, the reaction mixture was concentrated and purified by HPLC (Deltapak C18, acetonitrile: 0.1% trifluoroacetic acid), then neutralized using PL-HCO3 SPE to obtain 19 mg [6-(4-dimethylamino-piperidin-1-yl)-1H-benzoimidazol-2-yl]-(3-isoquinolin-4-yl-4-methoxy-phenyl)-methanone in 17% yield. MS m/z 506.5 (M+H)+.

Example 193

4-[2-(2-Isoquinolin-4-yl-pyridine-4-carbonyl)-3H-imidazo[4,5-b]pyridin-5-yl]-piperazine-1-carboxylic acid tert-butyl ester

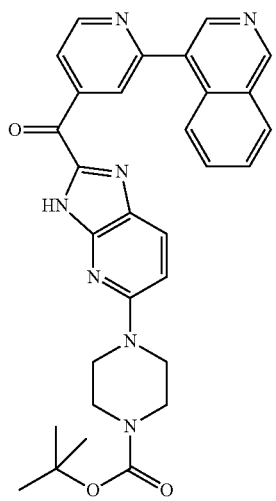 [SMILES: CC(C)(C)OC(=O)N1CCN(c2ccc3nc(C(=O)c4ccnc(-c5cncc6ccccc56)c4)[nH]c3n2)CC1]

Example 194

4-[2-(4-Cyano-3-isoquinolin-4-yl-benzoyl)-3H-imidazo[4,5-b]pyridin-5-yl]-piperazine-1-carboxylic acid tert-butyl ester

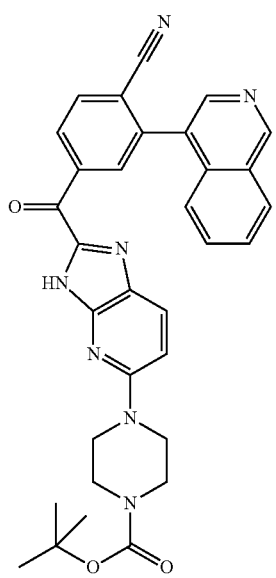 [SMILES: CC(C)(C)OC(=O)N1CCN(c2ccc3nc(C(=O)c4ccc(C#N)c(-c5cncc6ccccc56)c4)[nH]c3n2)CC1]

Example 195

[6-(4-Dimethylamino-piperidin-1-yl)-1H-benzoimidazol-2-yl]-(4-hydroxy-3-isoquinolin-4-yl-phenyl)methanone

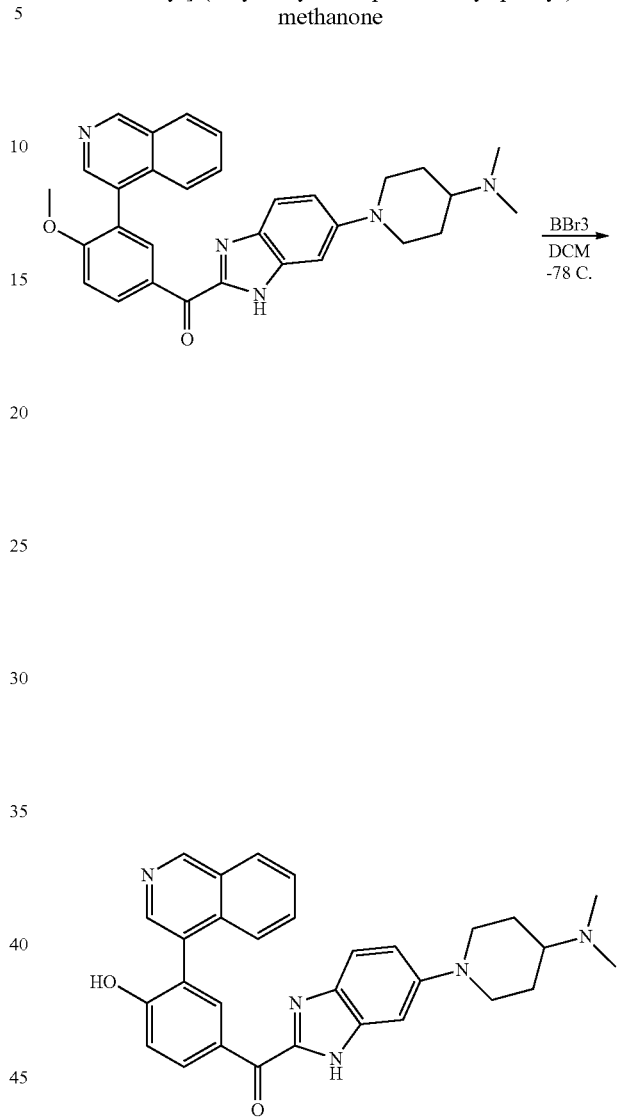

To a cooled (−78° C.) solution of [6-(4-Dimethylamino-piperidin-1-yl)-1H-benzoimidazol-2-yl]-(3-isoquinolin-4-yl-4-methoxy-phenyl)-methanone (6 mg, 0.012 mmol) in dichloromethane (6 mL) was added boron tribromide (0.118 mL, 10 eq) dropwise resulting in bright yellow solution. The reaction mixture was allowed to warm, diluted with saturated ammonium chloride solution, and extracted with dichloromethane. The organics were dried over Na2SO4, filtered, concentrated and purified by HPLC (Deltapak C18, acetonitrile: 0.1% trifluoroacetic acid), then neutralized using PL-HCO3 SPE to obtain 1 mg [6-(4-dimethylamino-piperidin-1-yl)-1H-benzoimidazol-2-yl]-(4-hydroxy-3-isoquinolin-4-yl-phenyl)-methanone in 20% yield. MS m/z 492.4 (M+H)+.

Example 196

4-[5-(4-Dimethylamino-piperidin-1-yl)-3H-imidazo[4,5-b]pyridine-2-carbonyl]-2-(2-methyl-5,6-dihydro-4H-pyrrolo[1,2-b]pyrazol-3-yl)-benzonitrile

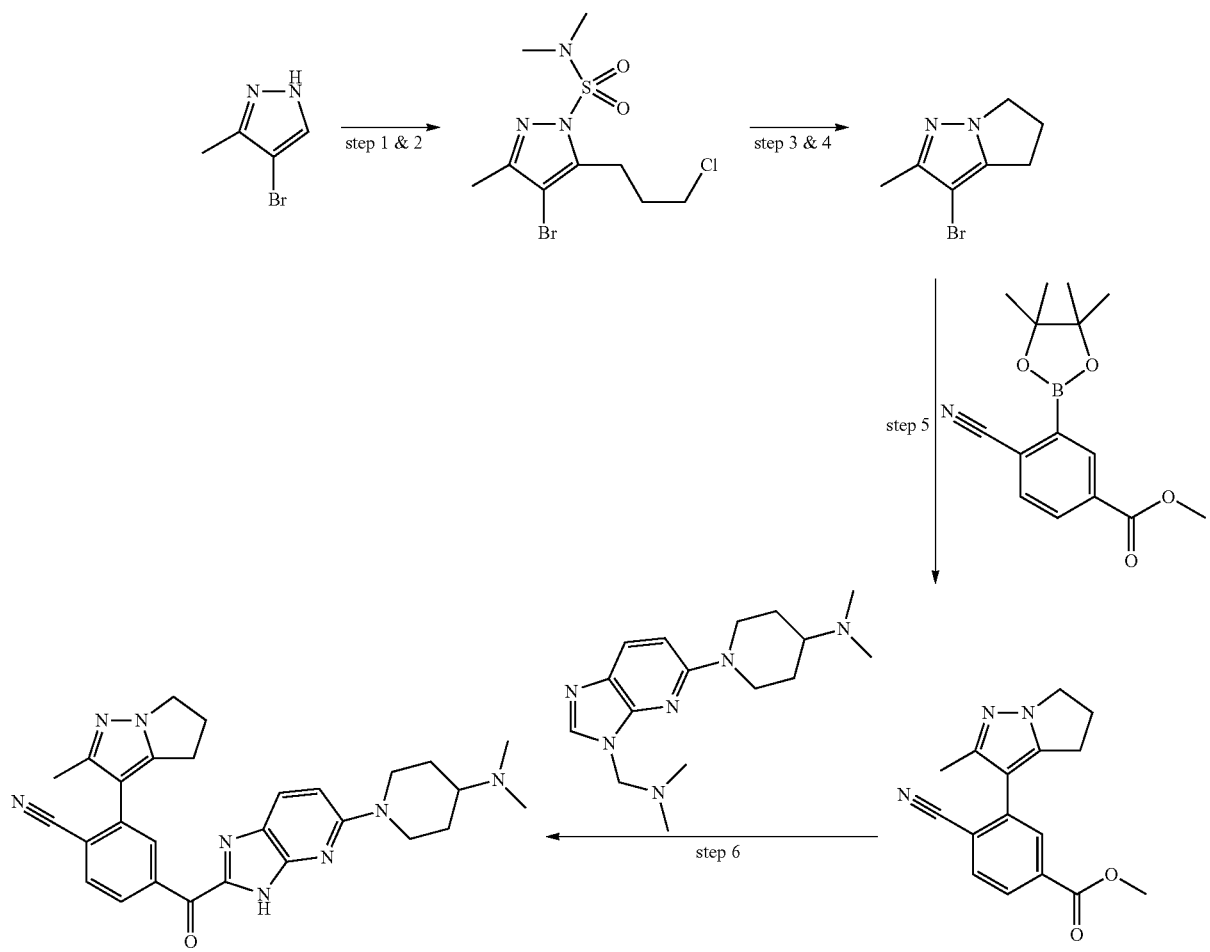

Step 1: 4-Bromo-3-methyl-pyrazole-1-sulfonic acid dimethylamide

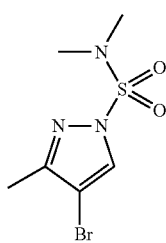

To a suspension of sodium hydride (60% mineral oil dispersion, 1.5 g, 37.3 mmol) in DMF (30 mL) at 0° C. was added dropwise over 15 m a solution of 4-bromo-3-methylpyrazole (5.0 g, 31 mmol) in DMF (30 mL). After stirring over 1 h at room temperature the reaction mixture was cooled to 0° C. and a solution of dimethyl sulfonyl chloride (4.5 g, 31 mmol) in DMF (20 mL) was added dropwise over 15 m. The reaction was warmed to room temperature and stirred for 3 h before quenching with a saturated aqueous solution of NH$_4$Cl. The quenched reaction mixture was extracted with heptane and the organic layer was dried over Na$_2$SO$_4$, filtered and concentrated. The crude product was purified over normal phase silica starting with 5% EtOAc in heptane for 10 m and then increasing to 50% EtOAc in heptane for 20 m to give the desired product as a clear yellow oil (8.0 g, 30.0 mmol) MS m/z 270.3 (M+H)+.

Step 2: 4-Bromo-5-(3-chloro-propyl)-3-methyl-pyrazole-1-sulfonic acid dimethylamide

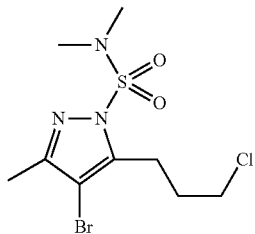 [SMILES: Cc1nn(S(=O)(=O)N(C)C)c(CCCCl)c1Br]

To a solution of 4-bromo-3-methyl-pyrazole-1-sulfonic acid dimethylamide (6.7 g, 25 mmol) in diethyl ether (75 mL) was added dropwise at −78° C. under N₂ phenyl lithium (1.8 M, 14.6 mL, 26.3 mmol) in dibutyl ether. After warming to 0° C. for 15 m, the reaction mixture was re-cooled to −78° C. and a solution of 3-chloro-iodopropane (15.3 g, 75 mmol) in 20 mL THF was added dropwise. The reaction was warmed to room temperature and stirred for 3 h before quenching with a saturated aqueous solution of NH₄Cl. The quenched reaction mixture was extracted with EtOAc and the organic layer was dried over Na₂SO₄, filtered and concentrated. The crude product was purified over normal phase silica starting with 5% EtOAc in heptane for 10 m and then increasing to 50% EtOAc in heptane for 20 m to give the desired product as a clear oil (3.85 g, 11.2 mmol) MS m/z 346.3 (M+H)+.

Step 3: 4-Bromo-5-(3-chloro-propyl)-3-methyl-1H-pyrazole

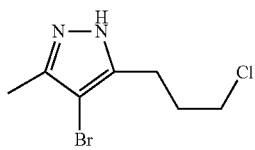

To a solution of 4-bromo-5-(3-chloro-propyl)-3-methyl-pyrazole-1-sulfonic acid dimethylamide (3.85 g, 11.2 mmol) in MeOH (50 ml) at 0° C. was added 6 N HCl (50 mL). The reaction was warmed to room temperature and stirred overnight. The reaction was quenched by adding concentrated NH₄OH until a pH of 8 was obtained. After concentrating to remove the MeOH, the remaining reaction solution was extracted with EtOAc and the organic layer was dried over Na₂SO₄, filtered and concentrated. The crude product was purified over normal phase silica starting with 10% EtOAc in heptane for 5 m and then increasing to 100% EtOAc over 40 m to give the desired product as a clear oil (2.42 g, 10.2 mmol). MS m/z 239.3 (M+H)+.

Step 4: 3-Bromo-2-methyl-5,6-dihydro-4H-pyrrolo[1,2-b]pyrazole

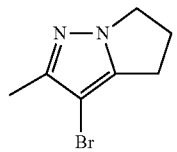

To a solution of 4-bromo-5-(3-chloro-propyl)-3-methyl-1H-pyrazole (2.42 g, 10.2 mmol) in isopropyl alcohol (35 mL) was added KOH (0.86 g, 15.3 mmol) dissolved in water (7 mL). The reaction was heated to reflux for 4 h. After cooling the reaction was partially concentrated, diluted with EtOAc and washed with brine. The organic layer was dried over Na₂SO₄, filtered and concentrated to give a light yellow oil as the desired product (1.01 g, 5.0 mmol). MS m/z 203.4 (M+H)+.

Step 5: 4-Cyano-3-(2-methyl-5,6-dihydro-4H-pyrrolo[1,2-b]pyrazol-3-yl)-benzoic acid methyl ester

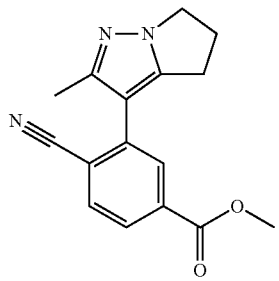 [SMILES: COC(=O)c1ccc(C#N)c(-c2c(C)nn3c2CCC3)c1]

In a pressure sealed flask a suspension of 3-bromo-2-methyl-5,6-dihydro-4H-pyrrolo[1,2-b]pyrazole (1.01 g, 5.0 mmol), 4-cyano-3-(4,4,5,5-tetramethyl-[1,3,2]dioxaborolan-2-yl)-benzoic acid methyl ester (1.8 g, 6.25 mmol), and K₃PO₄ (2.65 g, 12.5 mmol) in dioxane (50 mL) was degassed by bubbling N₂ for 30 m at room temperature. After the addition of tetrakis(triphenylphosphine)palladium (0.58 g, 0.5 mmol) the reaction flask was sealed and the contents heated to 95° C. for 5 h. After cooling the reaction mixture was diluted several fold with EtOAc, and washed with dilute aqueous NaHCO₃ followed by brine. The organic layer was dried over Na₂SO₄, filtered and concentrated. The crude product was purified over normal phase silica starting with 100% DCM for 5 m and then increasing to 10% MeOH in DCM over 25 m to give the desired product as a yellow solid (0.70 g, 2.49 mmol). MS m/z 282.5 (M+H)⁺.

Step 6: 4-[5-(4-Dimethylamino-piperidin-1-yl)-3H-imidazo[4,5-b]pyridine-2-carbonyl]-2-(2-methyl-5,6-dihydro-4H-pyrrolo[1,2-b]pyrazol-3-yl)-benzonitrile

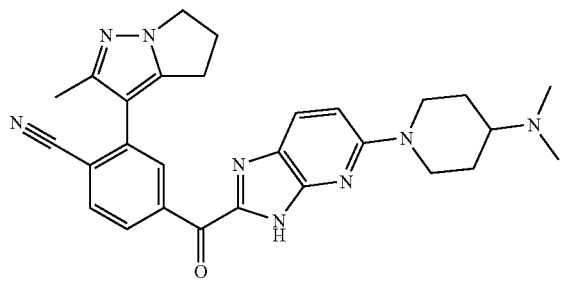 [SMILES: Cc1nn2c(c1-c1cc(C(=O)c3nc4ccc(N5CCC(N(C)C)CC5)nc4[nH]3)ccc1C#N)CCC2]

To a solution of [1-(3-dimethylaminomethyl-3H-imidazo[4,5-b]pyridin-5-yl)-piperidin-4-yl]-dimethyl-amine (0.36 g, 1.2 mmol) in THF (5 mL) at −78° C. under N₂ was added dropwise a freshly prepared solution of lithium diisopropylamine (1M, 1.5 mL, 1.5 mmol) in THF. After 10 m at −78° C. a solution of 4-cyano-3-(2-methyl-5,6-dihydro-4H-pyrrolo[1,2-b]pyrazol-3-yl)-benzoic acid methyl ester (0.28 g, 1.0 mmol) in THF (5 mL) was added. The reaction mixture was stirred at −78° C. under N₂ for 15 m before quenching with a 1:1 solution of acetic acid and water (2 mL). After warming to room temperature the quenched reaction was diluted several fold EtOAc and washed with dilute NH₄OH followed by brine. The organic layer was dried over Na₂SO₄, filtered and concentrated. After purifying the crude product by reverse phase HPLC, the product was neutralized with aqueous Na₂CO₃ yielding the desired product as a orange-colored solid (50 mg, 0.10 mmol). 1H NMR (400 MHz, DMSO-d₆) □ ppm 1.32-1.44 (m, J=12.00, 11.81, 11.81, 3.79 Hz, 2H) 1.85 (d, J=10.61 Hz, 2H) 2.20 (s, 6H) 2.25 (s, 3H) 2.33-2.46 (m, 1H) 2.53-2.63 (m, 2H) 2.89-3.02 (m, 4H) 4.43 (d, J=13.14 Hz, 2H) 7.04 (d, J=9.09 Hz, 1H) 7.95 (d, J=9.09 Hz, 1H) 8.10 (d, J=8.08 Hz, 1H) 8.36 (d, J=7.58 Hz, 1H) 8.52 (s, 1H); MS m/z 495.5 (M+H)⁺.

Example 197

Intermediate

4-{2-Cyano-5-[5-(4-hydroxy-piperidin-1-yl)-3H-imidazo[4,5-b]pyridine-2-carbonyl]-phenyl}-pyrrolo[2,3-c]pyridine-1-carboxylic acid tert-butyl ester

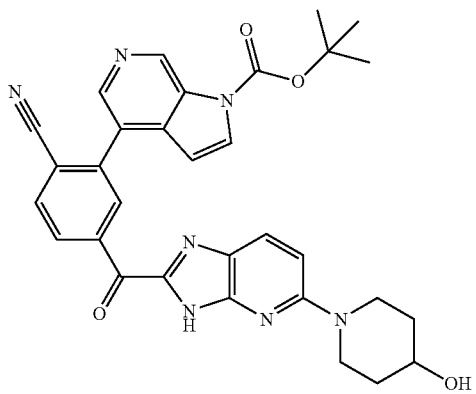

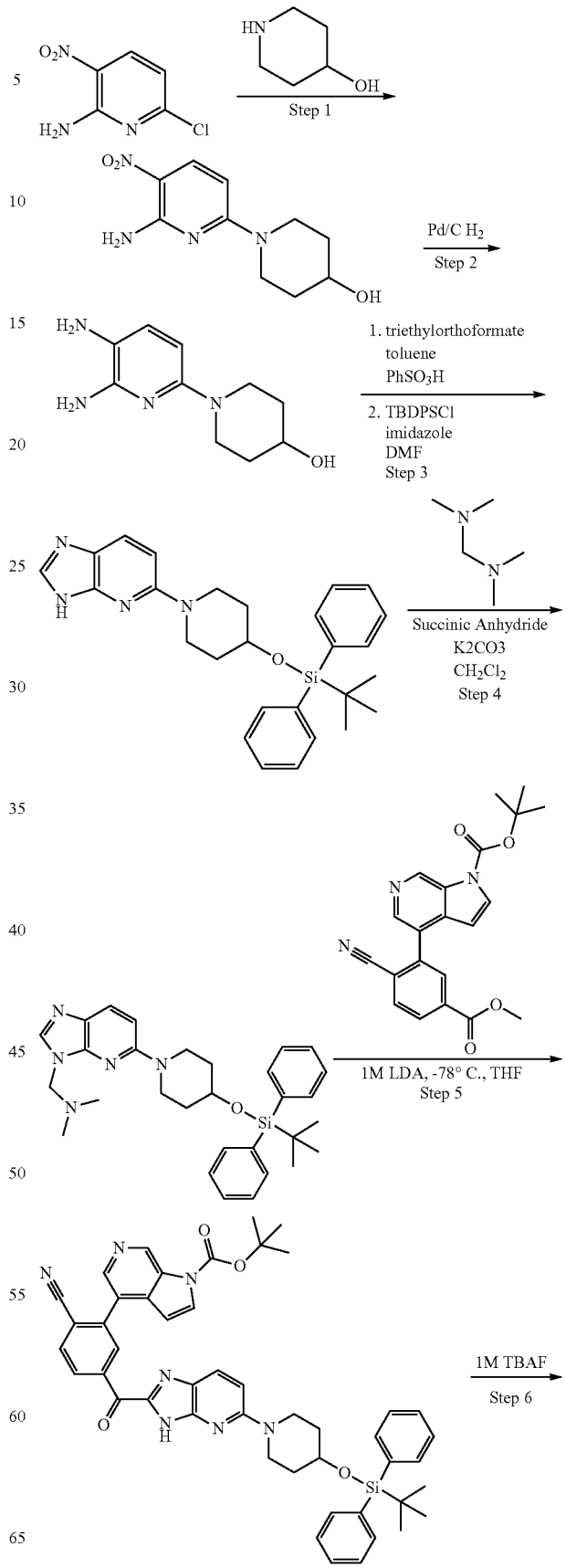

239
-continued

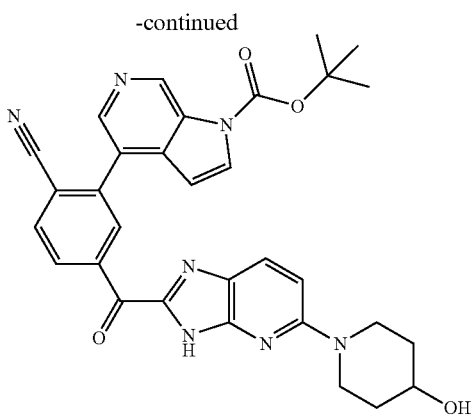

Step 1: To a solution of 2-chloro-5-nitroaniline (15.0 g, 87 mmol) and 4-hydroxypiperidine (9.0 g, 89 mmol, 1.0 eq) in Acetonitrile (200 mL) was added in one portion potassium carbonate (20 g, 145 mmol, 1.7 eq). The slurry was stirred at 50° C. for 16 hr then the solvent removed under reduced pressure and the resulting solid taken up in CH$_2$Cl$_2$ and water (100 mL) and partitioned. The layers were separated and the aqueous layer extract with CH$_2$Cl$_2$ (2×100 mL), the combined organics dried (MgSO4), and concentrated to a yellow solid that was further triturated with Acetonitrile giving 6'-Amino-5'-nitro-3,4,5,6-tetrahydro-2H-[1,2']bipyridinyl-4-ol as a yellow solid (16.9 g, 71.2 mmol. 82%). MS ESI m/z 239.1 (M+H)$^+$.

Step 2: To a parr flask was added 6'-Amino-5'-nitro-3,4,5,6-tetrahydro-2H-[1,2']bipyridinyl-4-ol (10.0 g, 42.0 mmol) (Step 1), 10% Pd/C (2.5 g) and MeOH (100 mL). The flask was pressurized to 50 psi with H$_2$ for 12 hr with shaking. The contents of the flask were filtered through Celite and the filtrate (dark green) was concentrated to afford 5',6'-Diamino-3,4,5,6-tetrahydro-2H-[1,2']bipyridinyl-4-ol as a dark purple solid (8.90 g, 39.7 mmol, 95%). MS ESI m/z 209.2 (M+H)$^+$.

Step 3: To a stirring suspension of 5',6'-Diamino-3,4,5,6-tetrahydro-2H-[1,2']bipyridinyl-4-ol (8.90 g, 39.7 mmol) and p-toluenesulfonic acid (1.63 g, 8.55 mmol, 0.2 eq) in toluene was added triethyl orthoformate (21.5 mL, 129 mmol, 3.0 eq) in two portions. The first (11 mL) was added in a fast dropwise addition manner the mixture stirred to 16 hr at 100° C. Methanol (10 mL) was added followed by the final portion of triethyl orthoformate (10.5 mL) and the reaction stirred an additional 1 hr at 110° C. The solution was cooled and concentrated to a dark solid. The resulting solid was triturated from Acetonitrile/Water (20:1) giving 6.0 g of benzimidazole as a brown powder. Benzimidazole (5.72 g, 26.2 mmol) was dissolved in DMF (100 mL) and imidazole (3.75 g, 55.1 mmol, 2.1 eq) followed by tert-butyl-diphenylsilylchloride (15.0 mL, 58.4 mmol, 2.2 eq) were added and the reaction stirred for 16 hr at 23° C. The reaction was quenched with sat'd NaHCO3 (20 mL) and then diluted (100 mL) with water. EtOAc (500 mL) was added and the layers partitioned. The organic was washed with brine, dried (Na$_2$SO$_4$), and concentrated. The crude product was purified by chromatography eluting with EtOAc/Heptane giving desired product as an oil, which was precipitated in Acetone to afford 5-[4-(tert-Butyl-diphenyl-silanyloxy)-piperidin-1-yl]-3H-imidazo[4,5-b]pyridine as an orange solid (4.75 g, 10.4 mmol, 40%). MS ESI m/z 457.3 (M+H)$^+$.

Step 4: To a solution of 5-[4-(tert-Butyl-diphenyl-silanyloxy)-piperidin-1-yl]-3H-imidazo[4,5-b]pyridine (4.65 g, 10.2 mmol) in CH$_2$Cl$_2$ (50 mL) was added potassium carbonate (1.60 g, 11.6 mmol, 1.1 eq), succinic anhydride (1.15 g, 11.5 mmol, 1.1 eq) and, N,N,N',N'-tetramethylmethanediamine (1.6 mL, 11.7 mmol, 1.1 eq) and the resulting suspension stirred for 16 hr at 23° C. The reaction was diluted with CH$_2$Cl$_2$ and washed with 20% NaOH (50 mL), water, dried over Na$_2$SO$_4$, and concentrated to afford {5-[4-(tert-Butyl-diphenyl-silanyloxy)-piperidin-1-yl]-imidazo[4,5-b]pyridin-3-ylmethyl}-dimethyl-amine orange oil (5.13 g, 9.89 mmol, 97%). $^1$H NMR (400 MHz, CDCl$_3$) δ: 7.81 (s, 1H), 7.72 (d, J=6.0 Hz), 4H), 7.42 (m, 6H), 6.67 (d, J=8.6 Hz, 1H), 4.99 (s, 2H), 4.01 (sept, 1H), 3.91 (m, 2H), 3.38 (m, 2H), 2.38 (s, 6H), 1.68-1.78 (m, 4H), 1.10 (s, 9H).

Step 5: To a solution of {5-[4-(tert-Butyl-diphenyl-silanyloxy)-piperidin-1-yl]-imidazo[4,5-b]pyridin-3-ylmethyl}-dimethyl-amine (574 mg, 1.12 mmol) and 4-(2-cyano-5-methoxycarbonyl-phenyl)-pyrrolo[2,3-c]pyridine-1-carboxylic acid tert-butyl ester (474 mg, 1.26 mmol, 1.1 eq) (Step 1 example 140) in THF (0.1M), cooled to −78° C., was slowly added 1M LDA (2 mol eq). After 1 hr, the reaction mixture was quenched with 50% acetic acid in water (0.25 vols.) at −78° C. The mixture was allowed to warm to room temperature and concentrated to remove most THF. The residue was diluted with EtOAc (20 mL) and basified with aqueous ammonium hydroxide (30%) until pH>8. The organic layer was washed with brine, dried (MgSO$_4$) and concentrated in vacuo. The residue was then purified by trituration from Acetonitrile affording 4-(5-{5-[4-(tert-Butyl-diphenyl-silanyloxy)-piperidin-1-yl]-3H-imidazo[4,5-b]pyridine-2-carbonyl}-2-cyano-phenyl)-pyrrolo[2,3-c]pyridine-1-carboxylic acid tert-butyl ester as a red solid (900 mg, 1.01 mmol, 90%). MS ESI m/z 802.7 (M+H)$^+$.

Step 6: To a solution of 4-(5-{5-[4-(tert-Butyl-diphenyl-silanyloxy)-piperidin-1-yl]-3H-imidazo[4,5-b]pyridine-2-carbonyl}-2-cyano-phenyl)-pyrrolo[2,3-c]pyridine-1-carboxylic acid tert-butyl ester in THF (0.2M) was added a 1M TBAF in THF solution at 23° C. After 24 hr, the reaction was quenched with sat'd NaHCO$_3$ and extracted with EtOAc (3×), the combined organics washed with brine, dried over Na$_2$SO$_4$, filtered, and concentrated to a red solid. The crude was purified using chromatography eluting with MeOH/DCM mixtures giving 4-{2-Cyano-5-[5-(4-hydroxy-piperidin-1-yl)-3H-imidazo[4,5-b]pyridine-2-carbonyl]-phenyl}-pyrrolo[2,3-c]pyridine-1-carboxylic acid tert-butyl ester as a red-orange solid (420 mg, 0.738 mmol, 66%). MS ESI m/z 564.5 (M+H)$^+$.

Example 198

4-[5-(4-Hydroxy-piperidin-1-yl)-3H-imidazo[4,5-b]pyridine-2-carbonyl]-2-(1H-pyrrolo[2,3-c]pyridin-4-yl)-benzonitrile

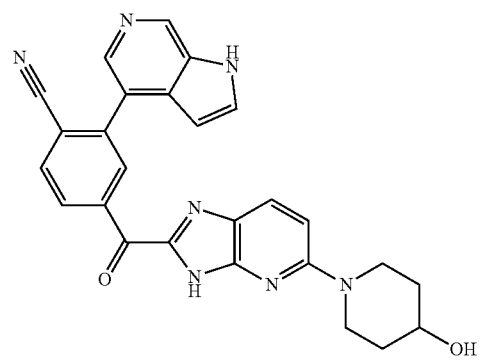 [SMILES: N#Cc1ccc(C(=O)c2nc3ccc(N4CCC(O)CC4)nc3[nH]2)cc1-c1cncc2[nH]ccc12]

The reaction for tert-butyldiphenylsilyl deprotection was performed as in Step 6 of Example A (430 mg, 0.536 mmol) with 1M TBAF in THF (2.1 mL, 4 eq) all in THF (0.05M). After purification, the resulting solid was taken up in DCM and to the solution added 4M HCl in dioxane (2.0 mL, 15 eq) at 23° C. and the solution stirred overnight during which time a precipitate formed on the sides of the flask. The reaction was concentrated under reduced pressure and the resulting solid washed with $CH_2Cl_2$. The solid was taken up in water and basified to pH ~10 using 1M NaOH, the aqueous extracted with 20% $IPA/CH_2Cl_2$ (3×), the combined organics dried ($Na_2SO_4$), filtered, and concentrated to a red solid (90 mg, 0.184 mmol, 34%). MS(ESI) m/z 564.6 (M+H)+. $^1$H NMR (400 MHz, DMSO-$d_6$) δ: 13.5 (br s, 1H), 11.9 (s, 1H), 8.89 (s, 1H), 8.74 (s, 1H), 8.51 (m, 1H), 8.32 (s, 1H), 8.23 (d, J=8 Hz, 1H), 7.95 (m, 1H), 7.78 (m, 1H), 7.02 (d, J=9.6 Hz, 1H), 6.63 (br s, 1H), 4.72 (d, J=4.5 Hz, 1H), 4.11 (m, 2H), 3.75 (m, 1H), 3.29 (m, 2H), 1.80 (m, 2H), 1.40 (m, 2H).

Example 199

(S)-2-Amino-3-methyl-butyric-acid-1-{2-[4-cyano-3-(1H-pyrrolo[2,3-c]pyridin-4-yl)-benzoyl]-3H-imidazo[4,5-b]pyridin-5-yl}-piperidin-4-yl ester

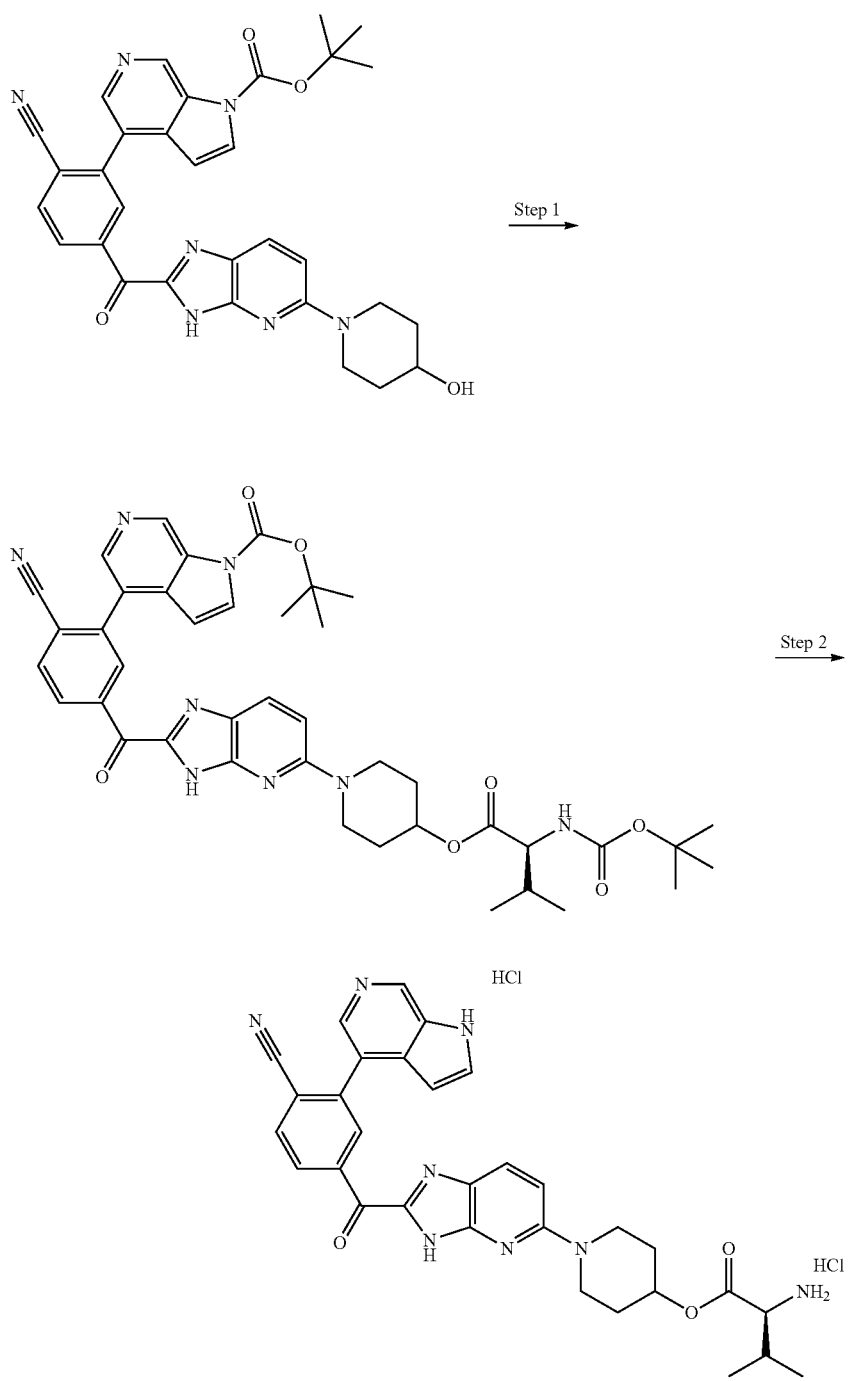

Step 1: Using Example A as starting material (100 mg, 0.177 mmol), 1-ethyl-3-(3-dimethylaminopropyl) carbodiimide (EDCI) (70 mg, 0.365 mmol, 2.0 eq), Boc-L-Valine (155 mg, 0.713, 4.0 eq), and 4-dimethylamino-pyridine (5 mg, 0.041 mmol, 0.2 eq) were added to a reaction vessel in $CH_2Cl_2$ (5 mL) at 23° C. To the reaction was added Hunig's base (0.250 mL, 1.43 mmol, 8.0 eq) and the reaction mixture stirred for 24 hr at 23° C. The reaction was quenched upon the addition of water (5 mL) and partitioned. The organic was washed with 5% KHSO4 followed by ½ sat'd NaHCO3 and water, dried ($Na_2SO_4$) and concentrated to an orange solid. Material was used without further purification (60 mg, 0.079 mmol, 44%). MS(ESI) m/z 763.5 $(M+H)^+$.

Step 2: To a stirring solution of step 1 in $CH_2Cl_2$ (5 mL) was added dropwise 4M HCl in dioxane at 23° C. After 16 hr the reaction was concentrated under reduced pressure giving the desired product as the di-hydrochloride salt. MS(ESI) m/z 563.2 $(M+H)^+$. $^1$H NMR (400 MHz, MeOD) δ: 9.26 (1H, s), 8.92 (s, 1H), 8.84 (d, J=8 Hz, 1H), 8.57 (s, 1H), 8.35 (d, J=2 Hz, 1H), 8.23 (t, J=7.8 Hz, 2H), 7.40 (d, J=9.6 Hz, 1H), 6.95 (d, J=3 Hz, 1H), 5.31 (br s, 1H), 4.05 (m, 2H), 4.00 (d, J=4.6 Hz, 1H), 3.82 (m, 2H), 2.34 (m, 1H), 2.18 (m, 2H), 1.95 (m, 2H), 1.10 (m, 6H).

Example 200

Phosphoric-acid-mono-(1-{2-[4-cyano-3-(1H-pyrrolo[2,3-c]pyridin-4-yl)-benzoyl]-3H-imidazo[4,5-b]pyridin-5-yl}-piperidin-4-yl)ester

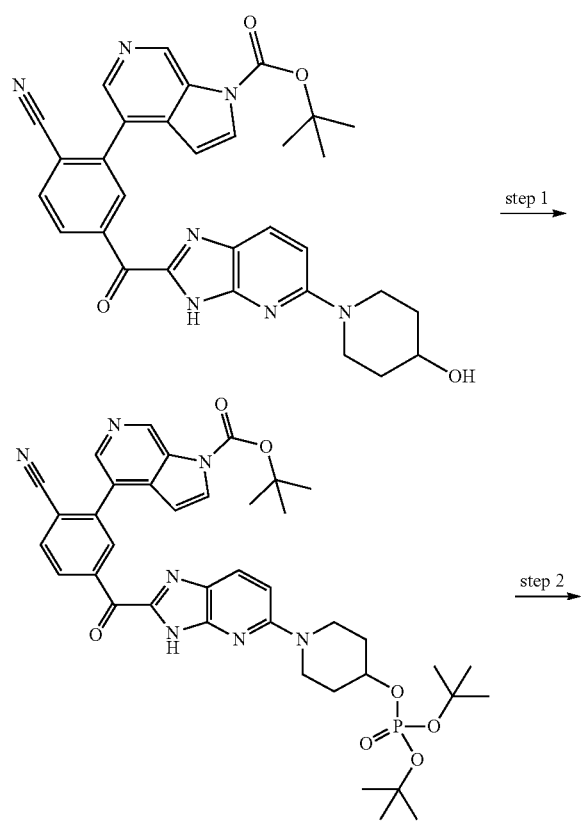

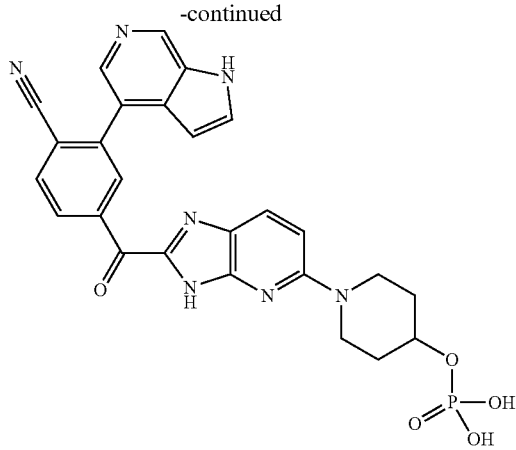

Using Example A as starting material (250 mg, 0.444 mmol) in anhydrous $CH_2Cl_2$ was added in succession, di-tert-butyl-diethylphosphoramidite (0.411 mL, 1.33 mmol, 3.0 eq), and tetrazole (0.45M in Acetonitrile, 2.96 mL, 3.0 eq) at 23° C. After 30 minutes, the reaction was cooled to 0° C. and 30% $H_2O_2$ (0.906 mL, 8.87 mmol, 20 eq) added dropwise. After an additional 45 minutes, the reaction was quenched with sat'd $NaS_2O_3$ (3 mL) at 0° C. and the reaction stirred vigorously for 2 hr. The reaction mixture was diluted with $CH_2Cl_2$ and water, the layers partitioned and separated. The organic was washed with water, brine, dried ($Na_2SO$), filtered, and concentrated. The crude was triturated from Acetonitrile, filtered, then purified by chromatography eluting with MeOH/$CH_2Cl_2$ giving 4-(2-Cyano-5-{5-[4-(di-tert-butoxy-phosphotyloxy)-piperidin-1-yl]-3H-imidazo[4,5-b]pyridine-2-carbonyl}-phenyl)-pyrrolo-[2,3-c]pyridine-1-carboxylic acid tert-butyl ester as an orange solid (194 mg, 0.254 mmol, 58%). HRMS m/z 756.3310 $(M+H)^+$.

Step 2: To a solution of 4-(2-Cyano-5-{5-[4-(di-tert-butoxy-phosphoryloxy)-piperidin-1-yl]-3H-imidazo[4,5-b]pyridine-2-carbonyl}-phenyl)-pyrrolo[2,3-c]pyridine-1-carboxylic acid tert-butyl ester (100 mg, 0.132 mmol) (Step 1) in anhydrous $CH_2Cl_2$ (5 mL) at 0° C. was added 4M HCl in Dioxane (0.331 mL, 1.32 mmol, 10 eq) and the solution warmed to 23° C. and stirred for 16 hr. The resulting suspension was concentrated under reduced pressure to afford Phosphoric-acid-mono-(1-{2-[4-cyano-3-(1H-pyrrolo[2,3-c]pyridin-4-yl)-benzoyl]-3H-imidazo-[4,5-b]pyridin-5-yl}-piperidin-4-yl)ester as a red-orange solid (75 mg, 0.122 mmol, 92%). HRMS m/z 544.1523 $(M+H)^+$. $^1$H NMR (400 MHz, MeOD) δ: 9.24 (1H, s), 8.90 (s, 1H), 8.81 (d, J=8 Hz, 1H), 8.58 (s, 1H), 8.34 (d, J=3 Hz, 1H), 8.23 (d, J=8 Hz, 1H), 8.11 (d, J=9 Hz, 1H), 7.29 (d, J=9.5 Hz, 1H), 6.98 (d, J=2.5 Hz, 1H), 4.63 (m, 1H), 3.98 (m, 2H), 3.77 (m, 2H), 2.08 (m, 2H), 1.94 (m, 2H).

Example 201

4-[5-(4-Dimethylamino-piperidin-1-yl)-3H-imidazo[4,5-b]pyridine-2-carbonyl]-2-(5-methoxy-1H-pyrrolo[2,3-c]pyridin-4-yl)-benzonitrile Synthetic Scheme:

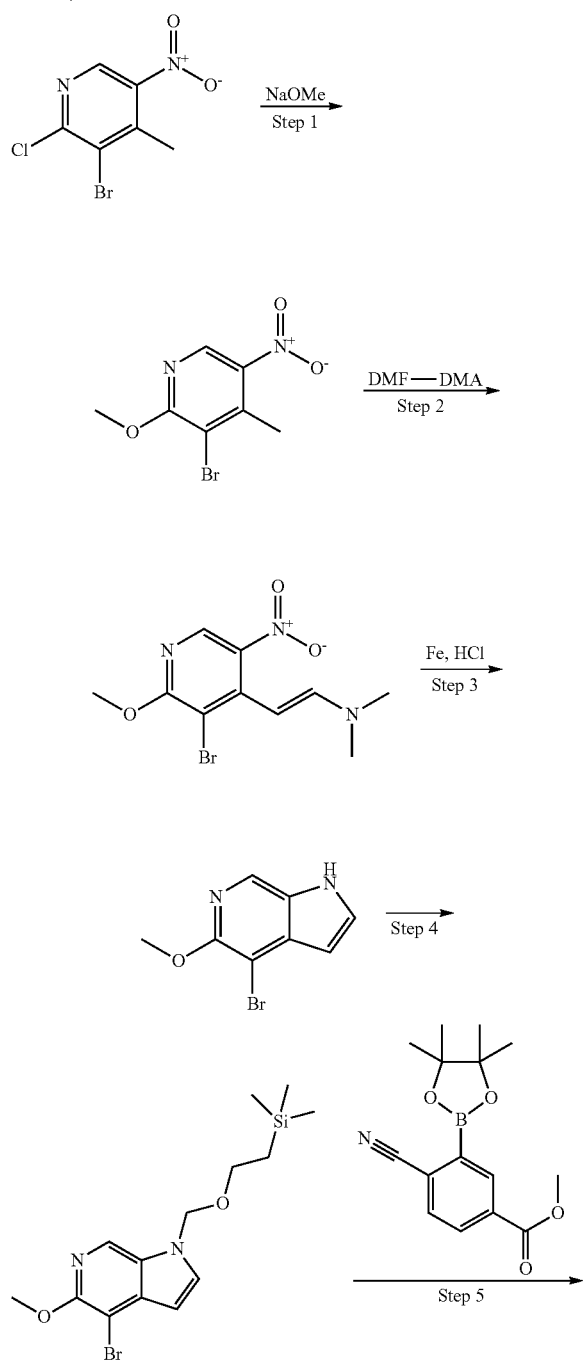

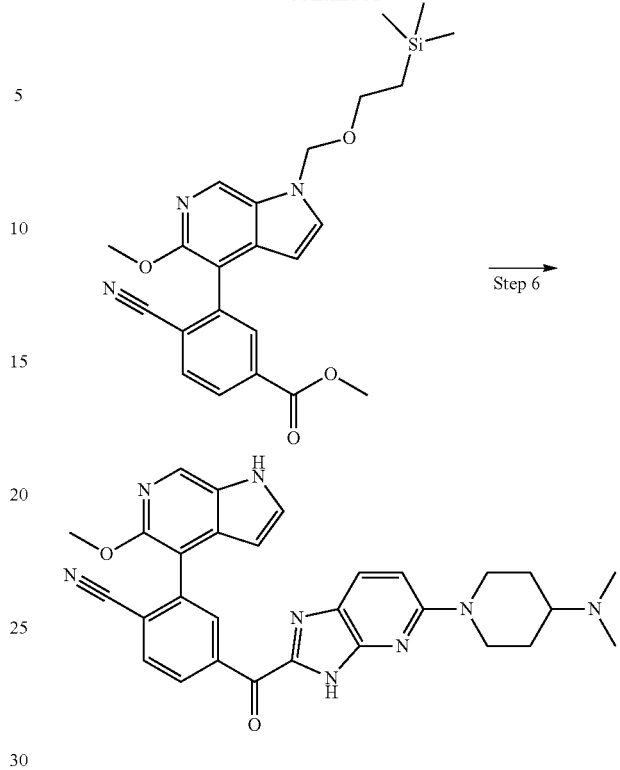

Step 1: To a solution of 3-Bromo-2-chloro-4-methyl-5-nitro-pyridine (5.00 g, 19.9 mmol) in anyhdrous Methanol was added a 25% methanolic NaOMe solution (10.7 mL, 2.5 eq). The reaction was stirred at room temperature for 24 hr. The solvent was removed under reduced pressure giving a solid. Water (100 mL) was added to the flask and the flask sonicated for 5 minutes. The precipitate was filtered and washed with water (50 mL) giving a beige powder. The aqueous mother liquor was extracted with EtOAc (1×), the organic washed with brine, and dried. The two solids were combined giving 3-Bromo-2-methoxy-4-methyl-5-nitro-pyridine (2.75 g, 10.6 mmol, 53%). $^1$H NMR (400 MHz, CDCl$_3$) δ 8.75 (s, 1H), 4.12 (s, 3H), 2.72 (s, 3H).

Step 2: To a solution of 3-Bromo-2-methoxy-4-methyl-5-nitro-pyridine (3.00 g, 12.1 mmol) in DMF (0.6M) was added via syringe N,N-dimethylformamide-dimethylacetal (3.0 mL, 22.4 mmol, 1.8 eq) in a fast dropwise manner. The solution was heated for 2 hr at 90° C., cooled to 23° C., then diluted with Ethyl Acetate (200 mL). The washed reaction mixture was washed with water, brine, dried (Na$_2$SO$_4$), and concentrated giving [(E)-2-(3-Bromo-2-methoxy-5-nitropyridin-4-yl)-vinyl]-dimethyl-amine as a red solid which was used without further purification (3.45 g, 10.9 mmol, 89%). MS ESI m/z 304.2 (M+2H)$^+$. $^1$NMR (400 MHz, CDCl$_3$) δ 8.36 (s, 1H), 7.03 (d, J=13.5 Hz, 1H), 5.30 (d, J=13.5 Hz, 1H), 4.05 (s, 3H), 2.97 (s, 3H).

Step 3: In A suspension of Iron powder (1.62 g, 28.9 mmol, 5.5 eq), [(E)-2-(3-Bromo-2-methoxy-5-nitro-pyridin-4-yl)-vinyl]-dimethyl-amine (1.59 g, 5.27 mmol), and EtOH (0.05M) were stirred while heating to 90° C. To the suspension was added dropwise concentrated HCl (1.6 mL) and the suspension refluxed (100° C.) for 2 hr. The reaction was cooled and neutralized by pouring reaction mixture into 200 mL of 1N NaOH and stirring. The resulting mixture was extracted with EtOAc (3×100 mL), the combined organics washed with brine and concentrated to a beige powder. The crude solid was further purified using chromatography eluting with EtOAc/Heptane giving 4-Bromo-5-methoxy-1H-pyrrolo[2,3-c]pyridine as a beige solid (0.980 g, 4.10 mmol, 78%). MS ESI m/z 229.2 (M+2H)⁺. ¹NMR (400 MHz, CDCl₃) δ 8.55 (br s, 1H), 8.36 (s, 1H), 7.47 (m, 1H), 6.60 (m, 1H), 4.12 (s, 3H).

Step 4: To a suspension of NaH (0.238 g, 5.95 mmol, 1.3 eq, 60%) in THF at 0° C. was added a solution of 4-Bromo-5-methoxy-1H-pyrrolo[2,3-c]pyridine (1.05 g, 4.62 mmol) in THF and the solution stirred until no effervescence was observed (approx. 5 minutes). To the reaction mixture was added (2-Chloromethoxy-ethyl)-trimethyl-silane (1.00 mL, 5.64 mmol, 1.2 eq) and the solution was warmed to 23° C. and stirred for 16 hr. The reaction was quenched using sat'd NaHCO3 (aq) and most of the THF removed under reduced pressure. The aqueous layer was partitioned between EtOAc (100 mL), the organic layer washed with water, brine, dried, and concentrated. The crude reaction was purified using chromatography eluting with 20% EtOAc/Heptane giving 4-Bromo-5-methoxy-1-(2-trimethylsilanyl-ethoxymethyl)-1H-pyrrolo[2,3-c]pyridine beige crystalline product (0.950 g, 2.53 mmol, 55%). MS ESI m/z 359.2 (M+2H)⁺. ¹NMR (400 MHz, CDCl₃) δ 8.46 (d, J=0.6 Hz 1H), 8.36 (s, 1H), 7.39 (d, J=3.2 Hz, 1H), 6.54 (dd, J=3.2 Hz, 0.6 Hz, 1H), 5.51 (s, 2H), 4.14 (s, 3H), 3.51 (m, 2H), 0.94 (m, 2H), 0.00 (s, 9H).

Step 5: A mixture of 4-Bromo-5-methoxy-1-(2-trimethyl-silanyl-ethoxymethyl)-1H-pyrrolo[2,3-c]pyridine (0.940 g, 2.63 mmol), 4-Cyano-3-(4,4,5,5-tetramethyl-[1,3,2]dioxaborolan-2-yl)-benzoic acid methyl ester (Example 140 Step 1 starting material) (0.840 g, 2.93 mmol, 1.1 eq), Bis(di-tertbutyl-(4-dimethylaminophenyl)-phosphine)-di-chloropalladium (II) (0.046 g, 0.066 mmol, 2 mol %), and tribasic potassium phosphate (1.12 g, 5.26 mmol, 2 eq) in a 10:1 mixture of dioxane and water was heated to 80° C. for 2.5 hr. The reaction was cooled to 23° C., the contents decanted into a separatory funnel and the residue in the vial was washed with copious amounts of ethyl acetate. The organic was washed with water, brine, dried (Na₂SO₄), and concentrated. The crude mixture was further purified by chromatography eluting with 30% EtOAc/Heptane giving 4-Cyano-3-[5-methoxy-1-(2-trimethylsilanyl-ethoxymethyl)-1H-pyrrolo[2,3-c]pyridin-4-yl]-benzoic acid methyl ester as a yellow amorphous solid (0.790 g, 1.81 mmol, 69%). MS ESI m/z 438.4 (M+H)⁺. ¹NMR (400 MHz, CDCl₃) δ 8.59 (s, 1H), 8.27 (d, J=1.6 Hz, 1H), 8.12 (dd, J=8.0 Hz, 1.6 Hz, 1H), 7.90 (d, J=8.0 Hz, 1H), 7.33 (d, J=3.2 Hz, 1H), 6.20 (d, J=3.2 Hz, 1H), 5.54 (d, J=5.0 Hz, 2H), 4.04 (s, 3H), 3.98 (s, 3H), 3.55 (m, 2H), 0.95 (m, 2H), 0.00 (s, 9H).

Step 6: To a −78° C. solution of 4-Cyano-3-[5-methoxy-1-(2-trimethylsilanyl-ethoxymethyl)-1H-pyrrolo[2,3-c]pyridin-4-yl]-benzoic acid methyl ester (125 mg, 0.285 mmol, 1.05 eq) and give [1-(3-dimethylaminomethyl-3H-imidazo[4,5-b]pyridin-5-yl)-piperidin-4-yl]-dimethyl-amine (Step 2 product from Example 140) (82 mg, 0.271 mmol) in THF (0.05M) was added 1M Lithium Diisopropylamide in THF (2 mol eq) dropwise. The reaction mixture was stirred at −78° C. for 1 hr, then quenched with 50% aqueous Acetic acid at −78° C. and the solution warmed to 23° C. The reaction mixture was diluted with EtOAc and neutralized with 30% NH₄OH until approximately pH 9. The biphasic layer was separated and the organic washed with brine, dried (Na₂SO₄), and concentrated. The crude mixture was purified by trituration with ACN giving 4-[5-(4-Dimethylamino-piperidin-1-yl)-3H-imidazo[4,5-b]pyridine-2-carbonyl]-2-[5-methoxy-1-(2-trimethylsilanyl-ethoxymethyl)-1H-pyrrolo[2,3-c]pyridin-4-yl]-benzonitrile as a yellow solid. This material was taken up in anhydrous CH₂Cl₂ (0.03M) and 4M HCl in dioxane (0.250 mL, 10 eq) added dropwise. After 48 hr, the solvent was removed and the dark solid taken up in water and neutralized with sat'd NaHCO₃, resulting in a red precipitate. The precipitate was extracted with CH₂Cl₂, the organic layer dried (Na₂SO₄), and concentrated giving 4-[5-(4-Dimethylamino-piperidin-1-yl)-3H-imidazo[4,5-b]pyridine-2-carbonyl]-2-(5-methoxy-1H-pyrrolo[2,3-c]pyridin-4-yl)-benzonitrile as a red solid (20 mg, 0.038 mmol, 39%). MS ESI m/z 551.4 (M+H)⁺. ¹NMR (400 MHz, CDCl₃) δ 13.6 (br s, 1H), 8.68 (s, 1H), 8.59 (s, 1H), 8.48 (d, J=8.0 Hz, 1H), 8.18 (d, J=8.0 Hz, 1H), 7.94 (br s, 1H), 7.73 (d, J=2.5 Hz, 1H), 7.02 (d, J=9.0 Hz, 1H), 6.69 (t, J=7.3 Hz, 1H), 6.31 (d, J=2.5 Hz, 1H), 5.62 (d, J=7.0 Hz, 2H), 4.43 (d, J=13 Hz, 2H), 3.91 (s, 3H), 2.94 (m, 2H), 2.33 (m, 1H), 1.83 (d, J=11.0 Hz, 2H), 1.37 (m, 2H).

Example 202

4-[5-(Pyrrolidin-3-yloxy)-3H-imidazo[4,5-b]pyridine-2-carbonyl]-2-(1H-pyrrolo[2,3-c]pyridin-4-yl)-benzonitrile

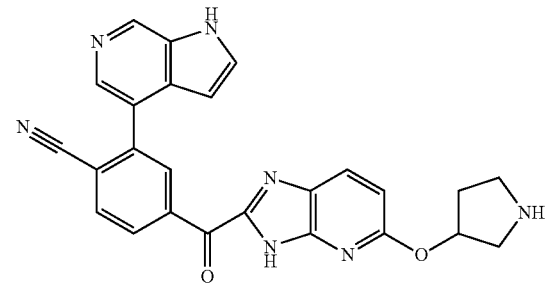 [SMILES: N#Cc1ccc(C(=O)c2nc3ccc(OC4CCNC4)nc3[nH]2)cc1-c1cncc2[nH]ccc12]

The title compound was made by methods as described above or methods analogous thereo.

HRMS (m/z): calculated 450.1678, observed 450.1684.

Example 203

4-[5-(1-Methyl-piperidin-4-yloxy)-3H-imidazo[4,5-b]pyridine-2-carbonyl]-2-(1,3,5-trimethyl-1H-pyrazol-4-yl)-benzonitrile

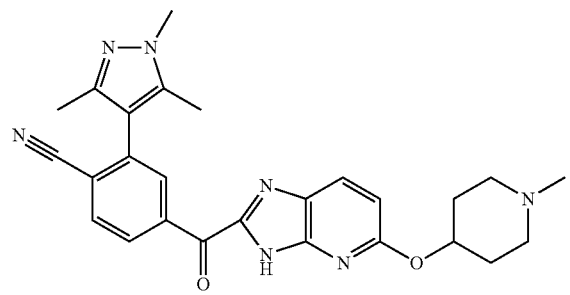 [SMILES: Cc1nn(C)c(C)c1-c1cc(C(=O)c2nc3ccc(OC4CCN(C)CC4)nc3[nH]2)ccc1C#N]

The title compound was made by methods as described above or methods analogous thereto.
HRMS (m/z): calculated 470.2304, observed 470.2320.

Example 204

4-{5-[2-(4-Methyl-piperazin-1-yl)-ethoxy]-3H-imidazo[4,5-b]pyridine-2-carbonyl}-2-(1,3,5-trimethyl-1H-pyrazol-4-yl)-benzonitrile

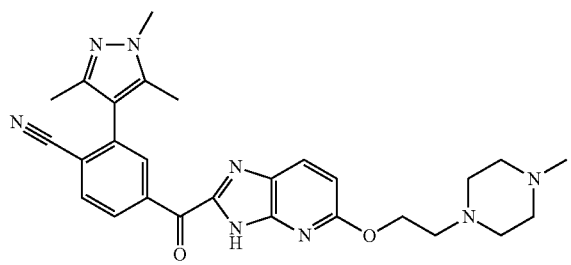 [SMILES: Cc1nn(C)c(C)c1-c1cc(C(=O)c2nc3ccc(OCCN4CCN(C)CC4)nc3[nH]2)ccc1C#N]

The title compound was made by methods as described above or methods analogous thereto.
HRMS (m/z): calculated 499.2570, observed 499.2585.

Example 205

4-[5-(5,6-Dihydro-8H-imidazo[1,2-a]pyrazin-7-yl)-3H-imidazo[4,5-b]pyridine-2-carbonyl]-2-(1,3,5-trimethyl-1H-pyrazol-4-yl)-benzonitrile

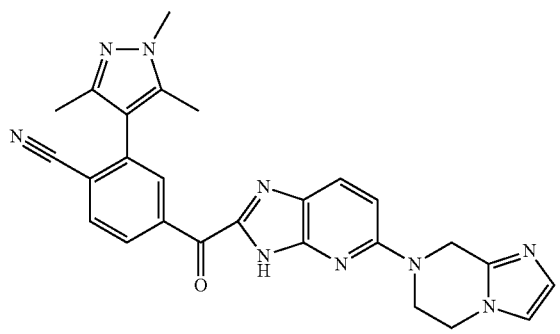 [SMILES: Cc1nn(C)c(C)c1-c1cc(C(=O)c2nc3ccc(N4CCn5ccnc5C4)nc3[nH]2)ccc1C#N]

The title compound was made by methods as described above or methods analogous thereto.
HRMS (m/z): calculated 478.2104, observed 478.2107.

Example 206

4-[5-(3,6-Diaza-bicyclo[3.2.0]hept-3-yl)-3H-imidazo[4,5-b]pyridine-2-carbonyl]-2-(1,3,5-trimethyl-1H-pyrazol-4-yl)-benzonitrile

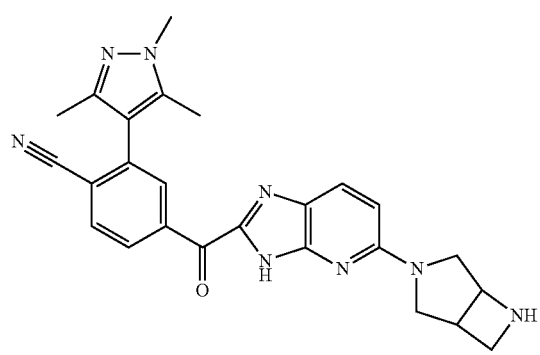 [SMILES: Cc1nn(C)c(C)c1-c1cc(C(=O)c2nc3ccc(N4CC5CNC5C4)nc3[nH]2)ccc1C#N]

The title compound was made by methods as described above or methods analogous thereto.
HRMS (m/z): calculated 453.2151, observed 453.2164.

Example 207

4-[5-(2,6-Diaza-spiro[3.3]hept-2-yl)-3H-imidazo[4,5-b]pyridine-2-carbonyl]-2-(1,3,5-trimethyl-1H-pyrazol-4-yl)-benzonitrile

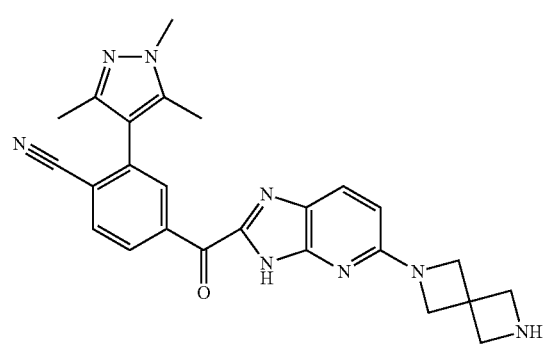 [SMILES: Cc1nn(C)c(C)c1-c1cc(C(=O)c2nc3ccc(N4CC5(CNC5)C4)nc3[nH]2)ccc1C#N]

The title compound was made by methods as described above or methods analogous thereto.
HRMS (m/z): calculated 453.2151, observed 453.2137.

Example 208

4-[5-(2,6-Diaza-spiro[3.3]hept-2-yl)-3H-imidazo[4,5-b]pyridine-2-carbonyl]-2-(1H-pyrrolo[2,3-c]pyridin-4-yl)-benzonitrile

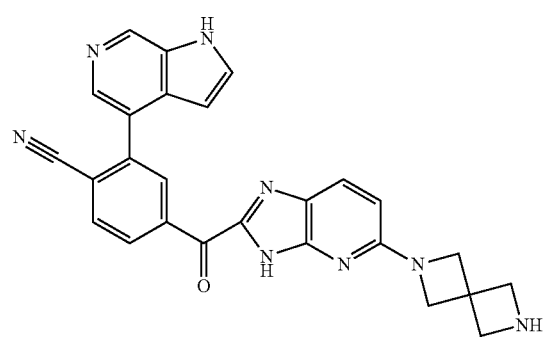 [SMILES: N#Cc1ccc(C(=O)c2nc3ccc(N4CC5(CNC5)C4)nc3[nH]2)cc1-c1cncc2[nH]ccc12]

The title compound was made by methods as described above or methods analogous thereto.

HRMS (m/z): calculated 461.1838, observed 461.1852.

Example 209

4-[5-(3,3-Dimethyl-2-oxo-piperazin-1-yl)-3H-imidazo[4,5-b]pyridine-2-carbonyl]-2-(1,3,5-trimethyl-1H-pyrazol-4-yl)-benzonitrile

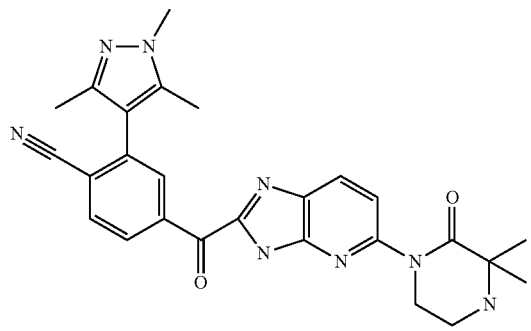 [SMILES: Cc1nn(C)c(C)c1-c1cc(C(=O)c2nc3ccc(N4CCNC(C)(C)C4=O)nc3[nH]2)ccc1C#N]

The title compound was made by methods as described above or methods analogous thereo.

Example 210

4-[5-(Pyrrolidin-3-ylamino)-3H-imidazo[4,5-b]pyridine-2-carbonyl]-2-(1,3,5-trimethyl-1H-pyrazol-4-yl)-benzonitrile

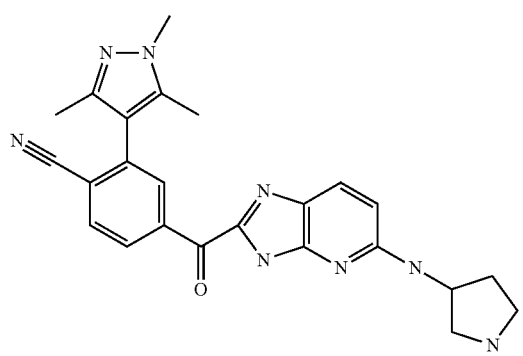 [SMILES: Cc1nn(C)c(C)c1-c1cc(C(=O)c2nc3ccc(NC4CCNC4)nc3[nH]2)ccc1C#N]

The title compound was made by methods as described above or methods analogous thereo.

Example 211

4-[5-(3-Amino-pyrrolidin-1-yl)-3H-imidazo[4,5-b]pyridine-2-carbonyl]-2-(1,3,5-trimethyl-1H-pyrazol-4-yl)-benzonitrile

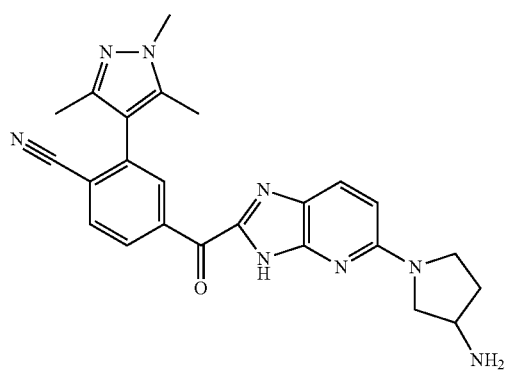 [SMILES: Cc1nn(C)c(C)c1-c1cc(C(=O)c2nc3ccc(N4CCC(N)C4)nc3[nH]2)ccc1C#N]

The title compound was made by methods as described above or methods analogous thereo.

Example 212

4-[5-(6-Amino-3-aza-bicyclo[3.1.0]hex-3-yl)-3H-imidazo[4,5-b]pyridine-2-carbonyl]-2-(1,3,5-trimethyl-1H-pyrazol-4-yl)-benzonitrile

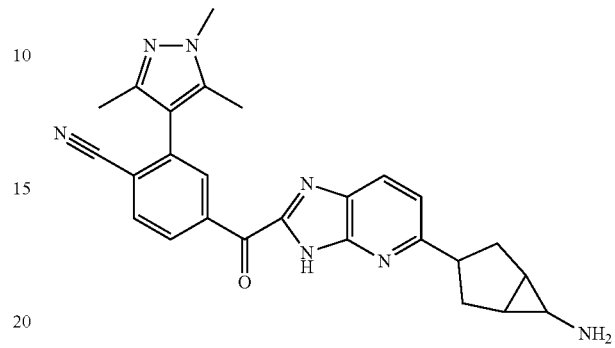

The title compound was made by methods as described above or methods analogous thereo.

Example 213

6-[5-(4-Dimethylamino-piperidin-1-yl)-3H-imidazo[4,5-b]pyridine-2-carbonyl]-2-(1,3,5-trimethyl-1H-pyrazol-4-yl)-nicotinonitrile

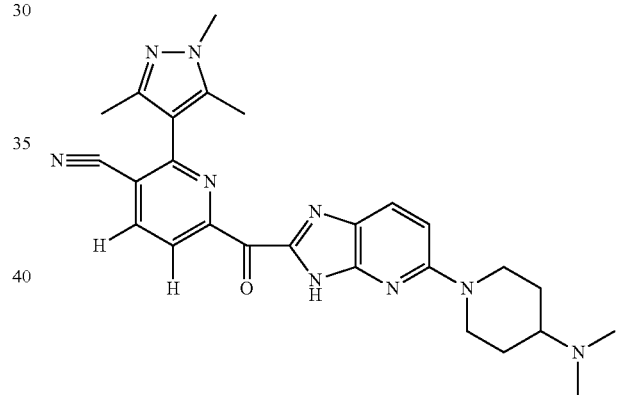

Step 1: Preparation of 6-chloro-5-cyano-pyridine-2-carboxylic acid methyl ester

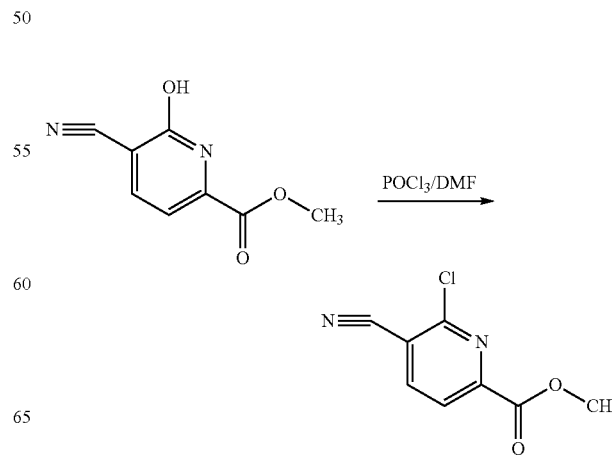

5-Cyano-6-hydroxy-pyridine-2-carboxylic acid methyl ester is treated with phosphorus oxychloride in dimethylformamide in accordance with known methods to give 6-chloro-5-cyano-pyridine-2-carboxylic acid methyl ester.

For a reference to methods that may be used to prepare the starting material, see Yonezawa, Yasuchika; Konn, Akihito; Shin, Chung-gi. Useful synthesis of 2,3,6-tri- and 2,3,5,6-tetrasubstituted pyridine derivatives from aspartic acid. Heterocycles (2004), 63(12), 2735-2746.

Step 2: Preparation of 5-cyano-6-(1,3,5-trimethyl-1H-pyrazol-4-yl)-pyridine-2-carboxylic acid methyl ester

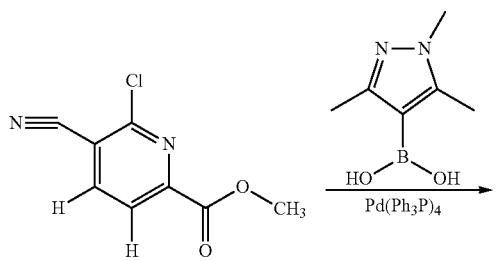

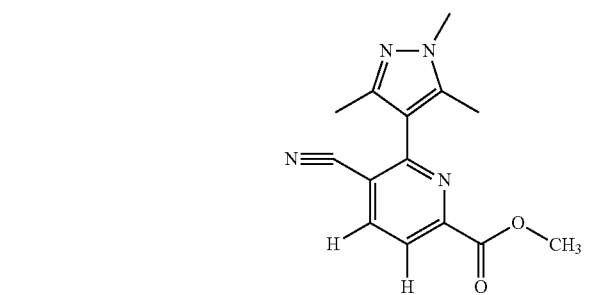

The title compound may be prepared from 6-chloro-5-cyano-pyridine-2-carboxylic acid methyl ester by reaction with 1,3,5-trimethylpyrazol-4-ylboronic acid under Suzuki reaction conditions as described in the previous examples.

Step 3: 6-[5-(4-Dimethylamino-piperidin-1-yl)-3H-imidazo[4,5-b]pyridine-2-carbonyl]-2-(1,3,5-trimethyl-1H-pyrazol-4-yl)-nicotinonitrile

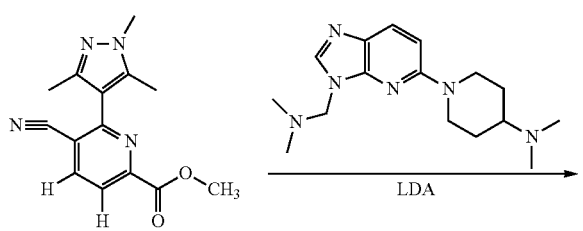

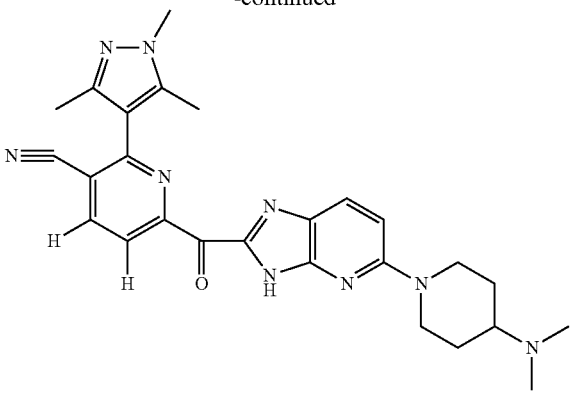

The title compound may be prepared by the reaction of 5-cyano-6-(1,3,5-trimethyl-1H-pyrazol-4-yl)-pyridine-2-carboxylic acid methyl ester with lithium diisopropylamide followed by [1-(3-dimethyl-aminomethyl-3H-imidazo[4,5-b]pyridin-5-yl)-piperidin-4-yl]-dimethyl-amine under the reaction conditions described in the previous examples.

Example 214

CDK4/cyclin D1 Enzymatic Activity Assay

Protocol A

A 384-well microtiter Lance TR-FRET (time-resolved-fluorescence energy transfer) endpoint assay was used for CDK4/cyclin D1 kinase activity measurements. The same assay was used for $IC_{50}$ determination of small molecule inhibitors. In general, the kinase reactions were carried out in 30 µL volumes in the reaction solution containing the following: 2 µL compound (in 20% DMSO), 18 uL CDK4/cyclin D1 in Assay Buffer (50 mM HEPES, pH 7.5, 5 mM $MgCl_2$, 2 mM $MnCl_2$, 1 mM DTT, 0.05% BSA, 0.02% Tween-20), 10 µL of the mixture of pRb152 and ATP. The final reaction mixture contains compound (inhibitor) with the concentration varying from 0.005-10 M, 2% DMSO, 0.3 nM CDK4/cyclin D1, 175 nM pRb152, and 3 µM ATP (Amersham Pharmacia, Cat. No. 27-2056-01). All reactions were run at room temperature in 384-well white flat-bottom OptiPlates (Perkin Elmer, Cat. No. 6007290) for 60 min then were quenched by the addition of 10 µL of 120 mM EDTA. The signals were captured by the addition of 40 µL of the Detection Solution containing the following: Detection Buffer (50 mM HEPES, pH 7.5, 30 mM EDTA, 0.1% Triton x-100, 0.05% BSA), 70 ng/mL anti-phospho-pRb(S780) (Cell Signaling Technology, Cat. No. 9307S), 1 nM Lance Eu-W1024-Rabbit anti-IgG (Perkin Elmer, Cat. No. AD0082), and 20 nM SureLight™ Allophycocyanin-Streptavidin (Perkin Elmer, Cat. No. CR130-100). The resulted solutions were incubated at room temperature for 2 hours before read on the Evision Multilabel Reader (Perkin Elmer, Envision 2102-0010). Note: $IC_{50}$<0.005 nM or $IC_{50}$>10 µM indicates the true $IC_{50}$ is out of detection range.

CDK4/cyclin D1 recombinant protein used in the enzymatic activity assay was prepared by coexpressing pDEST10-CDK4 (N-terminal $His_6$) and pFastBacDual-GST-hCyclinD1 viruses in Sf21 cells. The overexpressed protein was purified by Ni-NTA affinity pull down to >80% pure by Sizing HPLC.

The compounds of Examples 49, 50, 66, 73, 79A, 79B, 80-84, 86-90, 92-95, 98, 99, 101, 103, 105-115, 119, 120, 122-126, 129, 133, 135, 137-140, 144-146, 148-152, 155-

157, 159, 160, 163-174, 176-189, 207, 209 and 210-212 were found to have $IC_{50}$ values of less than 10 μM against CDK4 in the above assay.

Specific $IC_{50}$ values against CDK4 kinase for representative compounds of formula (I) are set out in the table below.

| Example | $IC_{50}$ (μM) |
|---------|----------------|
| 84 | 0.057 |
| 86 | 0.027 |
| 89 | 0.004 |
| 98 | 0.033 |
| 99 | 0.026 |
| 103 | 0.06 |
| 140 | 0.004 |
| 148 | 0.067 |
| 135 | 0.012 |
| 163 | 0.014 |
| 164 | 0.024 |
| 165 | 0.003 |
| 166 | 0.008 |
| 167 | 0.195 |
| 169 | 0.260 |
| 170 | 0.548 |
| 173 | 0.012 |
| 174 | 0.005 |
| 182 | 0.077 |
| 189 | 0.095 |

Example 215

Measurement of CDK2, 4 and 6 Enzyme Activity

Protocol B

CDK enzyme activity may be measured using an ELISA format. Briefly plates are coated with GST-pRb$^{769-92}$ (prepared in-house), washed with TBST (100 mM Tris pH7.5, 150 mM NaCl, 0.5% Tween-20) and blocked with Superblock (Perbio Science, Northumberland). Assay buffer (final concentrations:15 mM $MgCl_2$, 50 mM HEPES, pH 7.4, 1 mM DTT, 1 mM EGTA, pH 8.0, 0.02% Triton X-100 and 2.5% DMSO) and enzyme (CDK4-cyclin D1 or CDK2-cyclin D1 or CDK6) are added to each well and the reaction initiated with the addition of ATP. Plates are then washed with TBST and incubated for one hour with the primary antibody (CDK4 and CDK6: anti-p-Rb Serine 780, New England Biolab, Hitchin, UK. CDK2: p-Rb Theronine 821, Biosource, Paisley, Scotland) diluted in Superblock. Excess antibody is washed off and plates are then incubated with secondary antibody (alkaline phosphatase linked anti-rabbit (New England Biolab, Hitchin, UK) for a further hour. After removal of excess secondary antibody, plates are developed using the Attophos system (Promega, Southampton, UK) and the fluorescence read on a Spectramax Gemini plate reader (Molecular Devices) at excitation 450 nm and emission 580 nm. $IC_{50}$ values (the concentration of test compound required to inhibit 50% of the CDK activity) can be determined using a sigmoidal dose response equation from Prism Graph Pad Software.

Example 216

Measurement of CDK1 Enzyme Activity

Protocol C

CDK1/CyclinB (Upstate Discovery) activity may be determined using a radiometric assay to measure the incorporation of γ-phosphate from $γ^{33}P$-ATP into histone H1. Assay reactions containing 20 mM MOPS pH7.2, 25 mM β-glycerophosphate, 5 mM EDTA, 15 mM $MgCl_2$, 45 μM $γ^{33}P$-ATP (0.78 Ci/mmol), 0.1 mg/ml BSA, 1 mM sodium orthovanadate, 1 mM DTT, 0.12 μg/ml histone H1 and CDK1/cyclinB are set up in the presence of compound and allowed to proceed for 2 hours. Reactions are stopped by adding excess phosphoric acid and phosphorylated histone H1 is then separated from excess ATP on a Millipore MAPH filter plate. After washing, scintillant is added and plates counted on a Packard Topcount. $IC_{50}$ values calculated as described previously.

Example 217

Anti-Proliferative Activity

The anti-proliferative activities of compounds of the invention may be determined by measuring the ability of the compounds to inhibition of cell growth in a number of cell lines. Inhibition of cell growth is measured using the Alamar Blue assay (Nociari, M. M, Shalev, A., Benias, P., Russo, C. *Journal of Immunological Methods* 1998, 213, 157-167). The method is based on the ability of viable cells to reduce resazurin to its fluorescent product resorufin. For each proliferation assay cells are plated onto 96 well plates and allowed to recover for 16 hours prior to the addition of inhibitor compounds for a further 72 hours. At the end of the incubation period 10% (v/v) Alamar Blue is added and incubated for a further 6 hours prior to determination of fluorescent product at 535 nM ex/590 nM em. In the case of the non-proliferating cell assay cells are maintained at confluence for 96 hour prior to the addition of inhibitor compounds for a further 72 hours. The number of viable cells is determined by Alamar Blue assay as before. Cell lines can be obtained from the ECACC (European Collection of cell Cultures).

Example 218

JEKO-1 Cell Assay Protocol

This assay monitors phosphorylation of Rb at Ser780 in JEKO-1 cells after treatment with a test compound. This is performed using Capture ELISA, with Rb4H1 (Cell Signaling #9309) as capture Antibody and pRb Ser780 (Cell Signaling #9307) as primary Ab.

Jeko-1 cells are plated in 96 well plates (Corning #3598) at a density of 40,000 cells/well in RPMI media (Gibco #11875-093), 20% Fetal Bovine Serum (Gibco #1600-044), 2 mM L-Glutamine (Gibco #15140-122), 1% Penicillin/Streptomycin (Gibco #15140-122). The cells incubate overnight at 37° C., 5% $CO_2$. Cells are 60% confluent at treatment.

50 ng capture Antibody per well (Rb (4H1) Mouse mAb (Cell Signaling #9309); Lots 4 and 5 are at concentration of 1 mg/ml) is obtained by diluting 4H1 Ab to 1 ug/mL in DPBS (Gibco #14190-144). 50 uL/well is added to MaxiSorp 96 (Nunc#442404) well plate and coated overnight at 4° C. using shaker. Antibody is removed by flicking plate. The plate is washed with 200 uL TBST (Teknova #9501). 250 uL/well Superblock (in TBS) (Pierce #37535) is added and incubated for at least one hour at room temperature in shaker, changing Superblock once after 10 mins or incubated overnight to several days at 4° C.

Dilution plates are created by adding 100 μl of test compound (10 mM in DMSO) to Row A, and 75 μl DMSO to rows B-H, then serially diluted (e.g. 25 μl of row A to row B, 25 μl of row B to row C and so on) as outlined below.

| Dilution Plate | | | | | | | | | | | |
|---|---|---|---|---|---|---|---|---|---|---|---|
| 1 Cmpd A | 2 Cmpd B | 3 Cmpd C | 4 Cmpd D | 5 Cmpd E | 6 Cmpd F | 7 Cmpd G | 8 Cmpd H | 9 | 10 | 11 | 12 |
| A | 10 mM | 10 mM | 10 mM | 10 mM | 10 mM | 10 mM | 10 mM | 10 mM | | | |
| B | 2.5 | 2.5 | 2.5 | 2.5 | 2.5 | 2.5 | 2.5 | 2.5 | | | |
| C | 0.625 | 0.625 | 0.625 | 0.625 | 0.625 | 0.625 | 0.625 | 0.625 | | | |
| D | 0.156 | 0.156 | 0.156 | 0.156 | 0.156 | 0.156 | 0.156 | 0.156 | | | |
| E | 0.039 | 0.039 | 0.039 | 0.039 | 0.039 | 0.039 | 0.039 | 0.039 | | | |
| F | 0.010 | 0.010 | 0.010 | 0.010 | 0.010 | 0.010 | 0.010 | 0.010 | | | |
| G | 0.002 | 0.002 | 0.002 | 0.002 | 0.002 | 0.002 | 0.002 | 0.002 | | | |
| H | DMSO | DMSO | DMSO | DMSO | DMSO | DMSO | DMSO | DMSO | | | |

198 µl of media is added to each well 1-8 rows A-H, then 2 µl of stock compound added to the 198 µl of media (1 in 100 dilution). 10 µl of diluted compound is added to triplicate wells of the cell plate and incubated for 24 hrs.

| Cell Plate | | | | | | | | | | | |
|---|---|---|---|---|---|---|---|---|---|---|---|
| 1 Cmpd A | 2 Cmpd A | 3 Cmpd A | 4 Cmpd B | 5 Cmpd B | 6 Cmpd B | 7 Cmpd C | 8 Cmpd C | 9 Cmpd C | 10 Cmpd D | 11 Cmpd D | 12 Cmpd D |
| A | 10 uM | 10 uM | 10 uM | 10 uM | 10 uM | 10 uM | 10 uM | 10 uM | 10 uM | 10 uM | 10 uM | 10 uM |
| B | 2.5 | 2.5 | 2.5 | 2.5 | 2.5 | 2.5 | 2.5 | 2.5 | 2.5 | 2.5 | 2.5 | 2.5 |
| C | 0.63 | 0.63 | 0.63 | 0.63 | 0.63 | 0.63 | 0.63 | 0.63 | 0.63 | 0.63 | 0.63 | 0.63 |
| D | 0.16 | 0.16 | 0.16 | 0.16 | 0.16 | 0.16 | 0.16 | 0.16 | 0.16 | 0.16 | 0.16 | 0.16 |
| E | .04 | .04 | .04 | .04 | .04 | .04 | .04 | .04 | .04 | .04 | .04 | .04 |
| F | 0.01 | 0.01 | 0.01 | 0.01 | 0.01 | 0.01 | 0.01 | 0.01 | 0.01 | 0.01 | 0.01 | 0.01 |
| G | 0.002 | 0.002 | 0.002 | 0.002 | 0.002 | 0.002 | 0.002 | 0.002 | 0.002 | 0.002 | 0.002 | 0.002 |
| H | DM | DM | DM | DM | DM | DM | DM | DM | DM | DM | DM | DM |

In the table, DM refers to dimethylsulphoxide (DMSO)

Cells and supernatant are transferred to a Poly-lysine coated plate the following morning and allowed to adhere for 30 minutes to an hour before aspirating the supernatant and lysing them. Cells are lysed by adding 50 ul lysis buffer on ice (4 mL ice cold Doriano lysis buffer [25 ml 1M Tris pH 7.2; 12 ml 5M NaCl, 1 ml 0.5M EDTA, 6 ml 0.5M EGTA, 5 ml NP40 to 500 ml dH$_2$O], 400 uL 10× stock Protease inhibitor [dissolve one Roche Complete, Mini EDTA free Cat#11-836-170-001, Mini tablet in 1 mL Doriano lysis buffer] and 40 uL 100× stock phosphatase inhibitor cocktail [Calbiochem Phosphatase Inhibitor Cocktail Set II Cat#524625]. The cells are incubated in cold room at 4° C. for 5 min on rotating platform and then spun down at 1000 rpm for 5 minutes. Lysate is used immediately or frozen for future use. To 15 uL of cell lysate per well is added 35 uL of PBS/10% Superblock per well for 50 uL final volume. Allowed to bind for 2 hrs at room temperature on rotator (or o/n at 4° C.) and then washed 4× with 250 uL/well TBST.

50 uL/well pRb Ser780 (Cell Signaling #9307) at 1:1000 in PBS/10% Superblock is added and then incubated for 1 hr at room temperature on rotator. Then washed 4× with 250 uL/well TBST.

50 uL/well Goat-Anti-Rabbit-HRP (Promega Cat#W401B) at 1:2500 in PBS/10% Superblock is then added and incubated for 30 min at RT on rotator. Then wash 4×250 uL/well TBST.

Detection is performed by adding 50 uL/well Ultra TMB ELISA (Pierce #34028) and incubating for 5-10 min until color develops. 50 uL/well 2M Sulfuric Acid is added to stop reaction and absorbance read at 450 nm Lysate (15 µl) is added to Invitrogen Rb (total) Human ELISA kit (SKU#KHO0011) and the test protocol is performed according to the manufacturers instructions in the kit. pRb to total Rb is normalized and an IC$_{50}$ value is obtained using Prism.

Example 219

Pharmaceutical Formulations (i) Tablet Formulation

A tablet composition containing a compound of the formula (I) is prepared by mixing 50 mg of the compound with 197 mg of lactose (BP) as diluent, and 3 mg magnesium stearate as a lubricant and compressing to form a tablet in known manner.

(ii) Capsule Formulation

A capsule formulation is prepared by mixing 100 mg of a compound of the formula (I) with 100 mg lactose and filling the resulting mixture into standard opaque hard gelatin capsules.

(iii) Injectable Formulation I

A parenteral composition for administration by injection can be prepared by dissolving a compound of the formula (I) (e.g. in a salt form) in water containing 10% propylene glycol to give a concentration of active compound of 1.5% by weight. The solution is then sterilised by filtration, filled into an ampoule and sealed.

(iv) Injectable Formulation II

A parenteral composition for injection is prepared by dissolving in water a compound of the formula (I) (e.g. in salt form) (2 mg/ml) and mannitol (50 mg/ml), sterile filtering the solution and filling into sealable 1 ml vials or ampoules.

(v) Injectable Formulation III

A formulation for i.v. delivery by injection or infusion can be prepared by dissolving the compound of formula (I) (e.g. in a salt form) in water at 20 mg/ml. The vial is then sealed and sterilised by autoclaving.

(vi) Injectable Formulation IV

A formulation for i.v. delivery by injection or infusion can be prepared by dissolving the compound of formula (I) (e.g. in a salt form) in water containing a buffer (e.g. 0.2 M acetate pH 4.6) at 20 mg/ml. The vial is then sealed and sterilised by autoclaving.

(vii) Subcutaneous Injection Formulation

A composition for sub-cutaneous administration is prepared by mixing a compound of the formula (I) with pharmaceutical grade corn oil to give a concentration of 5 mg/ml. The composition is sterilised and filled into a suitable container.

(viii) Lyophilised Formulation

Aliquots of formulated compound of formula (I) are put into 50 mL vials and lyophilized. During lyophilisation, the compositions are frozen using a one-step freezing protocol at (−45° C.). The temperature is raised to −10° C. for annealing, then lowered to freezing at −45° C., followed by primary drying at +25° C. for approximately 3400 minutes, followed by a secondary drying with increased steps if temperature to 50° C. The pressure during primary and secondary drying is set at 80 millitor.

(ix) Solid Solution Formulation

The compound of formula (I) is dissolved in dichloromethane/ethanol (1:1) at a concentration of 5 to 50% (for example 16 or 20%) and the solution is spray dried using conditions corresponding to those set out in the table below. The data given in the table include the concentration of the compound of Formula (I), and the inlet and outlet temperatures of the spray drier.

| conc. sol. w/vol | temperature of inlet | temperature of outlet |
|---|---|---|
| 16% | 140° C. | 80° C. |
| 16% | 180° C. | 80° C. |
| 20% | 160° C. | 80° C. |
| 20% | 180° C. | 100° C. |

A solid solution of the compound of formula (I) and PVP can either be filled directly into hard gelatin or HPMC (hydroxypropylmethyl cellulose) capsules, or be mixed with pharmaceutically acceptable excipients such as bulking agents, glidants or dispersants. The capsules could contain the compound of formula (I) in amounts of between 2).

EQUIVALENTS

The foregoing examples are presented for the purpose of illustrating the invention and should not be construed as imposing any limitation on the scope of the invention. It will readily be apparent that numerous modifications and alterations may be made to the specific embodiments of the invention described above and illustrated in the examples without departing from the principles underlying the invention. All such modifications and alterations are intended to be embraced by this application.

The invention claimed is:
1. A compound of the formula (I):

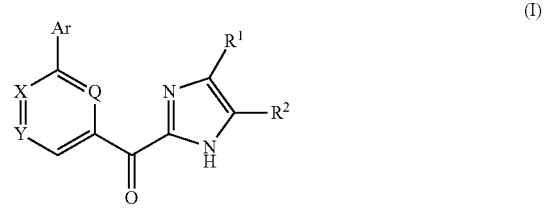

or a salt, tautomer, solvate or N-oxide thereof;
wherein:
Q is CH or N;
X is N, $N^+\!\!-\!\!O^-$ or $CR^3$;
Y is N, $N^+\!\!-\!\!O^-$ or $CR^{3a}$;
$R^1$ and $R^2$ are independently selected from hydrogen; halogen; cyano; hydroxyl; $C_{1-8}$ alkyl; $C_{1-8}$ alkoxyl; $C_{2-8}$ alkenyl; $C_{2-8}$ alkynyl; $C_{3-8}$ cycloalkyl; $C_{2-8}$ cycloalkenyl; aryl; heterocyclyl; heteroaryl; $OR^5$; $C\!\!=\!\!OR^5$; $C(\!\!=\!\!O)OR^5$; $OC\!\!=\!\!OR^5$; $S(O)_nR^5$; $NR^7R^8$; $N(R^7)C(\!\!=\!\!O)R^8$; $C(\!\!=\!\!O)NR^7R^8$; $SO_2NR^9R^{10}$; wherein the $C_{1-8}$ alkyl, $C_{1-8}$ alkoxyl, $C_{2-8}$ alkenyl and $C_{2-8}$ alkynyl moieties are each optionally substituted by one or more substituents $R^{11}$; and the $C_{3-8}$ cycloalkyl, $C_{2-8}$ cycloalkenyl, aryl, heterocyclyl and heteroaryl are each optionally substituted by one or more substituents $R^{12}$;
n is 0, 1 or 2;
m is 0, 1, 2, or 3;
or $R^1$ and $R^2$ together with the atoms to which they are attached, link to form an aromatic or non-aromatic ring of 4 to 7 members, wherein said aromatic or non-aromatic ring contains 0, 1 or 2 heteroatom ring members selected from O, N and S, wherein the aromatic or non-aromatic ring is optionally substituted by one or more substituents $R^{13}$;
$R^3$ is selected from hydrogen; hydroxy; halogen; cyano; $OR^5$; $C(\!\!=\!\!O)R^5$; $OC(\!\!=\!\!O)R^5$; $C(\!\!=\!\!O)OR^5$; $S(O)_nR^5$; $NR^7R^8$; $N(R^7)C(\!\!=\!\!O)R^8$; $C(\!\!=\!\!O)NR^7R^8$; $SO_2NR^9R^{10}$; $C_{1-6}$ alkyl; $C_{2-8}$ alkenyl; $C_{2-8}$ alkynyl; $O_{3-8}$ cycloalkyl; 5 or 6 membered aryl; and 5 or 6 membered heteroaryl;
$R^{3a}$ is selected from hydrogen; halogen; cyano; $OR^5$; $C(\!\!=\!\!O)R^5$; $OC(\!\!=\!\!O)R^5$; $C(\!\!=\!\!O)OR^5$; $S(O)_nR^5$; $NR^7R^8$; $N(R^7)C(\!\!=\!\!O)R^8$; $C(\!\!=\!\!O)NR^7R^8$; $SO_2NR^9R^{10}$; $C_{1-6}$ alkyl; $C_{2-6}$ alkenyl; $C_{2-6}$ alkynyl; $C_{3-6}$ cycloalkyl; 5 or 6 membered aryl; and 5 or 6 membered heteroaryl;
wherein, in $R^3$ and $R^{3a}$, the $C_{1-6}$ alkyl, $C_{1-6}$ alkoxyl, $C_{2-6}$ alkenyl and $C_{2-6}$ alkynyl moieties are each optionally substituted by one or more substituents $R^{11}$; and the $C_{3-6}$ cycloalkyl, 5- or 6-membered aryl, and 5- or 6-membered heteroaryl moieties are each optionally substituted by one or more substituents $R^{12}$;
$R^5$ is selected from $C_{1-8}$ alkyl; $C_{3-8}$ cycloalkyl; aryl; heteroaryl; and heterocyclyl;
$R^7$ and $R^8$ are the same or different, and independently are selected from hydrogen; $C_{1-8}$ alkyl; $C_{3-8}$ cycloalkyl; aryl; heteroaryl; and heterocyclyl; or $NR^7R^8$ forms a non-aromatic four to seven membered ring optionally containing a second heteroatom selected from O, N and S, and optionally substituted by one or more substituents $R^{12}$;

$R^9$ and $R^{10}$ are the same or different, and independently are selected from hydrogen; $C_{1-8}$ alkyl; $C_{3-8}$ cycloalkyl; aryl; heteroaryl; and heterocyclyl; or $NR^9R^{10}$ forms a non-aromatic four to seven membered ring optionally containing a second heteroatom selected from O, N and S, and optionally substituted by one or more substituents $R^{12}$;

wherein, in $R^5$, $R^7$, $R^8$, $R^9$ and $R^{10}$, the $C_{1-8}$ alkyl moiety is optionally substituted by one or more substituents $R^{11}$; and the $C_{3-8}$ cycloalkyl, aryl, heteroaryl and heterocyclyl moieties are each optionally substituted by one or more substituents $R^{12}$;

$R^{11}$ is selected from the group consisting of halogen; cyano; =O; hydroxyl; $C_{1-6}$ alkyl; $C_{1-6}$ alkoxy; $C_{2-6}$ alkenyl; $C_{2-6}$ alkynyl; $C_{3-6}$ cycloalkyl; $C_{3-6}$ cycloalkenyl; aryl; heteroaryl; heterocyclyl; —$(CH_2)_m$—$NR^{7a}R^{8a}$; —$(CH_2)_m$—C(=O)$OR^{5a}$; —$(CH_2)_m$—OC(=O)$R^{5a}$; —$(CH_2)_m$—C(=O)$R^{5a}$; —$(CH_2)_m$—S(O)$_nR^5$; —$(CH_2)_m$—N($R^{7a}$)C(=O)$R^{8a}$; —$(CH_2)_m$—C(=O)$NR^{7a}R^{8a}$; —$(CH_2)_m$—SO$_2NR^{9a}R^{10a}$; —$(CH_2)_m$-aryl; —$(CH_2)_m$-O-aryl; —O—$(CH_2)_m$-aryl; —$(CH_2)_m$-heterocyclyl; —O—$(CH_2)_m$-heterocyclyl; and —$(CH_2)_m$—O-heterocyclyl;

$R^{12}$ is selected from the group consisting of halogen; cyano; =O; hydroxyl; —O—P(O)(OH)$_2$; $C_{1-6}$ alkyl; $C_{1-6}$ alkoxyl; $C_{2-6}$ alkenyl; $C_{2-6}$ alkynyl; $C_{3-6}$ cycloalkyl; $C_{3-6}$ cycloalkenyl; —$(CH_2)_m$—$NR^{7a}R^{8a}$; —$(CH_2)_m$—C(=O)$OR^{5a}$; —$(CH_2)_m$—OC(=O)$R^{5a}$; —$(CH_2)_m$—C(=O)$R^{5a}$; —$(CH_2)_m$—S(O)$_nR^{5a}$; —$(CH_2)_m$—N($R^7$)C(=O)$R^{8a}$; —$(CH_2)_m$—C(=O)$NR^{7a}R^{8a}$; —$(CH_2)_m$—SO$_2NR^{9a}R^{10a}$; —$(CH_2)_m$-aryl; —$(CH_2)_m$-O-aryl; —O—$(CH_2)_m$-aryl; —$(CH_2)_m$-heterocyclyl; —O—$(CH_2)_m$-heterocyclyl; and —$(CH_2)_m$—O-heterocyclyl;

wherein, in $R^{11}$ and $R^{12}$, the $C_{1-6}$ alkyl, $C_{1-6}$ alkoxyl, $C_{2-6}$ alkenyl and $C_{2-6}$ alkynyl moieties are each optionally substituted by one or more substituents $R^{14}$; and the $C_{3-8}$ cycloalkyl, $C_{3-6}$ cycloalkenyl, aryl, heterocyclyl and heteroaryl moieties are each optionally substituted by one or more substituents $R^{15}$;

$R^{13}$ is selected from the group consisting of halogen; cyano; hydroxyl; =O; an oxide (when $R^{13}$ is attached to N or S); a dioxide (when $R^{13}$ is attached to S); $C_{1-6}$ alkyl optionally substituted by one or more substituents $R^{11}$; $C_{1-6}$ alkoxyl optionally substituted by one or more substituents $R^{11}$; $C_{2-6}$ alkenyl optionally substituted by one or more substituents $R^{11}$; $C_{2-6}$ alkynyl optionally substituted by one or more substituents $R^{11}$; $C_{3-6}$ cycloalkyl optionally substituted by one or more substituents $R^{12}$; $C_{3-6}$ cycloalkenyl optionally substituted by one or more substituents $R^{12}$; aryl optionally substituted by one or more substituents $R^{12}$; heteroaryl optionally substituted by one or more substituents $R^{12}$; heterocyclyl optionally substituted by one or more substituents $R^{12}$; —$(CH_2)_m$—$NR^7R^8$; —$(CH_2)_m$—C(=O)$OR^5$; —$(CH_2)_m$—OC(=O)$R^5$; —$(CH_2)_m$—C(=O)$R^5$; —$(CH_2)_m$—S(O)$_nR^5$; —$(CH_2)_m$—N($R^7$)C(=O)$R^8$; —$(CH_2)_m$—C(=O)$NR^7R^8$; —$(CH_2)_m$—SO$_2NR^9R^{10}$; —$(CH_2)_m$-aryl; —$(CH_2)_m$-O-aryl; —O—$(CH_2)_m$-aryl; —$(CH_2)_m$-heterocyclyl; —O—$(CH_2)_m$-heterocyclyl; and —$(CH_2)_m$—O-heterocyclyl wherein the aryl or heterocyclyl can be optionally substituted by one or more substituents $R^{12}$; and Ar is selected from 6-membered aryl optionally substituted by one or more substituents $R^{13}$; 5 or 6-membered heteroaryl optionally substituted by one or more substituents $R^{13}$; bicyclic aryl optionally substituted by one or more substituents $R^{13}$; and bicyclic heteroaryl optionally substituted by one or more substituents $R^{13}$;

$R^{14}$ is selected from hydroxy; halogen; cyano; $C_{1-4}$ alkyl; $C_{1-4}$ alkoxy; $C_{1-4}$ alkoxy-$C_{2-4}$ alkoxy; hydroxy-$C_{2-4}$ alkoxy; $(CH_2)_m$—$NR^{7a}R^{8a}$; —$(CH_2)_m$—C(=O)$OR^{5a}$; —$(CH_2)_m$—OC(=O)$R^{5a}$; —$(CH_2)_m$—C(=O)$R^{5a}$; —$(CH_2)_m$—S(O)$_nR^{5a}$; —$(CH_2)_m$—N($R^{7a}$)C(=O)$R^{8a}$; —$(CH_2)_m$—C=ONR$^{7a}R^{8a}$; and —$(CH_2)_m$—SO$_2NR^{9a}R^{10a}$;

$R^{15}$ is selected from hydroxy; halogen; cyano; $C_{1-4}$ alkyl; $C_{1-4}$ alkoxy; $C_{1-4}$ alkoxy-$C_{2-4}$ alkoxy; hydroxy-$C_{2-4}$ alkoxy; $(CH_2)_m$—$NR^{7a}R^{8a}$; —$(CH_2)_m$—C(=O)$OR^{5a}$; —$(CH_2)_m$—OC(=O)$R^{5a}$; —$(CH_2)_m$—C(=O)$R^{5a}$; —$(CH_2)_m$—S(O)$_nR^{5a}$; —$(CH_2)_m$—N($R^{7a}$)C(=O)$R^{8a}$; —$(CH_2)_m$—C(=O)$NR^{7a}R^{8a}$; and —$(CH_2)_m$—SO$_2NR^{9a}R^{10a}$;

$R^{5a}$ is selected from $C_{1-8}$ alkyl optionally substituted by one or more substituents selected from amino, hydroxy, $C_{1-4}$ alkoxy, halogen and cyano; $C_{3-8}$ cycloalkyl optionally substituted by one or more substituents selected from hydroxy, $C_{1-4}$ alkyl, $C_{1-4}$ alkoxy, halogen and cyano; aryl optionally substituted by one or more substituents selected from hydroxy, $C_{1-4}$ alkyl, $C_{1-4}$ alkoxy, halogen and cyano; heteroaryl optionally substituted by one or more substituents selected from hydroxy, $C_{1-4}$ alkyl, $C_{1-4}$ alkoxy, halogen and cyano; and heterocyclyl optionally substituted by one or more substituents selected from hydroxy, $C_{1-4}$ alkyl, $C_{1-4}$ alkoxy, halogen and cyano;

$R^{7a}$ and $R^{8a}$ are the same or different, and independently are selected from hydrogen; $C_{1-8}$ alkyl optionally substituted by one or more substituents selected from hydroxy, $C_{1-4}$ alkoxy, halogen and cyano; $C_{3-8}$ cycloalkyl optionally substituted by one or more substituents hydroxy, $C_{1-4}$ alkyl, $C_{1-4}$ alkoxy, halogen and cyano; aryl optionally substituted by one or more substituents hydroxy, $C_{1-4}$ alkyl, $C_{1-4}$ alkoxy, halogen and cyano; heteroaryl optionally substituted by one or more substituents selected from hydroxy, $C_{1-4}$ alkyl, $C_{1-4}$ alkoxy, halogen and cyano; and heterocyclyl optionally substituted by one or more substituents selected from hydroxy, $C_{1-4}$ alkyl, $C_{1-4}$ alkoxy, halogen and cyano; or $NR^{7a}R^{8a}$ forms a non-aromatic four to seven membered ring optionally containing a second heteroatom selected from O, N and S, and optionally substituted by one or more substituents selected from hydroxyl, $C_{1-4}$ alkyl, $C_{1-4}$ acyl, $C_{1-4}$ alkoxycarbonyl and $C_{1-4}$ alkylsulphonyl; and $R^{9a}$ and $R^{10a}$ are the same or different, and independently are selected from hydrogen; $C_{1-8}$ alkyl optionally substituted by one or more substituents selected from hydroxy, $C_{1-4}$ alkoxy, halogen and cyano; $C_{3-8}$ cycloalkyl optionally substituted by one or more substituents selected from hydroxy, $C_{1-4}$ alkyl, $C_{1-4}$ alkoxy, halogen and cyano; aryl optionally substituted by one or more substituents selected from hydroxy, $C_{1-4}$ alkyl, $C_{1-4}$ alkoxy, halogen and cyano; heteroaryl optionally substituted by one or more substituents selected from hydroxy, $C_{1-4}$ alkyl, $C_{1-4}$ alkoxy, halogen and cyano; and heterocyclyl optionally substituted by one or more substituents selected from hydroxy, $C_{1-4}$ alkyl, $C_{1-4}$ alkoxy, halogen and cyano.

2. A compound of the formula (I) according to claim 1, or a salt, tautomer, solvate or N-oxide thereof,
wherein:
X is N, $N^+$—$O^-$ or $CR^3$;
Y is N, $N^+$—$O^-$ or $CR^{3a}$;
$R^1$ and $R^2$ are independently selected from hydrogen; halogen; cyano; hydroxyl; $C_{1-8}$ alkyl; $C_{1-8}$ alkoxyl; $C_{2-8}$ alkenyl; $C_{2-8}$ alkynyl; $C_{3-8}$ cycloalkyl; $C_{2-8}$ cycloalkenyl; aryl; heterocyclyl; heteroaryl; $OR^5$; C=$OR^5$; C=$OOR^5$; OC=$OR^5$; $S(O)_nR^5$; $NR^7R^8$; $NR^7C$=$OR^8$; C=$ONR^7R^8$; $SO_2NR^9R^{10}$; wherein the $C_{1-8}$ alkyl, $C_{1-8}$ alkoxyl, $C_{2-8}$ alkenyl and $C_{2-8}$ alkynyl moieties are each optionally substituted by one or more substituents $R^{11}$; and the $C_{3-8}$ cycloalkyl, $C_{2-6}$ cycloalkenyl, aryl, heterocyclyl and heteroaryl are each optionally substituted by one or more substituents $R^{12}$;
n is 0, 1 or 2;
m is 0, 1, 2, or 3;
or $R^1$ and $R^2$ together with the atoms to which they are attached, link to form an aromatic or non-aromatic ring of 4 to 7 members, wherein said aromatic or non-aromatic ring contains 0, 1 or 2 heteroatom ring members selected from O, N and S, wherein the aromatic or non-aromatic ring is optionally substituted by one or more substituents $R^{13}$;
$R^3$ is selected from hydrogen; halogen; cyano; $OR^5$; C=$OR^5$; OC=$OR^5$; C=$OOR^5$; $S(O)_nR^5$; $NR^7R^8$; $NR^7C$=$OR^8$; C=$ONR^7R^8$; $SO_2NR^9R^{10}$; $C_{1-6}$ alkyl; $C_{2-6}$ alkenyl; $C_{2-6}$ alkynyl; $C_{3-6}$ cycloalkyl; 5 or 6 membered aryl; and 5 or 6 membered heteroaryl;
$R^{3a}$ is selected from hydrogen; halogen; cyano; $OR^5$; C=$OR^5$; OC=$OR^5$; C=$OOR^5$; $S(O)_nR^5$; $NR^7R^8$; $NR^7C$=$OR^8$; C=$ONR^7R^8$; $SO_2NR^9R^{10}$; $C_{1-6}$ alkyl; $C_{2-6}$ alkenyl; $C_{2-6}$ alkynyl; $C_{3-6}$ cycloalkyl; 5 or 6 membered aryl; and 5 or 6 membered heteroaryl;
wherein, in $R^3$ and $R^{3a}$, the $C_{1-8}$ alkyl, $C_{1-8}$ alkoxyl, $C_{2-6}$ alkenyl and $C_{2-6}$ alkynyl moieties are each optionally substituted by one or more substituents $R^{11}$; and the $C_{3-6}$ cycloalkyl, 5- or 6-membered aryl, and 5- or 6-membered heteroaryl moieties are each optionally substituted by one or more substituents $R^{12}$;
$R^5$ is selected from $C_{1-8}$ alkyl; $C_{3-8}$ cycloalkyl; aryl; heteroaryl; and heterocyclyl;
$R^7$ and $R^8$ are the same or different, and independently are selected from hydrogen; $C_{1-8}$ alkyl; $C_{3-8}$ cycloalkyl; aryl; heteroaryl; and heterocyclyl; or $NR^7R^8$ forms a non-aromatic four to seven membered ring optionally containing a second heteroatom selected from O, N and S, and optionally substituted by one or more substituents $R^{12}$;
$R^9$ and $R^{10}$ are the same or different, and independently are selected from hydrogen; $C_{1-8}$ alkyl; $C_{3-8}$ cycloalkyl; aryl; heteroaryl; and heterocyclyl; or $NR^9R^{10}$ forms a non-aromatic four to seven membered ring optionally containing a second heteroatom selected from O, N and S, and optionally substituted by one or more substituents $R^{12}$;
wherein, in $R^5$, $R^7$, $R^8$, $R^9$, and $R^{10}$, the $C_{1-8}$ alkyl moiety is optionally substituted by one or more substituents $R^{11}$; and the $C_{3-8}$ cycloalkyl, aryl, heteroaryl and heterocyclyl moieties are each optionally substituted by one or more substituents $R^{12}$;
$R^{11}$ is selected from the group consisting of halogen; cyano; =O; hydroxyl; $C_{1-6}$ alkyl; $C_{1-6}$ alkoxy; $C_{2-6}$ alkenyl; $C_{2-6}$ alkynyl; $C_{3-6}$ cycloalkyl; $C_{3-6}$ cycloalkenyl; aryl; heteroaryl; heterocyclyl; —$(CH_2)_m$—$NR^{7a}R^{8a}$; —$(CH_2)_m$—$COOR^{5a}$; —$(CH_2)_m$—OC=$OR^{5a}$; —$(CH_2)_m$—C=$OR^{5a}$; —$(CH_2)_m$—$S(O)_nR^5$; —$(CH_2)_m$—$NR^{7a}C$=$OR^{8a}$; —$(CH_2)_m$—C=$ONR^{7a}R^{8a}$; —$(CH_2)_m$—$SO_2NR^{9a}R^{10a}$; —$(CH_2)_m$-aryl; —$(CH_2)_m$—O-aryl; —O—$(CH_2)_m$-aryl; —$(CH_2)_m$-heterocyclyl; —O—$(CH_2)_m$-heterocyclyl; and —$(CH_2)_m$—O-heterocyclyl;
$R^{12}$ is selected from the group consisting of halogen; cyano; =O; hydroxyl; $C_{1-6}$ alkyl; $C_{1-6}$ alkoxyl; $C_{2-6}$ alkenyl; $C_{2-6}$ alkynyl; $C_{3-6}$ cycloalkyl; $C_{3-6}$ cycloalkenyl; —$(CH_2)_m$—$NR^{7a}R^{8a}$; —$(CH_2)_m$—$COOR^{5a}$; —$(CH_2)_m$—OC=$OR^{5a}$; —$(CH_2)_m$—C=$OR^{5a}$; —$(CH_2)_m$—$S(O)_nR^{5a}$; —$(CH_2)_m$—$NR^7C$=$OR^{8a}$; —$(CH_2)_m$—C=$ONR^{7a}R^{8a}$; —$(CH_2)_m$—$SO_2NR^{9a}R^{10a}$; —$(CH_2)_m$-aryl; —$(CH_2)_m$—O-aryl; —O—$(CH_2)_m$-aryl; —$(CH_2)_m$-heterocyclyl; —O—$(CH_2)_m$-heterocyclyl; and —$(CH_2)_m$—O-heterocyclyl;
wherein, in $R^{11}$ and $R^{12}$, the $C_{1-6}$ alkyl, $C_{1-6}$ alkoxyl, $C_{2-6}$ alkenyl and $C_{2-6}$ alkynyl moieties are each optionally substituted by one or more substituents $R^{14}$; and the $C_{3-8}$ cycloalkyl, $O_{3-6}$ cycloalkenyl, aryl, heterocyclyl and heteroaryl moieties are each optionally substituted by one or more substituents $R^{15}$;
$R^{13}$ is selected from the group consisting of halogen; cyano; hydroxyl; =O; an oxide (when $R^{13}$ is attached to N or S); a dioxide (when $R^{13}$ is attached to S); $C_{1-6}$ alkyl optionally substituted by one or more substituents $R^{11}$; $C_{1-6}$ alkoxyl optionally substituted by one or more substituents $R^{11}$; $C_{2-6}$ alkenyl optionally substituted by one or more substituents $R^{11}$; $C_{2-6}$ alkynyl optionally substituted by one or more substituents $R^{11}$; $C_{3-6}$ cycloalkyl optionally substituted by one or more substituents $R^{12}$; $C_{3-8}$ cycloalkenyl optionally substituted by one or more substituents $R^{12}$; aryl optionally substituted by one or more substituents $R^{12}$; heteroaryl optionally substituted by one or more substituents $R^{12}$; heterocyclyl optionally substituted by one or more substituents $R^{12}$; $(CH_2)_m$—$NR^7R^8$; —$(CH_2)_m$—$COOR^5$; —$(CH_2)_m$—OC=$OR^5$; —$(CH_2)_m$—C=$OR^5$; —$(CH_2)_m$—$S(O)_nR^5$; —$(CH_2)_m$—$NR^7C$=$OR^8$; —$(CH_2)_m$—C=$ONR^7R^8$; —$(CH_2)_m$—$SO_2NR^9R^{10}$; —$(CH_2)_m$-aryl; —$(CH_2)$, —O-aryl; —O—$(CH_2)_m$-aryl; —$(CH_2)_m$-heterocyclyl; —O—$(CH_2)_m$-heterocyclyl; and —$(CH_2)_m$—O-heterocyclyl wherein the aryl or heterocyclyl can be optionally substituted by one or more substituents $R^{12}$; and
Ar is selected from 6-membered aryl optionally substituted by one or more substituents $R^{13}$; 5 or 6-membered heteroaryl optionally substituted by one or more substituents $R^{13}$; bicyclic aryl optionally substituted by one or more substituents $R^{13}$; and bicyclic heteroaryl optionally substituted by one or more substituents $R^{13}$;
$R^{14}$ is selected from hydroxy; halogen; cyano; $C_{1-4}$ alkyl; $C_{1-4}$ alkoxy; $C_{1-4}$ alkoxy-$C_{2-4}$ alkoxy; hydroxy-$C_{2-4}$ alkoxy; $(CH_2)$, $NR^{7a}R^{8a}$; —$(CH_2)_m$—$COOR^{5a}$; —$(CH_2)_m$—OC=$OR^{5a}$; —$(CH_2)_m$—C=$OR^{5a}$; —$(CH_2)_m$—$S(O)_nR^{5a}$; —$(CH_2)_m$—$NR^{7a}C$=$OR^{8a}$; —$(CH_2)_m$—C=$ONR^{7a}R^{8a}$; and —$(CH_2)_m$—$SO_2NR^{9a}R^{10a}$;
$R^{15}$ is selected from hydroxy; halogen; cyano; $C_{1-4}$ alkyl; $C_{1-4}$ alkoxy; $C_{1-4}$ alkoxy-$C_{2-4}$ alkoxy; hydroxy-$C_{2-4}$ alkoxy; $(CH_2)$, $NR^{7a}R^{8a}$; —$(CH_2)_m$—$COOR^{5a}$; —$(CH_2)_m$—OC=$OR^{5a}$; —$(CH_2)_m$—C=$OR^{5a}$;

—(CH$_2$)$_m$—S(O)$_n$R$^{5a}$; —(CH$_2$)$_m$—NR$^{7a}$C═OR$^{8a}$; —(CH$_2$)$_m$—C═ONR$^{7a}$R$^{8a}$; and —(CH$_2$)$_m$SO$_2$NR$^{9a}$R$^{10a}$;

R$^{5a}$ is selected from C$_{1-8}$ alkyl optionally substituted by one or more substituents selected from hydroxy, C$_{1-4}$ alkoxy, halogen and cyano; C$_{3-8}$ cycloalkyl optionally substituted by one or more substituents selected from hydroxy, C$_{1-4}$ alkyl, C$_{1-4}$ alkoxy, halogen and cyano; aryl optionally substituted by one or more substituents selected from hydroxy, C$_{1-4}$ alkyl, C$_{1-4}$ alkoxy, halogen and cyano; heteroaryl optionally substituted by one or more substituents selected from hydroxy, C$_{1-4}$ alkyl, C$_{1-4}$ alkoxy, halogen and cyano; and heterocyclyl optionally substituted by one or more substituents selected from hydroxy, C$_{1-4}$ alkyl, C$_{1-4}$ alkoxy, halogen and cyano;

R$^{7a}$ and R$^{8a}$ are the same or different, and independently are selected from hydrogen; C$_{1-8}$ alkyl optionally substituted by one or more substituents selected from hydroxy, C$_{1-4}$ alkoxy, halogen and cyano; C$_{3-8}$ cycloalkyl optionally substituted by one or more substituents hydroxy, C$_{1-4}$ alkyl, C$_{1-4}$ alkoxy, halogen and cyano; aryl optionally substituted by one or more substituents hydroxy, C$_{1-4}$ alkyl, C$_{1-4}$ alkoxy, halogen and cyano; heteroaryl optionally substituted by one or more substituents selected from hydroxy, C$_{1-4}$ alkyl, C$_{1-4}$ alkoxy, halogen and cyano; and heterocyclyl optionally substituted by one or more substituents selected from hydroxy, C$_{1-4}$ alkyl, C$_{1-4}$ alkoxy, halogen and cyano; or NR$^{7a}$R$^{8a}$ forms a non-aromatic four to seven membered ring optionally containing a second heteroatom selected from O, N and S, and optionally substituted by one or more substituents selected from hydroxyl, C$_{1-4}$ alkyl, C$_{1-4}$ acyl, C$_{1-4}$ alkoxycarbonyl and C$_{1-4}$ alkylsulphonyl; and R$^{9a}$ and R$^{10a}$ are the same or different, and independently are selected from hydrogen; C$_{1-8}$ alkyl optionally substituted by one or more substituents selected from hydroxy, C$_{1-4}$ alkoxy, halogen and cyano; C$_{3-8}$ cycloalkyl optionally substituted by one or more substituents selected from hydroxy, C$_{1-4}$ alkyl, C$_{1-4}$ alkoxy, halogen and cyano; aryl optionally substituted by one or more substituents selected from hydroxy, C$_{1-4}$ alkyl, C$_{1-4}$ alkoxy, halogen and cyano; heteroaryl optionally substituted by one or more substituents selected from hydroxy, C$_{1-4}$ alkyl, C$_{1-4}$ alkoxy, halogen and cyano; and heterocyclyl optionally substituted by one or more substituents selected from hydroxy, C$_{1-4}$ alkyl, C$_{1-4}$ alkoxy, halogen and cyano.

3. A compound according to claim 1 wherein Q is CH, Y is CH and X is N or C—CN.

4. A compound according to claim 1 wherein Ar is selected from phenyl; naphthyl; 5-membered heteroaryl rings containing a nitrogen ring member and optionally a further heteroatom ring member selected from O, N and S; 6-membered heteroaryl ring rings containing one or two nitrogen ring members; bicyclic heteroaryl rings containing 9 or 10 ring members of which one or two are heteroatoms selected from O, N and S; each of the moieties Ar being optionally substituted by one or more substituents R$^{13}$.

5. A compound according to claim 4 wherein Ar is selected from phenyl, pyridyl, pyrazolyl, imidazolyl, thiazolyl, pyrimidinyl, naphthyl, isoquinolinyl, benzoimidazolyl, azobenzoimidazolyl, pyridopyrazolyl, quinolinyl, indolyl, azaindolyl, isoquinolinyl, and 2,3-dihydrobenzfuranyl, each optionally substituted by one or more substituents R$^{13}$.

6. A compound according to claim 5 wherein Ar is an isoquinolinyl ring optionally substituted by one or more substituents R$^{13}$, a pyrazolyl ring optionally substituted by one or more substituents R$^{13}$ or an azaindolyl ring optionally substituted by one or more substituents R$^{13}$.

7. A compound according to claim 1 wherein R$^1$ and R$^2$ together with the carbon atoms to which they are attached form a 6-membered aromatic ring optionally containing one or two nitrogen ring members, and optionally substituted by one or more substituents R$^{13}$.

8. A compound according to claim 7 wherein R$^1$ and R$^2$ together with the carbon atoms to which they are attached form a benzene ring optionally substituted by one or more substituents R$^{13}$ or a pyridine ring optionally substituted by one or more substituents R$^{13}$.

9. A compound according to claim 7 wherein one or two substituents R$^{13}$ are present and are selected from the group consisting of halogen; cyano; hydroxyl; C$_{1-6}$ alkyl optionally substituted by one or more substituents R$^{11}$; C$_{1-6}$ alkoxyl optionally substituted by one or more substituents R$^{11}$; heteroaryl optionally substituted by one or more substituents R$^{12}$; heterocyclyl optionally substituted by one or more substituents R$^{12}$; (CH$_2$)$_m$—NR$^7$R$^8$; and —(CH$_2$)$_m$—C═ONR$^7$R$^8$.

10. A compound according to claim 2 having the formula (II):

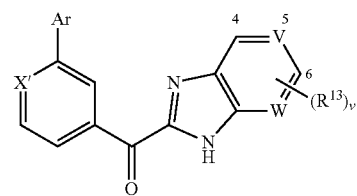

(II)

or a salt, solvate, tautomer or N-oxide thereof; wherein X' is N or C—CN; V and W are selected from N, CH and C—R$^{13}$; and v is 0, 1 or 2.

11. A compound according to claim 10 having the formula (IIa):

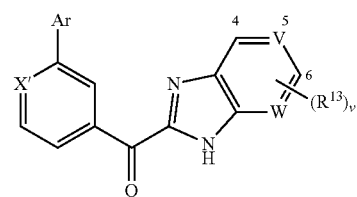

(IIa)

or a salt, solvate, tautomer or N-oxide thereof; wherein:
X' is N or C—CN;
V and W are selected from N, CH and C—R$^{13}$;
v is 0, 1 or 2;
R$^{13}$ is selected from the group R$^{13a}$ consisting of halogen; cyano; hydroxyl; ═O; an oxide (when R$^{13}$ is attached to N or S); C$_{1-6}$ alkyl optionally substituted by one or more substituents R$^{11a}$; C$_{1-6}$ alkoxyl optionally substituted by one or more substituents R$^{11a}$; C$_{3-6}$ cycloalkyl optionally substituted by one or more substituents R$^{12a}$; heterocyclyl optionally substituted by one or more substituents R$^{12a}$; (CH$_2$)$_m$—NR$^{7b}$R$^{8b}$;

—(CH$_2$)$_m$—C(=O)OR$^{5b}$; —(CH$_2$)$_m$—C(=O)NR$^{7b}$R$^{8b}$; —(CH$_2$)$_m$-heterocyclyl; —O—(CH$_2$)$_m$-heterocyclyl; and —(CH$_2$), O-heterocyclyl wherein the heterocyclyl can be optionally substituted by one or more substituents R$^{12a}$;

R$^{11a}$ is selected from the group consisting of halogen; cyano; =O; hydroxyl; C$_{1-6}$ alkyl; C$_{1-6}$ alkoxy; heterocyclyl; —(CH$_2$)$_m$NR$^{7b}$R$^{8b}$; —(CH$_2$)$_m$—C(=O)NR$^{7b}$R$^{8b}$; —(CH$_2$)$_m$-heterocyclyl; —O—(CH$_2$)$_m$-heterocyclyl; and —(CH$_2$), O-heterocyclyl;

R$^{12a}$ is selected from the group consisting of hydroxyl; OP(=O)(OH)$_2$, —(CH$_2$)$_m$—C(=O)OR$^{5b}$C$_{1-6}$ alkyl; C$_{1-6}$ alkoxyl; —(CH$_2$)$_m$—NR$^{7b}$R$^{8b}$; —(CH$_2$)$_m$—C(=O)NR$^{7b}$R$^{8b}$; —(CH$_2$)$_m$-heterocyclyl; —O—(CH$_2$)$_m$-heterocyclyl; and —(CH$_2$)$_m$—O-heterocyclyl;

R$^{5b}$ is hydrogen, C$_{1-4}$ alkyl or amino-C$_{1-4}$ alkyl;

R$^{7b}$ and R$^{8b}$ are the same or different, and independently are selected from hydrogen; C$_{1-8}$ alkyl optionally substituted by one or more substituents selected from hydroxyl and C$_{1-4}$ alkoxy and cyano; C$_{3-8}$ cycloalkyl optionally substituted by one or more substituents hydroxy, C$_{1-4}$ alkyl, C$_{1-4}$ alkoxy and cyano; and heterocyclyl optionally substituted by one or more substituents selected from hydroxy, C$_{1-4}$ alkyl, C$_{1-4}$ alkoxy and cyano; or NR$^{7b}$R$^{8b}$ forms a non-aromatic four to seven membered ring optionally containing a second heteroatom selected from O, N and S, and optionally substituted by one or more substituents selected from hydroxyl, C$_{1-4}$ alkyl, C$_{1-4}$ acyl, C$_{1-4}$ alkoxycarbonyl and C$_{1-4}$ alkylsulphonyl.

12. A compound according to claim 1 having the formula (IIb):

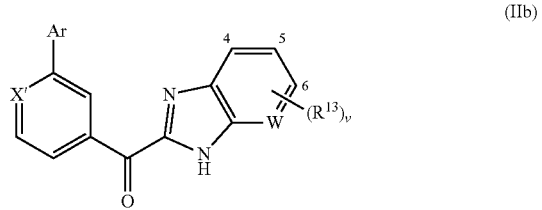

(IIb)

or a salt, solvate, tautomer or N-oxide thereof; wherein X' is N or C—CN; W is selected from N, CH and C—R$^{13}$; v is 0, 1 or 2; and v is 0, 1 or 2.

13. A compound according to claim 1 having the formula (III):

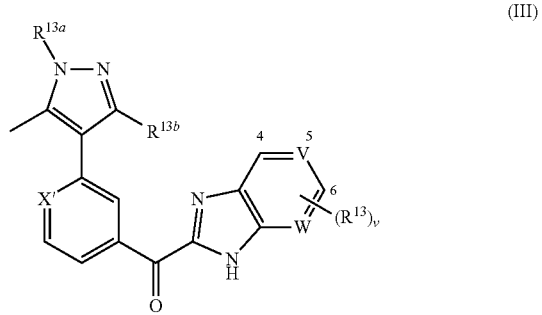

(III)

or a salt, solvate, tautomer or N-oxide thereof; X' is N or C—CN; W is CH or N; V is CH, N or C—R$^{13}$; R$^{13a}$ and R$^{13b}$ are each selected from R$^{13}$; and v is 0, 1 or 2.

14. A compound according to claim 10 having the formula (IV):

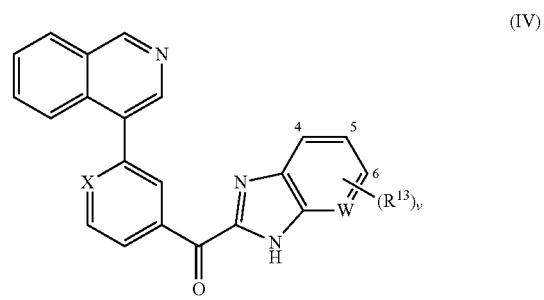

(IV)

or a salt, solvate, tautomer or N-oxide thereof; wherein v is 0, 1 or 2.

15. A compound according to claim 1 wherein one substituent R$^{13}$ is selected from:

(a) —O$_m$—(C$_{1-4}$-alkylene)$_n$-[Sol], where m is 0 or 1 and n is 0 or 1 and the alkylene is straight chain or branched, provided that when m and n are both 1 and Sol is linked by a nitrogen atom to C$_{1-4}$-alkylene, there must be at least two carbon atoms in the C$_{1-4}$-alkylene in line between O and [Sol];

(b) —(C=O)-[Sol];

(c) (SO$_2$)-[Sol]

(d) mono- or dihydroxy-C$_{2-4}$-alkoxy, provided that when two hydroxyl groups are present, they are not attached to the same carbon atom; and wherein [Sol] is selected from:

(i) NR$^{18}$R$^{19}$ where R$^{18}$ is selected from hydrogen and C$_{1-3}$ alkyl where the C$_{1-3}$ alkyl is optionally substituted by hydroxyl, amino or mono- or di-methylamino; and R$^{19}$ is selected from R$^{18}$ and monocyclic and bicyclic saturated heterocyclic rings containing from 4 to 8 ring members and containing a nitrogen ring member and optionally a second heteroatom ring member selected from N and O; and wherein the monocyclic and bicyclic saturated heterocyclic rings are optionally substituted by one or more substituents selected from C$_{1-4}$ alkyl, hydroxy, amino, mono-C$_{1-2}$-alkylamino and mono-C$_{1-2}$-alkylamino and optionally substituted 4 to 6 membered saturated heterocyclic rings containing a nitrogen ring member and optionally a second ring member selected from nitrogen and oxygen wherein the optional substituents for the 4 to 6 membered saturated heterocyclic rings are selected from hydroxyl and methyl; and (ii) monocyclic and bicyclic saturated heterocyclic rings containing from 4 to 8 ring members and containing a nitrogen ring member and optionally a second heteroatom ring member selected from N and O; and wherein the monocyclic and bicyclic saturated heterocyclic rings are optionally substituted by one or more substituents selected from C$_{1-4}$ alkyl, hydroxy, —OP(=O)(OH)$_2$, amino, amino-C$_{1-4}$alkanoyloxy, mono-C$_{1-2}$-alkylamino and mono-C$_{1-2}$-alkylamino and optionally substituted 4 to 6 membered saturated heterocyclic rings containing a nitrogen ring member and optionally a second ring member selected from nitrogen and oxygen wherein the optional substituents for the 4 to 6 membered saturated heterocyclic rings are selected from hydroxyl and methyl.

16. A compound according to claim 15 wherein [Sol] is
(i) NR$^{18}$R$^{19}$ where R$^{18}$ is selected from hydrogen and C$_{1-3}$ alkyl where the C$_{1-3}$ alkyl is optionally substituted by hydroxyl, amino or mono- or di-methylamino; and R$^{19}$ is selected from R$^{18}$ and monocyclic and bicyclic saturated heterocylic rings containing from 4 to 8 ring members and containing a nitrogen ring member and optionally a second heteroatom ring member selected from N and O; and wherein the monocyclic and bicyclic saturated heterocylic rings are optionally substituted by one or more substituents selected from C$_{1-4}$ alkyl, hydroxy, amino, mono-C$_{1-2}$-alkylamino and mono-C$_{1-2}$-alkylamino and optionally substituted 4 to 6 membered saturated heterocylic rings containing a nitrogen ring member and optionally a second ring member selected from nitrogen and oxygen wherein the optional substituents for the 4 to 6 membered saturated heterocyclic rings are selected from hydroxyl and methyl; and
(ii) monocyclic and bicyclic saturated heterocylic rings containing from 4 to 8 ring members and containing a nitrogen ring member and optionally a second heteroatom ring member selected from N and O; and wherein the monocyclic and bicyclic saturated heterocylic rings are optionally substituted by one or more substituents selected from C$_{1-4}$ alkyl, hydroxy, amino, mono-C$_{1-2}$-alkylamino and mono-C$_{1-2}$-alkylamino and optionally substituted 4 to 6 membered saturated heterocylic rings containing a nitrogen ring member and optionally a second ring member selected from nitrogen and oxygen wherein the optional substituents for the 4 to 6 membered saturated heterocyclic rings are selected from hydroxyl and methyl.

17. A compound according to claim 1 selected from:
[2-(2,6-Difluoro-phenyl)-pyridin-4-yl]-[5-(1-methyl-1H-pyrazol-4-yl)-1H-imidazol-2-yl]-methanone;
[2-(2-Fluoro-6-methoxy-phenyl)-pyridin-4-yl]-[6-(4-methyl-piperazin-1-yl)-1H-benzoimidazol-2-yl]-methanone;
[6-(4-Dimethylamino-piperidin-1-yl)-1H-benzoimidazol-2-yl]-[2-(2-fluoro-6-methoxy-phenyl)-pyridin-4-yl]-methanone;
(6'-Fluoro-2'-methoxy-biphenyl-3-yl)-(5-morpholin-4-ylmethyl-1H-benzoimidazol-2-yl)-methanone;
1H-Imidazol-2-yl)-[3-(2-methyl-thiazol-4-yl)-phenyl]methanone;
(1H-Imidazol-2-yl)-(2-phenyl-pyridin-4-yl)-methanone;
(1H-Imidazol-2-yl)-[3-(2H-pyrazol-3-yl)-phenyl]-methanone;
(1H-Imidazol-2-yl)-(3-thiophen-3-yl-phenyl)-methanone;
[2-(4-Hydroxymethyl-phenyl)-pyridin-4-yl]-(1H-imidazol-2-yl)-methanone;
(1H-Imidazol-2-yl)-[2-(3-methoxy-phenyl)-pyridin-4-yl]-methanone;
(3-Chloro-5-thiophen-3-yl-phenyl)-(1H-imidazol-2-yl)-methanone;
(3'-Amino-biphenyl-3-yl)-(1H-imidazol-2-yl)-methanone;
(3-Chloro-5-thiazol-4-yl-phenyl)-(1H-imidazol-2-yl)-methanone;
(3,5-Di-thiophen-3-yl-phenyl)-(1H-imidazol-2-yl)-methanone;
(1H-Imidazol-2-yl)-[3-(1-methyl-1H-pyrazol-3-yl)-5-thiophen-3-yl-phenyl]-methanone;
[2-(2,3-Difluoro-6-methoxy-phenyl)-pyridin-4-yl]-(1H-imidazol-2-yl)-methanone;
[2-(2,3-Difluoro-6-methoxy-phenyl)-pyridin-4-yl]-(5-dimethylaminomethyl-1H-benzoimidazol-2-yl)-methanone;
[2-(3,5-Dimethyl-isoxazol-4-yl)-pyridin-4-yl]-(5-morpholin-4-ylmethyl-1H-benzoimidazol-2-yl)-methanone;
(5-Morpholin-4-ylmethyl-1H-benzoimidazol-2-yl)-(2-phenyl-pyridin-4-yl)-methanone;
[2-(2,6-Difluoro-phenyl)-pyridin-4-yl]-(5-morpholin-4-ylmethyl-1H-benzoimidazol-2-yl)-methanone;
[2-(2,6-Difluoro-phenyl)-pyridin-4-yl]-(1H-imidazol-2-yl)-methanone;
[2-(4-Hydroxymethyl-phenyl)-pyridin-4-yl]-(5-morpholin-4-ylmethyl-1H-benzoimidazol-2-yl)-methanone;
[2-(2-Fluoro-6-methoxy-phenyl)-pyridin-4-yl]-(5-morpholin-4-ylmethyl-1H-benzoimidazol-2-yl)-methanone;
[2-(2,3-Difluoro-6-methoxy-phenyl)-pyridin-4-yl]-(5-morpholin-4-ylmethyl-1H-benzoimidazol-2-yl)-methanone;
[2-(2-Methoxy-phenyl)-pyridin-4-yl]-(5-morpholin-4-ylmethyl-1H-benzoimidazol-2-yl)-methanone;
[4-(4-Dimethylamino-piperidin-1-ylmethyl)-1H-imidazol-2-yl]-[2-(2-fluoro-6-methoxy-phenyl)-pyridin-4-yl]-methanone;
(6-Chloro-2'-methoxy-biphenyl-3-yl)-(5-dimethylaminomethyl-1H-benzoimidazol-2-yl)-methanone;
[2-(2-Fluoro-6-methoxy-phenyl)-1-oxy-pyridin-4-yl]-[5-(4-oxy-morpholin-4-ylmethyl)-1H-benzoimidazol-2-yl]-methanone;
(4-Dimethylaminomethyl-1H-benzoimidazol-2-yl)-(2-isoquinolin-4-yl-pyridin-4-yl)-methanone (formate salt);
[2-(2,3-Difluoro-6-methoxy-phenyl)-pyridin-4-yl]-(4-dimethylaminomethyl-1H-benzoimidazol-2-yl)-methanone (hydrochloride salt);
(4-Hydroxy-1H-benzoimidazol-2-yl)-(2-isoquinolin-4-yl-pyridin-4-yl)-methanone (methanesulfonate salt);
(2-Isoquinolin-4-yl-pyridin-4-yl)-[4-(1-methylaminoethyl)-1H-benzoimidazol-2-yl]-methanone (trifluoroacetate salt);
(5,6-Dimethoxy-1H-benzoimidazol-2-yl)-(5'-ethylaminomethyl-[2,3']bipyridinyl-4-yl)-methanone (formate salt);
[5-(2-Dimethylamino-ethoxy)-1H-benzoimidazol-2-yl]-(2-isoquinolin-4-yl-pyridin-4-yl)-methanone;
(6-Dimethylaminomethyl-1H-benzoimidazol-2-yl)-(2-isoquinolin-4-yl-pyridin-4-yl)-methanone;
2-(2-Isoquinolin-4-yl-pyridine-4-carbonyl)-3H-benzoimidazole-5-carboxylic acid piperidin-4-ylamide (formate salt);
(2-Isoquinolin-4-yl-pyridin-4-yl)-[5-(4-methyl-piperazin-1-ylmethyl)-1H-benzoimidazol-2-yl]methanone (formate salt);
(2-Isoquinolin-4-yl-pyridin-4-yl)-[6-(piperazine-1-carbonyl)-1H-benzoimidazol-2-yl]-methanone (formate salt);
5-[5-(4-Dimethylamino-piperidin-1-yl)-1H-benzoimidazole-2-carbonyl]-2'-methoxy-biphenyl-2-carbonitrile (trifluoroacteate salt);
[5-(4-Dimethylamino-piperidin-1-yl)-1H-benzoimidazol-2-yl]-(2-isoquinolin-4-yl-pyridin-4-yl)-methanone (hydrochloride salt);
(2-Isoquinolin-4-yl-pyridin-4-yl)-[5-(4-methyl-piperazin-1-yl)-1H-benzoimidazol-2-yl]-methanone;
(2-Isoquinolin-4-yl-pyridin-4-yl)-(5-piperazin-1-yl-1H-benzoimidazol-2-yl)-methanone;

[5-(3-Amino-pyrrolidin-1-yl)-1H-benzoimidazol-2-yl]-(2-isoquinolin-4-yl-pyridin-4-yl)-methanone;

(5-[1,4]Diazepan-1-yl-1H-benzoimidazol-2-yl)-(2-isoquinolin-4-yl-pyridin-4-yl)-methanone;

(5,7-Difluoro-1H-benzoimidazol-2-yl)-(5'-ethylaminomethyl-[2,3']bipyridinyl-4-yl)-methanone (hydrochloride salt);

(5,7-Difluoro-1H-benzoimidazol-2-yl)-(5'-ethylaminomethyl-4'-methyl-[2,3']bipyridinyl-4-yl)-methanone (hydrochloride salt);

[6-(4-Dimethylamino-piperidin-1-yl)-1H-benzoimidazol-2-yl]-(5'-ethylaminomethyl-[2,3']bipyridinyl-4-yl)-methanone (formate salt);

(2-Isoquinolin-4-yl-pyridin-4-yl)-[6-(4-methyl-piperazine-1-carbonyl)-1H-benzoimidazol-2-yl]methanone;

[5-(2,3-Dihydroxy-propoxy)-1H-benzoimidazol-2-yl]-(2-isoquinolin-4-yl-pyridin-4-yl)-methanone;

2-(2-Isoquinolin-4-yl-pyridine-4-carbonyl)-3H-benzoimidazole-5-carboxylic acid methyl-piperidin-4-yl amide;

2-(2-Isoquinolin-4-yl-pyridine-4-carbonyl)-3H-benzoimidazole-5-carboxylic acid (1-methyl-piperidin-4-yl)-amide;

4-(5,6-Dimethoxy-1H-benzoimidazole-2-carbonyl)-2-(5-ethylaminomethyl-pyridin-3-yl)-benzonitrile;

[2-(2,3-Difluoro-6-methoxy-phenyl)-pyridin-4-yl]-[5-(4-dimethylamino-piperidin-1-yl)-1H-benzoimidazol-2-yl]methanone;

[5-(4-Isopropyl-piperazin-1-yl)-1H-benzoimidazol-2-yl]-(2-isoquinolin-4-yl-pyridin-4-yl)-methanone;

4-{4-[6-(4-dimethylamino-piperidin-1-yl)-1H-benzoimidazole-2-carbonyl]-4'-methyl[2,3']bipyridinyl-6'-yl}piperazine-1-carboxylic acid tert-butyl ester;

[6-(4-Dimethylamino-piperidin-1-yl)-1H-benzoimidazol-2-yl]-(4'-methyl-6'-piperazin-1-yl-[2,3']bipyridinyl-4-yl)-methanone;

[6-(4-Dimethylamino-piperidin-1-yl)-1H-benzoimidazol-2-yl]-[2-(7-methyl-1H-indol-3-yl)-pyridin-4-yl]-methanone;

[6-(4-Dimethylamino-piperidin-1-yl)-1H-benzoimidazol-2-yl]-[2-(5-methyl-1H-pyrazol-4-yl)-pyridin-4-yl]methanone;

[6-(4-Dimethylamino-piperidin-1-yl)-1H-benzoimidazol-2-yl]-(4'-methyl-[2,3']bipyridinyl-4-yl)-methanone;

[6-(4-Dimethylamino-piperidin-1-yl)-1H-benzoimidazol-2-yl]-[2-(1H-indol-3-yl)-pyridin-4-yl]-methanone;

[6-(4-Dimethylamino-piperidin-1-yl)-1H-benzoimidazol-2-yl]-[2-(1H-indol-4-yl)-pyridin-4-yl]-methanone;

[6-(4-Dimethylamino-piperidin-1-yl)-1H-benzoimidazol-2-yl]-(2-pyrazolo[1,5-a]pyridin-3-yl-pyridin-4-yl)-methanone (methaneulfonate salt);

[6-(4-Dimethylamino-piperidin-1-yl)-1H-benzoimidazol-2-yl]-[2-(1H-pyrrolo[2,3-b]pyridin-5-yl)-pyridin-4-yl]-methanone;

[6-(4-Dimethylamino-piperidin-1-yl)-1H-benzoimidazol-2-yl]-[2-(1H-pyrrolo[3,2-b]pyridin-6-yl)-pyridin-4-yl]-methanone;

[6-(4-Dimethylamino-piperidin-1-yl)-1H-benzoimidazol-2-yl]-(2-quinolin-3-yl-pyridin-4-yl)-methanone;

[6-(4-Dimethylamino-piperidin-1-yl)-1H-benzoimidazol-2-yl]-(2-naphthalen-1-yl-pyridin-4-yl)-methanone;

[2,4']Bipyridinyl-4-yl-[6-(4-dimethylamino-piperidin-1-yl)-1H-benzoimidazol-2-yl]-methanone;

[2,3']Bipyridinyl-4-yl-[6-(4-dimethylamino-piperidin-1-yl)-1H-benzoimidazol-2-yl]-methanone;

[6-(4-Dimethylamino-piperidin-1-yl)-1H-benzoimidazol-2-yl]-(4'-methoxy-[2,3']bipyridinyl-4-yl)-methanone;

[6-(4-Dimethylamino-piperidin-1-yl)-1H-benzoimidazol-2-yl]-(6'-fluoro-4'-methyl-[2,3']bipyridinyl-4-yl)-methanone;

2-{4-[6-(4-Dimethylamino-piperidin-1-yl)-1H-benzoimidazole-2-carbonyl]-pyridin-2-yl}-N-methyl-benzenesulfonamide;

[6-(4-Dimethylamino-piperidin-1-yl)-1H-benzoimidazol-2-yl]-[2-(1,5-dimethyl-1H-pyrazol-4-yl)-pyridin-4-yl]-methanone;

[6-(4-Dimethylamino-piperidin-1-yl)-1H-benzoimidazol-2-yl]-[2-(4-isopropyl-pyrimidin-5-yl)-pyridin-4-yl]-methanone;

[6-(4-Dimethylamino-piperidin-1-yl)-1H-benzoimidazol-2-yl]-[2-(2,4-dimethyl-thiazol-5-yl)-pyridin-4-yl]-methanone;

[6-(4-Dimethylamino-piperidin-1-yl)-1H-benzoimidazol-2-yl]-[2-(2-methyl-2H-pyrazol-3-yl)-pyridin-4-yl]-methanone;

[6-(4-Dimethylamino-piperidin-1-yl)-1H-benzoimidazol-2-yl]-[2-(5-fluoro-2-methoxy-phenyl)-pyridin-4-yl]-methanone;

[6-(4-Dimethylamino-piperidin-1-yl)-1H-benzoimidazol-2-yl]-[2-(1,3,5-trimethyl-1H-pyrazol-4-yl)-pyridin-4-yl]-methanone;

[6-(4-Dimethylamino-piperidin-1-yl)-1H-benzoimidazol-2-yl]-[2-(4-piperidin-1-yl-phenyl)-pyridin-4-yl]-methanone (trifluoroacetate salt);

[2-(2,3-Dihydro-benzofuran-7-yl)-pyridin-4-yl]-[6-(4-dimethylamino-piperidin-1-yl)-1H-benzoimidazol-2-yl]-methanone (hydrochloride salt);

[6-(4-Dimethylamino-piperidin-1-yl)-1H-benzoimidazol-2-yl]-[2-(3,5-dimethyl-1H-pyrazol-4-yl)-pyridin-4-yl]-methanone (formate salt);

(5'-Amino-[2,3']bipyridinyl-4-yl)-[6-(4-dimethylamino-piperidin-1-yl)-1H-benzoimidazol-2-yl]-methanone (formate salt);

[2-(2,3-Dihydro-benzo[1,4]dioxin-6-yl)-pyridin-4-yl]-[6-(4-dimethylamino-piperidin-1-yl)-1H-benzoimidazol-2-yl]-methanone;

[6-(4-Dimethylamino-piperidin-1-yl)-7-fluoro-1H-benzoimidazol-2-yl]-(2-isoquinolin-4-yl-pyridin-4-yl)-methanone (trifluoroacetate salt);

[2-(4-Dimethylamino-piperidin-1-yl)-9H-purin-8-yl]-(2-isoquinolin-4-yl-pyridin-4-yl)-methanone;

(2-[1,4]-Diazepan-1-yl-9H-purin-8-yl)-(2-isoquinolin-4-yl-pyridin-4-yl)-methanone;

[5-(4-Dimethylamino-piperidin-1-yl)-3H-imidazo[4,5-b]pyridin-2-yl]-(2-isoquinolin-4-yl-pyridin-4-yl)-methanone;

[5-(4-Dimethylamino-piperidin-1-yl)-3H-imidazo[4,5-b]pyridin-2-yl]-[2-(1,3,5-trimethyl-1H-pyrazol-4-yl)-pyridin-4-yl]-methanone;

4-[6-(4-Dimethylamino-piperidin-1-yl)-1H-benzoimidazole-2-carbonyl]-2-isoquinolin-4-yl-benzonitrile;

4-[5-(4-Dimethylamino-piperidin-1-yl)-1H-benzoimidazole-2-carbonyl]-2-(3,5-dimethyl-1H-pyrazol-4-yl)-benzonitrile;

4-[5-(4-Dimethylamino-piperidin-1-yl)-1H-benzoimidazole-2-carbonyl]-2-pyridin-3-yl-benzonitrile;

4-[5-(4-Dimethylamino-piperidin-1-yl)-3H-imidazo[4,5-b]pyridine-2-carbonyl]-2-(1H-pyrrolo[2,3-c]pyridin-4-yl)-benzonitrile;

446-(4-Dimethylamino-piperidin-1-yl)-1H-benzoimidazole-2-carbonyl]-2-(1H-pyrrolo[2,3-c]pyridin-4-yl)-benzonitrile;

4-[6-(4-Dimethylamino-piperidin-1-yl)-1H-benzoimidazole-2-carbonyl]-2-[1,6]naphthyridin-8-yl-benzonitrile;

4-[5-(4-Dimethylamino-piperidin-1-yl)-3H-imidazo[4,5-b]pyridine-2-carbonyl]-2-[1,6]naphthyridin-8-yl-benzonitrile;

4-[5-(4-Dimethylamino-piperidin-1-yl)-3H-imidazo[4,5-b]pyridine-2-carbonyl]-2-(3,5-dimethyl-1H-pyrazol-4-yl)-benzonitrile;

[5-(4-dimethylamino-piperidin-1-yl)-3H-imidazo[4,5-b]pyridin-2-yl]-[2-(2,3-difloro-6-methoxy-phenyl)-pyridin-4-yl]-methanone;

[6-(4-dimethylamino-piperidin-1-yl)-1H-benzoimidazol-2-yl]-[2-(5-methyl-imidazol-1-yl)-pyridin-4-yl]-methanone (hydrochloride salt);

[6-(4-Dimethylamino-piperidin-1-yl)-1H-benzoimidazol-2-yl]-[2-(4-methyl-imidazol-1-yl)-pyridin-4-yl]-methanone (hydrochloride salt);

[6-(4-Dimethylamino-piperidin-1-yl)-1H-benzoimidazol-2-yl]-[2-(2-methyl-benzoimidazol-1-yl)-pyridin-4-yl]-methanone;

[6-(4-Dimethylamino-piperidin-1-yl)-1H-benzoimidazol-2-yl]-[2-(2,5-dimethyl-imidazol-1-yl)-pyridin-4-yl]-methanone;

[6-(4-Dimethylamino-piperidin-1-yl)-1H-benzoimidazol-2-yl]-[2-(2,4-dimethyl-imidazol-1-yl)-pyridin-4-yl]-methanone;

[6-(4-Dimethylamino-piperidin-1-yl)-1H-benzoimidazol-2-yl]-(2-imidazo[4,5-c]pyridin-3-yl-pyridin-4-yl)-methanone;

[6-(4-Dimethylamino-piperidin-1-yl)-1H-benzoimidazol-2-yl]-(2-imidazo[4,5-c]pyridin-1-yl-pyridin-4-yl)-methanone;

[6-(4-Dimethylamino-piperidin-1-yl)-1H-benzoimidazol-2-yl]-(2-imidazo[4,5-b]pyridin-3-yl-pyridin-4-yl)-methanone;

[6-(4-Dimethylamino-piperidin-1-yl)-1H-benzoimidazol-2-yl]-(2-imidazo[4,5-b]pyridin-1-yl-pyridin-4-yl)-methanone;

(2-Benzoimidazol-1-yl-pyridin-4-yl)-[6-(4-dimethylamino-piperidin-1-yl)-1H-benzoimidazol-2-yl]-methanone;

[5-(2,3-Difluoro-6-methoxy-phenyl)-pyridin-3-yl]-(5-dimethylaminomethyl-1H-benzoimidazol-2-yl)-methanone;

[5-(4-Dimethylamino-piperidin-1-yl)-3H-imidazo[4,5-b]pyridin-2-yl]-(2-isoquinolin-4-yl-pyridin-4-yl)-methanone;

[5-(4-Dimethylamino-piperidin-1-yl)-3H-imidazo[4,5-b]pyridin-2-yl]-[2-(1,3,5-trimethyl-1H-pyrazol-4-yl)-pyridin-4-yl]-methanone;

[5-(4-dimethylamino-piperidin-1-yl)-3H-imidazo[4,5-b]pyridin-2-yl]-[2-(2,3-difloro-6-methoxy-phenyl)-pyridin-4-yl]-methanone;

(5-[1,4]Diazepan-1-yl-3H-imidazo[4,5-b]pyridine-2-yl)-(2-isoquinolin-4-yl-pyridin-4-yl)-methanone;

(2-Isoquinolin-4-yl-pyridin-4-yl)-5-piperazin-1-yl-3H-imidazo[4,5-b]pyridin-2-yl)-methanone;

4-[5-(4-Dimethylamino-piperidin-1-yl)-3H-imidazo[4,5-b]pyridine-2-carbonyl]-2-isoquinolin-4-yl-benzonitrile;

2-Isoquinolin-4-yl-4-(5-piperazin-1-yl-3H-imidazo[4,5-b]pyridine-2-carbonyl)-benzonitrile;

[5-(4-Dimethylamino-piperidin-1-yl)-3H-imidazo[4,5-b]pyridine-2-yl]-[2-(3,5-dimethyl-1H-pyrazol-4-yl)-pyridin-4-yl]-methanone;

4-[5-(4-Dimethylamino-piperidin-1-yl)-3H-imidazo[4,5-b]pyridine-2-carbonyl]-[2-(3,5-dimethyl-1H-pyrazol-4-yl)-benzonitrile;

[2-(3,5-Dimethyl-1H-pyrazol-4-yl)-pyridin-4-yl]-(5-piperazin-1-yl-3H-imidazo[4,5-b]pyridine-2-yl)-methanone;

(5-[1,4]Diazepan-1-yl-3H-imidazo[4,5-N-pyridin-2-yl)₄₂-(3,5-dimethyl-1H-pyrazol-4-yl)-pyridin-4-yl]-methanone;

(5-[1,4]Diazepan-1-yl-3H-imidazo[4,5-N-pyridin-2-yl)₄₂-(1,3,5-trimethyl-1H-pyrazol-4-yl)-pyridin-4-yl]-methanone;

[5-(3-Amino-pyrrolidin-1-yl)-3H-imidazo[4,5-b]pyridin-2-yl]-(2-isoquinolin-4-yl-pyridin-4-yl)-methanone;

4-[5-(4-Dimethylamino-piperidin-1-yl)-3H-imidazo[4,5-b]pyridine-2-carbonyl]-2-(1,3,5-trimethyl-1H-pyrazol-4-yl)-benzonitrile;

2-(3-Methyl-isoquinolin-4-yl)-4-[5-(piperazine-1-carbonyl)-1H-benzoimidazole-2-carbonyl]-benzonitrile;

5-[5-(4-Dimethylamino-piperidin-1-yl)-1H-benzoimidazole-2-carbonyl]-2-methoxy-biphenyl-2-carboxylic acid amide;

4-[5-(4-Dimethylamino-piperidin-1-yl)-3H-imidazo[4,5-b]pyridine-2-carbonyl]-2-(2-methyl-imidazo[1,2-a]pyridin-3-yl)-benzonitrile;

2-(3,5-Dimethyl-1H-pyrazol-4-yl)-4-[6-(piperazine-1-carbonyl)-1H-benzoimidazole-2-carbonyl]-benzonitrile;

(2-Isoquinolin-4-yl-pyridin-4-yl)-[5-(piperazine-1-carbonyl)-3H-imidazo[4,5-b]pyridin-2-yl]-methanone;

4-(5-[1,4']Bipiperidinyl-1'-yl-3H-imidazo[4,5-b]pyridine-2-carbonyl)-2-(3,5-dimethyl-1H-pyrazol-4-yl)-benzonitrile;

2-Isoquinolin-4-yl-4-[6-(piperazine-1-carbonyl)-1H-benzoimidazole-2-carbonyl]-benzonitrile;

4-(6-Chloro-1H-benzoimidazole-2-carbonyl)-2-[1,6]naphthyridin-8-yl-benzonitrile;

(2-Isoquinolin-4-yl-pyridin-4-yl)-[6-(piperazine-1-sulfonyl)-1H-benzoimidazol-2-yl]-methanone;

[6-(piperazine-1-carbonyl)-1H-benzoimidazol-2-yl]-[2-(1,3,5-trimethyl-1H-pyrazol-4-yl)-pyridin-4-yl]-methanone;

4-[6-(piperazine-1-carbonyl)-1H-benzoimidazole-2-carbonyl]-2-(1,3,5-trimethyl-1H-pyrazol-4-yl)-benzonitrile;

2-(3,5-Dimethyl-1-phenyl-1H-pyrazol-4-yl)-4-[6-(piperazine-1-carbonyl)-1H-benzoimidazole-2-carbonyl]-benzonitrile;

2-(4-Cyano-3-isoquinolin-4-yl-benzoyl)-3H-benzoimidazole-5-sulfonic acid (2-amino-ethyl)-methyl-amide;

2-(3,5-Dimethyl-isoxazol-4-yl)-4-[6-(piperazine-1-carbonyl)-1H-benzoimidazole-2-carbonyl]-benzonitrile;

6-(4-Dimethylamino-piperidin-1-yl)-1H-benzoimidazol-2-yl]-[3-(3,5-dimethyl-1H-pyrazol-4-yl)-4-fluoro-phenyl]methanone;

4-(5-piperazin-1-yl-3H-imidazo[4,5-b]pyridine-2-carbonyl)-2-(1,3,5-trimethyl-1H-pyrazol-4-yl)-benzonitrile;

(5-[1,4']Bipiperidinyl-1'-yl-3H-imidazo[4,5-b]pyridin-2-yl)-(2-isoquinolin-4-yl-pyridin-4-yl)-methanone;

4-[2-(2-Isoquinolin-4-yl-pyridine-4-carbonyl)-3H-imidazo[4,5-b]pyridin-6-yl]-[1,4]diazepane-1-carboxylic acid tert-butyl ester;

(2-Isoquinolin-4-yl-pyridin-4-yl)-[6-(piperazine-1-carbonyl)-1H-benzoimidazol-2-yl]-methanone;

4-[2-(2-Isoquinolin-4-yl-pyridine-4-carbonyl)-3H-imidazo[4,5-b]pyridin-5-yl]-piperazine-1-carboxylic acid tert-butyl ester;

4-[2-(4-Cyano-3-isoquinolin-4-yl-benzoyl)-3H-imidazo[4,5-b]pyridin-5-yl]-piperazine-1-carboxylic acid tert-butyl ester;

4-[5-(pyrrolidin-3-yloxy)-3H-imidazo[4,5-b]pyridine-2-carbonyl]-2-(1,3,5-trimethyl-1H-pyrazol-4-yl)-benzonitrile;

4-[5-(4-dimethylamino-piperidin-1-yl)-3H-imidazo[4,5-b]pyridine-2-carbonyl]-2-(1,3,5-trimethyl-1H-pyrazol-4-yl)-benzamide;

4-[5-(4-dimethylamino-piperidin-1-yl)-3H-imidazo[4,5-b]pyridine-2-carbonyl]-N,N-dimethyl-2-(1,3,5-trimethyl-1H-pyrazol-4-yl)-benzamide;

[6-(4-dimethylamino-piperidin-1-yl)-1H-benzoimidazol-2-yl]-(3-isoquinolin-4-yl-4-methoxy-phenyl)-methanone;

[6-(4-dimethylamino-piperidin-1-yl)-1H-benzoimidazol-2-yl]-(4-hydroxy-3-isoquinolin-4-yl-phenyl)-methanone;

4-[5-(4-dimethylamino-piperidin-1-yl)-3H-imidazo[4,5-b]pyridine-2-carbonyl]-2-(2-methyl-5,6-dihydro-4H-pyrrolo[1,2-b]pyrazol-3-yl)-benzonitrile;

4-[5-(4-hydroxy-piperidin-1-yl)-3H-imidazo[4,5-b]pyridine-2-carbonyl]-2-(1H-pyrrolo[2,3-c]pyridin-4-yl)-benzonitrile;

(S)-2-amino-3-methyl-butyric-acid-1-{2-[4-cyano-3-(1H-pyrrolo[2,3-c]pyridin-4-yl)-benzoyl]-3H-imidazo[4,5-b]pyridin-5-yl}-piperidin-4-yl ester;

phosphoric-acid-mono-(1-{2-[4-cyano-3-(1H-pyrrolo[2,3-c]pyridin-4-yl)-benzoyl]-3H-imidazo[4,5-b]pyridin-5-yl]-piperidin-4-yl)ester;

4-[5-(4-dimethylamino-piperidin-1-yl)-3H-imidazo[4,5-b]pyridine-2-carbonyl]-2-(5-methoxy-1H-pyrrolo[2,3-c]pyridin-4-yl)-benzonitrile;

4-[5-(pyrrolidin-3-yloxy)-3H-imidazo[4,5-b]pyridine-2-carbonyl]-2-(1H-pyrrolo[2,3-c]pyridin-4-yl)-benzonitrile;

4-{5-[2-(4-methyl-piperazin-1-yl)-ethoxy]-3H-imidazo[4,5-b]pyridine-2-carbonyl}-2-(1,3,5-trimethyl-1H-pyrazol-4-yl)-benzonitrile;

4-[5-(5,6-dihydro-8H-imidazo[1,2-a]pyrazin-7-yl)-3H-imidazo[4,5-b]pyridine-2-carbonyl]-2-(1,3,5-trimethyl-1H-pyrazol-4-yl)-benzonitrile;

4-[5-(3,6-diaza-bicyclo[3.2.0]hept-3-yl)-3H-imidazo[4,5-b]pyridine-2-carbonyl]-2-(1,3,5-trimethyl-1H-pyrazol-4-yl)-benzonitrile;

4-[5-(2,6-diaza-spiro[3.3]hept-2-yl)-3H-imidazo[4,5-b]pyridine-2-carbonyl]-2-(1,3,5-trimethyl-1H-pyrazol-4-yl)-benzonitrile;

4-[5-(2,6-diaza-spiro[3.3]hept-2-yl)-3H-imidazo[4,5-b]pyridine-2-carbonyl]-2-(1H-pyrrolo[2,3-c]pyridin-4-yl)-benzonitrile;

4-[5-(3,3-dimethyl-2-oxo-piperazin-1-yl)-3H-imidazo[4,5-b]pyridine-2-carbonyl]-2-(1,3,5-trimethyl-1H-pyrazol-4-yl)-benzonitrile;

4-[5-(pyrrolidin-3-ylamino)-3H-imidazo[4,5-b]pyridine-2-carbonyl]-2-(1,3,5-trimethyl-1H-pyrazol-4-yl)-benzonitrile;

4-[5-(3-amino-pyrrolidin-1-yl)-3H-imidazo[4,5-b]pyridine-2-carbonyl]-2-(1,3,5-trimethyl-1H-pyrazol-4-yl)-benzonitrile; and 4-[5-(6-amino-3-aza-bicyclo[3.1.0]hex-3-yl)-3H-imidazo[4,5-b]pyridine-2-carbonyl]-2-(1,3,5-trimethyl-1H-pyrazol-4-yl)-benzonitrile;

and salts, solvates, tautomers and N-oxides thereof.

18. A pharmaceutical composition comprising a compound according to claim 1, or a salt, solvate, tautomer or N-oxide thereof, and a pharmaceutically acceptable carrier.

* * * * *

UNITED STATES PATENT AND TRADEMARK OFFICE
CERTIFICATE OF CORRECTION

PATENT NO. : 8,598,217 B2  Page 1 of 1
APPLICATION NO. : 13/266976
DATED : December 3, 2013
INVENTOR(S) : Howard et al.

It is certified that error appears in the above-identified patent and that said Letters Patent is hereby corrected as shown below:

In the Claims:

Column 260, Line 44: Claim 1, Delete "$C_{2-8}$ alkenyl; $C_{2-8}$ alkynyl;" and insert -- $C_{2-6}$ alkenyl; $C_{2-6}$ alkynyl; --

Column 260, Line 45: Claim 1, Delete "$O_{3-8}$" and insert -- $C_{3-6}$ --

Column 263, Line 37: Claim 2, Delete "$C_{1-8}$ alkyl, $C_{1-8}$ alkoxyl" and insert -- $C_{1-6}$ alkyl, $C_{1-6}$ alkoxyl --

Column 264, Line 59: Claim 2, Delete "$(CH_2),NR^{7a}R^{8a}$" and insert -- $(CH_2)_m\text{-}NR^{7a}R^{8a}$ --

Column 264, Line 66: Claim 2, Delete "$(CH_2),NR^{7a}R^{8a}$" and insert -- $(CH_2)_m\text{-}NR^{7a}R^{8a}$ --

Column 272, Line 65: Claim 17, Delete "446-(4-" and insert -- 4-[6-(4- --

Column 273, Line 1: Claim 17, Delete "446-(4-" and insert -- 4-[6-(4- --

Column 274, Line 7: Claim 17, Delete "[4,5-N]-" and insert -- [4,5-b]- --

Column 274, Line 8: Claim 17, Delete "$_{42}$-(3,5-" and insert -- -[2-(3,5- --

Column 274, Line 10: Claim 17, Delete "[4,5-N]-" and insert -- [4,5-b]- --

Column 274, Line 11: Claim 17, Delete "$_{42}$-(1,3,5-" and insert -- -[2-(1,3,5- --

Signed and Sealed this
Eighteenth Day of March, 2014

Michelle K. Lee
*Deputy Director of the United States Patent and Trademark Office*

UNITED STATES PATENT AND TRADEMARK OFFICE
CERTIFICATE OF CORRECTION

| | | |
|---|---|---|
| PATENT NO. | : 8,598,217 B2 | Page 1 of 1 |
| APPLICATION NO. | : 13/266976 | |
| DATED | : December 3, 2013 | |
| INVENTOR(S) | : Howard et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 203 days.

Signed and Sealed this
Thirtieth Day of December, 2014

Michelle K. Lee
*Deputy Director of the United States Patent and Trademark Office*